United States Patent
Brody et al.

(10) Patent No.: US 6,323,002 B1
(45) Date of Patent: Nov. 27, 2001

(54) METHODS FOR MODIFYING THE PRODUCTION OF A POLYPEPTIDE

(75) Inventors: Howard Brody; Deborah S. Yaver; Michael Lamsa, all of Davis, CA (US); Kim Hansen, Vaerlose (DK)

(73) Assignee: Novozymes Biotech, Inc, Davis, CA (US)

( * ) Notice: Subject to any disclaimer, the term of this patent is extended or adjusted under 35 U.S.C. 154(b) by 0 days.

(21) Appl. No.: 09/339,972

(22) Filed: Jun. 25, 1999

Related U.S. Application Data

(63) Continuation of application No. 08/928,692, filed on Sep. 12, 1997, now Pat. No. 5,958,727, which is a continuation-in-part of application No. 08/713,312, filed on Sep. 13, 1996, now abandoned.

(51) Int. Cl.[7] ........................... C12N 15/09; C12N 15/63; C12N 1/15; C12P 21/06; C07H 21/04
(52) U.S. Cl. ................ 435/69.1; 435/254.3; 435/320.1; 435/471; 435/243; 435/455; 435/468; 536/23.1
(58) Field of Search ........................... 435/69.1, 41, 325, 435/243, 455, 254.3, 410, 440, 320.1, 468, 471; 536/23.1

(56) References Cited

PUBLICATIONS

Studier, et al. Journal of Molecular Biology, pp37–44, 1991.*

Robyt, et al. "Biochemical Techniques: Theory and Practice" chapters 4,5, and 8–10, 1991.*

* cited by examiner

*Primary Examiner*—David Guzo
*Assistant Examiner*—Gerald G. Leffeis, Jr.
(74) *Attorney, Agent, or Firm*—Robert L. Starnes

(57) ABSTRACT

The present invention relates to methods for modifying the production of a polypeptide, comprising: (a) introducing a nucleic acid construct into a cell, wherein the cell comprises a DNA sequence encoding a polypeptide, under conditions in which the nucleic acid construct integrates into the genome of the cell at a locus not within the DNA sequence encoding the polypeptide to produce a mutant cell, wherein the integration of the nucleic acid construct modifies the production of the polypeptide by the mutant cell relative to the cell when the mutant cell and the cell are cultured under the same conditions; and (b) identifying the mutant cell with the modified production of the polypeptide.

19 Claims, 46 Drawing Sheets

```
ACAGGCGACTGGGATGGTGAATATCTGAGCGGATAGCCCCCGACACAGCACCAAGGGTAAGCTTCCATAGCGG    70
TTCCAGGTGGCTTAGATACGCTCTTCGATGCCATATAAAGGCTTCTAACCACGCTGTACCAGTAGAAGTA       140
CGCAAAGTTGGTCGAGGCCACGCCAAGCAAAGAACCATCCCGAATATAAACCTTCAATTCCCTCT            210
TTCTCCACAATCTTGTTGATGGCATCTAGGGTCGACTCGTAATGTACTACATCTCCGCTTTTCGATTCAG       280
GTGCGTTCTTCACTTGGACTTGAAGTTTGGTTTGACACGCACAGTGAACGAGTCAGTCTCAGTCTA           350
CACCACTAAGCCAAACTGGCAAGGCTATGTGTACGCAGTCCAGTGGATAGACGATAGCATTGCGAGAAC        420
AGCACCAGTTGCACCTGCGACAGCACTACCCCAAGGGGAGAGCGCGGGTTTCGATTGGCCGGCCATTATG       490
CAGGATGAGCTAAAGTGCCTCTGCCAATTCCGTGTGCGATTCGGGGGGTTTAGCGTTCGGCTTGAAGGCTTACCG  560
CCAAGACCGGCGAATGAGGCAGGACTCTGTGCGAGTAAGGTGAATGCCGAGTAAGGTGAAAGACCCCAGCTCCCAAGCAACAGTAAG 630
GATCGACTGATAGAGAAAAAGTTGAATGCCGAGTAAGGTGAAAGACCCCAGCTCCCAAGCAACAGTAAG        700
TGGAAGAGCTTAAGGATAGAAAATAAATAGGATTAAGAAAAAAGAAACCTCAAGACTGGTCACA             770
CAGTCCCGGCATCCTGAACGTAAAATGCGGGAAGGATAGAGTCGGCAGGCCAGTTGCACCTCGG             840
CGCTCTGGGTTTGCGCATGAGCGAAATGAGCGAGGTTCGTTTTTTGGAGGCCAATTCTGAACACCGACCT       910
TCGAATTCCCGTTCCTCCCCACCGACACGCTAGTGAATGATCCAGCAAGCATACTTGGTGTGTTTGAC         980
CTCATTCCACTGCCGTGTGATTGGCCCTTCATAAAACTTGACAAGGAAGTTTGATCGACCTCGGATGTCGCGCTT  1050
TCATCATCGTCTTGATTGGCCCTTCATAAAACTTGACAAGGAAGTTTGATCGACCTCGGATGTCGCGCTT       1120
TCGGAAATTTCACGGAGCCTATGCCTATCGCGGGAAGATCTCGGAGTGTCACGGTGTTGAAGATCCCAGGC      1190
ACGCTAGTTGAACTGTTATGCCTATCGCGGGAAGATCTCGGAGTGTCACGGTGTTGAAGATCCCAGGC         1260
GCTCGTCAAAATACTGCCCGGCCTGCCAGTATGCCGAACCGCCTCAGCCGAAGTCCTTTATAA              1330
           M  S  R  P  N  A  S  A  Q  K  S  F  I
CTCAGGCACTGGTACTTGACCCTTTTTTTTATGGTTTTTTGTTTCTTCTTGTTACACCTTATTTTCT           1400
T  Q  A  L
TCTTCTCGTTTTTTGTAGATAATACTGACCACTGGCTAGAAAGCCGAGCGGGATGTATCGTCCGCCACTT       1470
                       K  A  E  R  D  V  S  S  A  T
```

Fig. 10A

```
CTCAAAGGCAAGCTTTAGAAGCTGCCATTGATGCTGCTGAAACACTATATGAAAGCCTTAAATCTGGCATC 1540
 S  Q  R  Q  A  L  E  A  A  I  D  A  A  E  H  Y  M  K  A  L  N  L  A  S
TGTTCAGAGAAAGACAAACATGGATGCAAAGTGTAAAGAGCTCACAAGAGCGGAAAAGATCAAA 1610
 V  Q  K  D  K  H  A  L  D  A  K  C  K  E  W  L  T  R  A  E  K  I  K
GAATCTAAGGACTGGCAAGCTGCTGCCCGTTTCCATGACAAAACTGTTCCAGAGCCACGGTGCCTGTAT 1680
 E  S  K  D  W  Q  A  A  A  R  F  H  D  K  T  V  P  E  P  R  L  P  V
CTACTCGTAAGCTCACCACACGGGAGGAGATCATTCTGCTAGAGGGAGCCAAGTTGAATGGCTTCATATT 1750
 S  T  R  K  L  T  T  R  E  E  I  I  L  E  G  A  K  L  N  G  F  I  F
CCCTCCATGGTCCACCTCCCCAGGCTCTGACGAGTTCAAACGAGAGGATGGTGAATCCCCGTTTACGTAA 1820
 P  P  W  S  T  S  P  G  S  D  E  F  K  R  E  D  G  E  S  P  F  T  *
GTTCTGGTGGTCTGCATCGTCAATGTTGCATGTATACCCAGATGACTGCTGGATATTCTAACCGATAACA 1890
 V  L  V  V  C  I  V  N  V  A  C  I  P  D  D  C  W  I  F  *  P  I  T
GCGACAAACCCGATCTTCATCTATCTTCAAAGGAAAGTTTTTGATGGCTGAAAACGACCTTCCGA 1960
 A  T  N  P  D  L  H  L  S  S  K  E  S  F  *  W  L  K  T  T  F  R
DKPDLHLSYPQRKVFDGWKRPSE
GCTTCTCGCGAAAGACAACGGAAGAGTGTACACAAAGGTGGTTCCTGTGATGTCTGTTCCAGGAAAGACA 2030
 L  L  A  K  D  T  E  D  V  Y  T  K  V  V  P  V  M  S  V  P  G  K  T
GATCTAGTCCAGGATATGCTGACGGACTGTTCTGTGTTGCTAGCCTTTGTGCTACTACGTCAATGCTAG 2100
 D  L  V  Q  D  M  L  T  D  C  S  V  V  A  S  L  C  A  T  T  S  M  L
AACGCGGGCCAGTGTACTGTAAGAAGATTGATCCCCTTCCGGCTGACCTGCATGGTTCGCTGTGACTAATAG 2170
 N  A  G  Q  C  T  V  K  K  I  D  P  L  P  A  D  L  H  G  S  L  *  L  *
ERGQCT
GTGTAGCATTTCTTCCAATGATATACCCTAGCCGGGAGCTCTCAGCCTTCACCGTCAGGCAAGTATA 2240
 V  *  H  F  F  Q  *  Y  T  L  A  G  S  S  Q  P  S  P  H  R  Q  V  *
 HFLPMIYPSRGSSQPSPSGKY
TATTTCGCTTTTATTTCAATGGGTGCTTCCGGAAAGTCATTGACGACGTTGCCATCGTCTAAGAC 2310
 Y  F  A  L  F  S  M  G  A  S  G  K  S  L  T  T  L  P  S  S  K  T
IFRFYFNGCFRKVIIDDRLPSSKT
```

Fig. 10B

```
ATCAAGATCACTCCACGTGATCGACCGGAAAAATCCCAATTTCCTTTGGCCGGCGCTCGTAGAGAAGGCG  2380
 S  R  S  L  H  V  I  D  R  K  N  P  N  F  L  W  P  A  L  V  E  K  A
TATTTGAAATTGCGCGGAGGCTATGATTTTCCCGGAAGCAATTCCGGGACAGATCTCTGGGTGCTGACAG  2450
 Y  L  K  L  R  G  G  Y  D  F  P  G  S  N  S  G  T  D  L  W  V  L  T
GTTGGATTCCCGAGCAAGTCTTTCTCCATAATGACGATGTGACTGGCGACCAGTTGTGGAAGCGACTTTA  2520
 G  W  I  P  E  Q  V  F  L  H  N  D  D  V  T  G  D  Q  L  W  K  R  L  Y
CAGATCCTTTCACCAAGGAGATGTTCTCTTGACTATAGGTACCGGTGAACTGACTGAGAGGAACAAAGA  2590
 R  S  F  H  Q  G  D  V  L  L  T  I  G  T  G  E  L  T  E  R  E  Q  R
GAACTAGGCCTCGTGAGTGAGCATGATTATGCTATTCTGGATATGAAGGAATCTAAAGGTCGCCGACAAT  2660
 E  L  G  L  V  S  E  H  D  Y  A  I  L  D  M  K  E  S  K  G  R  R  Q
TACTCGTGAAAAACCCTTGGGCTGGAGCAGAGATACTGCCCCCGGCAGAAGCCTCTCTGCATCGCA  2730
 L  L  V  K  N  P  W  A  G  A  D  T  A  P  G  D  N  G  S  L  S  A  S  Q
GGATTACCCCATAACCCGCCCTCATTGAGCCGGGTACCTTTTGAGCCGGGTACCTTTGAGCGAAAAGCTGCTTCAA  2800
 D  L  P  H  N  P  P  S  F  E  P  G  T  F  W  M  D  C  E  K  L  L  Q
CATTTTGAAAACCTCTATTGAATTGAACCCTGAGATTTCAAATACCGGCGAAGACGTTCCACTTTACGT  2870
 H  F  E  N  L  Y  L  N  W  N  P  E  I  F  K  Y  R  E  D  V  H  F  T
GGGACCTCAACAACGGGAGAGGTGTAGCGGTGTGTTCCGCGGCTGTCTAGGCAGTTCGCAGTGTCAACCGA  2940
 W  D  L  N  N  G  R  G  V  A  G  C  F  V  N  N  P  Q  F  A  V  S  T  E
GAACGGTGGGATTGTCTGTTACTTCTAGGCAAGCATTTCAGAACACAGGCGAACGACCTCTT  3010
 N  G  I  V  W  L  L  G  K  H  F  R  T  T  G  Q  P  E  R  P  L
GACGAATACCAAGCGAATGAGGAGTCGGCTTTTATAAGCATATATGTCTTTAACGCAGATGGCAAACGGG  3080
 D  E  Y  Q  A  N  E  E  S  A  F  I  S  I  Y  V  F  N  A  D  G  K  R
TCTCTTTGAGTGATGATGGGGCTCTACATCGTGCCCCTATGGTGGATTCCCCTAATACGCTCATGAGGTTAGA  3150
 V  S  L  S  D  G  A  L  H  R  G  P  Y  V  D  S  P  N  T  L  M  R  L  E
```

Fig. 10C

```
GATGCCCCCAGAACAACATACACAGTCGTGGTCTCCGAGCAATCACTGCCATCTTTGAATCAAAACTTT  3220
  M   P   P   R   T   T   Y   T   V   V   V   S   E   Q   S   L   P   S   L   N   Q   N   F
ACTTTGTCTGCCTTCTCTACCTGCCCTGCCGTGAGGATGGCAAAAGCCCAAGATAAATACATGTGTCAGGA  3290
  T   L   S   A   F   S   T   C   P   V   R   M   A   K   A   Q   D   K   Y   M   C   V   R
AGATTCAAGGGTCTTGGACACCTTCGATATCTTCTGATATCCACTCAACCC  3360
  K   I   Q   G   S   W   T   P   S   T   A   G   G   N   A   E   S   R   Y   P   L   N   P
CCAATTTAGGTTGGAGATAGAATGACACAGATGTTTCACTCCTGCTGAATGCCAAACACGGAACTC  3430
  Q   F   R   L   E   I   E   N   D   T   D   V   S   L   L   E   C   P   N   T   E   L
GCGACCCATGTTAAGTTATTCTGGTCCAATGGAAATCGTGTGTCGCGAGTACGCAGTCGCGACATAATCG  3500
  A   T   H   V   K   L   F   W   S   N   G   N   R   V   S   R   V   R   S   R   D   I   I
CTGATAGTGGTGACTATCGCCGTGGTGGCGCCGATCAACTTGGCCGAGCTCTGGTATCCTCCTTAGTTCCT  3570
  A   D   S   G   D   Y   R   R   G   G   S   L   V   E   K   K   A   L   E   P   G   S   Y   T
AATCGTCTGTTCCACATTCGCCGCCGATCAACTTGGCCGAGCTCTGGTATCCTCCTTAGTTCCT  3640
  I   V   C   S   T   F   A   P   D   Q   L   G   R   F   T   L   W   V   S   S   L   V   P
TGCAAGACGAGCCCGCTCCCACCAGAGCCTGAAGCAGGTCAGTTCATTTCAGATATTGGCTACTGC  3710
  C   K   T   S   P   L   P   P   E   A   A   G   R   R   T   V   I   S   D   I   G   V   L
CTCCCGGGAGACCGAATGTTAGCTCTCTGCAAGTGTTCCTGCACCCCGTTTTAATGACAGTGGAGCTCGGG  3780
  P   P   G   R   D   R   M   L   A   S   L   Q   V   P   R   L   T   R   I   K   L   I   T   R
AAGTAGGCAATCATCATGGGAGCCATCCTGTTGGACCCTCGCCCGTTTAATGACAGTGGAGCTCGGG  3850
  K   *   A   I   I   M   G   A   I   L   L   D   P   R   P   V   *   *   Q   *   ELG
CAAGGGCCATACAAACAGATCCTGGCGACTTGCAGCCTGGCTAGAGGAGAGTGTATCGGGGGTAC  3920
  S   R   Q   S   I   G   S   H   P   V   G   P   S   P   V   L   M   T   V   E   L   G
GTGTTGAGGACTTTGACTTGCAGCCTGGCTAGAGGAGAGTGTTATTGGATTGTTATTGAGAGGAT  3990
  R   V   E   D   F   D   L   Q   P   G   L   E   E   S   G   G   I   W   I   V   I   E   R   I
```

Fig. 10D

```
TGGGGGTCCTGGAGGGCAGGTAGAGGACCACTTTGAGGTGGAAGCTTTGGCTGAAGAGAGGGTTGAGATT  4060
 G  G  P  G  G  Q  V  E  D  H  F  E  V  E  A  L  A  E  E  R  V  E  I
GGGGAGTGGATACTTGAAGATGCTTGATCTCTCTTATCCTGCAGAAGCTCTGAAGCTCTGACGGTCTTAGT  4130
 G  E  W  I  L  E  D  A  .
TGAGCTTTTTTGATCGTCGTTGTGATTAGCACGTTAGAGAGTAGAAGAGCGGAAACAATGATAGACATGAAT  4200
TTCTCTTATTGTCTCTATTGGCCAGAAGAAAGGCATTAAATCATTAAAAGCAAGAGTTTA  4270
TCTATAGATACCGAGCAGCCTCAGGATTTGAGCTGAGGTTTGTCGCGATCGCCAAAAATGGAGTT  4340
AGCTTGCTTTACTCCGCATAAATTAAATCCCTCGGCTGTGTGTTAAATCCTCCGAGTGCTTTCAAC  4410
GTCATCCCGTTTGCTTGCTGTGTGCATTGTGCCTCCCACCTTTAACAATTGGAGCTCTGTCCAAGGACAAATC  4480
CTTATTCTCGCGGCCTCCATGGCGACTTCAGCTTGAACGTGTAAAGCCCGTCGCCTACTGGTGTGAGTATTGGGCGCTTTG  4550
CCGTCAGAGACAGCTCAGCTTGAACGTGTAAAGCCCGTCGCCTACTGGTGTGAGTATTGTGATTAT  4620
ACCCAGTACGAACTACGAGCTGATGAGCGGCCTCTGCTGATCGCAGGCAACTTCTGGATCGTCAACCAGA  4690
TTATTGAGAA  4700
```

Fig. 10E

```
TATTCTGCTAGTAGTTAGATCTTACTGAGGGGGTATAACTCTTCGGTAGCCGGTGCGTATGCAGTTGTATTGTGACTGTATTGTGATGAGAAGA        90
AGGGCGTTTACTGAAACTGAGTATATGCAAGAGAATGATGTTATGCTTGCATATAAGAGAGATGGAATTATTACTGATATGTCTAAAATTACAATGATT      180
TGTTTTACTGAAACTGAGTATAATGCCAGTTTGACTTAGCCGCGTAGGTAGCCGCGTAGGTGATACTTAATCCGACCAAATTATGAGACCTCGATAGTAC    270
AATGCTATTGGACTTGTAAGATAATAGTCTAGTTCTTCATAGACAAACCTGAGAGAGGCCAGAACGTCGAAGTCATTTCGACAAGCCATAGT              360
ATGATTAGGCATCTAGGAGCTGAACGGAAACCGGTTTAAAGACTGGGCGTCCTCGTACCTCACAGTGCAGATGCATGCCAGATCGAGCATTCGAGCATTATCTGAGCATTATCTGAGCATT    450
ATATATGGAAACCGGTTCAATGCAACCGTACCCACCCGGCGTNTACTATATCGCAGATGTGGCGCACACATTCCCAGATCGGCT                     540
GGAGCCTATCGCAATGCAACCGTACCCACCCGGCGTNTACTATATCGCAGATGTGGCGCACACATTCCCAGATCGGCT                          630
GGTCCGTTGAGCTTCTTTTTCCGATATGGTAGCTGACAGTGTACTAGTGTGACAGTGTACTACCGGCACCAGTGCCTCGCGAAATGTGAGATCGGA        720
GCATGTCTTGCTTCAGCGACCGAAGCCACGGCTTTGTGTGATAGAGTTCAAGACCGAGATTTACAACGTGACTAATCGCAGATATCAGCACAGT          810
ATGTATATGCCAAGATGCCACGATGCCAACTGAGTCACACTTTATTAGTACGACAAGTATAAGCAATACACATACCCACACATTAACCGCTTTCATCGTTTATCCTGGGCATGCTATGCCTCTTTGCAGGA    900
ACCGGCAAGATGTCAACTGAGAGCAACATACAGATGTCTTCACGGTGTGTGAGCTTCTTGTGAGCGGGACTTCTTGTACTGCACTGTCTTGTAGAGCGGGACTAACGACAGG              990
ACGAAACACAAACCTTTATTAGATACGACAAGTATAAGCAATACACATACCCACACATTAACCGCTTTCATCGTTTATCCTGGGCATGCTATGCCTCTTTGCAGGA   1080
CGAAGATATACGACAAGTATAAGCAATACACATACCCACACATTAACCGCTTTCATCGTTTATCCTGGGCATGCTATGCCTCTTTGCAGGA             1170
ATGCAGAAATCGAAACTCGTTATCCAGCCTGGGATGCCGAGTTCCATCACCGAGTTCCATCACGATGATCCATCATGCGACAGAAGCGTTCGGTGCATCGCAGTATGGGTGTCT           1260
ACAACACCTCGTTATCCAGCCTGGGATGCCGAGTTCCATCACCGAGTTCCATCACGATGATCCATCATGCGACAGAAGCGTTCGGTGCATCGCAGTATGGGTGTCT                  1350
TCTACTGTATTGGGATAGGATTAGCGGACTGGCGGTTTGAACGATTGTGGTTCGTGATCGCAAGAGGGCCAGAGAGTCAGTTACTGACGTTACTGACGTTGTAG     1440
AAGTTTCTTCTCTATCATCGCAACGGTCGTTGCCCTTACAATTTGTGGGTTCGGGTTTGCTCTAGACAATTGTGCCCTTACAATTGTGAGCCTCATCATGGTGGTGCCGCTCATCATGGTGGTG   1530
ATACCGTCTATCATCGCAACGGTCGTTGCCCTTACAATTTGTGGGTTCGGGTTTGCTCTAGACAATTGTGAGCCTCATCATGGTGGTGCCGCTCATCATGGTGGTG                  1620
GGACATCAATTTTAGGAATGACGTGGAATGACGTGGACCAGTAATGGAGAAGGAACGAATCGGACGGCCCAAACTCGACCTTATTTTCCGACGTCAATACAATAGCAGCAGCCGATGCCCCAAACTCGACCTTATTTTCCGACGTCAATACAATAGCAGCAGCCG   1710
AACCGATCGGCAGACCAGTATGAACGATGAACGGAATAATCATAAGAGAACGAATCGGACGGCCCAAACTCGACCTTATTTTCCGACGTCAATACAATAGCAGCAGCCG              1800
TAAGAAAGGACAGAAGCCAAGAAAGAACCAAGACGAATCGGACGGCCCAAACTCGACCTTATTTTCCGACGTCAATACAATAGCAGCAGCCG                                1890
GAAGACCGGAGAAGAACCAAGAAAGAACCAAGACGAATCGGACGGCCCAAACTCGACCTTATTTTCCGACGTCAATACAATAGCAGCAGCCG                                1980
ACTCCGTACTGTAGTCGAAAGAACAGTGTTGTAACGTGGTTGAAGTGAACGTCTCCCGCGATGCCGACGATGGACTTATTTTCCGACGTCAATACAATAGCAGCAGCCG              2070
TCTGATCGATGATGTTGTAACAGTGTTGTAACGTGGTTGAAGTGAACGTCTCCCGCGATGCCGACGATGGACTTATTTTCCGACGTCAATACAATAGCAGCAGCCG                 2160
CATAGTCATAGTGTAAGAAAAATTGGGTCTGCCTGCGATTCTATCATGATATGGTCACTGGATCAAGGATGTCAAATGATGAGCTT                                      2250
CGGTTCCCTCCGTTCCAACCGCTATGCCTGTGTCATGCAGGAAATTATCGGGATGACTCGATCTTATTCGGAGGAGGAGTGAAGAGACTA                                  2340
AAGTTGACTACGACTGTTCAGTTCAGTCTTGCGTGTCATGCAGGAAATTATCGGGATGACTCGATCTTATTCGGAGGAGGAGTGAAGAGACTA                               2430
GGAGTCGTTCAGTTCAGTCTTGCGTGTCATGCAGGAAATCCACTCGGGATGAGCAGGAGGAGCAGGGTTAACCTCATGGACGACTACTCCGTACAGGACGG                      2520
AGTACAGAATGTCGAATTCACCCGTTCGGTGACATTAGGATCGGGTGACATTAGGATCGGATCCGGATCAGAATTCCACCCGTGACAGAATCAAATCATGACGAAAACCAA            2610
GAAAAGAGAATTAGGATCGGTGACATTAGGATCGGATCCGGATCAGAATTTCTGAGGTTCGTTGGATTGATGACCTGAATAATACCAATATCATGACGAAAACCAA                 2700
GACGATCACGGAATGGTCCGGATCAGAATTTCTGAGGTTCGTTGGATTGATGACCTGAATAATACCAATATCATGACGAAAACCAA                                      2790
TCCCCCTCATTTCCTGTTTTTGCACGGGAATAGCCACAATTTCCCCCCCAGAAAACCGAAATGAAGTCTGAGCCCTC                                                2880
```

```
CGGGCGTTCTTCGCCGGCGCCCTCCGACCTAAGAAATCCCGTCAGGTCCTCCGAAAGGCATCGACACCGAATCTAAAGGAAGGTCTACAA  1980
AGCAAAGATGACGTCCCGGCGATGCCTTCACTGACCCCATTGGAGGCCCACCGAGAAGTAAATCTTCAGAAAGACACA              2070
CAGCTAGGCGAAACCACGATCATACCGCAATGCTGCATTCAATCGGTTGCATTCAAATCGGTTGGAGAGCTCGATCCGTCCGATCCACACGCAACTACAC  2160
GAATTCGACAATAGACCCCAGGCGAGCGCTTACATGGAGCCTTAACATCGGAGCTTAACATCGGACCTTCTGGGCCGCGAGCCCTGAGCCCTGATAACAATAAACCTCCAGAAACCAC  2250
GAAAGAGCCAGTCTTGCCTTCTCATCTCCCAAGACCGAACACTATACGCTCGTCTGGCCGCGAGCCCTGAGCCCTGATAACAATAAACCTCCAGAAACCAC  2340
GACTACAAAGCGGACTTTCTCATCTCCCAAGATAGACTACTACTCCCTCCTCTGTTTCCCCTGCGCAAATACCACCGCGCACA  2430
CAAGAAGGCTACGAAAGCTCCAACCCGCAGAACATAATCAACCCGCTCTTGATTGCCCAACGCCCGCAACAACGCCCTCCCAGCACCC  2520
CGCCACCGATCACCCACGGCCCATGCCCGTCTGCCCGGGACGGCTGGTCCCAGCCAGTCCATCCGCCCAGTAGTCATGCGCCATACCGATACCATCCGCTAGTCATGCGCCATACCAGGTCATCATCAGGTCATCATCATCGAGGTCATCATCATCGAGGTCATCATCATCGAGGTCATCATCATCGAGGTCATCATCATCGAGGTCATCATCATCGAGGTCATCATCATCGAGGTCATCATCATCGAGGTCATCATCATCGAGGTCATCATCATCGAGGTCATCATCATCGAGGTCATCATCATCGAGGTCATCATCATCGAGGTCATCATCATCGAGGTCATCATCATCGAGGTCATCATCATCGA  2610
```

Fig. 17B

```
ATATCGACTGTAGTAATATCTCAGGTCTCTGGGATAGCTGATGGAATGTTAAGTGAATAATATTGATTTA    70
AAGTTCCTCTAGTTCCAAGCTCTTATGTAGCTTCATTTCTATATATATATTCTATTTAGTGGTGTTG      140
CAGGCGGTGAGCCTATCGGCCAATCATAGTAAAAAACCCGTTAGTTGCAATACCCTGTTAGTTGCAAGGC   210
GAATTCCTGGCTGATATCCTTGCAACTAACGGGGTTTCTCAGTACTCGAATTGAATATATTCGCACA      280
AAGTTATTTCGCAAACTTGGGGCCCTGGGGGTCATACAACCCAAGCCACAAGCTTTATTTAATTCG       346
```

Fig. 20

```
GATTTAATGACTACCTTGATGATACTGCCAATATAGTTAGATAATACAAATCCTGGCTGCCATATAACGC   70
CCTCGCAAACGACATCTTGTTCTTATTNTCCCTCAATCGAGCTTGCCTATGCCCAAGCTTCGAACTATAC  140
GAGCATTGTAAATTGATTTTGATACGGGCCTGCCATATCAGATTGACTC  188
```

Fig. 21

* methylated site

```
AACCCTGTATGTGAGCCTGATTCAAGACTTCGGATTTACTTTCAAGGCTTCGAATCACTGTTAAGGCAGA         70
 N  P  V  C  E  P  D  S  R  L  R  I  Y  F  Q  G  F  E  S  L  L  R  Q
AGAAAGTAGTACTAATGGTTATCAATATAGGAGGCAAGCGGGAGGTTATCGCCAACGAAGAAGGAGG            140
 K  K  V  V  L  M  V  I  N  I  .  E  G  K  R  E  V  I  A  N  E  E  G  G
TTAGTCCACTACTGCTTGGTGGCGGGTAATCTTAAGAGACACAAACTAACGGATACACAGATCGTCAAATC        210
 .  S  T  T  A  W  W  R  V  I  L  R  A  Q  T  N  G  Y  T  D  R  Q  I
CCTTCCGTCCTCTTTCATATGATGGTGAGGAGTACCACGGTACTCAAGCCAAGGCCCAGTTGGTCCGCA         280
 P  S  V  L  S  Y  I  D  G  E  E  Y  H  G  T  Q  A  K  A  Q  L  V  R
ACTCCCAGAACACTGTCGGCATACTTCAGAGATTACCTTGGCAAGGAGTTCAAGTTCGATAGACGCCACACC      350
 N  S  Q  N  T  V  A  Y  F  R  D  Y  L  G  K  E  F  K  S  I  D  A  T  P
ATGCCATAACTCGGCGCATCCTCAGCCTCACGAGTCTACCGTTGCTTTCTCCATTGTGAAGCAGTCCGCTT       420
 C  H  N  S  A  H  P  Q  P  H  E  S  T  V  A  F  S  I  V  D  S  T  N
GAGACCCCCAGCACTGTCACCGTCTCCGAGATTGCCACCCGCCATCTCCGTCGTTTGAAGCAGTCCGCCT        490
 E  T  P  S  T  V  T  V  S  E  I  A  T  R  H  L  R  R  L  K  Q  S  A
CTGACTACCTGGGCAAGGAAGTCAATGCCGCCGTCATCACTGTCCCCACTGACTTCTCCGATGCTCAGCG        560
 S  D  Y  L  G  K  E  V  N  A  A  V  I  T  V  P  T  D  F  S  D  A  Q  R
CGAGGCTTTGACCGCTTCCGCTAAGGCTGCTGGCCTTGAGGTCCTACAGCTTCATCCATGAGCCTGTTGCC       630
 E  A  L  T  A  S  A  K  A  A  G  L  E  V  L  Q  L  I  H  E  P  V  A
GCTGCCCTGGCTTACGATGCCAGGCCCGAGGCTGTTACTGTTGACAAGCTTGTTGTCGCCGACCTCG           700
 A  A  L  A  Y  D  A  R  P  E  A  T  V  T  D  K  L  V  V  A  D  L
GTGGTACCCGATCCGACGCTGCTGTTCTCGCTTGGACACAAGATCATCGCCATGTACAGTATCCTGCAACTGCTCA  770
 G  G  T  R  S  D  A  A  V  L  A  C  R  G  G  M  Y  S  I  L  A  T  A  H
TGACTACGAGTTGGGTGGAGCTTCGTTGGAGACAAGATCATCATCGACCATTTCGCCAAGGAGTTCATTAAG      840
 D  Y  E  L  G  G  A  S  L  D  K  I  I  I  D  H  F  A  K  E  F  I  K
AAGCACAAGACCGATCCTCGCGAGAACGCCAGACTTCGCGTCTGGTCTCGCGCCAAGTTGAGCATTGAGATCTTCGCAGATGGCATTGATTTCGG  910
 K  H  K  T  D  P  R  E  N  A  R  G  L  A  K  L  K  L  E  G  E  A  A
GCAAGACCTTGAGCTTGGGTACCAACGCCAGCCAAGCTTCTTCCGGCAAGACCTTCGCCCAGTTCACCGGCTTGATC   980
 R  K  T  L  S  L  G  T  N  A  S  L  S  I  E  I  F  A  D  G  I  D  F  G
CTCCACTGTCAACCGTACTCGNTACGAACTTCTTTCCGGACAGTTTTGGATGTTTGGACATTGACGAGGTTAGTCCCCTTGTGATTTTTT       1050
 S  T  V  N  R  T  R  Y  E  L  L  S  G  K  T  F  A  Q  F  T  G  L  I
GAGCAGGTTATCCAGAAGGCTGTTTTGGATGTTTGGACATTGACGAGGTTAGTCCCCTTGTGATTTTTTT        1120
 E  Q  V  I  Q  K  A  G  L  D  V  L  D  I  D  E  V  S  P  L  .  F  F
TTTTTTTTCAG       1132
 F  F  F  S

Fig. 32
```

```
ATTTCCCAGCGTCGTCGTTGGTTGAACGGTTCTTTTGCGGCCGGTCTCTATTCGCTCATGCATTTCGGTC    70
 I  S  Q  R  R  R  W  L  N  G  S  F  A  A  G  L  Y  S  L  M  H  F  G
GGATGTACAAGAGTGGACATAACATCCGTATGTTCTTCTTGCACATTCAGATGTTGTACAACGTTTT      140
 R  M  Y  K  S  G  H  N  I  I  R  M  F  F  L  H  I  Q  M  L  Y  N  V  F
CAACACTATCCTTACATGGTTCTCCCTGGCATCTTACTGGTTGACCACCGTCATCATGGACTTGGTC      210
 N  T  I  L  T  W  F  S  L  A  S  Y  W  L  T  T  V  I  M  D  L  V
GGAACGCCCAGTGAGAGCAACGGTAACAAAGGATTCCCCTTCGGTAAATCGGCGACCCTTATCAACA      280
 G  T  P  S  E  S  N  G  N  K  G  F  P  F  G  K  S  A  T  P  I  I  N
CAATTGTGAAGTATGTCTACCTCGGATTGTTGCTCCTTCAGTTCATTCTCGCTAACCGCCCCAA        350
 T  I  V  K  Y  V  Y  L  G  L  L  L  Q  F  I  L  A  L  G  N  R  P  K
GGGATCCCGCTTCTCGTACCCAGATCTTTCGTCGTATTCATTCAAATCTACGTTGTCGTCGAC        420
 G  S  R  F  S  Y  L  T  S  F  V  V  F  G  I  I  Q  I  Y  V  V  V  D
GCTCTGTACTTGGTGGTTCGTGCATTCACAAACAGTGATGCGATAGATTTCGTCACCGATCAAGGTGTTG   490
 A  L  Y  L  V  V  R  A  F  T  N  S  D  A  I  D  F  V  T  D  Q  G  V
GCGAATTCCTCAAGTCGTTCTTCTCGTCTTCGTCTTCCGGCGCCAGCGCCA                      535
 G  E  F  L  K  S  F  F  S  S  S  G  A  S  A
```

Fig. 33

```
AGGGCCACAGCNTGTGCTAAGCGCCCTTGACGGGACCCCTTGGGACTTTCAAGTCTCCTTGGACCCGGAATT   70
  G  P  Q  ?  V  L  S  A  L  T  G  T  L  G  L  S  S  L  L  G  P  G  I
GAATCCTCACAGAACAGCTTTCAACACTGCTCTAAGGCTGAACTGAGCTGCGCGACTCCGTATCATGGCC  140
  E  S  S  Q  N  S  F  Q  H  C  S  K  A  E  L  S  C  A  T  P  Y  H  G
AAGACAAATGCTGCTTCAACTATCCCGGGGGCAGTTCCTTCAATCGCTGTTTTGGGACGCCGACCCGGC  210
  Q  D  K  C  C  F  N  Y  P  G  G  Q  F  L  Q  S  L  F  W  D  A  D  P  A
CATTGGACCGGAAGATTCCTGGACTATCCATGGCTTATGGT   251
  I  G  P  E  D  S  W  T  I  H  G  L  W
```

Fig. 35

```
CTACTGAACGCTTAAAGGTGCTTAAGGAGCAACTTCATATTATGCGGACCAACGGATCCAGGAAGTCTT    70
GAGCAATAAGAAGGGTCGAACGCAGCACGGACACTCGCACAAGCGACCGGTTTGGGGACTCAACGGT   140
TCTCGGCTAAAGGAGGCCTTTGTGGGACGTCGAATCGGGAAGAATTCCAAGGCATTGGCCGAATTGGCCA   210
CCCC   214
```

Fig. 36

```
AGCACCTTATAATCTATGCTGTCCCACTATCACACATCTATATGTTGTACAAGCCTGATACAATCAATAAT  70
GATGTAATAATTGACTCTGGAAAGTTGGCTATAAAACTCACCATACAAGTCCAGATAACCCTGCCAAACT  140
CCACTCCCAGGGCATTAATCTTCATTTATATCGACCAGCCATACCTATGGTCAAATCACACGCAACGCCA  210
CAGATATATTTGAATCAAATTTCTCTTTTGAAGAAGAAGGGTGGTTTATGAGGAAGAATATCCCAAT  280
ATGCCAATCTGACTGTTCCGGATTGGAATAATGCACAAGCATTGCTCCTCTTATAGAAAACTGACAGGA  350
CAAGACCTACCCCATGACATATAAATTCGAATATAAATATA  390
```

Fig. 37

```
CAAGGGAACGGGAATAAAATACACATAACAAAGGATTCGAAGAAAAAAAAGGGGGAGGTGTGT    70
CCAAGAGGAAAGAAGAAGAAAAAAAATTTAATTTCGCCACCCTATCGCGGAGTGTTCCGCCCTTCAGGAGAGAT   140
AGAAAAGAGGAGGAGAAGGAGAAGGAGAAGAATTCCCACAGAAGAATTCCCACAGACAAGAAAGCTTAACCG   210
GGTCACGAAAAAGCACAATACAGGTGAACAACTGAGGGGAAGGGGCCAAAAAGAAAAAATAATTCCTA   280
A   281
```

Fig. 38

METHODS FOR MODIFYING THE PRODUCTION OF A POLYPEPTIDE

CROSS-REFERENCE TO RELATED APPLICATION

This application is a continuation of U.S. application Ser. No. 08/928,692 filed on Sep. 12, 1997, now U.S. Pat. No. 5,958,727, which is a continuation-in-part of U.S. application Ser. No. 08/713,312 filed on Sep. 13, 1996, now abandoned, which applications are fully incorporated herein by reference.

BACKGROUND OF THE INVENTION

1. Field of the Invention

This invention relates to methods for modifying the production of a polypeptide by a cell.

2. Description of the Related Art

Several methods have been used to modify the production of polypeptides by mutagenizing cells. For example, the production of proteins has been altered by producing mutant cells by classical mutagenesis which involves treating cells with chemical, physical, and biological agents as mutagenic (mutation inducing) agents to increase the frequency of mutational events.

Production of proteins also has been modified by mutagenesis of a cell with short sections of double-stranded DNA, consisting of more than 2000 base pairs, called transposons which usually code for resistance to one or sometimes several antibiotics. Transposons are able to move or jump within the genome, even between a bacterial chromosome and a plasmid, and they are able to become integrated in a number of different sites on the genome. An insertion of a transposon within a structural gene interrupts the normal nucleotide sequence of the gene so that it can no longer deliver the information for the synthesis of the normal, functional polypeptide (Seifert et al., 1986, *Proceedings of the National Academy of Sciences USA* 83: 735–739). An insertion also may disrupt a gene whose gene product is required for expression (Márquez-Magaña and Chamberlin, 1994, *Journal of Bacteriology* 176: 2427–2434). In addition, Errede et al. (1980, *Cell* 22: 427–436) disclose the insertion of a transposable element adjacent to the structural gene coding for iso- 2-cytochrome c causing overproduction. Furthermore, WO 96/29414 discloses that transposable elements may be constructed containing a transposon and a DNA sequence capable of regulating a targeted gene where upon introduction into a cell the transposable element integrates into the genome of the cell in a manner which regulates the expression of the gene.

A widely used method for increasing production of a polypeptide is amplification to produce multiple copies of the gene encoding the polypeptide. For example, U.S. Pat. No. 5,578,461 discloses the inclusion via homologous recombination of an amplifiable selectable marker gene in tandem with the gene where cells containing amplified copies of the selectable marker can be selected for by culturing the cells in the presence of the appropriate selectable agent.

In addition, the production of polypeptides has been increased by replacing one promoter with a different promoter or one signal peptide coding region with another. See, e.g., U.S. Pat. No. 5,641,670.

Methods for altering gene expression by disrupting genes encoding various regulatory elements have also been described. For example, Toma et al. (1986, *Journal of Bacteriology* 167: 740–743) showed that a deletion from −156 to −90 in the npr promoter region caused overexpression of the neutral protease encoded by the npr gene. Pero and Sloma (1993, In A. L. Sonensheim, J. A. Hoch, and R. Losick, editors, *Bacillus subtilis* and *Other Gram-Positive Bacteria*, pp. 939–952, American Society for Microbiology, Washington, D.C.) disclose that mutating the sporulation gene spoOA results in deficient synthesis of proteases and that mutations in the abrB gene restore synthesis.

The production of polypeptides also has been increased by disrupting DNA sequences encoding a protease capable of hydrolyzing the polypeptide under the conditions for producing the polypeptide.

The secretion of polypeptides has also been modified by overproduction of secretion proteins (Ruohonen et al., 1997, *Yeast*, 3: 337–351), and producing a super-secreting cell (U.S. Pat. No. 5,312,735).

Methods for increasing the production of metabolites have also been described. For example, WO 96/41886 discloses that increased production of clavam produced by an organism having at least part of the clavam pathway and at least part of a cephalosporin pathway by interfering with the conversion of L-lysine to L-alpha-aminoadipic acid in the cephalosporin pathway. WO 94/13813 discloses the disruption of gene which encodes a protein which degrades betaine, an enzyme inducer.

It is an object of the present invention to provide new and improved methodologies for altering production of polypeptides and metabolites.

BRIEF SUMMARY OF THE INVENTION

The present invention is drawn to methods for modifying the production of a polypeptide by a cell. In the methods of the present invention, a nucleic acid construct is introduced into a cell which contains a DNA sequence encoding a specific polypeptide. The introduced nucleic acid construct integrates into the host genome at a locus not within the DNA sequence of interest to produce a mutant cell. The integration of the nucleic acid construct into the locus modifies the production of the polypeptide by the mutant cell relative to the parent cell. Mutant cells are then identified in which the polypeptide's production is modified by the mutant cell relative to the parent cell. Modification is determined by comparing production of the polypeptide when the mutant cell and the parent cell are cultured under the same conditions.

An advantage of the present invention is that the mutation can be recovered and leads to a modification of the production of a polypeptide encoded by a DNA sequence which does not contain the mutation.

BRIEF DESCRIPTION OF THE FIGURES

FIG. 9(Panels 9A–9B) is the nucleic acid sequence and the deduced amino acid sequence of the rescued locus of mutant *Aspergillus oryzae* DEBY599.3 (SEQ ID NOS:9 and 10, respectively).

FIG. 10(10A–10E) is the nucleic acid sequence and the deduced amino acid sequence of the rescued locus of mutant *Aspergillus oryzae* DEBY10.3 (SEQ ID NOS: 16 and 17).

FIG. 16(Panels 16A–16C) is the nucleic acid sequence and the deduced amino acid sequence of the rescued locus of mutant *Aspergillus oryzae* DEBY932 (SEQ ID NOS:25 and 26).

FIG. 17(Panels 17A–17B) is the nucleic acid sequence and deduced amino acid sequence of the rescued locus of mutant *Aspergillus oryzae* DEBY1058 (SEQ ID NOS:29 and 30).

FIG. 20 is the nucleic acid sequence of the rescued locus of mutant *Aspergillus oryzae* 1204.3.3 (SEQ ID NO:34).

FIG. 21 is the nucleic acid sequence of the rescued locus of mutant *Aspergillus oryzae* H603 (SEQ ID NO:39).

FIG. 32 is the nucleic acid sequence and deduced amino acid sequence of the rescued locus of mutant *Aspergillus oryzae* P4-8.1 (SEQ ID NOS:50 and 51).

FIG. 33 is the nucleic acid sequence and deduced amino acid sequence of the rescued locus of mutant *Aspergillus oryzae* P7-14.1 (SEQ ID NOS:56 and 57).

FIG. 35 is the nucleic acid sequence and deduced amino acid sequence of the rescued locus of mutant Aspergillus oryzae DEBY7-17.2 (SEQ ID NOS:63 and 64).

FIG. 36 is the nucleic acid sequence of the rescued locus of mutant *Aspergillus oryzae* DEBY3-2.1 (SEQ ID NO:66).

FIG. 37 is the nucleic acid sequence of the rescued locus of mutant *Aspergillus oryzae* DEBY5-7.1 (SEQ ID NO:71).

FIG. 38 is the nucleic acid sequence of the rescued locus of mutant *Aspergillus oryzae* DEBY8-10.1 (SEQ ID NO:76).

DETAILED DESCRIPTION OF THE INVENTION

Figure 1:
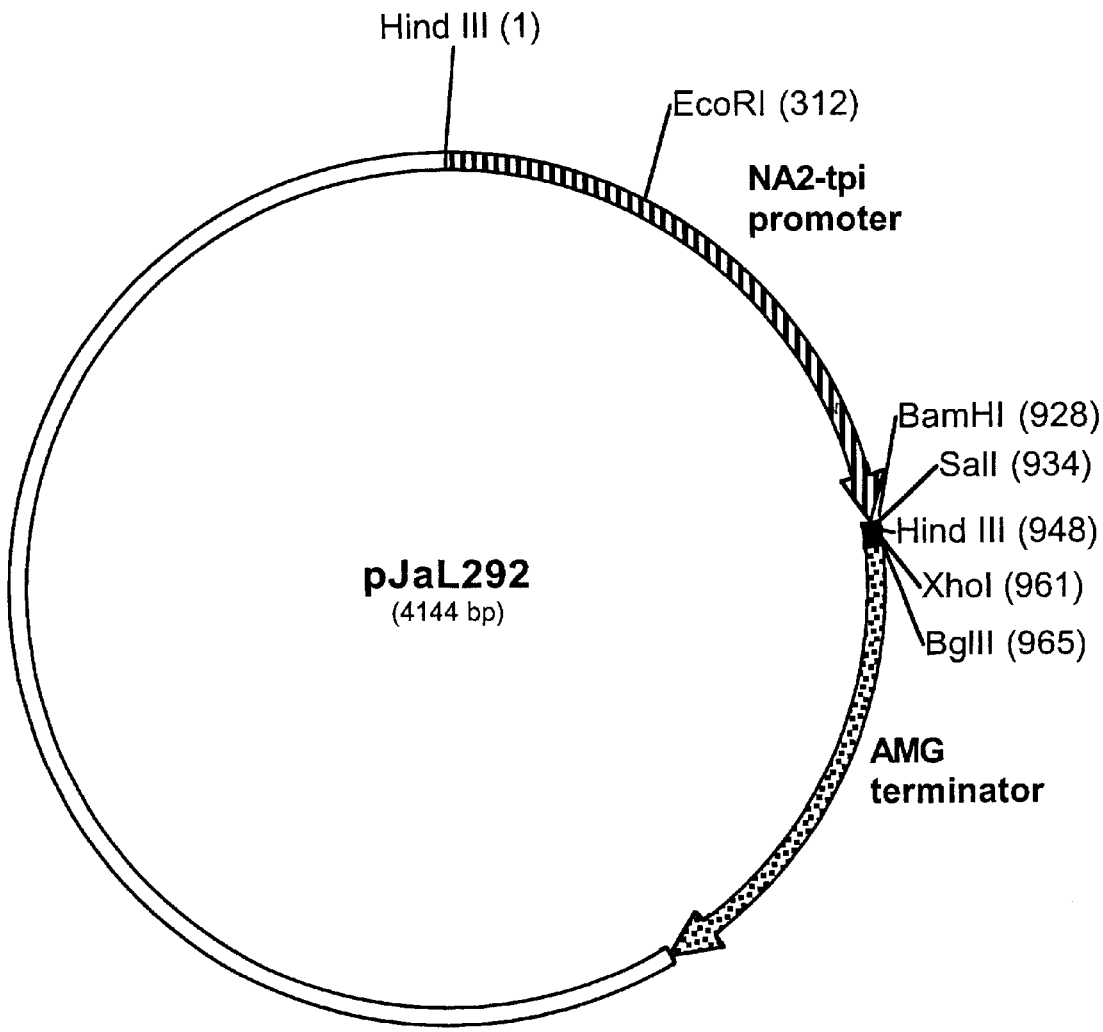
FIG. 1 is a restriction map of pJaL292.

In a first embodiment, the present invention relates to methods of producing a polypeptide, comprising (a) cultivating a mutant cell under conditions conducive for production of the polypeptide, wherein (i) the mutant cell is related to a parent cell, which comprises a first DNA sequence encoding the polypeptide, by the introduction of a nucleic acid construct into the genome of the parent cell at a locus which is not within the first DNA sequence, not within a second DNA sequence encoding a protein that negatively regulates transcription, translation or secretion of the polypeptide, and not within a third DNA sequence encoding a protease capable of hydrolyzing the polypeptide under the conditions; and (ii) the mutant cell produces more of the polypeptide than the parent cell when both cells are cultivated under the conditions; and (b) recovering the polypeptide.

A "protein that negatively regulates transcription" is defined herein as a repressor that negatively affects the process of RNA synthesis by RNA polymerase to produce a single-stranded RNA complementary to a DNA sequence, or as a protein that degrades an enzyme inducer which is generally a chemical agent produced by a biosynthetic or catabolic pathway of a cell. The repressor consists of distinct domains that are required for DNA-binding, transcription repression, and inducer or repressor binding.

A "protein that negatively regulates translation" is defined herein as a protein or a substance, the production of which is catalyzed by the protein, that negatively affects the process of protein synthesis carried out by ribosomes which de-code the information contained in mRNA derived from transcription of a gene. For example, the substance may be a cap-dependent translation initiation factor, e.g., p20 (Altmann et al., 1997, *EMBO Journal* 16: 1114–1121); or a sex-lethal protein, e.g., the sex-lethal protein of Drosophila which regulates the translation of ms1-2 (Bashaw and Baker, 1997, *Cell* 89: 789–798).

A "protein that negatively regulates secretion" is defined herein as a protein or a substance, the production of which is catalyzed by the protein, that negatively affects the process of transferring a protein molecule through a membrane into (i) an intracellular compartment, e.g., a vacuole or mitochrondrion, (ii) the periplasmic space, or (iii) the culture medium and, in eukaryotic cells, the process of vesicular transport that ultimately results in exocytic release of secreted proteins from the cell. The secretory process oversees and promotes correct protein folding, mediates any required post-translational modifications (such as glycosylation), and sorts, processes, and targets proteins to specific cellular sites all at a rate consistent with the function of the cell as a whole. Such substances include a protein with $Ca^{2+}$-ATPase activity which upon inactivation increase levels of secreted heterologous or mutant proteins (for example, see Rudolph et al., 1989, *Cell* 58: 133–145); or the binding protein BiP which is an ATP-dependent hsp70-class chaperone found in the endoplasmic reticulum of eukaryotic cells which when decreased in mammalian cells through the use of anti-sense RNA results in up to a three-fold increase in secreted levels of a mutant protein (Dorner et al., 1988, *Molecular and Cellular Biology* 8: 4063–4070). In a specific embodiment, the substance is a protein with ATPase activity or the binding protein BiP.

In a second embodiment, the present invention relates to methods of producing a polypeptide, comprising (A) cultivating a mutant cell under conditions conducive for production of the polypeptide, wherein (i) the mutant cell is related to a parent cell, which comprises a first DNA sequence encoding the polypeptide, by the introduction of a nucleic acid construct into the genome of the parent cell at a locus which is not within the first DNA sequence, wherein the introduction of the nucleic acid construct disrupts a gene encoding an oxidoreductase, a transferase, a hydrolase, a lyase, an isomerase, a ligase, or regulatory or control sequences thereof, other than a gene encoding a protease which is capable of hydrolyzing the polypeptide under the conditions; and (ii) the mutant cell produces more of the polypeptide than the parent cell when both cells are cultivated under the conditions; and (B) recovering the polypeptide.

A mutant cell that "produces" more of a polypeptide is defined herein as a cell from which more of the polypeptide is recovered relative to the parent cell.

In a third embodiment, the present invention relates to methods of producing a polypeptide, comprising (a) cultivating a mutant cell under conditions conducive for production of the polypeptide, wherein (i) the mutant cell is related to a parent cell, which comprises a first DNA sequence encoding the polypeptide, by the introduction of a nucleic acid construct into the genome of the parent cell at a locus which is not within the first DNA sequence, not within a second DNA sequence encoding a protein that negatively regulates transcription of the polypeptide, and not within a third DNA sequence encoding a protease capable of hydrolyzing the polypeptide under the conditions; and (ii) the mutant cell expresses more of the polypeptide than the parent cell when both cells are cultivated under the conditions; and (b) recovering the polypeptide.

In a fourth embodiment, the present invention relates to methods of producing a polypeptide, comprising (A) cultivating a mutant cell under conditions conducive for production of the polypeptide, wherein (i) the mutant cell is related to a parent cell, which comprises a first DNA sequence encoding the polypeptide, by the introduction of a nucleic acid construct into the genome of the parent cell at a locus which is not within the first DNA sequence, wherein the introduction of the nucleic acid construct disrupts a gene encoding an oxidoreductase, a transferase, a hydrolase, a lyase, an isomerase, a ligase, or regulatory or control sequences thereof, other than a gene encoding a protease which is capable of hydrolyzing the polypeptide under the conditions; and (ii) the mutant cell expresses more of the polypeptide than the parent cell when both cells are cultivated under the conditions; and (B) recovering the polypeptide.

A mutant cell that "expresses" more of a polypeptide is defined herein as a cell that contains an increase in functional mRNA encoding the polypeptide relative to the parent cell.

It will be understood that an increase in functional mRNA may result from an increase in the absolute rate of transcription of the gene encoding the polypeptide and/or from alterations in post-transcriptional processing or modification of the transcripts, including nuclear-cytoplasmic transport and/or cytoplasmic stabilization of the mRNA. Such mutant cells may be identified using conventional techniques, including without limitation Northern blot analysis, run-off transcription assays, and the like.

In a fifth embodiment, the present invention relates to methods of producing a polypeptide, comprising (a) cultivating a mutant cell under conditions conducive for production of the polypeptide, wherein (i) the mutant cell is related to a parent cell, which comprises a first DNA sequence encoding the polypeptide, by the introduction of a nucleic acid construct into the genome of the parent cell at a locus which is not within the first DNA sequence, not within a second DNA sequence encoding a protein that negatively regulates translation of the polypeptide, and not within a third DNA sequence encoding a protease capable of hydrolyzing the polypeptide under the conditions; and (ii) the mutant cell synthesizes more of the polypeptide than the parent cell when both cells are cultivated under the conditions; and (b) recovering the polypeptide.

In a sixth embodiment, the present invention relates to methods of producing a polypeptide, comprising (A) cultivating a mutant cell under conditions conducive for production of the polypeptide, wherein (i) the mutant cell is related to a parent cell, which comprises a first DNA sequence encoding the polypeptide, by the introduction of a nucleic acid construct into the genome of the parent cell at a locus which is not within the first DNA sequence, wherein the introduction of the nucleic acid construct disrupts a gene encoding an oxidoreductase, a transferase, a hydrolase, a lyase, an isomerase, a ligase, or regulatory or control sequences thereof, other than a gene encoding a protease which is capable of hydrolyzing the polypeptide under the conditions; and (ii) the mutant cell synthesizes more of the polypeptide than the parent cell when both cells are cultivated under the conditions; and (B) recovering the polypeptide.

A mutant cell that "synthesizes" more of a polypeptide is defined herein as a cell that accumulates larger amounts of the polypeptide relative to a parent cell. Accumulation refers to the total amount of the polypeptide in the culture as a whole, i.e., in both intracellular and extracellular compartments taken together. Such mutant cells may be identified using any suitable technique, including without limitation pulse-labelling or steady-state labelling using radiolabelled amino acids; immunoblot analysis of cell and medium fractions using an antibody specific to the polypeptide; assays of biological activity; separation by conventional chromatographic methods; and the like.

In a seventh embodiment, the present invention relates to methods of producing a polypeptide, comprising (a) cultivating a mutant cell under conditions conducive for production of the polypeptide, wherein (i) the mutant cell is related to a parent cell, which comprises a first DNA sequence encoding the polypeptide, by the introduction of a nucleic acid construct into the genome of the parent cell at a locus which is not within the first DNA sequence, not within a second DNA sequence encoding a protein that negatively regulates secretion of the polypeptide, and not within a third DNA sequence encoding a protease capable of hydrolyzing the polypeptide under the conditions; and (ii) the mutant cell secretes more of the polypeptide than the parent cell when both cells are cultivated under the conditions;

(b) recovering the polypeptide.

In an eighth embodiment, the present invention relates to methods of producing a polypeptide, comprising (A) cultivating a mutant cell under conditions conducive for production of the polypeptide, wherein (i) the mutant cell is related to a parent cell, which comprises a first DNA sequence encoding the polypeptide, by the introduction of a nucleic acid construct into the genome of the parent cell at a locus which is not within the first DNA sequence, wherein the introduction of the nucleic acid construct disrupts a gene encoding an oxidoreductase, a transferase, a hydrolase, a lyase, an isomerase, a ligase, or regulatory or control sequences thereof, other than a gene encoding a protease which is capable of hydrolyzing the polypeptide under the conditions; and (ii) the mutant cell secretes more of the polypeptide than the parent cell when both cells are cultivated under the conditions; and (B) recovering the polypeptide.

A mutant cell that "secretes" more of a polypeptide is defined herein as a cell in which the amount of the polypeptide released into the extracellular medium is increased relative to the parent cell. Such mutant cells may be identified using, e.g., pulse-chase labelling in conjunction with immunoprecipitation to quantify the proportion of the newly synthesized polypeptide that is externalized as well as the absolute amount released in the mutant cell relative to the parent cell. Immunoblot analysis, biological activity assays, and physical-chemical separation methods may also be used to quantify the absolute amounts of the polypeptide released in mutant vs. parent cells.

In a ninth embodiment, the present invention relates to methods of producing a polypeptide, comprising (a) cultivating a mutant cell under conditions conducive for production of the polypeptide, wherein (i) the mutant cell is related to a parent cell, which comprises a first DNA sequence encoding the polypeptide, by the random integration of a nucleic acid construct into the genome of the parent cell at a locus wherein the nucleic acid construct is not homologous with the locus and wherein the locus is not within the first DNA sequence nor within a second DNA sequence encoding a protease capable of hydrolyzing the polypeptide under the conditions; and (ii) the mutant cell produces more of the polypeptide than the parent cell when both cells are cultivated under the conditions; and (b) recovering the polypeptide.

In a tenth embodiment, the present invention relates to methods of producing a polypeptide, comprising (a) cultivating a mutant cell under conditions conducive for production of the polypeptide, wherein (i) the mutant cell is related to a parent cell, which comprises a first DNA sequence encoding the polypeptide, by the introduction of a nucleic acid construct into the genome of the parent cell at a locus which is not within the first DNA sequence and a second DNA sequence encoding a protein that positively regulates transcription, translation or secretion of the polypeptide; and (ii) the mutant cell produces less of the polypeptide than the parent cell when both cells are cultivated under the conditions; and (b) recovering the polypeptide.

A mutant cell that "produces" less of a polypeptide is defined herein as a cell from which less of the polypeptide is recovered relative to the parent cell.

A "protein that positively regulates transcription" is defined herein as an activator or an inducer that positively affects the process of RNA synthesis by RNA polymerase to produce a single-stranded RNA complementary to a DNA sequence. The activator consists of distinct domains that are required for DNA-binding, transcription activation, and inducer or repressor binding. An inducer is generally a chemical agent produced by a biosynthetic or catabolic pathway of a cell. In a specific embodiment, the substance is an activator or an inducer.

A "protein that positively regulates translation" is defined herein as a protein or a substance, the production of which is catalyzed by the protein, that positively affects the process of protein synthesis carried out by ribosomes which de-code the information contained in mRNA derived from transcription of a gene. In a specific embodiment, the substance is an initiation factor or an elongation factor.

A "protein that positively affects secretion" is defined herein as a protein or a substance, the production of which is catalyzed by the protein, that positively affects the process of transferring a protein molecule through a membrane into (i) an intracellular compartment, e.g., a vacuole or mitochrondrion, (ii) the periplasmic space, or (iii) the culture medium or positively affects vesicular transport as described above. Such substances include folding proteins, e.g., protein disulfide isomerase and peptidyl prolyl isomerase isoforms; chaperones, e.g., heat shock proteins, signal recognition particles, PrsA, SecD, SecF, and BiP; translocating chain-associating membrane proteins (TRAM); translocase complexes; and processing enzymes, e.g., glycosylating enzymes; signal peptidases; pro region peptidases. In a specific embodiment, the substance is a folding protein, a chaperone, a signal recognition particle, PrsA, SecD, SecF, BiP, a translocating chain-associating membrane, a translocase complex, or a processing enzyme.

Other embodiments of the present invention relate to methods for producing polypeptides as described in the tenth embodiment, except that the mutant cells express, synthesize or secrete less of the polypeptide than the parent cell when both cells are cultivated under the conditions.

A mutant cell that "expresses" less of a polypeptide is defined herein as a cell that contains a decrease in functional mRNA encoding the polypeptide relative to the parent cell. It will be understood that a decrease in functional mRNA may result from a decrease in the absolute rate of transcription of the gene encoding the polypeptide and/or from alterations in post-transcriptional processing or modification of the transcripts, including nuclear-cytoplasmic transport and/or cytoplasmic stabilization of the mRNA. Such mutant cells may be identified using conventional techniques, including without limitation Northern blot analysis, run-off transcription assays, and the like.

A mutant cell that "synthesizes" less of a polypeptide is defined herein as a cell that accumulates smaller amounts of the polypeptide relative to a parent cell. Accumulation refers to the total amount of the polypeptide in the culture as a whole, i.e., in both intracellular and extracellular compartments taken together. Such mutant cells may be identified using any suitable technique, including without limitation pulse-labelling or steady-state labelling using radiolabelled amino acids; immunoblot analysis of cell and medium fractions using an antibody specific to the polypeptide; assays of biological activity; separation by conventional chromatographic methods; and the like.

A mutant cell that "secretes" less of a polypeptide is defined herein as a cell in which the amount of the polypeptide released into the extracellular medium is decreased relative to the parent cell. Such mutant cells may be identified using, e.g., pulse-chase labelling in conjunction with immunoprecipitation to quantify the proportion of the newly synthesized polypeptide that is externalized as well as the absolute amount released in the mutant cell relative to the parent cell. Immunoblot analysis, biological activity assays, and physical-chemical separation methods may also be used to quantify the absolute amounts of the polypeptide released in mutant vs. parent cells.

The present invention also relates to methods of producing a metabolite, comprising (A) cultivating a mutant cell under conditions conducive for production of the metabolite, wherein
  (i) the mutant cell is related to a parent cell, which comprises one or more first DNA sequences encoding first polypeptides in the biosynthetic pathway of the metabolite, by the introduction of a nucleic acid construct into the genome of the parent cell at a locus which is not within (a) the first DNA sequences, (b) a second DNA sequence encoding a substance that negatively regulates transcription, translation or secretion of the polypeptides, (c) a third DNA sequence encoding a protease capable of hydrolyzing any of the first polypeptides under the conditions, and (d) one or more fourth DNA sequences encoding a second polypeptide in the second biosynthetic pathway of a second metabolite wherein the biosynthetic pathway and the second biosynthetic pathway involve the production of the same intermediate and the second polypeptide catalyzes a step after the production of the intermediate; and
  (ii) the mutant cell produces more of the metabolite than the parent cell when both cells are cultivated under the conditions; and
(B) recovering the metabolite.

The present invention also relates to methods of producing a metabolite, comprising (A) cultivating a mutant cell under conditions conducive for production of the metabolite, wherein
  (i) the mutant cell is related to a parent cell, which comprises one or more first DNA sequences encoding first polypeptides in the biosynthetic pathway of the metabolite, by the introduction of a nucleic acid construct into the genome of the parent cell at a locus which is not within (a) the first DNA sequences, (b) a second DNA sequence encoding a protein that negatively regulates transcription, translation or secretion of the polypeptides, and (c) one or more third DNA sequences encoding a second polypeptide in the second biosynthetic pathway of a second metabolite wherein the biosynthetic pathway and the second biosynthetic pathway involve the production of the same intermediate and the second polypeptide catalyzes a step prior to the production of the intermediate; and
  (ii) the mutant cell produces less of the metabolite than the parent cell when both cells are cultivated under the conditions; and
(B) recovering the metabolite.

The present invention also relates to methods of producing a first polypeptide, comprising (a) forming a mutant cell by introducing a nucleic acid construct into the genome of the parent cell at a locus which is not within the first DNA sequence, a second DNA sequence encoding a protein that negatively regulates transcription, translation or secretion of a second polypeptide, and a third DNA sequence encoding a protease capable of hydrolyzing the polypeptide under conditions conducive to the production of the first polypeptide;

(b) isolating the mutant cell which produces more of the polypeptide than the parent cell when both cells are cultivated under the conditions;

(c) identifying the locus wherein the nucleic acid construct has been integrated;

(d) producing a cell in which a corresponding locus has been disrupted;

(e) culturing the cell under the conditions conducive; and (f) recovering the first polypeptide.

A corresponding locus is defined herein as a locus which encodes a polypeptide with has the same function as the polypeptide encoded by the rescued locus.

The present invention also relates to methods of producing a polypeptide, comprising (a) cultivating a mutant cell under conditions conducive for production of the polypeptide, wherein
  (i) the mutant cell is related to a parent cell, which comprises a first DNA sequence encoding the polypeptide, by the introduction of a nucleic acid construct into the genome of the parent cell at a locus which is not within the first DNA sequence and a second DNA sequence encoding a protease capable of hydrolyzing the polypeptide under the conditions, wherein the introduction of the nucleic acid construct specifically enhances transcription, translation or secretion of the polypeptide; and
  (ii) the mutant cell produces nore of the polypeptide than the parent cell when both cells are cultivated under the conditions; and
(b) recovering the polypeptide.

"Specific" enhancement of transcription, translation, or secretion as used herein refers to an enhancement of one or more aspects of the biogenesis and production of the polypeptide that is limited to the polypeptide of interest and is not accompanied by a global effect on other polypeptides in the cell. Preferably, specific enhancement affects only a small number of polypeptides, including the polypeptide of interest. Most preferably, specific enhancement affects only the polypeptide of interest.

Global enhancement of these biogenetic processes can be distinguished from specific enhancement using conventional methods that are well known in the art. For example, biosynthetic pulse-labelling with $^3$H-uridine (followed by quantitation of total radioactivity incorporated into RNA) can be used to determine that a mutant cell does not generally synthesize mRNA at a higher or lower rate than the parent cell to which it is related. Similarly, pulse-labelling with, e.g., $^{35}$S-methionine (followed by quantitation of total radioactivity incorporated into protein) can be used to determine that a mutant cell does not generally synthesize proteins at a higher or lower rate than the parent cell to which it is relate. General rates of secretion can be compared between mutant and parent cells by pulse-chase labelling using radioactive amino acids or sugars followed by quantitation of extracellular vs. intracellular radioactivity.

These methods can also be used to determine if transcription, translation, or secretion of a limited number of other polypeptides might also be affected in the mutant cell. For example, capture of specific radiolabelled RNA transcripts by hybridization to an immobilized oligonucleotide probe can be used to assess transcription rates of individual genes. For translation and secretion, resolution of radiolabelled nascent proteins by, e.g., SDS-PAGE (with or without immunoprecipitation of individual proteins) can be used to compare instantaneous rates of translation and/or secretion of individual proteins.

Polypeptides

The term "polypeptide" encompasses peptides, oligopeptides, and proteins and, therefore, is not limited to a specific length of the encoded product. The polypeptide may be native to the cell or may be a heterologous polypeptide. Preferably, it is a heterologous polypeptide. The polypeptide may also be a recombinant polypeptide which is a polypeptide native to a cell, which is encoded by a nucleic acid sequence which comprises one or more control sequences foreign to the gene. The polypeptide may be a wild-type polypeptide or a variant thereof. The polypeptide may also be a hybrid polypeptide which contains a combination of partial or complete polypeptide sequences obtained from at least two different polypeptides where one or more of the polypeptides may be heterologous to the cell. Polypeptides further include naturally occurring allelic and engineered variations of the above mentioned polypeptides.

In a preferred embodiment, the polypeptide is an antibody or portions thereof.

In a preferred embodiment, the polypeptide is an antigen.

In a preferred embodiment, the polypeptide is a clotting factor.

In a preferred embodiment, the polypeptide is an enzyme.

In a preferred embodiment, the polypeptide is a hormone or a hormone variant.

In a preferred embodiment, the polypeptide is a receptor or portions thereof.

In a preferred embodiment, the polypeptide is a regulatory protein.

In a preferred embodiment, the polypeptide is a structural protein.

In a preferred embodiment, the polypeptide is a reporter.

In a preferred embodiment, the polypeptide is a transport protein.

In a more preferred embodiment, the polypeptide is an oxidoreductase,

In a more preferred embodiment, the polypeptide is a transferase.

In a more preferred embodiment, the polypeptide is a hydrolase.

In a more preferred embodiment, the polypeptide is a lyase.

In a more preferred embodiment, the polypeptide is an isomerase.

In a more preferred embodiment, the polypeptide is a ligase.

In an even more preferred embodiment, the polypeptide is an aminopeptidase

In an even more preferred embodiment, the polypeptide is an amylase.

In an even more preferred embodiment, the polypeptide is a carbohydrase.

In an even more preferred embodiment, the polypeptide is a carboxypeptidase.

In an even more preferred embodiment, the polypeptide is a catalase.

In an even more preferred embodiment, the polypeptide is a cellulase.

In an even more preferred embodiment, the polypeptide is a chitinase.

In an even more preferred embodiment, the polypeptide is a cutinase.

In an even more preferred embodiment, the polypeptide is a deoxyribonuclease.

In an even more preferred embodiment, the polypeptide is a dextranase.

In an even more preferred embodiment, the polypeptide is an esterase.

In an even more preferred embodiment, the polypeptide is an alpha-galactosidase.

In an even more preferred embodiment, the polypeptide is a beta-malactosidase.

In an even more preferred embodiment, the polypeptide is a glucoamylase.

In an even more preferred embodiment, the polypeptide is an alpha-glucosidase.

In an even more preferred embodiment, the polypeptide is a beta-llucosidase.

In an even more preferred embodiment, the polypeptide is a haloperoxidase.

In an even more preferred embodiment, the polypeptide is an invertase.

In an even more preferred embodiment, the polypeptide is a laccase.

In an even more preferred embodiment, the polypeptide is a lipase.

In an even more preferred embodiment, the polypeptide is a mannosidase.

In an even more preferred embodiment, the polypeptide is a mutanase.

In an even more preferred embodiment, the polypeptide is an oxidase.

In an even more preferred embodiment, the polypeptide is a pectinolytic enzyme.

In an even more preferred embodiment, the polypeptide is a peroxidase.

In an even more preferred embodiment, the polypeptide is a phytase.

In an even more preferred embodiment, the polypeptide is a polyphenoloxidase.

In an even more preferred embodiment, the polypeptide is a proteolytic enzyme.

In an even more preferred embodiment, the polypeptide is a ribonuclease.

In an even more preferred embodiment, the polypeptide is a transglutaminase.

In an even more preferred embodiment, the polypeptide is a xylanase.

In an even more preferred embodiment, the polypeptide is human insulin or an analog thereof.

In an even more preferred embodiment, the polypeptide is human growth hormone.

In an even more preferred embodiment, the polypeptide is erythropoietin.

In an even more preferred embodiment, the polypeptide is insulinotropin.

The polypeptide also may be an enzyme involved in the biosynthesis of a specific metabolite. The biosynthesis of a metabolite generally involves a biosynthetic pathway containing an array of enzyme-catalyzed chemical reaction steps in which one or more steps may be rate-limiting. In this embodiment of the present invention, the integration of the nucleic acid construct into the cell's genome modifies the production of the metabolite by modifying one or more of these enzyme-catalyzed steps.

The metabolite may be any organic compound of a cell which has been produced by transformation of a precursor organic compound by an enzyme-catalyzed chemical reaction of the cell. The metabolite may be a primary metabolite or a secondary metabolite. Furthermore, the metabolite may be a biosynthetic pathway intermediate or a biosynthetic pathway product. Preferably, the metabolite is an alkaloid, an amino acid, an antibiotic, a cofactor, a drug, a fatty acid, a fungicide, a herbicide, an insecticide, an organic acid, a prosthetic group, a rodenticide, a sweetener, a vitamin, a deoxysugar, a surfactant, a mycotoxin, an organic acid, a sugar alcohol, a toxic metabolite, or a toxin.

Nucleic Acid Constructs

The nucleic constructs used in the methods of the present invention may be termed "tagged nucleic acid constructs". "A tagged nucleic acid construct" is a nucleic acid molecule containing an identifiable nucleic acid sequence which integrates into the cell's genome at one or more loci thereby marking the loci. The genome is the complete set of DNA of a cell including chromosomal and artificial chromosomal DNA and extrachromosomal DNA, i.e., self-replicative genetic elements.

The nucleic acid constructs may be any nucleic acid molecule, either single- or double-stranded, which is synthetic DNA, isolated from a naturally occurring gene, or has been modified to contain segments of nucleic acid which are combined and juxtaposed in a manner which would not otherwise exist in nature. The nucleic acid constructs may be circular or linear. Furthermore, the nucleic acid constructs may be contained in a vector, may be a restriction enzyme cleaved linearized fragment, or may be a PCR amplified linear fragment.

The nucleic acid constructs may contain any nucleic acid sequence of any size. In one embodiment, the nucleic acid constructs are between about 1–20,000 bp in length, preferably 100–15,000 bp in length, more preferably 500–15,000 bp in length, even more referably 1000–15,000 bp in length, and most preferably 1,000–10,000 bp in length.

Preferably, the nucleic acid constructs have less than 40% homology, preferably less than 30% homology, more preferably less than 20% homology, even more preferably less than 10% homology, and most preferably no homology with the locus.

Preferably, the nucleic acid constructs have less than 40% homology, preferably less than 30% identity, more preferably less than 20% identity, even more preferably less than 10%, and most preferably no homology with the DNA sequence encoding the polypeptide of interest.

The nucleic acid construct can be introduced into a cell as two or more separate fragments. In the event two fragments are used, the two fragments share DNA sequence homology (overlap) at the 3' end of one fragment and the 5' end of the other. Upon introduction into a cell, the two fragments can undergo homologous recombination to form a single fragment. The product fragment is then in a form suitable for recombination with the cellular sequences. More than two fragments can be used, designed such that they will undergo homologous recombination with each other to ultimately form a product suitable for recombination with a cellular sequence.

It will be further understood that two or more nucleic acid constructs may be introduced into the cell as circular or linear fragments using the methods of the present invention, wherein the fragments do not contain overlapping regions as described above. It is well known in the art that for some organisms, the introduction of multiple constructs into a cell results in their integration at the same locus.

The nucleic acid constructs can contain coding or non-coding DNA sequences. Coding sequences are sequences which are capable of being transcribed into mRNA and translated into a polypeptide when placed under the control of the appropriate control sequences. The boundaries of a coding sequence are generally determined by a translation start codon ATG at the 5'-terminus and a translation stop codon at the 3'-terminus. A coding sequence can include, but is not limited to, DNA, cDNA, and recombinant nucleic acid sequences.

In a preferred embodiment, the nucleic acid constructs contain a selectable marker as the identifiable nucleic acid sequence. A selectable marker is a gene, the product of which provides for biocide or viral resistance, resistance to heavy metals, prototrophy to auxotrophs, and the like. Integration of a selectable marker into the genome of a host cell permits easy selection of transformed cells. Selectable marker genes for use in the methods of the present invention include, but are not limited to, acetamidase (amdS), 5-aminolevulinic acid synthase (hemA), anthranilate synthase (trpC), glufosinate resistance genes, hygromycin phosphotransferase (hygB), nitrate reductase (niaD), ornithine carbamoyltransferase (argB), orotidine-5'-phosphate decarboxylase (pyrG), phosphinothricin acetyltransferase (bar), and sulfate adenyltransferase (sC), as well as equivalents from other species. In a more preferred embodiment, the selectable marker is the amdS gene of *Aspergillus nidulans* or *Aspergillus oryzae*, the bar gene of *Streptomyces hygroscopicus*, the hemA gene of *Aspergillus oryzae* or the pyrG gene of *Aspergillus nidulans* or *Aspergillus oryzae*. Other selectable markers for use in the methods of the present invention are the dal genes from *Bacillus subtilis* or *Bacillus licheniformis*, or markers which confer antibiotic resistance such as ampicillin (amp), kanamycin (kan), chloramphenicol (cam) or tetracycline resistance (tet). A frequently used mammalian marker is the dihydrofolate reductase gene (dfhr). Suitable markers for yeast host cells are ADE2, HIS3, LEU2, LYS2, MET3, TRP1, and URA3.

In another preferred embodiment, the constructs comprise vector sequences alone or in combination with a selectable marker, including vector sequences containing an origin of replication, e.g., *E. coli* vector sequences such as pUC19, pBR322, or pBluescript. For example, an *E. coli* vector sequence containing an origin of replication can facilitate recovery of the construct from the host genome after integration due to the *E. coli* origin of replication. The construct can be recovered from the host genome by digestion of the genomic DNA with a restriction endonuclease followed by ligation of the recovered construct and transformation of *E. coli*.

In a preferred embodiment, the nucleic acid constructs do not contain the coding sequence of the DNA sequence for the polypeptide or portions thereof. In another preferred embodiment, the nucleic acid constructs contain a sequence which is not homologous to the DNA sequence encoding the polypeptide in order to block the construct from integrating or disrupting the DNA sequence of interest.

In another preferred embodiment, the nucleic acid constructs contain one or more copies of the DNA sequence coding for the polypeptide operably linked to control sequences. In this embodiment, the production of the polypeptide will be modified by both gene inactivation and the introduction of one or more copies of the DNA sequence.

In another preferred embodiment, the nucleic acid constructs do not contain transposable elements, i.e., transposons. A transposon is a discrete piece of DNA which can insert itself into many different sites in other DNA sequences within the same cell. The proteins necessary for the transposition process are encoded within the transposon. A copy of the transposon may be retained at the original site after transposition. The ends of a transposon are usually identical but in inverse orientation with respect to one another.

In another preferred embodiment, the nucleic acid constructs may contain one or more control sequences, e.g., a promoter alone or in combination with a selectable marker, wherein the control sequences upon integration are not operably linked to the DNA sequence encoding the polypeptide of interest. The term "operably linked" is defined herein as a configuration in which a control sequence is appropriately placed at a position relative to the coding sequence of the DNA sequence such that the control sequence directs the production of a primary RNA transcript. Such control sequences are a promoter, a signal sequence, a propeptide sequence, a transcription terminator, a polyadenylation sequence, an enhancer sequence, an attenuator sequence, and an intron splice site sequence. Each control sequence may be native or foreign to the cell or to the polypeptide-coding sequence.

The presence of a strong promoter in the nucleic acid construct allows for additional genetic effects in addition to gene inactivation via insertion into a structural gene (or functional transcriptional promoter or mRNA termination regions). The promoter may insert upstream of a structural gene so as to enhance its transcription. Alternatively, if the promoter sequences insert in reverse gene orientation so as to generate antisense RNA, there is the possibility of gene inactivation in diploid or higher ploidy cells. By the same mechanism, insertion of the promoter sequences in reverse orientation may result in inactivation of multiple gene family encoded gene product activities.

In another preferred embodiment, the nucleic acid constructs contain a control sequence other than a promoter.

In another preferred embodiment, the nucleic acid constructs do not contain control sequences.

Locus

In the methods of the present invention, the nucleic acid constructs are introduced at a "locus not within the DNA sequence of interest" or a "locus not within DNA sequences encoding polypeptides in the biosynthetic pathway of a metabolite" which means that the nucleic acid construct is not introduced into the polypeptide-coding sequence, the control sequences thereof, and any intron sequences within the coding sequence.

Control sequences include all components which are operably linked to the DNA sequence and involved in the expression of the polypeptide-coding sequence. Such control sequences are a promoter, a signal sequence, a propeptide sequence, a transcription terminator, a polyadenylation sequence, an enhancer sequence, an attenuator sequence, and an intron splice site sequence. Each of the control sequences may be native or foreign to the coding sequence.

The promoter sequence contains transcriptional control sequences which mediate the expression of the polypeptide. The promoter may be any promoter sequence including mutant, truncated, and hybrid promoters.

The signal peptide coding region codes for an amino acid sequence linked to the amino terminus of the polypeptide which can direct the expressed polypeptide into the cell's secretory pathway.

The propeptide coding region codes for an amino acid sequence positioned at the amino terminus of the polypeptide. The resultant polypeptide is known as a proenzyme or propolypeptide (or a zymogen in some cases). A propolypeptide is generally inactive and can be converted to mature active polypeptide by catalytic or autocatalytic cleavage of the propeptide from the propolypeptide.

The terminator is a sequence operably linked to the 3' terminus of the polypeptide coding sequence, and is recognized by the cell to terminate transcription of the polypeptide coding sequence.

The polyadenylation sequence is a sequence which is operably linked to the 3' terminus of the DNA sequence and which, when transcribed, is recognized by the cell as a signal to add polyadenosine residues to the transcribed mRNA.

The enhancer sequence is a sequence which can increase transcription from a gene when located up to several kilobases from the gene. The enhancer sequencer is usually upstream of the gene.

The attenuator sequence is a sequence which regulates the expression of a gene by determining whether the mRNA molecule containing its transcript will be completed or not.

The intron sequence is a sequence of a gene which is not represented in the protein product of the gene. Intron sequences are transcribed into RNA and must be excised and the RNA molecule religated through a process called intron splicing before it can be translated.

The locus may be noncontiguous or contiguous with the above-noted sequences. Preferably the locus is noncontiguous. The locus may be on the same chromosome or the same extrachromosomal element or on a different chromosome or a different extrachromosomal element as that of the DNA sequence of interest. Furthermore, the locus may be native or foreign to the cell.

In a preferred embodiment, the locus is at least 1,000 bp, more preferably at least 2,000 bp, and even more preferably at least 3,000 bp, even more preferably at least 4,000 bp, even more preferably at least 5,000 bp, and most preferably at least 10,000 bp from the 5' or 3' terminus of the DNA sequence of interest.

In another preferred embodiment, the locus is on a different chromosome than the DNA sequence encoding the polypeptide of interest.

In various methods of the present invention, the nucleic acid constructs are introduced at a locus not within a DNA sequence encoding a protease capable of hydrolyzing the polypeptide under physiological conditions, which means that the nucleic acid construct is not introduced into the protease-coding sequence, the control sequences thereof, any intron sequences within the coding sequence, and any DNA sequences encoding proteins that positively regulate transcription, translation or secretion of the protease.

In another preferred embodiment, the locus encodes a polypeptide different from the polypeptide encoded by the DNA sequence.

In another preferred embodiment, the locus encodes a glucose transporter. Preferably, the locus has at least 60% homology, more preferably at least 70% homology, even more preferably at least 80% homology, even more preferably at least 90% homology, and most preferably at least 95% homology with the nucleic acid sequence of SEQ ID NO:9.

In another preferred embodiment, the locus encodes a mannitol-1-phosphate dehydrogenase. Preferably, the locus has at least 60% homology, more preferably at least 70% homology, even more preferably at least 80% homology, even more preferably at least 90% homology, and most preferably at least 95% homology with the nucleic acid sequence of SEQ ID NO:25.

In another preferred embodiment, the locus encodes a chitin synthase. Preferably, the locus has at least 60% homology, more preferably at least 70% homology, even more preferably at least 80% homology, even more preferably at least 90% homology, and most preferably at least 95% homology with the nucleic acid sequence of SEQ ID NO:56.

In another preferred embodiment, the locus encodes a heat shock protein. Preferably, the locus has at least 60% homology, more preferably at least 70% homology, even more preferably at least 80% homology, even more preferably at least 90% homology, and most preferably at least 95% homology with the nucleic acid sequence of SEQ ID NO:50.

In another preferred embodiment, the locus encodes a manganese superoxide dismutase. Preferably, the locus has at least 60% homology, more preferably at least 70% homology, even more preferably at least 80% homology, even more preferably at least 90% homology, and most preferably at least 95% homology with the nucleic acid sequence of SEQ ID NO:29.

In another preferred embodiment, the locus is a gene required for activation of pacC, preferably a palB gene. Preferably, the locus has at least 60% homology, more preferably at least 70% homology, even more preferably at least 80% homology, even more preferably at least 90% homology, and most preferably at least 95% homology with the nucleic acid sequence of SEQ ID NO:16.

In another preferred embodiment, the locus has at least 60% homology, more preferably at least 70% homology, even more preferably at least 80% homology, even more preferably at least 90% homology and most preferably at least 95% homology with the nucleic acid sequence of SEQ ID NO:34.

In another preferred embodiment, the locus has at least 60% homology, more preferably at least 70% homology, even more preferably at least 80% homology, even more preferably at least 90% homology, and most preferably at least 95% homology with the nucleic acid sequence of SEQ ID NO:39.

In another preferred embodiment, the locus has at least 60% homology, more preferably at least 70% homology, even more preferably at least 80% homology, even more preferably at least 90% homology, and most preferably at least 95% homology with the nucleic acid sequence of SEQ ID NO:63.

In another preferred embodiment, the locus has at least 60% homology, more preferably at least 70% homology, even more preferably at least 80% homology, even more preferably at least 90% homology, and most preferably at least 95% homology with the nucleic acid sequence of SEQ ID NO:66.

In another preferred embodiment, the locus has at least 60% homology, more preferably at least 70% homology, even more preferably at least 80% homology, even more preferably at least 90% homology, and most preferably at least 95% homology with the nucleic acid sequence of SEQ ID NO:71.

In another preferred embodiment, the locus has at least 60% homology, more preferably at least 70% homology, even more preferably at least 80% homology, even more preferably at least 90% homology, and most preferably at least 95% homology with the nucleic acid sequence of SEQ ID NO:76.

In another preferred embodiment, the locus encodes an aminopeptidase.

In another preferred embodiment, the locus encodes an amylase.

In another preferred embodiment, the locus encodes a carbohydrase.

In another preferred embodiment, the locus encodes a carboxypeptidase.

In another preferred embodiment, the locus encodes a catalase.

In another preferred embodiment the locus encodes a catalase.

In another preferred embodiment, the locus encodes a cellulase.

In another preferred embodiment, the locus encodes a chitinase.

In another preferred embodiment, the locus encodes a cutinase.

In another preferred embodiment, the locus encodes a deoxyribonuclease.

In another preferred embodiment, the locus encodes a dextranase.

In another preferred embodiment, the locus encodes an esterase.

In another preferred embodiment, the locus encodes an alpha-galactosidase.

In another preferred embodiment, the locus encodes a beta-galactosidase.

In another preferred embodiment, the locus encodes a glucoamylase.

In another preferred embodiment, the locus encodes an alpha-glucosidase.

In another preferred embodiment, the locus encodes a beta-galactosidase.

In another preferred embodiment, the locus encodes a glucoamylase.

In another preferred embodiment, the locus encodes an alpha-glucosidase.

In another preferred embodiment, the locus encodes a beta-glucosidase.

In another preferred embodiment, the locus encodes a haloperoxidase.

In another preferred embodiment, the locus encodes an invertase.

In another preferred embodiment, the locus encodes a laccase.

In another preferred embodiment, the locus encodes a lipase.

In another preferred embodiment, the locus encodes a mannosidase.

In another preferred embodiment, the locus encodes a mutanase.

In another preferred embodiment, the locus encodes an oxidase.

In another preferred embodiment, the locus encodes a pectinolytic enzyme.

In another preferred embodiment, the locus encodes a peroxidase.

In another preferred embodiment, the locus encodes a phytase.

In another preferred embodiment, the locus encodes a polyphenoloxidase.

In another preferred embodiment, the locus encodes a proteolytic enzyme.

In another preferred embodiment, the locus encodes a ribonuclease.

In another preferred embodiment, the locus encodes a transglutaminase .

In another preferred embodiment, the locus encodes a xylanase.

In a more preferred embodiment, the locus is the sequence contained in pDSY109.

In a more preferred embodiment, the locus is the sequence contained in pDSY112.

In a more preferred embodiment, the locus is the sequence contained in pDSY138.

In a more preferred embodiment, the locus is the sequence contained in pDSY141.

In a more preferred embodiment, the locus is the sequence contained in pDSY162.

In a more preferred embodiment, the locus is the sequence contained in pMT1936.

In a more preferred embodiment, the locus is the sequence contained in pSMO1204.

In a more preferred embodiment, the locus is the sequence contained in pSMOH603.

In a more preferred embodiment, the locus is the sequence of SEQ ID NO:9.

In a more preferred embodiment, the locus is the sequence of SEQ ID NO:16.

In a more preferred embodiment, the locus is the sequence of SEQ ID NO:25.

In a more preferred embodiment, the locus is the sequence of SEQ ID NO:29.

In a more preferred embodiment, the locus is the sequence of SEQ ID NO:34.

In a more preferred embodiment, the locus is the sequence of SEQ ID NO:39.

In another more preferred embodiment, the locus is the sequence contained in p4–8.1.

In another more preferred embodiment, the locus is the sequence contained in p7–14.1.

In another more preferred embodiment, the locus is the sequence contained in pHB220.

In another more preferred embodiment, the locus is the sequence contained in pSMO717.

In another more preferred embodiment, the locus is the sequence contained in pSMO321.

In another more preferred embodiment, the locus is the sequence contained in pHowB571.

In another more preferred embodiment, the locus is the sequence contained in pSMO810.

In another more preferred embodiment, the locus is the sequence of SEQ ID NO:50.

In another more preferred embodiment, the locus is the sequence of SEQ ID NO:56.

In another more preferred embodiment, the locus is the sequence of SEQ ID NO:63.

In another more preferred embodiment, the locus is the sequence of SEQ ID NO:66.

In another more preferred embodiment, the locus is the sequence of SEQ ID NO:71.

In another more preferred embodiment, the locus is the sequence of SEQ ID NO:76.

In another preferred embodiment, the locus does not encode a trans factor of the DNA sequence of interest. A "trans factor" is a factor which is encoded by a gene separate from the DNA sequence of interest which activates or represses transcription of the DNA sequence. In a more preferred embodiment, the locus does not encode a repressor of the DNA sequence of interest. In a more preferred embodiment, the locus does not encode an activator of the DNA sequence of interest.

Cells

The methods of the present invention may be used with any cell containing a DNA sequence encoding a polypeptide of interest including prokaryotic cells such as bacteria, or eukaryotic cells such as marnmalian, insect, plant, and fungal cells. The DNA sequence may be native or foreign to the cell. The cell may be a unicellular microorganism or a non-unicellular microorganism. Furthermore, the cell may be wild-type or a mutant cell. For example, the mutant cell may be a cell which has undergone classical mutagenesis or genetic manipulation.

Useful prokaryotic cells are bacterial cells such as gram positive bacteria including, but not limited to, a Bacillus cell, e.g., *Bacillus alkalophilus, Bacillus amyloliquefaciens, Bacillus brevis, Bacillus circulans, Bacillus coagulans, Bacillus lautus, Bacillus lentus, Bacillus lichenifonnis, Bacillus megaterium, Bacillus stearothermophilus, Bacillus subtilis*, and *Bacillus thuringiensis*; or a *Streptomyces cell*, e.g., *Streptornyces lividans* or *Streptomyces murinus*, or gram negative bacteria such as *E. coli* and Pseudomonas sp.

In a preferred embodiment, the bacterial cell is a *Bacillus lentus, Bacillus licheniformis, Bacillus stearotheifnophiltis*, or *Bacillus subtilis* cell.

In a preferred embodiment, the cell is a fungal cell. "Fungi" as used herein includes the phyla Ascomycota, Basidiomycota, Chytridiomycota, and Zygomycota (as defined by Hawksworth et al., In, Ainsworth and Bisby's Dictionary of The Fungi, 8th edition, 1995, CAB International, University Press, Cambridge, UK) as well as the Oomycota (as cited in Hawksworth et al., 1995, supra, page 171) and all mitosporic fungi (Hawksworth et al., 1995, supra). Representative groups of Ascomycota include, e.g., Neurospora, Eupenicillium (=Penicillium), Emericella (=Aspergillus), Eurotiuim (=Aspergillus), and the true yeasts. Examples of Basidiomycota include mushrooms, rusts, and smuts. Representative groups of Chytridiomycota include, e.g., Allomyces, Blastocladiella, Coelomomyces, and aquatic fungi. Representative groups of Oomycota include, e.g., Saprolegniomycetous aquatic fungi (water molds) such as Achlya. Examples of mitosporic fungi include Alternaria, Aspergillus, Candida, and Penicillium. Representative groups of Zygomycota include, e.g., Mucor and Rhizopus.

In a preferred embodiment, the fungal cell is a yeast cell. "Yeast" as used herein includes ascosporogenous yeast (Endomycetales), basidiosporogenous yeast, and yeast belonging to the Fungi Imperfecti (Blastomycetes). The ascosporogenous yeasts are divided into the families Spermophthoraceae and Saccharomycetaceae. The latter is comprised of four subfamilies, Schizosaccharomycoideae (e. g., genus Schizosaccharomyces), Nadsonioideae, Lipomycoideae, and Saccharomycoideae (e. g., genera Kluyveromyces, Pichia, and Saccharotnyces). The basidiosporogenous yeasts include the genera Filobasidiella, Filobasidium, Leucosporidim, Rhodosporiditum, and Sporidiobolus. Yeast belonging to the Fungi Imperfecti are divided into two families, Sporobolomycetaceae (e.g., genera Bullera and Sorobolomyces) and Cryptococcaceae (e.g., genus Candida). Since the classification of yeast may change in the future, for the purposes of this invention, yeast shall be defined as described in Biology and Activities of Yeast (Skinner et al., 1980, Soc. App. Bacteriol. Symposium Series No. 9, 1980. The biology of yeast and manipulation of yeast genetics are well known in the art (see, e.g., Biochemistry and Genetics of Yeast, (Bacil, M., Horecker, B. J., and Stopani, A. O. M., editors), 2nd edition, 1987; The Yeasts (Rose, A. H., and Harrison, J. S., editors), 2nd edition, 1987; and The Molecular Biology of the Yeast Saccharomyces, Strathern et al., editors, 1981).

In a more preferred embodiment, the yeast cell is a cell of a species of Candida, Kluyveromyces, Pichia, Saccharomyces, Schizosaccharomyces, or Yarrowia.

In a most preferred embodiment, the yeast cell is a *Saccharomyces carlsbergensis, Saccharomyces cerevisiae, Saccharomyces diastaticus, Saccharomyces douglasii, Saccharomyces kluyveri, Saccharomyces norbensis*, or *Saccharomiyces oviformis* cell. In another most preferred embodiment, the yeast cell is a *Kluyveromyces lactis* cell. In another most preferred embodiment, the yeast cell is a *Yarrowia lipolytica* cell.

In another preferred embodiment, the fungal cell is a filamentous fungal cell. "Filamentous fungi" include all filamentous forms of the subdivision Eumycota and Oomycota (as defined by Hawksworth et al., 1995, supra). The filamentous fungi are characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomvces cerevisiae* is by budding of a unicellular thallus and carbon catabolism may be fermentative. In a more preferred embodiment, the filamentous fungal cell is a cell of a species of, but not limited to, Acremonium, Aspergillus, Fusarium, Humicola, Mucor, Mycetiophthora, Neurospora, Penicillium, Scytalidium, Thielavia, Tolypocladium, and Trichodernna.

In an even more preferred embodiment, the filamentous fungal cell is an Aspergillus cell. In another even more preferred embodiment, the filamentous fungal cell is an Acremonium cell. In another even more preferred embodiment, the filamentous fungal cell is a Fusarium cell. In another even more preferred embodiment, the filamentous fungal cell is a Humicola cell. In another even more preferred embodiment, the filamentous fungal cell is a Mucor cell. In another even more preferred embodiment, the filamentous fungal cell is a Myceliophthora cell. In another even more preferred embodiment, the filamentous fungal cell is a Neurospora cell. In another even more preferred embodiment, the filamentous fungal cell is a Penicillium cell. In another even more preferred embodiment, the filamentous fungal cell is a Thielavia cell. In another even more preferred embodiment, the filamentous fungal cell is a Tolypocladium cell. In another even more preferred embodiment, the filamentous fungal cell is a Trichoderma cell.

In a most preferred embodiment, the filamentous fungal cell is an *Aspergillus awamnori, Aspergillus foetidus, Aspergillus japonicus, Aspergillus nidulans, Aspergillus niger*, or *Aspergillus oryzae* cell. In another most preferred embodiment, the filamentous fungal cell is a *Fitsariuin bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sulphureum, Fusarium toruloseum, Fusarium trichothecioides*, or *Fusarium venenatum* cell. In a most preferred embodiment, the filamentous fungal cell is a *Fusarium venenatum* cell (Nirenberg sp. nov.). In another most preferred embodiment, the filamentous fungal cell is a *Humicola insolens* cell or a *Humicola lanuginosa* cell. In another most preferred embodiment, the filamentous fungal cell is a *Mucor miehei* cell. In another most preferred embodiment, the filamentous fungal cell is a *Myceliophthora thermophila* cell. In another most preferred embodiment, the filamentous fungal cell is a *Neurospora crassa* cell. In another most preferred embodiment, the filamentous fungal cell is a *Penicillium purpurogenum* cell. In another most preferred embodiment, the filamentous fungal cell is a *Thielavia terrestris* cell. In another most preferred embodiment, the filamentous fungal cell is a *Trichodermna harzianum, Trichoderma koningii, Trichoderma longibrachiatumn, Trichoderma reesei*, or *Trichoderma viride* cell.

Useful mammalian cells include Chinese hamster ovary (CHO) cells, HeLa cells, baby hamster kidney (BHK) cells, COS cells, or any number of immortalized cells available, e.g., from the American Type Culture Collection.

Introduction of Nucleic Acid Constructs into Cells

The nucleic acid construct(s) may be introduced into a cell by a variety of physical or chemical methods known in the art including, but not limited to, transfection or transduction, electroporation, microinjection, microprojectile bombardment, alkali salts, or protoplast-mediated transformation.

The introduction of the nucleic acid construct into a cell for insertional mutagenesis is referred to as "DNA-tagged mutagenesis". "DNA-tagged mutagenesis" is defined herein as the introduction of a nucleic acid molecule into a cell, which leads to one or more insertions of the nucleic acid molecule into one or more loci of the genome of the cell thereby marking the loci into which the nucleic acid molecule is inserted. The mutant cell roduced by DNA-tagged mutagenesis is called a tagged mutant.

Suitable procedures for transformation of Aspergillus cells are described in EP 238 023 and Yelton et al., 1984, *Proceedings of the National Academy of Sciences USA* 81: 1470–1474. A suitable method of transforming Fusarium species is described by Malardier et al., 1989, *Gene* 78: 147–156 or in WO 96/00787. Yeast may be transformed using the procedures described by Becker and Guarente, In Guide to Yeast Genetics and Molecular Biology, *Methods of Enzymology* 194: 182–187; Ito et al., 1983, *Journal of Bacteriology* 153: 163; and Hinnen et al., 1978, *Proceedings of the National Academy of Sciences USA* 75: 1920.

The transformation of a bacterial cell may, for instance, be accomplished by protoplast transformation (see, e.g., Chang and Cohen, 1979, *Molecular General Genetics* 168: 111–115), by using competent cells (see, e.g., Young and Spizizin, 1961, *Journal of Bacteriology* 81: 823–829, or Dubnau and Davidoff-Abelson, 1971, *Journal of Molecular Biology* 56: 209–221), by electroporation (see, e.g., Shigekawa and Dower, 1988, *Biotechniques* 6: 742–751), or by conjugation (see. e.g., Koehler and Thorne, 1987, *Journal of Bacteriology* 169: 5771–5278).

Mammalian cells may be transformed by direct uptake using the calcium phosphate precipitation method of Graham and Van der Eb, 1978, *Virology* 52: 546. Other processes, e.g., electronoration, known to the art, may be used.

When the nucleic acid construct is a vector, integration into the cell's genome occurs randomly by homologous and/or non-homologous recombination depending on the cell of choice.

In a preferred embodiment, the nucleic acid construct is introduced into the parent cell by restriction enzyme-mediated integration (REMI). REMI, which is described in Schiestl and Petes, 1991, *Proceedings of the National Academiy of Sciences USA* 88: 7585–7589, is the introduction of plasmid DNA digested with a restriction enzyme along with the restriction enzyme into a cell which subsequently leads to integration of the plasmid DNA into the genome often at a site specified by the restriction enzyme added. The advantage of REMI DNA-tagged mutagenesis is it can generate mutations whose molecular basis can be easily identified.

When the nucleic acid construct is a restriction enzyme cleaved linear DNA fragment, insertion of the construct into the cell's genome through REMI in the presence of the appropriate restriction enzyme is random by virtue of the randomness of the restriction sites present in the genome. The nucleic acid construct may insert into the cell's genome as a single copy or as multiple copies at a single locus or at a different locus or at different loci. It is preferable that the nucleic acid construct insert as a single copy to facilitate the identification and recovery of the tagged locus.

Screening of Mutant Cells

The present invention also relates to mutant cells which produce, express, synthesize or secrete more of a polypeptide or metabolite than the parent cell when both cells are cultivated under the conditions.

The present invention also relates to mutant cells which produce, express, synthesize or secrete more of a polypeptide or metabolite than the parent cell when both cells are cultivated under the conditions.

Following the introduction of a nucleic acid construct into a cell, the next step is to isolate the mutant cell with the modified production of a polypeptide from a population of presumptive mutant cells. The isolation of the mutant cell preferably relies on measurement of the production of the polypeptide or the metabolite by the mutant cell relative to the parent cell when the mutant cell and the parent cell are cultured under the same conditions.

The phrase "modified production of a polypeptide" includes an alteration or change of a step in the production of a polypeptide or a metabolite by the mutant cell relative to the parent cell. Such steps include, but are not limited to, transcription, post-transcriptional modification, translation, post-translational modification, secretion, fermentation, proteolysis, down-stream processing, recovery, and purification.

The mutant cell may be a mutant cell, for example, with improved production of a specific polypeptide or metabolite or a mutant cell which is no longer capable or has a diminished capability of producing a specific polypeptide or metabolite. Furthermore, the mutant cell may be a mutant cell having an increased uptake of an inorganic cofactor.

The mutant cell may also have a more desirable phenotype than the parent cell which modifies the production of a polypeptide or a metabolite. The term "phenotype" is defined herein as an observable or outward characteristic of a cell determined by its genotype and modulated by its environment. Such a mutant cell having a desired phenotype includes, but is not limited to, a morphological mutant cell, a secretion mutant cell, an auxotrophic mutant cell, a conditional mutant, a mutant cell exhibiting an altered growth rate under desired conditions relative to the parent cell, a mutant cell resulting in the relief of overexpression mediated growth inhibition, or a mutant cell able to tolerate low oxygen conditions.

Furthermore, the mutant cell may be characterized as being a mutant cell exhibiting altered production of a transcriptional activator of a promoter or a cryptic intron-splicing-deficient mutant cell.

The isolation of a mutant cell may involve screening methods known in the art specific to the desired phenotype and/or the polypeptide or the metabolite of interest. In general where a desired phenotype is involved, a method specific to the desired phenotype may be used initially to identify the mutant cell, but then may be followed by a method specific to the polypeptide or the metabolite.

The population of presumptive mutants obtained by introducing a nucleic acid construct into the cells of an organism to produce a mutant cell are first purified using standard plating techniques such as those used in classical mutagenesis (see, for example, Lawrence. C. W., 1991, In Christine Guthrie and Gerald R. Fink, editors, *Methods in Enzymology*. Volume 194, pages 273–281, Academic Press, Inc., San Diego), single spore isolation, or enrichment techniques. The standard plating techniques are preferably conducted in combination with a means of detecting the desired phenotype and/or the polypeptide or the metabolite. Different enrichment techniques may be used for increasing the percentage of mutant cells in comparison to their wild-type or parent equivalents such as (1) direct selection which utilizes growth conditions that greatly favor the growth of the mutant; (2) counterselection, which makes use of conditions that kill the parent cells; (3) physical selection, which involves unique properties of the mutant cells that enable them to be physically separated from their parent cells; and (4) direct measurements of the amount of desired substances. However, whether or not a means for identifying the mutant cell with respect to the desired phenotype and/or the polypeptide or the metabolite of interest can be incorporated into the plating medium, the purified presumptive mutants may require further characterization to confirm the identity of the mutant. Examples of the methods used to further characterize and confirm the identity of the mutant are illustrated below.

A mutant with improved production of a specific polypeptide or a specific metabolite may be identified by using a detection method known in the art that is specific for the polypeptide or the metabolite. Detection methods for polypeptides may include, but are not limited to, use of specific antibodies, enzymatic activity by measuring formation of an enzyme product or disappearance of an enzyme substrate, clearing zones on agar plates containing an enzyme substrate, and biological activity assays. Detection methods for metabolites may include, but are not limited to, thin layer chromatography, high performance liquid chromatography, gas chromatography, mass spectroscopy, biological activity assays, bioassays, and fluorescent activating cell sorting.

In a preferred embodiment, the specifically desired mutant cell is a mutant cell with improved production of a specific polypeptide.

In another preferred embodiment, the specifically desired mutant is a mutant with improved production of a specific metabolite- more preferably an alkaloid, an amino acid, an antibiotic, a cofactor, a drug, a fatty acid, a fungicide, a herbicide, an insecticide, an organic acid, a pigment, a plastic precursor, a polyester precursor, a prosthetic group, a rodenticide, a sweetner, or a vitamin; and most preferably citric acid or lactic acid.

A prosthetic group or an organic cofactor which is a constituent of a polypeptide and/or required for biological activity may be overproduced by isolating a mutant according to the methods of the present invention. Such a mutant would be particularly important where biosynthesis of the prosthetic group or the cofactor is a rate-limiting event in the production of a polypeptide in a biologically active form, e.g., a hemoprotein containing heme including, but not limited to, a cytochrome, specifically cytochrome P450, cytochrome b, cytochrome $c_1$, or cytochrome c; a globin, specifically, hemoglobin or myoglobin; an oxidoreductase, specifically a catalase, an oxidase, an oxygenase, a haloperoxidase, or a peroxidase; or any other polypeptide containing a heme as a prosthetic group.

In a more preferred embodiment, the specifically desired mutant cell is a mutant cell overproducing an adenosine phosphate, S-adenosyl-L-methionine, biocytin, biotin, coenzyme A, coenzyme Q (ubiquinone), 5'-deoxyadenosylcobalamine, a ferredoxin, a flavin coenzyme, heme, lipoic acid, a nucleoside diphosphate, a nicotinamide adenine dinucleotide, a nicotinamide adenine dinucleotide phosphate, phosphoadenosine, phosphosulfate, pyridoxal phosphate, tetrahydrofolic acid, thiamine pyrophosphate, or a thioredoxin.

In another preferred embodiment, the specifically desired mutant cell is a mutant cell characterized with an increased uptake of an inorganic cofactor. The uptake by a cell of an inorganic cofactor which is a constituent of a polypeptide and/or required for biological activity may be increased by isolating a mutant according to the methods of the present invention. Such a mutant would be particularly important where uptake of the inorganic cofactor is a rate-limiting event in the production of a polypeptide in a biologically active form. In a more preferred embodiment, the specifically desired mutant cell is a mutant cell characterized with an increased uptake of $Co^{2+}$, $CU^{2+}$, $Fe^{2+}$, $Fe^{3+}$, $K^+$, $Mg^{2+}$, $Mn^{2+}$, Mo, $Ni^{2+}$, Se, or $Zn^{2+}$.

In a preferred embodiment, the polypeptide or the metabolite is produced by the mutant cell in an amount which is at least 20% greater, preferably at least 50%, more preferably at least 75%, more preferably at least 100%, more preferably at least 100%–1000%, even more preferably at least 200%–1000%, and most preferably at least 500%–1000% or more greater than the cell.

In another preferred embodiment, the specifically desired mutant cell is a mutant cell which is no longer capable or has a diminished capability of producing a specific polypeptide. A mutant cell which is no longer capable or has a diminished capability of producing a specific polypeptide may be identified using the same methods described above for polypeptides, but where no or diminished production is measured relative to the parent cell.

In a more preferred embodiment, the specifically desired mutant cell is a mutant cell which is no longer capable or has a diminished capability of producing a polypeptide.

In another preferred embodiment, the polypeptide is produced by the mutant cell in an amount which is at least 20%, more preferably at least 50%, even more preferably at least 75%, and most preferably 100% lower than the cell.

In another preferred embodiment, the specifically desired mutant cell is a mutant cell which is no longer capable or has a diminished capability of producing a specific metabolite. A mutant cell which is no longer capable or has a diminished capability of producing a specific metabolite may be identified using the same or similar methods described above for metabolites, but where no or diminished production is measured relative to the parent cell.

In a more preferred embodiment, the specifically desired mutant cell is a mutant cell which is no longer capable or has a diminished capability of producing a deoxysugar, a surfactant, a mycotoxin, an organic acid, a sugar alcohol, a toxic metabolite, or a toxin; and most preferably an aflatoxin, beta-exotoxin, cyclopiazonic acid, an enniatin, a fusarin, kanosamine, mannitol, oxalic acid, surfactin, a tricothecene, a zearalenol, or a zearalenone.

In another preferred embodiment, the metabolite is produced by the mutant cell in an amount which is at least 20% lower than the cell, more preferably 50%, even more preferably 75%, and most preferably 100% lower than the cell.

In another preferred embodiment, the mutant cell is a morphological mutant cell. A "morphological mutant cell" is defined herein as a mutant cell which has a desired morphology. A morphological mutant cell may be identified, for example, by using standard plating techniques employing a growth medium which elicits the desired morphology relative to the parent cell, by microscopic examination, or by sorting vegetatively growing cells by fluorescence activated cell sorting. Such morphological mutants include, but are not limited to, a mutant characterized as having superior rheological properties, e.g., a highly-branched fungal mutant, a restricted colonial fungal mutant, or a highly-branched restricted colonial fungal mutant which possesses rapid growth and low viscosity growth characteristics; a mutant which possesses a filamentous form during fermentation in contrast to a pellet form; a mutant which is less "sticky" preventing the colonization of fermentor surfaces; a mutant with a predictable viscosity during the course of a fermentation; a color mutant which aids in monitoring and maintaining the purity of a culture and high production of a polypeptide by the culture; a wettable cell which lacks, for example, a cell wall or structural hydrophobic protein, e.g., hydrophobin; an osmotic stress-insensitive mutant which improves growth of a cell; a desiccation-insensitive mutant which improves growth of a cell; a non-spore-forming mutant which enhances the production of a polypeptide; and a non-slime-producing mutant with low viscosity growth.

Preferably, the morphological mutant cell is a color mutant, a wettable mutant cell, a mutant characterized as having superior rheological properties, an osmotic stress-insensitive mutant, a desiccation-insensitive mutant, a non-spore-forming mutant, or a non-slime-producing mutant, and most preferably a highly-branched fungal mutant, a restricted colonial fungal mutant, or a highly-branched restricted colonial fungal mutant.

In another preferred embodiment, the mutant cell is a secretion mutant cell. A "secretion mutant cell" is defined herein as a mutant cell which produces higher yields of one or more secreted proteins. A secretion mutant cell may be identified by using a detection method known in the art that is specific for the polypeptide and comparing the yield to one or more known secreted polypeptides at the same time. Detection methods for polypeptides may include, but are not limited to, use of specific antibodies, enzymatic activity by measuring formation of an enzyme product or disappearance of an enzyme substrate, clearing zones on agar plates containing an enzyme substrate, biological activity assays, and fluorescent activating cell sorting.

In another preferred embodiment, the specifically desired mutant cell is an auxotrophic mutant cell. An "auxotrophic mutant cell" is defined herein as a mutant cell which has lost its ability to synthesize one or more essential metabolites or to metabolize one or more metabolites which modifies the production of a polypeptide by the mutant cell. An auxotrophic mutant cell may be identified using standard plating techniques by growing the presumptive mutant both in the absence and presence of an essential metabolite. The auxotrophic mutant will not grow in the absence of the essential metabolite. The auxotrophic mutant can be advantageously used to selectively screen for a mutant producing a specific polypeptide of interest.

In a more preferred embodiment, the specifically desired mutant cell is an auxotrophic mutant cell unable to metabolize or synthesize one or more of an amino acid, a fatty acid, an organic acid, a pyrimidine, a purine, or a sugar; and more preferably 5-aminolevulinic acid. biotin, glucose, lactose, or maltose.

In another preferred embodiment, the specifically desired mutant cell is a conditional mutant cell. A "conditional mutant cell" is defined herein as a mutant cell which contains one or more mutations whose phenotypes are only observed under certain conditions and modifies the production of a polypeptide or a metabolite by the mutant cell. Conditional mutations can occur in virtually all genes, including those that control the steps in macromolecular synthesis, modification, and assembly into supermolecular structures. A conditional mutant cell may be identified using standard plating techniques by growing the presumptive mutant both under permissive and restrictive conditions. For example, a mutant strain which does not produce undesirable proteolytic activity under nitrogen limited conditions would be desirable compared to the parent strain which produces proteolytic activity under nitrogen limited conditions. An additional example is an alkaline pH sensitive mutant that does not grow at alkaline pH, but may have increased or decreased production of a desired polypeptide. A further example is a mutant which is unable to grow under specifc growth conditions.

In a more preferred embodiment, the conditional mutant cell is a temperature-sensitive, acid pH sensitive, alkaline pH sensitive, antibiotic-resistant, antibiotic-sensitive, toxin-resistant, toxin-sensitive, virus-resistant, or paraquat-sensitive cell; and most preferably an alkaline pH sensitive mutant cell.

In another preferred embodiment, the specifically desired mutant cell is a mutant cell exhibiting an altered growth rate relative to the parent cell. A "mutant cell exhibiting an altered growth rate" is defined herein as a mutant cell which has a doubling time that is different than that of the parent cell. Such a mutant cell may be identified by comparing the growth of the mutant cell and the parent cell under controlled fermentation conditions. Such a mutant cell may have improved fermentation characteristics like a shorter fermentation time to increase productivity, or a longer fermentation time to provide control of the oxygen demand of a culture.

In another preferred embodiment, the specifically desired mutant cell is a mutant cell resulting in the relief of overexpression mediated growth inhibition. A "mutant cell resulting in the relief of overexpression mediated growth inhibition" is defined herein as a mutant cell whose growth is not inhibited by the overproduction of a desired polypeptide or metabolite when grown under conditions that induce high level production of the polypeptide or the metabolite. Such a mutant may be identified by standard plating techniques on plates with an inducing carbon source, e.g., maltose. Mutants would be able to grow well on the inducing carbon source while the parent cells would grow poorly. Such a mutant would be useful since it is known in some cells that overexpression of a polypeptide is toxic to the cells.

In another preferred embodiment, the specifically desired mutant cell is a mutant cell able to tolerate low oxygen conditions. A "mutant cell able to tolerate low oxygen conditions" is defined herein as a mutant cell which is able to grow and produce a desired polypeptide or metabolite under growth conditions where the dissolved oxygen concentration is low. Such a mutant cell is particularly advantageous for fermentations where the productivity of high cell densities decreases due to oxygen transfer. A low oxygen tolerant mutant is preferably detected by growing the mutant cell relative to the parent cell on a solid or in a liquid medium in the presence of low levels of oxygen.

In a more preferred embodiment, the specifically desired mutant cell is a mutant cell able to tolerate low oxygen conditions in the range of about 0 to about 50% saturation, preferably about 0 to about 40% saturation, even more preferably about 0% to about 30% saturation, more preferably about 0% to about 20% saturation, most preferably about 0% to about 10% saturation, and even most preferably about 0% to about 5% saturation.

In another preferred embodiment, the specifically desired mutant cell is a signal transduction pathway mutant cell. A "signal transduction pathway mutant cell" is defined herein as a mutant cell with a mutation in one or more of the genes of the pathway which modifies the production of a polypeptide encoded by a DNA sequence of interest. The term "signal transduction pathway" is defined herein as a cascade of genes encoding polypeptides that are all required for the activation or deactivation of another single polypeptide. The pathway senses a signal and through the cascade of genes, the signal is transduced and leads to the activation or deactivation of one or more polypeptides. Such a mutant is preferably detected using a method which is specific to the desired phenotype which modifies the production of a polypeptide of interest.

In a more preferred embodiment, the signal transduction pathway mutant cell is a glucose transport signal transduction pathway mutant or a pH signal transduction pathway mutant, even more preferably a mutant in which gene required for activation of pacC has been disrupted, and most preferably a gluT gene mutant or a palB gene mutant.

In another preferred embodiment, the specifically desired mutant cell is a mutant cell exhibiting altered production of a transcriptional activator of a promoter. A "mutant cell exhibiting altered production of a transcriptional activator of a promoter" is defined herein as a mutant cell with a mutation in a gene encoding a transcriptional activator which 'turns-up' or 'turns-down' a promoter of a DNA sequence encoding a polypeptide of interest.

Examples of such promoters in a bacterial cell are promoters of the genes of the *Bacillus amyloliquefaciens* alpha-amylase gene (amyQ), the *Bacillus licheniformis* alpha-amylase gene (amyL), the *Bacillus licheniformis* penicillinase gene (penP), the *Bacillus stearothermophilus* maltogenic amylase gene (amyM), the *Bacillus subtilis* levansucrase gene (sacB), the *Bacillus subtilis* xylA and xylB genes, the *E. coli* lac operon, the *Streptomyces coelicolor* agarase gene (dagA), and the prokaryotic beta-lactamase gene (Villa-Kamaroff et al., 1978, *Proceedings of the National Academy of Sciences USA* 75:3727–3731), as well as the tac promoter (DeBoer et al., 1983. *Proceedings of the National Academy of Sciences USA* 80:21–25). Further promoters are described in "Useful proteins from recombinant bacteria" in *Scientific American*, 1980, 242:74–94; and in J. Sambrook, E. F. Fritsch, and T. Maniatus, 1989, *Molecular Cloning, A Laboratory Manual*, 2d edition, Cold Spring Harbor, N.Y.

Examples of such promoters in a filamentous fungal cell are promoters of the genes encoding *Aspergillus nidulans* acetamidase, *Aspergillus niger* acid stable alpha-amylase, *Aspergillus niger* neutral alpha-amylase, *Aspergillus awamori* or *Aspergillus niger* glucoamylase (glaA), *Aspergillus oryzae* alkaline protease, *Aspergillus oryzae* TAKA amylase, *Aspergillus oryzae* triose phosphate isomerase, *Fusarium oxysporum* trypsin-like protease (as described in U.S. Pat. No. 4,288,627, which is incorporated herein by reference), *Rhizomucor miehei* aspartic proteinase, *Rhizomucor miehei* lipase, and mutant, truncated, and hybrid promoters thereof. Particularly preferred promoters in filamentous fungal cells are the TAKA amylase, NA2-tpi (a hybrid of the promoters from the genes encoding *Aspergillus niger* neutral alpha-amylase and *Aspergillus oryzae* triose phosphate isomerase), and glaA promoters.

Examples of such promoters in a yeast cell are promoters of the genes encoding *Saccharonyces cerevisiae* enolase (ENO-1) gene, the *Saccharomyces cerevisiae* galactokinase gene (GAL1) the *Saccharomyces cerevisiae* alcohol dehydrogenase/glyceraldehyde-3-phosphate dehydrogenase genes (ADH2/GAP), and the *Saccharomyces cerevisiae* 3-phosphoglycerate kinase gene. Other yeast promoters are described by Romanos et al., 1992, Yeast 8:423–488.

Examples of such promoters in a mammalian cell are viral promoters such as those of Simian Virus 40 (SV40), Rous sarcoma virus (RSV), adenovirus, and bovine papilloma virus (BPV).

In a more preferred embodiment, the mutant cell exhibits altered production of a transcriptional activator of the TAKA, TAKA/NA2, *Fusarium oxysporum* trypsin-like protease, or a glucoamylase promoter.

In another preferred embodiment, the specifically desired mutant cell is a cryptic intron-splicing-deficient mutant cell. A "cryptic intron-splicing-deficient mutant cell" is defined herein as a mutant cell which no longer recognizes and erroneously splices a cryptic intron as an authentic intron during mRNA synthesis. A cryptic intron-splicing-deficient mutant cell would be particularly useful to prevent the excision or splicing of an erroneous cryptic nuclear pre-mRNA intron from a primary transcript so a biologically active substance is produced. In this situation, the cryptic intron is actually part of the coding sequence and, therefore, is not an authentic intron but incorrectly recognized as such and erroneously spliced during mRNA synthesis and processed by the parent cell. The introduction of a DNA sequence encoding a heterologous polypeptide into a parent cell such as a fungal host cell, particularly a filamentous fungal host cell, may result in this type of erroneous or aberrant splicing of the coding sequence. A cryptic intron-splicing-deficient mutant cell may be identified by screening for increased production of a polypeptide encoded by a DNA sequence that is known to have a cryptic intron which leads to little or no production of the polypeptide.

In another preferred embodiment, the specifically desired mutant may be a mutant which contains two or more of the mutations described above.

Identification of Mutant Cells of the Present Invention

The present inventors have discovered that when certain loci in a parent cell are disrupted, the resulting mutant cell has a modified production of a polypeptide. As described above, the nucleic acid construct itself can have an effect on the production of a polypeptide. For example, the nucleic acid construct may comprise one or more copies of the nucleic acid sequence encoding the polypeptide. In addition, the nucleic acid construct may comprise a promoter, transcriptional activators and repressors, etc.

When the nucleic acid construct itself can have an effect on the amount of polypeptide produced, expressed, synthesized or secreted, in order to determine whether a mutant cell of the present invention has been produced, one would have to rescue the locus as described below and introduce another nucleic acid construct which does not have an effect, e.g., a selectable marker, at the same locus. If the mutant cell produced by introducing the other nucleic acid construct at the same locus also has an effect on the amount of polypeptide produced, expressed, synthesized or secreted, then the original mutant cell is a mutant cell of the present invention.

Rescue of a Locus with the Inserted Nucleic Acid Construct and Use of a Targeting Construct The present invention further relates to methods for rescuing a locus with the inserted nucleic acid construct comprising isolating from the identified mutant cell (i) the nucleic acid construct and (ii) the 3' and 5' flanking regions of the locus of the genome where the nucleic acid construct has been integrated; and identifying the 3' and 5' flanking regions of the locus.

The nucleic acid construct and flanking regions can be isolated or rescued by methods well known in the art such as cleaving with restriction enzymes and subsequent ligation and transformation of *E. Coli*, inverse PCR, random primed gene walking PCR, or probing a library of the tagged mutant. The isolated nucleic acid construct with either or both the 3' and 5' flanking regions is defined herein as a "targeting construct".

The targeting construct includes between 100–9,000 bp, preferably 200–9,000 bp, more preferably 500–7,000 bp, even more preferably 1,000–7,000 bp, and most preferably 1,000–3,000 bp upstream and/or downstream of the integration site of the nucleic acid construct.

The targeting construct of the invention may be introduced into a different cell to modify the production of a polypeptide similar or identical to or completely different from the polypeptide modified in the original cell. The other cell may be of the same or a different species or of a different genera as the original cell. If the original cell was a fungal cell, the other cell is preferably a fungal cell. If the original cell was a bacterial cell, the other cell is preferably a bacterial cell. If the original cell was a mammalian cell, the other cell is preferably a mammalian cell.

When the cell is a different cell, integration of the targeting construct preferably occurs at a target locus which is homologous to the locus sequence of the original cell from which the targeting construct was obtained, i.e., identical or sufficiently similar such that the targeting sequence and cellular DNA can undergo homologous recombination to produce the desired mutation. The sequence of the targeting construct is preferably, therefore, homologous to a preselected site of the cellular chromosomal DNA with which homologous recombination is to occur. However, it will be understood by one of ordinary skill in the art that the likelihood of a targeting construct reinserting at a target locus will depend on the cell since homologous recombination frequencies range from almost 100% in the yeast *Saccharomyces cerevisiae* to as low as 1% in Aspergillus. The targeting construct may integrate by non-homologous recombination at a non-target locus which is not within the DNA sequence encoding the polypeptide of interest, but results in the modification of the production of the polypeptide.

Preferably, the target locus includes DNA sequences that have greater than 40% homology, preferably greater than 60% homology, more preferably greater than 70% homology, even more preferably greater than 80% homology, and most preferably greater than 90% homology with the flanking sequences of the targeting construct.

The targeting construct may contain either or both of the 3' and 5' regions depending on whether a single cross-over or a replacement is desired. Furthermore, the targeting construct may be modified to correct any aberrant events, such as rearrangements, repeats, deletions, or insertions, which occurred during the introduction and integration of the original nucleic acid construct into the cell's genome at the locus from which it was originally rescued.

The targeting construct described above may be used as is. i.e., a restriction enzyme cleaved linear nucleotide sequence, or may be circularized or inserted into a suitable vector. For example, a circular plasmid or DNA fragment preferably employs a single targeting sequence. A linear plasmid or DNA fragment preferably employs two targeting sequences. The targeting construct upon introduction into a cell, in which the cell comprises a DNA sequence encoding a polypeptide of interest, integrates into the genome of the cell at a target locus or at a nontarget locus, but preferably at a target locus, not within the DNA sequence encoding the polypeptide of interest. The target locus may be on the same chromosome or the same extrachromosomal element or on a different chromosome or a different extrachromosomal element as that of the DNA sequence of interest. The integration modifies the production of the polypeptide or a metabolite by the mutant cell relative to the parent cell when the mutant cell and the parent cell are cultured under the same conditions. In a preferred embodiment, the targeting construct contains a selectable marker.

Optionally, the targeting construct can be introduced into a cell as two or more separate fragments. In the event two fragments are used, the fragments share DNA sequence homology (overlap) at the 3' end of one fragment and the 5' end of the other, while one carries a first targeting sequence and the other carries a second targeting sequence. Upon introduction into a cell, the two fragments can undergo homologous recombination to form a single fragment with the first and second targeting sequences flanking the region of overlap between the two original fragments. The product fragment is then in a form suitable for homologous recombination with the cellular target sequences. More than two fragments can be used, designed such that they will undergo homologous recombination with each other to ultimately form a product suitable for homologous recombination with the cellular target sequences.

Upon introduction of the targeting construct into a cell, the targeting construct may be further amplified by the inclusion of an amplifiable selectable marker gene which has the property that cells containing amplified copies of the selectable marker gene can be selected for by culturing the cells in the presence of the appropriate selectable agent.

In a specific embodiment, the targeting construct is SphI linearized pDSY109, HpaI linearized pDSY112, AsnI/PvuI linearized pMT1936, NdeI linearized pDSY138, AsnI/PvuI linearized pDSY162, BglII linearized p4–8.1, BglII linearized p4–8.1, NarI linearized p7–14.1, BglII linearized pSMO717, BglII linearized pSMO321, NdeI linearized pHowB571, or NdeI linearized pSMO810.

In a most preferred embodiment, the nucleic acid construct is pDSY109.

In a most preferred embodiment, the nucleic acid construct is pDSY112.

In a most preferred embodiment, the nucleic acid construct is pMT1936.

In a most preferred embodiment, the nucleic acid construct is pDSY138.

In a most preferred embodiment, the nucleic acid construct is pDSY162.

In a most preferred embodiment, the nucleic acid construct is pDSY163.

In a most preferred embodiment, the nucleic acid construct is pDSY141.

In a most preferred embodiment, the nucleic acid construct is pSMO1204.

In a most preferred embodiment, the nucleic acid construct is pSMOH603.

In a most preferred embodiment, the nucleic acid construct is p4–8.1.

In a most preferred embodiment, the nucleic acid construct is p7–14.1.

In a most preferred embodiment, the nucleic acid construct is pHB220.

In a most preferred embodiment, the nucleic acid construct is pSMO717.

In a most preferred embodiment, the nucleic acid construct is pSMO321.

In a most preferred embodiment, the nucleic acid construct is pHowB571.

In a most preferred embodiment, the nucleic acid construct is pSMO810.

In a preferred embodiment, one or more targeting constructs are introduced into target loci. In another preferred embodiment, each targeting construct modifies the production of a different polypeptide or a different metabolite or a combination thereof, or results in different phenotypes which modify the production of different polypeptides or different metabolites or a combination thereof. In another preferred embodiment, two or more targeting constructs together when introduced into target loci act additively or synergistically to modify the production of a polypeptide or a metabolite.

Methods of Producing a Desired Polypeptide or Metabolite from Mutant Cells

The present invention further relates to the mutant cells with a desired phenotype as host cells. Mutant cells selected for increased production of a desired polypeptide or metabolite are cultivated in a nutrient medium suitable for production of the polypeptide or metabolite using methods known in the art. For example, the cell may be cultivated by shake flask cultivation, small-scale or large-scale fermentation (including continuous, batch, fed-batch, or solid state fermentations) in laboratory or industrial fermentors performed in a suitable medium and under conditions allowing the polypeptide or metabolite to be expressed and/or isolated. The cultivation takes place in a suitable nutrient medium comprising carbon and nitrogen sources and inorganic salts, using procedures known in the art (see, e.g., references for bacteria and yeast; Bennett, J. and LaSure, L., editors, More Gene Manipulations in Fungi, Academic Press, CA, 1991). Suitable media are available from commercial suppliers or may be prepared according to published compositions (e.g., in catalogues of the American Type Culture Collection). If the polypeptide or metabolite is secreted into the nutrient medium, the polypeptide can be recovered directly from the medium. If the polypeptide or metabolite is not secreted, it is recovered from cell lysates.

The polypeptides and metabolites may be detected using methods known in the art that are specific for the polypeptides and metabolites such as those methods described earlier or the methods described in the Examples.

The resulting polypeptide or metabolite may be recovered by methods known in the art. For example, the polypeptide or metabolite may be recovered from the nutrient medium by conventional procedures including, but not limited to, centrifugation, filtration, extraction. spray-drying, evaporation, or precipitation.

The polypeptides and metabolites of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), or extraction (see, e.g., Protein Purification, J.-C. Janson and Lars Ryden, editors, VCH Publishers, New York, 1989).

EXAMPLES

The following examples are put forth so as to provide those of ordinary skill in the art with a complete disclosure and description of how to make and use various constructs and perform the various methods of the present invention and are not intended to limit the scope of what the inventors regard as their invention. Unless indicated otherwise, parts are parts by weight, temperature is in degrees centigrade, and pressure is at or near atmospheric pressure. Efforts have been made to ensure accuracy with respect to numbers used (e.g., length of DNA sequences, molecular weights, amounts, particular components, etc.), but some deviations should be accounted for.

Example 1

Strains and Materials

The starting strains were pyrG-minus *Aspergillus oryzae* HowB425, pyrG-minus *Aspergillus oryzae* HowB101, *Aspergillus oryzae* JaL250, *Aspergillus niger* strain JRoy3 (pyrGΔ), *E. coli* DH5α (GIBCO-BRL, Gaithersburg, Md.), and *E. coli* HB101 (GIBCO-BRL, Gaithersburg, Md.).

PDA plates contained 39 g/l Potato Dextrose Agar (Difco) and were supplemented with 10 mM uridine for pyrG auxotrophs unless otherwise indicated.

MY25 medium at pH 6.5 was composed per liter of 25 g of maltose, 2.0 g of $MgSO_4$-$7H_2O$, 10 g of $KH_2PO_4$, 2.0 g of citric acid, 10 g of yeast extract, 2.0 g of $K_{2,0}$ g of $K_2SO_4$, 2.0 g of urea, and 0.5 ml of trace metals solution. MY25 shake-flask medium was diluted 1:100 or 1:1000 with glass distilled water for use in microtiter growth experiments (MY25/100 or MY25/1000). Cultures were grown at 34° C.

2×MY Salts pH 6.5 solution was composed per liter of 4 g of $MgSO_4$-$7H_2O$, 4 g of $K_2SO_4$, 20 g of $KH_2PO_4$, 4 g of citric acid, 1 ml of trace metals, and 2 ml of $CaCl_2$-$2H_2O$ (100 g/l stock solution.

Minimal medium transformation plates were composed per liter of 6 g of $NaNO_3$, 0.52 g of KCl, 1.52 g of $KH_2PO_4$, 1 ml of trace metals solution, 1 g of glucose, 500 mg of $MgSO_4$-$7H_2O$, 342.3 g of sucrose and 20 g of Noble agar per liter (pH 6.5). Minimal medium transfer plates (pH 6.5) were composed per liter of 6 g of $NaNO_3$, 0.52 g of KCl, 1.52 g of $KH_2PO_4$, 1 ml of trace elements, 1 g of glucose, 500 mg of $MgSO_4$-$7H_2O$, and 20 g Noble agar.

The trace metals solution (1000×) was composed per liter of 22 g of $ZnSO_4$-$7H_2O$, 11 g of $H_3BO_3$, 5 g of $MnCl_2$-$4H_2O$, 5 g of $FeSO_4$-$7H_2O$, 1.6 g of $CoCl_2$-$5H_2O$, 1.6 g of $(NH_4)_6Mo_7O_{24}$, and 50 g of $Na_4EDTA$.

COVE plates were composed per liter of 343.3 g of sucrose, 20 ml of COVE salts solution, 10 ml of 1 M acetamide, 10 ml of 3 M CsCl, and 25 g of Nobel agar. The COVE salts (50×) solution was comprised of 26 g of KCl, 26 g of $MgSO_4$-$7H_2O$, 76 g of $KH_2PO_4$, and 50 ml of COVE trace metals solution. COVE trace metals solution was composed of (per liter): 0.04 g of $NaB_4O_7$-$10H_2O$, 0.040 g of $CuSO_4$-$5H_2O$, 0.70 g of $FeSO_4$—$H_2O$, 0.80 g of $Na_2MoO_2$-$2H_2O$, and 10 g of $ZnSO_4$.

YEG medium was composed per liter of 5 g yeast extract and 20 g dextrose.

CM-1 agar plates at pH 6.5 were composed per liter of 0.25 g of NaCl, 0.5 g of $MgSO_4$-$7H_2O$, 1.9 g of $K_2HPO_4$, 3.6 g of $KH_2PO_4$, 0.1 ml of trace metals solution, 30 g of Bacto agar (Difco), pH 6.5.11 ml of 10% urea, and 67 ml of 30% maltose.

CD medium was composed per liter of 1 g of $MgSO_4$-$7H_2O$, 1 g of $K_2SO_4$, 15 g of $KH_2PO_4$, 0.25 ml of trace metals solution, 0.7 g of yeast extract (Difco), 20 g of beta-cyclodextrin (Sigma C-4767). 3 ml of 50% urea, and 2 ml of 15% $CaCl_2$-$2H_2O$.

G1-gly medium was composed per liter of 18 g of yeast extract (Difco), 80 g of 75% glycerol, and 0.5 g of $CaCl_2$-$2H_2O$.

OL-1 medium (pH 7.0) was composed per liter of 15 g of $KH_2PO_4$, 1 g of $MgSO_4$-$7H_2O$. 1 g of $K_2SO_4$, 0.25 ml of trace metals solution, 0.3 g of $CaCl_2$-$2H_2O$ (autoclaved separately), 2 g of Difco yeast extract (Difco), 0.5 g of urea (autoclaved separately), and 10 g of glucose.

OL-6 medium (pH 7.0) was composed per liter of 15 g of $KH_2PO_4$, 1 g of $MgSO_4$-$7H_2O$, 1 g of $K_2SO_4$, 0.25 ml of trace metals solution, 0.3 g of $CaCl_2$-$2H_2O$ (autoclaved separately), 2 g of Difco yeast extract (Difco), 3 g of urea (autoclaved separately), and 60 g of glucose.

YPM medium was composed of 10 g of Bactopeptone and 5 g of yeast extract dissolved in 500 ml of water and autoclaved, to which 50 ml of a sterilized 20% maltose solution was added.

MTBCDUY was composed per liter of 0.3 g of $MgSO_4$-$7H_2O$, 0.3 g of $K_2SO_4$, 5 g of $KH_2PO_4$, 0.013 g of urea, 0.01 g of yeast extract, 0.1 g of maltose, 4.88 g of uridine, and 0.25 ml of trace metal solution 1 adjusted to pH 6.5.

4×MTBCDUY was composed per liter of 0.3 g of $MgSO_4$-$7H_2O$, 0.3 g of $K_2SO_4$, 5 g of $KH_2PO_4$, 0.052 g of urea, 0.04 g of yeast extract, 0.4 g of maltose, 4.88 g of uridine, and 0.25 ml of trace metal solution 1.

MDU1B was composed per liter of 45 g of Maltodextrin MD01, 1.0 g of $MgSO_4$-$7H_2O$, 1.0 g of NaCl, 2.0 g of $K_2SO_4$, 12.0 g of $KH_2PO_4$, 7.0 g of yeast extract, 0.5 ml of trace metal solution, and 0.1 ml of pluronic acid. The trace metal solution consisted of 13.9 g of $FeSO_4$-$7H_2O$, 8.45 g of $MnSO_4$—$H_2O$, 6.8 g of $ZnCl_2$, 2.5 g of $CuSO_4$-$5H_2O$, 2.5 g of $NiCl_2$-$6H_2O$, and 3 g of citric acid. The pH of the shake flask medium was adjusted to 5.0 before being autoclaved.

1/5MDU2BP was composed per liter of 9 g of maltose, 0.2 g of $MgSO_4$-$7H_2O$, 0.4 g of $K_2SO_4$, 0.2 g of NaCl, 2.4 g of $KH_2PO_4$, 1.0 g of urea, 1.4 g of yeast extract, and 0.1 ml of trace metal solution 1.

Trace metal solution 1 was composed per liter of 13.8 g of $FeSO_4$-$7H_2O$, 8.5 g of $MnSO_4$—$H_2O$, 14.3 g of $ZnSO_4$-$7H_2O$, 2.5 g of $CuSO_4$-$5H_2O$, 0.5 g of $NiCl_2$-$6H_2O$, and 3.0 g of citric acid.

YPG plates was composed per liter of 4.0 g yeast extract, 1.0 g of $K_2HPO_4$, 0.5 g of $MgSO_4$-$7H_2O$, 15.0 g of dextrose, and 20.0 g of agar.

Example 2

Construction of *Aspergillus oryzae* HowB430

*Aspergillus oryzae* HowB430 was constructed to contain a lipase gene from *Humicola lanuginosa* (LIPOLASE™ gene, Novo Nordisk A/S, Bagsværd, Denmark).

pBANe8 was constructed as described below to contain the TAKA/NA2-tpi leader hybrid promoter, the lipase gene from *Humnicola lanuginosa*, the AMG terminator, and the full-length *Aspergillus nidulans* amdS gene as a selectable marker.

PCR was employed to insert NsiI sites flanking the full-length amdS gene of pToC90 (Christensen et al., 1988, *Biotechnology* 6: 1419–1422) using primers 1 and 2 below and to insert an EcoRI site at the 5' end and a SwaI site at the 3' end of the NA2-tpi leader hybrid promoter of pJaL292 (FIG. 1) using primers 3 and 4 below. The primers were synthesized with an Applied Biosystems Model 394 DNA/RNA Synthesizer (Applied Biosystems, Inc., Foster City, Calif.) according to the manufacturer's instructions.

Primer 1: 5'-ATGCATCTGGAAACGCAACCCTGA-3' (SEQ ID NO:1)

Primer 2: 5'-ATGCATTCTACGCCAGGACCGAGC-3' (SEQ ID NO:2)

Primer 3: 5'-TGGTGTACAGGGGCATAAAAT-3' (SEQ ID NO:3)

Primer 4: 5'-ATTTAAATCCAGTTGTGTATATAGA GGATTGTGG-3' (SEQ ID NO:4)

Amplification reactions (100 µl) were prepared using approximately 0.2 µg of either pToC90 or pJaL292 as the template. Each reaction contained the following components: 0.2 µg of plasmid DNA, 48.4 pmol of the forward primer, 48.4 pmol of the reverse primer, 1 mM each of dATP, dCTP, dGTP, and dTTP, 1×Taq polymerase buffer, and 2.5 U of Taq polymerase (Perkin-Elmer Corp., Branchburg, N.J.). The reactions were incubated in an Ericomp Thermal Cycler programmed as follows: One cycle at 95° C. for 5 minutes followed by 30 cycles each at 95° C. for 1 minute, 55° C. for 1 minute and 72° C. for 2 minutes The PCR products were electrophoresed on a 1% agarose gel to confirm the presence of a 2.7 kb amdS fragment and a 0.6 kb NA2-tpi fragment.

Figure 2:
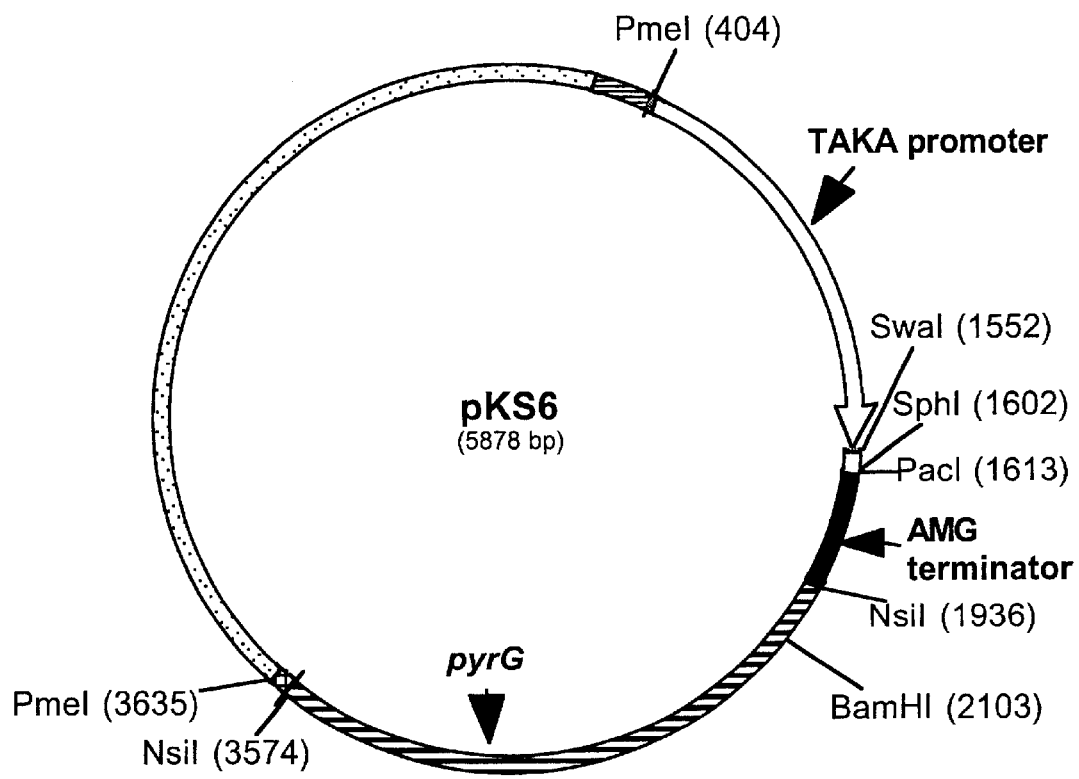
FIG. 2 is a restriction map of pKS6.
Figure 3:
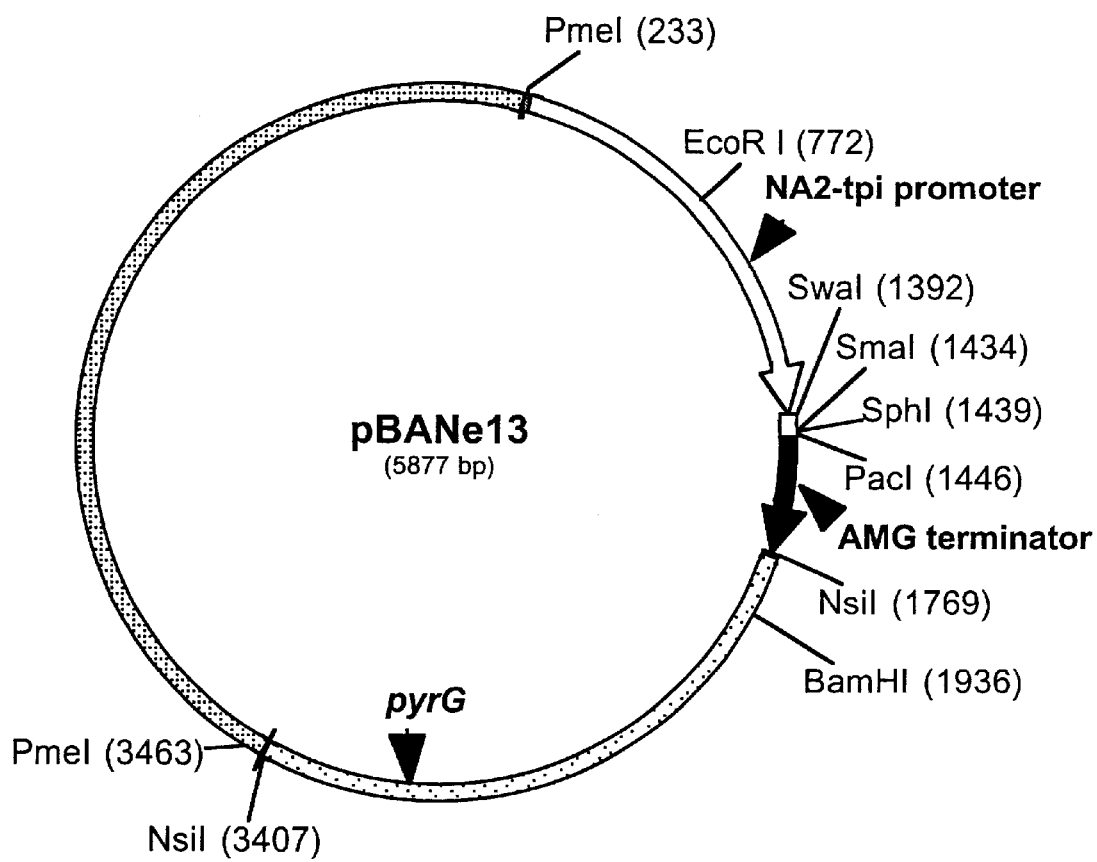
FIG. 3 is a restriction map of pBANe13.
Figure 4:
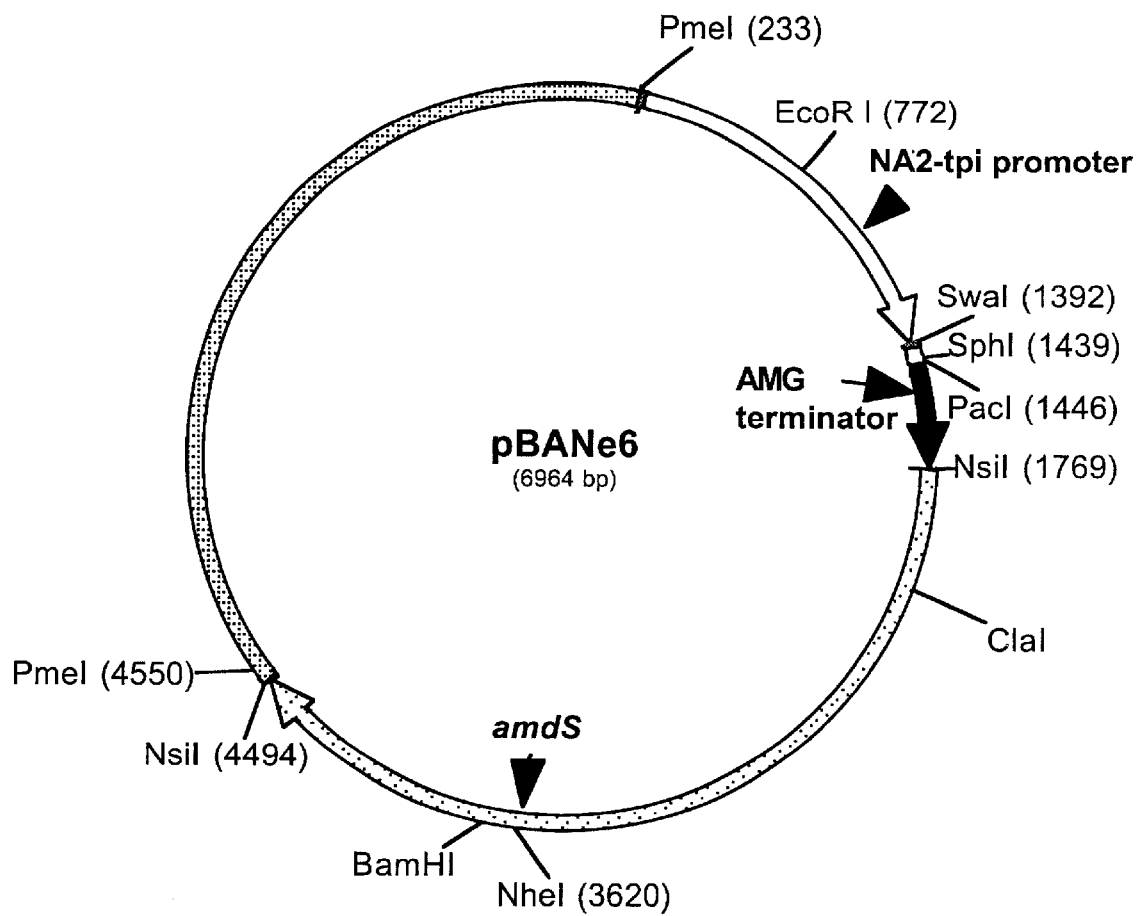
FIG. 4 is a restriction map of pBANe6.

The PCR products were subsequently subcloned into pCRII using a TA Cloning Kit (Invitrogen. San Diego, Calif.) according to the manufacturer's instructions. The transformants were then screened by extracting plasmid DNA from the transformants using a QIAwell-8 Plasmid Kit (Qiagen, Inc., Chatsworth, Calif.) according to the manufacturer's instructions, and restriction digesting the plasmid DNA with either NsiI or EcoRI/SwaI followed by agarose electrophoresis to confirm the presence of the correct size fragments, 2.7 kb and 0.6 kb, respectively, for the NsiI amdS fragment and SwaI/EcoRI NA2-tpi fragment. In order to confirm the PCR products, the products were sequenced with with an Applied Biosystems Model 373A Automated DNA Sequencer (Applied Biosystems, Inc., Foster City, Calif.) on both strands using the primer walking technique with dye-terminator chemistry (Giesecke et al., 1992, *Journal of Virol. Methods* 38: 47–60) using the M13 reverse (-48) and M13 forward (-20) primers (New England Biolabs, Beverly, Mass.) and primers unique to the DNA being sequenced. The plasmids from the correct transformants were then digested with the restriction enzymes for which the plasmids were designed, separated on a 1% agarose gel, and purified using a FMC SpinBind Kit (FMC, Rockland, Me.) according to the manufacturer's instructions.

pKS6 (FIG. 2), which contains the TAKA promoter, a polylinker, the AMG terminator, and the *Aspergillus nidulans* pyrG gene, was digested with EcoRI and SwaI to remove a portion of the TAKA promoter. This region was replaced with the NA2-tpi PCR product to produce pBANe13 (FIG. 3).

pBANe13 was digested with NsiI to remove the *Aspergillus nidulans* pyrG gene. This region was then replaced with the full length amdS gene PCR product described above to produce pBANe6 (FIG. 4).

Figure 5:
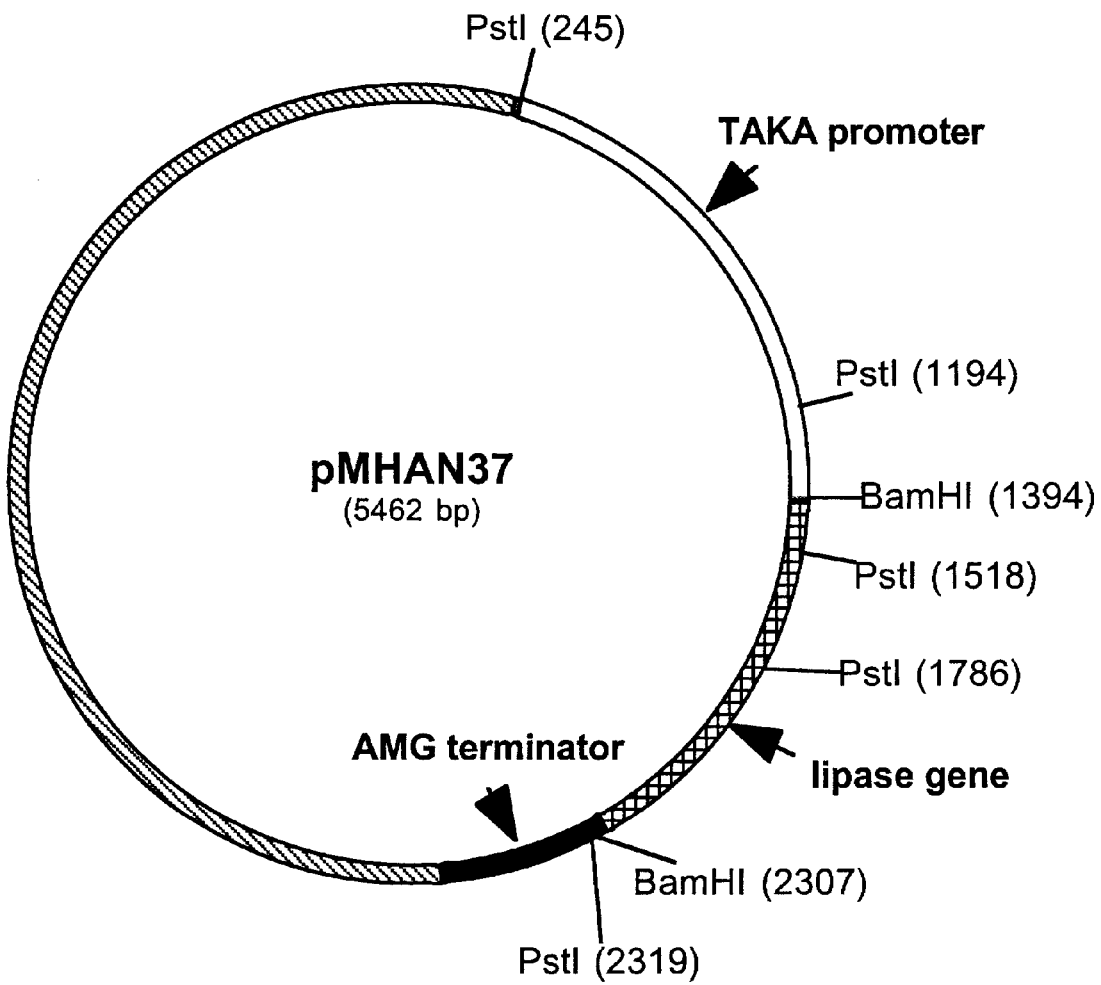
FIG. 5 is a restriction map of pMHan37.

PCR was used to insert SwaI and PacI flanking sites on the full-length *Humicola lanuginosa* lipase gene of pMHan37 (FIG. 5) using primers 5 and 6 below. Primers 5 and 6 were synthesized as described above.

Primer 5:
5'-ATTTAAATGATGAGGAGCTCCCTTGTGCTG-3' (SEQ ID NO:5)

Primer 6:
5'-TTAATTAACTAGAGTCGACCCAGCCGCGC-3' (SEQ ID NO:6)

The amplification reaction (100 µl) contained the following components: 0.2 µg of pMHan37, 48.4 pmol of primer 5, 48.4 pmol of primer 6, 1 mM each of dATP, dCTP, dGTP, and dTTP, 1×Taq polymerase buffer, and 2.5 U of Taq polymerase. The reaction was incubated in an Ericomp Thermal Cycler programmed as follows: One cycle at 95° C. for 5 minutes followed by 30 cycles each at 95° C. for 1 minute, 55° C. for 1 minute, and 72° C. for 2 minutes. Two µl of the reaction was electrophoresed on an agarose gel to confirm the amplification of the lipase gene product of approximately 900 bp.

The PCR amplified lipase gene product was then subcloned into pCRII using a TA Cloning Kit. The transformants were screened by extracting plasmid DNA from the transformants using a QIAwell-8 Plasmid Kit, restriction digesting the plasmid DNA with SwaI/PacI, and sequencing the DNA according to the method described above to confirm the PCR product.

Figure 6:
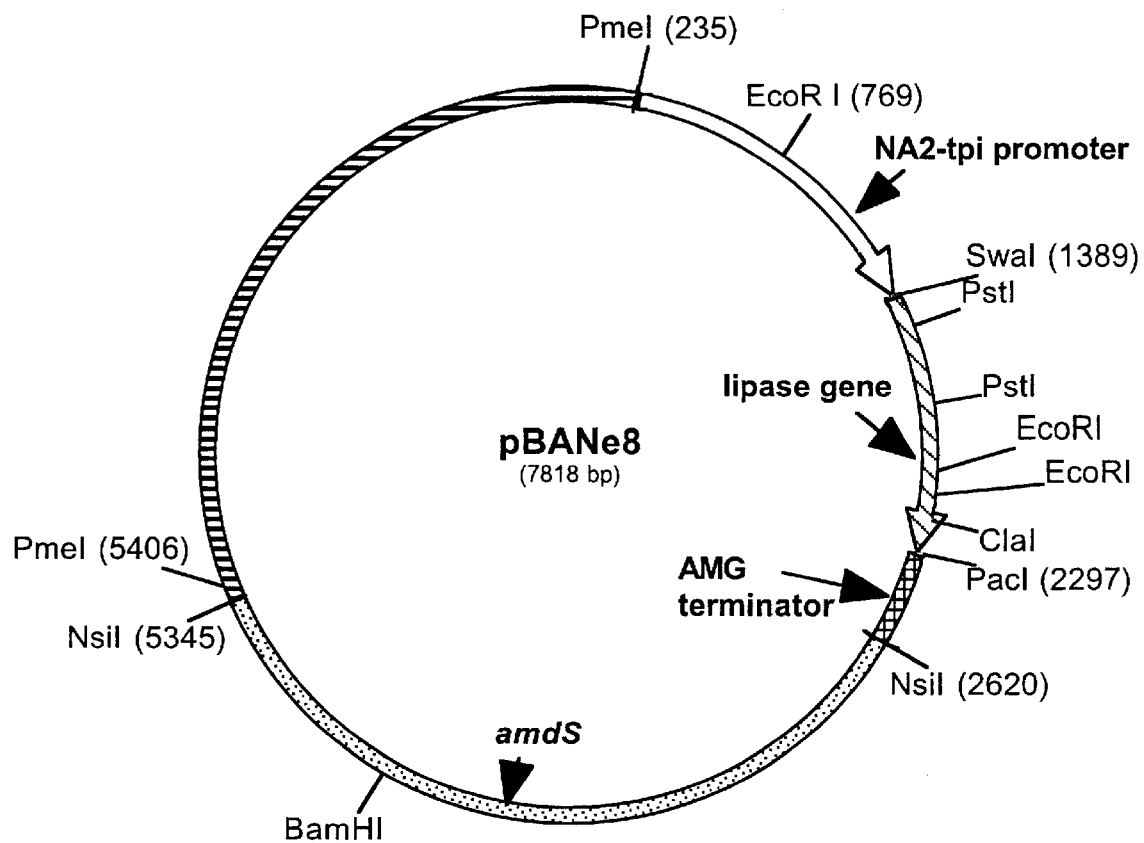
FIG. 6 is a restriction map of pBANe8.

The lipase gene was excised from the pCRII plasmid by digesting with SwaI and PacI and subsequently subcloned into SwauIPacI digested pBANe6 to produce pBANe8 (FIG. 6).

pBANe8 was digested with PmeI and the linear PmeI fragment containing the NA2-tpi promoter, the lipase gene from *Humicola lanuginosa*, and the AMG terminator was isolated by preparative agarose electrophoresis using 40 mM Tris-acetate-1 mM disodium EDTA (TAE) buffer.

*Aspergillus oryzae* HowB430 was generated by transformation of *Aspergillus oryzae* HowB425 with the linear PmeI fragment according to the following procedure.

*Aspergillus oryzae* HowB425 was grown in 100 ml of 1% yeast extract-2% peptone-1% glucose at 32° C. for 16–18 hours with agitation at 150 rpm. The mycelia were recovered by filtration through a 0.45 µm filter until approximately 10 ml remained on the filter, washed with 25 ml of 1.0–1.2 M $MgSO_4$-10 mM sodium phosphate pH 6.5, filtered as before, washed again as before until 10 ml remained, and then resuspended in 10 ml of 5 mg/ml NOVOZYM 234™ (Novo Nordisk A/S, Bagsvzrd, Denmark) in 1.2 M $MgSO_4$-10 mM sodium phosphate pH 6.5 (0.45 µm filtered) in a 125 ml Ehrlenmeyer flask. The suspension was incubated with gentle agitation at 50 rpm for approximately one hour at 37° C. to generate protoplasts. A volume of 10 ml of the protoplast/mycelia preparation was added to a 30 ml Corex centrifuge tube, overlaid with 5 ml of 0.6 M sorbitol-10 mM Tris-HCl pH 7.5, and centrifuged at 3600×g for 15 minutes in a swinging bucket rotor to recover the protoplasts. The protoplasts were recovered from the buffer interface with a Pasteur pipet. The protoplasts were then washed with five volumes of STC, centrifuged, and then rewashed and centrifuged as before. The protoplasts were resuspended in STC to a final concentration of $2\times10^7$ protoplasts per ml.

Transformation of *Aspergillus oryzae* HowB425 for amdS selection was conducted with protoplasts at a concentration of $2\times10^7$ protoplasts per ml. Ten µg of DNA were added to 100 µl of protoplasts. A volume of 250 µl of PEG solution (60% PEG 4000–10 mM $CaCl_2$-10 mM Tris-HCl pH 8.0) was then added and the mixture was placed at 37° C. for 30 minutes. Three ml of 1 M sorbitol-10 mM $CaCl_2$-10 mM Tris pH 7.5 (STC) was added and the mixture was plated on Cove plates supplemented with 10 mM uridine selecting for amdS. The plates were incubated 7–10 days at 34° C. Transformants were transferred to plates of the same medium and incubated 3–5 days at 37° C. The transformants were purified by streaking spores and picking isolated colonies using the same plates of the same medium without sucrose under the same conditions.

Example 3

Construction of *Aspergillus oryzae* HowB427

Figure 7:
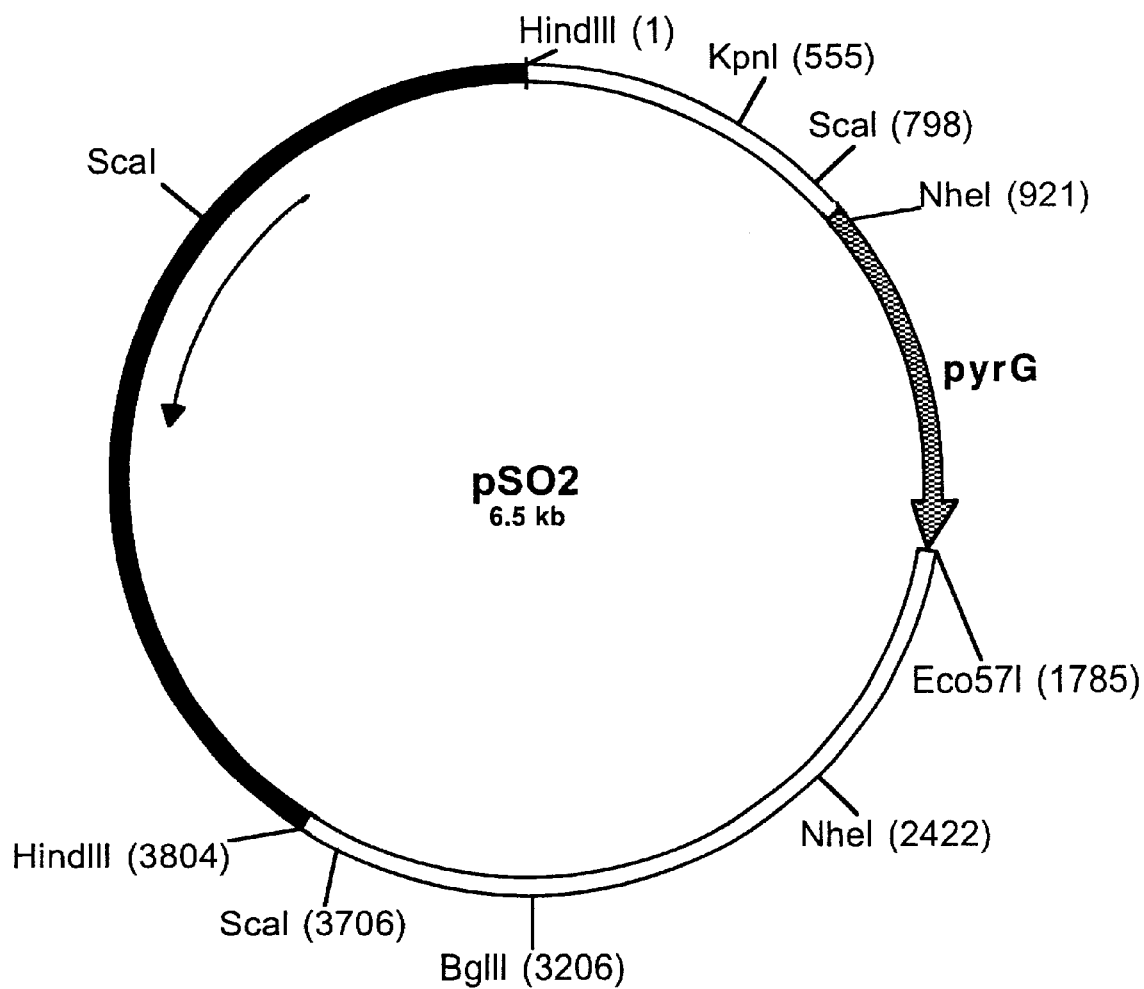
FIG. 7 is a restriction map of pSO2.

*Aspergillus oryzae* HowB425 was co-transformed with pMHan37 and pSO2 (FIG. 7) to construct *Aspergillus oryzae* HowB427 to contain the lipase gene from *Humicola lanuginosa* behind the TAKA promoter.

pSO2 (FIG. 7) was constructed from a genomic library of *Aspergillus oryzae* 1560. The genomic library of *Aspergillus oryzae* 1560 was constructed by first partially digesting *Aspergillus oryzae* 1560 genomic DNA with Sau3A (New England Biolabs, Beverly, Mass.). Four units of Sau3A were used to digest 10 µg of *Aspergillus oryzae* 1560 genomic DNA using conditions recommended by the manufacturer. The reaction was carried out at 65° C., and samples were taken at 5 minute intervals (from 0 to 50 minutes). The reactions were placed on ice and stopped by the addition of EDTA to 10 mM. These digests were then run on a 1% agarose gel with ethidium bromide, and the region of the gel containing DNA from 3kb to 9 kb was excised. The DNA was then purified from the gel slice using Beta-Agarase I using a protocol provided by the manufacturer (New England Biolabs, Beverly, Mass.). The size-selected DNA was then ligated into EMBL 4 arms according to the manufacturer's instructions (Clontech, Palo Alto, Calif.) at 16° C. overnight using conditions recommended by the manufacturer. The ligation reaction was packaged and titered using a Gigapack II Packaging Kit (Stratagene, La Jolla, Calif.) according to the manufacturer's protocol. A total of 16,000 recombinant plaques were obtained, and the library was amplified using a protocol provided by the manufacturer.

Appropriate dilutions of the genomic library were made to obtain 7000 plaques per 150 mm petri plate as described in the protocols provided with the EMBL 4 arms. The plaques were lifted to Hybond-N plus circular filters (Amersham, Cleveland, Ohio) using standard protocols (Sambrook et al., 1989, supra). The filters were fixed using UV crosslinking, and prehybridized at 42° C. (5×SSPE, 35% formamide). The genomic library was probed at low stringency (35% formamide, 5×SSPE at 42° C.) with a 500 bp fragment consisting of the *Aspergillus niger* pyrG gene which was labeled with $^{32}p$ using a random prime DNA labeling kit (Boehringer Mannheim, Indianapolis, Ind.). A 3.8 kb HindIII fragment was isolated from one phage and subcloned into a pUC118 cloning vector to produce pSO2.

The co-transformation of *Aspergillus oryzae* HowB425 was conducted using the procedure described in Example 2 except selection was on Minimal medium transformation plates. Transformants were transferred to Minimal medium transfer plates and incubated 3–5 days at 37° C. The transformants were then purified by streaking spores and picking isolated colonies using the same transfer plates under the same conditions.

Example 4

Construction of Plasmids pSO122, pDSY81, and pDSY82 pSO122 was constructed as described below to contain a 1.5 kb fragment of the *Aspergillus oryzae* pyrG gene.

PCR was used to generate pSO122 by introducing a BamHI restriction site at the 5' end of the pyrG gene of pSO2 using primers 7 and 8 shown below. Primers 7 and 8 were synthesized with an Applied Biosystems Model 394 DNA/RNA Synthesizer according to the manufacturer's instructions.

Primer 7:
5'-GCGGGATCCCTAGAGTAGGGGGTGGTGG-3'
(SEQ ID NO:7)
Primer 8:
5'-GCGGGATCCCCCCTAAGGATAGGCCCTA-3'
(SEQ ID NO:8)

The amplification reaction (50 µl) contained the following components: 2 ng of pSO2, 48.4 pmoles of the forward primer, 48.4 pmoles of the reverse primer, 1 mM each of dATP, dCTP, dGTP, and dTTP, 1×Taq polymerase buffer, and 2.5 U of Taq polymerase (Perkin-Elmer Corp., Branchburg, N.J.). The reaction was incubated in an Ericomp Thermal Cycler programmed as follows: One cycle at 95° C. for 5 minutes followed 30 cycles each at 95° C. for 1 minute, 55° C. for 1 minute and 72° C. for 2 minutes PCR product was isolated by electrophoresis on a 1% agarose gel.

Figure 8:
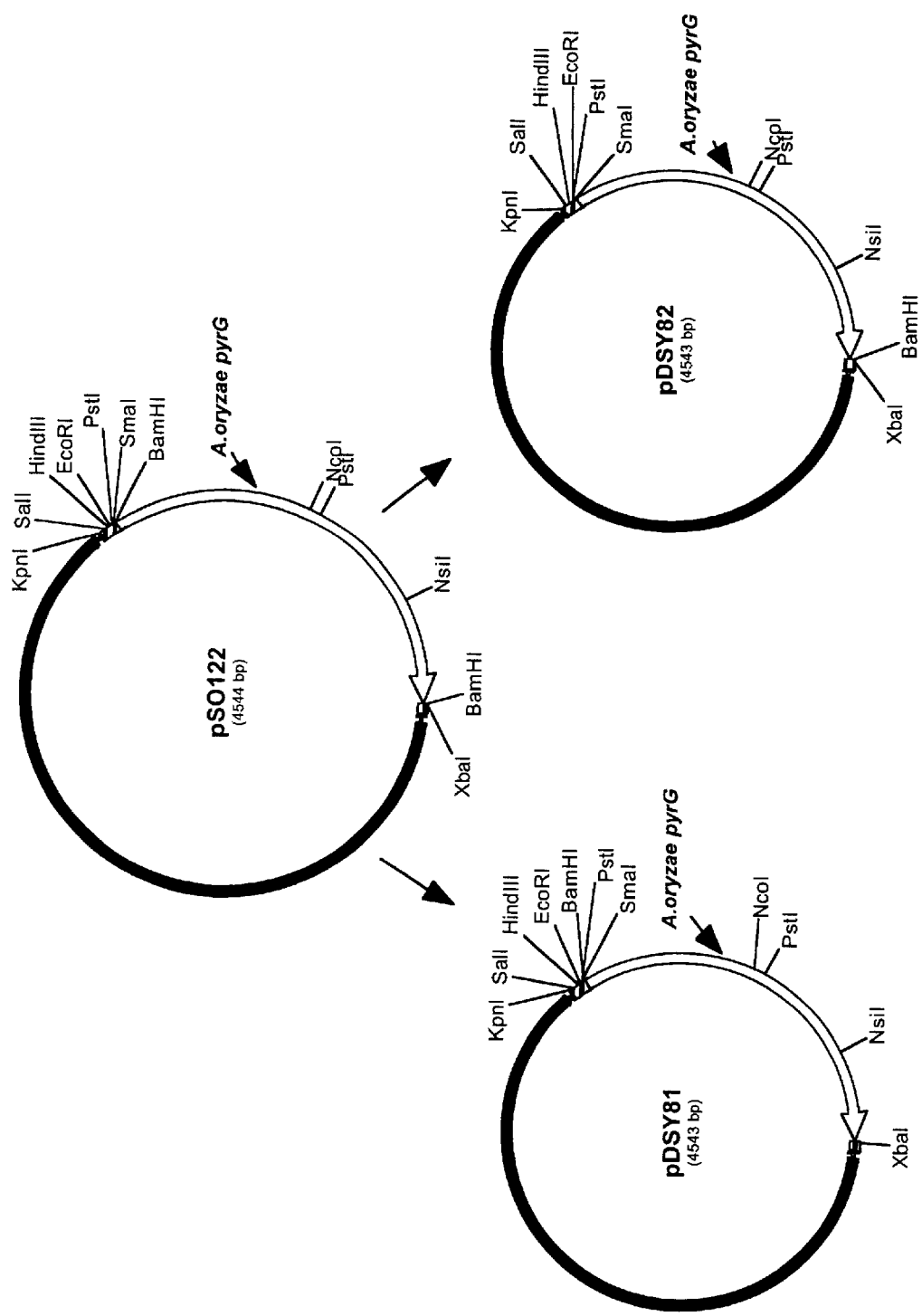
FIG. 8 is a restriction map of pSO122 and shows the construction of pDSY81 and pDSY82 from pSO122.

The isolated PCR product was digested with BamHI and cloned into the BamHI site of pBluescript SK- (Stratagene, La Jolla, Calif.) to yield pSO122 (FIG. 8). The only homology between the genome of *Aspergillus oryzae* HowB430 and pSO122 was in the 5' end of the pyrG insert since the rest of the pyrG fragment was deleted from *Aspergillus oryzae* HowB430 as described in Example 2.

In order to reduce the frequency of targeting to this homologous region in the genome and since pSO122 contains two BamHI sites, two derivatives of pSO122, pDSY81 and pDSY82 (FIG. 8), were constructed in which one of the BamHI sites was destroyed. The plasmids pDSY81 and pDSY82 were constructed by partially digesting pSO122 with BamHI, filling-in the 5' overhangs with the Klenow fragment, closing down the plasmid by ligation and subsequent transformation into *E. coli* DH5α (Sambrook et al., 1989, supra). The transformants were then screened by extracting plasmid DNA from the transformants using a QIAwell-8 Plasmid Kit and restriction digesting the plasmid DNA with BamHI to determine if one of the BamHI sites had been destroyed. Plasmids with one of the BamHI sites destroyed were digested with NsiI/BamHI to determine which BamHI site had been destroyed.

Example 5

*Aspergillus oryzae* HowB430 Transformation with pSO122, pDSYS1, or pDSY82

Protoplasts of *Aspergillus oryzae* HowB430 were prepared as described in Example 2. A 5–15 µl aliquot of DNA (circular pSO122, pDSY81 linearized with 4 to 12 U of EcoRI, or pDSY82 linearized with 15 U of BamHI) was added to 0.1 ml of the protoplasts at a concentration of $2 \times 10^7$ protoplasts per ml in a 14 ml Falcon polypropylene tube followed by 250 µl of 60% PEG 4000–10 mM $CaCl_2$-10 mM Tris-HCl pH 7, gently mixed, and incubated at 37° C. for 30 minutes. The transformations were made either with 5 µg of circular pSO122, 6 µg of linearized pDSY81, or 6 µg of linearized pDSY82. Three ml of SPTC (1.2 M sorbitol-10 mM $CaCl_2$-10 mM Tris pH 8) were then added and the suspension was gently mixed. The suspension was mixed with 12 ml of molten overlay agar (1×COVE salts, 1% NZ amine, 0.8 M sucrose, 0.6% Noble agar) or 3 ml of STC medium and the suspension was poured onto a Minimal medium plate. The plates were incubated at 37° C. for 3–5 days.

The transformation frequencies of the circular pSO122 transformations ranged from about 100 to 200 transformants/µg. A library of ~120,000 DNA-tagged transformants of *Aspergillus oryzae* HowB430 was obtained.

The transformation frequencies of the EcoRI REMI pDSY81 transformations ranged from about 60 to 100 per µg. An EcoRI REMI library of ~28,000 DNA-tagged transformants of *Aspergillus oryzae* HowB430 was generated.

The transformation frequencies of the BamHI REMI pDSY82 transformations ranged from about 80 to 110 transformants/µg. A BamHI REMI library of ~27,000 DNA-tagged transformants of *Aspergillus oryzae* HowB430 was obtained.

HindJII and SalI REMI libraries of *Aspergillus oryzae* HowB430 were also prepared using pDSY81 as described above.

The transformation frequencies of the HindIII REMI pDSY81 transformations ranged from about 80 to 120 per µg. A HindIII REMI library of 35,000 DNA-tagged transformants of *Aspergillus oryzae* HowB430 was generated.

The transformation frequencies of the SalI REMI pDSY81 transformations ranged from about 80 to 120 per µg. A SalI REMI library of 25,000 DNA-tagged transformants of *Aspergillus oryzae* HowB430 was generated.

The *Aspergillus oryzae* HowB430 tagged mutant library pools were designated "h" for pSO122; "e" for pDSY81 digested with EcoRI with subsequent transformation in the presence of EcoRI; "b" for pDSY82 digested with BamHI with subsequent transformation in the presence of BamHI; "hIII" for pDSY81 digested with HindIII with subsequent transformation in the presence of HindIII; and "s" for pDSY81 digested with SalI with subsequent transformation in the presence of SalI. There were 123 "h" pools, 28 "e" pools, 23 "b" pools, 55 "hIII" pools, and 25 "s" pools.

The libraries described above were pooled into groups of ~1000 transformants and stored in 10% glycerol at −80° C.

Example 6

Characterization of Integration Events in "REMI" *Aspergillus oryzae* HowB430 Transformants Genomic DNA was isolated from 26 of the EcoRl REMI transformants ("e" pool) described in Example 5 according to the following procedure. Each transformant was grown in 5 ml of YEG medium for 24 hours at 37° C. in a small Petri plate. Mycelia were then collected from each culture by filtration through Whatman filter paper No. 1 (Whatman, Springfield Mill, England) and transferred to a 1.7 ml centrifuge tube. The mycelia preparations were frozen in dry ice and dried in a SpeedVac (Savant Instruments, Inc., Farmingdale, N.Y.) overnight at room temperature. The frozen mycelia preparations were ground to a fine powder with a speared spatula and then the ground mycelia were resuspended in 0.5 ml of lysis buffer (100 mM EDTA, 10 mM Tris pH 8.0, 1 % Triton X-100, 50 mM guanidine-HCl, 200 mM NaCl). RNase was added to each preparation to a final concentration of 20 μg/ml, and the preparations were incubated at 37° C. for 30 minutes. Protease K was then added to each preparation to a final concentration of 0.1 mg/ml, and the preparations were incubated at 50° C. for 1 hour. The preparations were centrifuged at 13,000×g for 15 ninutes, and the supernatants were applied to QIAprep-8-well strips (Qiagen, Chatsworth, Calif.). The wells were washed once with 0.5 ml of PB and 0.75 ml of PE supplied by the manufacturer (Qiagen, Chatsworth, Calif.). After removing excess PE from each well, the DNAs were eluted from the wells in 200 μl of TE buffer (10 mM Tris-1 mM EDTA pH 7.0).

The genomic DNA was digested with either EcoRI to determine whether integration occurred into genomic EcoRI sites or SnaBI to determine whether or not the integration events were random throughout the genome by Southern hybridization according to the procedure described by Sambrook et al., 1989, supra. Southern blots of the digests were probed with a 1.6 kb NheI pyrG fragment obtained from pSO122 (FIG. 8) labeled with dioxygenin using a Genius Kit according to the manufacturer's instructions. The blot was prehybridized for 2 hours and hybridized overnight at 42° C. in DIG Easy Hyb. The blot was washed and processed as recommended by the manufacturer.

The Southern blot demonstrated that in 13 of 26 transformants, EcoRI linearized pDSY81 integrated into an EcoRI site in the genome, and the distribution of the integration events appeared to be random. In 20 of the 26 transformants, only a single copy of the plasmid was integrated while in 6 of the transformants at least 2 copies were integrated at the same locus. In order to determine if the bias (of 50%) towards integration at EcoRI sites was due to REMI, genomic DNA was isolated as described above from 16 Asperg illus oryzae HowB425 transformants, in which the EcoRl enzyme was heat inactivated before transformation with EcoRI linearized pDSY81 according to the procedure described in Example 5, and submitted to Southern blot analysis as described above. Southern analysis of these transformants demonstrated that in none of the transformants did the plasmid integrate at an EcoRI site in the genome.

Example 7

Lipase Expression Screening

The *Aspergillus oryzae* HowB430 tagged mutant library "h", "e", and "b" pools described in Example 5 were assayed for lipase expression.

For 96-well plate screens, MY25 medium was diluted 1000-fold using a diluent made of equal volumes of sterile water and 2×MY Salts pH 6.5 solution. For 24-well plate methods, MY25 medium was diluted 100-fold using a diluent made of equal volumes of sterile water and 2×MY Salts pH 6.5 solution.

Primary 96-well plate screens involved the dilution of spores from distinct pools into MY25/1000 so that one spore on average was inoculated per well when 50 μl of medium was dispensed into the wells. After inoculation, the 96-well plates were grown for 7 days at 34° C. under static conditions. Cultures were then assayed for lipase activity as described below. Mutants of interest were inoculated directly into 24-well plates containing MY25/100 and were grown for 7 days at 34° C. Cultures were then assayed for lipase activity as described below. Mutants of interest were then plated on COVE plates to produce spores, spread on PDA plates to produce single colonies, and then 4 single colonies from each isolate were tested in the 24-well plate method described above.

The lipase assay substrate was prepared by diluting 1:50 a p-nitrophenylbutyrate stock substrate (21 μl of p-nitrophenylbutyrate/ml DMSO) into MC buffer (4 mM $CaCl_2$-100 mM MOPS pH 7.5) immediately before use. Standard lipase (LIPOLASE™, Novo Nordisk A/S, Bagsværd, Denmark) was prepared to contain 40 LU/ml of MC buffer containing 0.02% alpha olefin sulfonate (AOS) detergent. The standard was stored at 4° C until use. Standard lipase was diluted 1/40 in MC buffer just before use. Broth samples were diluted in MC buffer containing 0.02% AOS detergent and 20 μl aliquots were dispensed to wells in 96-well plates followed by 200 μl of diluted substrate. Using a plate reader, the absorbance at 405 nm was recorded as the difference of two readings taken at approximately 1 minute intervals. Lipase units/ml (LU/ml) were calculated relative to the lipase standard.

The results of the 96-well screen followed by the 24-well screen identified for further evaluation 53 transformants from the pSO122 transformations and 44 transformants from the pDSY81 or pDSY82 REMI transformations. These identified transformants produced higher levels of lipase than the control strains *Aspergillus oryzae* HowB427 and *Aspergillus oryzae* HowB430.

Example 8

Shake Flask and Fermentation Evaluation

The highest lipase-producing DNA-tagged mutants described in Example 7 were then plated onto COVE plates to produce spores for shake flask and fermentation evaluations.

Shake flask evaluations were performed by inoculating 300–500 μl of a spore suspension (0.02% Tween-80 plus spores from the COVE plates) into 25 ml of MY25 medium at pH 6.5 in a 125 ml shake flask. The shake flasks were incubated at 34° C. for 3 days at 200 rpm. Samples were taken at day 2 and day 3 and lipase activity was measured as described in Example 7.

The same DNA-tagged mutants were grown in a 2 liter lab fermentor containing medium composed of Nutriose, yeast extract, $(NH_4)_2HPO_4$, $MgSO_4$-$7H_2O$, citric acid, $K_2SO_4$, $CaCl_2$—$H_2O$, and trace metals solution at 34° C. pH 7, 1000–1200 rpm for 8 days. Lipase activity was measured as described in Example 7.

The results obtained are shown in Table 1 below where the lipase yield of either *Aspergillus oryzae* HowB427 or *Aspergillus oryzae* HowB430 as a control is normalized to 1.0.

fine powder with a mortar and pestle. The powdered mycelia preparations were each transferred to a 50 ml tube and 20 ml of lysis buffer was added. RNAse was added to each preparation to a final concentration of 20 µg/ml, and the preparations was incubated at 37° C. for 30 minutes. Protease K was then added to each preparation to a final concentration of 0.1 mg/ml, and the preparations were incubated at 50° C. for 1 hour. The preparations were then centrifuged at 15,000×g for 20 minutes to pellet the insoluble material. Each supernatant was applied to a Qiagen MAXI column (Qiagen, Chatsworth, Calif.) which was equilibrated with QBT provided by the manufacturer. The columns were then washed with 30 ml of QC provided by the manufacturer. DNA was eluted from each column with 15 ml of QF provided by the manufacturer and then recovered by precipitation with a 0.7 volume of isopropanol

TABLE I

Lipase Expression by DNA Tagged Mutants

| Strain Description | Construction | Pool | # Screened in 96-well Plates | 24-well Plate Results (LU/ml) | Shake Flask Results (LU/ml) | Ferm. Results (LU/ml) |
|---|---|---|---|---|---|---|
| HowB427 | HowB425 + pMHan37 | NA | NA | 1.2 | 0.6 | 1.0 |
| HowB430 | HowB425 + pBANe8 | NA | NA | 1.0 | 1.0 | NA |
| DEBY10.3 | pDSY81 + BamHI | b1 | 808 | 1.7 | 2.2 | 3.9 |
| DEBY203.3 | pDSY81 + EcoRI | e1 | 707 | 2.4 | 2.1 | 1.8 |
| DEBY599.3 | pDSY81 + BamHI | b18 | 443 | 1.5 | 2.4 | 4.1 |
| DEBY932 | pDSY81 + EcoRI | e21 | 1092 | 1.9 | 1.9 | 3.6 |
| DEBY1058 | pDSY81 + BamHI | b22 | 80 | 2.3 | 2.4 | 3.8 |
| DEBY1204.3.3 | pDSY81 + EcoRI | e26 | 1260 | 1.9 | 2.0 | 3.0 |
| HINL603 | pDSY81 + HindIII | hi3-7 | NA | 2.8 | 2.0 | 3.3 |
| HowL91.1 | pSO122 | h32 | 1134 | 1.9 | 2.3 | 3.3 |
| HowL214.2 | pSO122 | h9 | 861 | 1.9 | 2.3 | 3.0 |
| HowL301.4 | pSO122 | h58 | 731 | 2.3 | 2.8 | 3.6 |
| HowL371.3 | pSO122 | h92 | 592 | 1.8 | 2.5 | 3.5 |
| HowL442.1 | pSO122 | h7 | 1095 | 2.3 | 2.6 | 4.5 |
| HowL465.2 | pSO122 | h8 | 1003 | 2.3 | 2.2 | 3.2 |
| HowL500.1 | pSO122 | h99 | 885 | 2.3 | 2.7 | 3.4 |
| HowL554.1 | pSO122 | h120 | 892 | 1.9 | 2.3 | 3.6 |
| HowL795.4 | pSO122 | h29 | 1029 | 3.0 | 3.8 | 4.9 |

As shown in Table I, the mutants produced approximately 2- to 4-fold more lipase than the control strain *Aspergillus oryzae* HowB427 and approximately 3- to 6-fold more lipase than the control strain *Aspergillus oryzae* HowB430 when grown in shake flasks. The mutants also produced approximately 2- to 5-fold more lipase than the control strain *Aspergillus oryzae* HowB427 when grown in fermentors.

Example 9

Rescue of Plasmid DNA and Flanking DNA from High Lipase Expressing Mutants

The plasmid DNA (pSO122, pDSY81, or pDSY82) and genomic flanking loci were isolated from mutants *Aspergillus oryzae* DEBY10.3, DEBY599.3, DEBY932, DEBY1058, DEBY1204.3.3, and HIN603.

Genomic DNA was isolated from mutants *Aspergillus oryzae* DEBY10.3, DEBY599.3, DEBY932, DEBY1058, DEBY1204.3.3, and HIN603 according to the following procedure. Spore stocks of each mutant were inoculated into 150 ml of YEG medium and were grown overnight at 37° C. and 250 rpm. The mycelia were harvested from each culture by filtration through Miracloth (Calbiochem, La Jolla, Calif.) and rinsed twice with TE. The mycelia preparations were then frozen quickly in liquid nitrogen and ground to a and centrifugation at 15,000×g for 20 minutes. The pellets were finally washed with 5 µl of 70% ethanol, air-dried, and dissolved in 200 µl of TE.

Two µg aliquots from each of the *Aspergillus oryzae* DEBY10.3, DEBY599.3, DEBY932, DEBY1058, DEBY1204.3.3, and HIN603 genomic DNA preparations were digested separately with BglII HpaI, NarI, NdeI, SphI, and StuI. The restriction endonucleases did not cut pDSY82 which allowed the isolation of the integrated plasmid and the flanking genomic DNA. The digested genomic DNAs were then ligated in a 20 l reaction with T4 DNA ligase.

The ligated DNA preparations were each transformed into *E. coli* HB101 or *E. coli* DH5α. The transformants were then screened by extracting plasmid DNA from the transformants, restriction digesting the inserts to confirm they are derived from pDSY82, and sequencing the inserts according to the method described above using primers specific to pDSY82.

Transformant *E. coli* HB101-pDSY112 contained the HpaI rescued locus from mutant *Aspergillus oryzae* DEBY599.3. Transformant *E. coli* HB101-pDSY109 contained the SphI rescued locus from mutant *Aspergillus oryzae* DEBY10.3. Transformant *E. coli* HB101-pDSY138 contained the NdeI rescued locus from mutant DEBY932. Transformant *E. coli* HB101-pDSY141 contained the BglII rescued locus from mutant DEBY1058. Transformant *E.* coli DH5α-pSMO1204 contained the BglII rescued locus from mutant *Aspergillus oryzae* DEBY1204.3.3. Transformant *E. coli* DH5α-pSMOH603 contained the BglII rescued locus from mutant *Aspergillus oryzae* HIN603.

Example 10

Characterization of *Aspergillus oryzae* DEBY599.3 Rescued Locus pDSY112

Figure 9B:
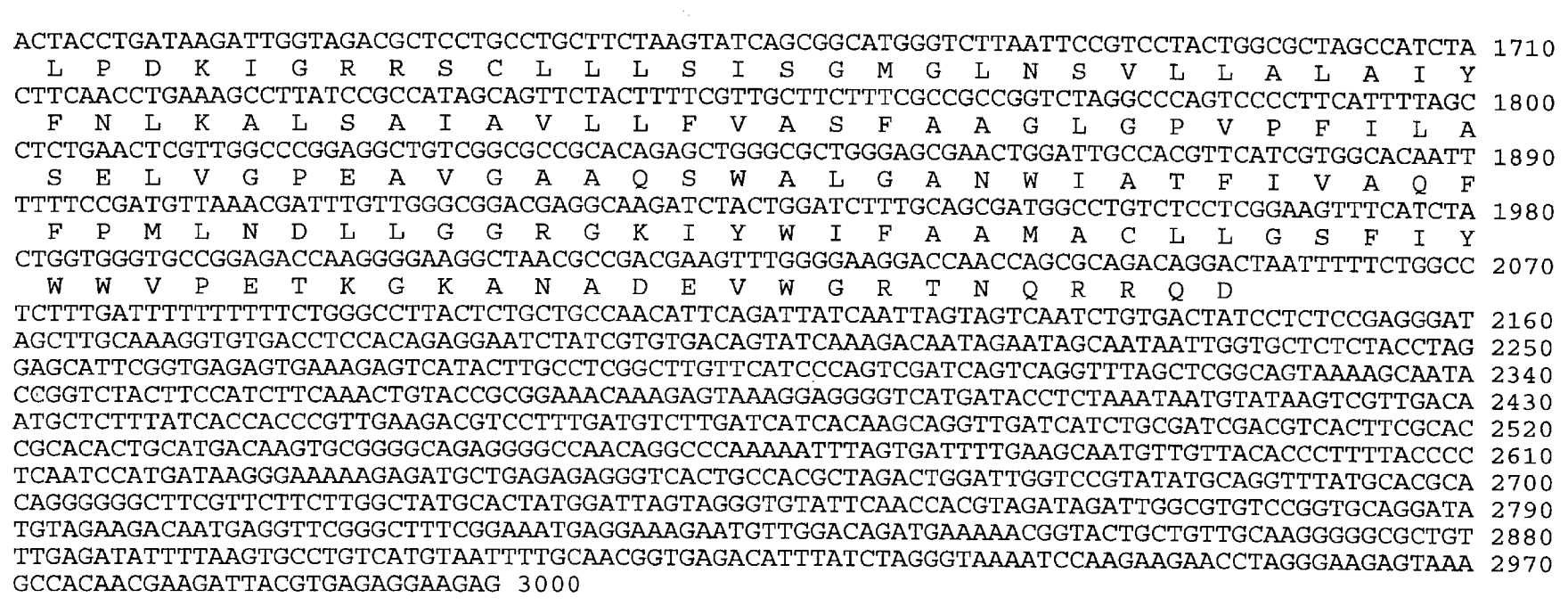

The *Aspergillus oiyzae* DEBY599.3 rescued locus pDSY112 containing 1625 bp was sequenced according to the method described in Example 2. The nucleic acid sequence (SEQ ID NO:9) and the deduced amino acid sequence (SEQ ID NO:10) are shown in FIG. 9. The nucleic acid sequence suggested that integration occurred within the promoter of a glucose transporter about 150 bp upstream of the ATG start codon. The open reading frame was punctuated by an intron. The predicted protein (SEQ ID NO:10) shared 31.6% and 24.8% identity with the glucose transporters from yeast (SEQ ID NO:11) and human (SEQ ID NO:12), respectively, and 20.1% identity with an inositol transporter from yeast (SEQ ID NO:13). Glucose transporters have very distinct predicted secondary structures with 12 membrane spanning domains. Kyte-Doolittle plots of the *Aspergillus oryzae* DEBY599.3 rescued locus predicted 12 membrane spanning domains similar to the yeast and human glucose transporters.

In order to confirm that the rescued flanking DNA was the gene disrupted in *Aspergillus oryzae* DEBY599.3, a Southern blot of *Aspergillus oryzae* HowB101 and *Aspergillus oryzae* DEBY599.3 genomic DNA preparations digested with BglII was prepared and analyzed according to the procedure described in Example 6. The blot was probed with the *Aspergillus oryzae* DEBY599.3 rescued flanking DNA at 42° C. in DIG Easy Hyb. The blot was then washed and processed using protocols provided with a Genius Kit.

A BglII band of 2.7 kb from *Aspergillus oryzae* HowB101 hybridized with the probe, while an ~8 kb BglII band from *Aspergillus oryzae* DEBY599.3 hybridized to the probe. The size difference corresponded to the length of the plasmid integrated during REMI confirming the DNA rescued from *Aspergillus oryzae* DEBY599.3 was flanking the insertion.

Example 11

*Aspergillus oryzae* Transformation with HpaI Linearized pDSY112 and Lipase Expression Screening

*Aspergillus oryzae* HowB430 was transformed with HpaI digested pDSY112 and the transformants were recovered using the methods described in Example 5. Totally, 216 transformants were grown in 24 well microtiter plates in 1/100 strength MY25 medium. Samples were taken at 4 and 6 days and assayed for lipase activity as described in Example 7. An equal number of low, average and high producing lipase transformants were spore purified and retested in 24 well microtiter cultures as described above. These purified transformants were also tested in shake flasks in full-strength MY25 medium as described in Example 8. The top five producing transformants were then grown in a 2 liter fermentor as described in Example 8. Lipase activity was measured as described in Example 7.

The results obtained are shown in Table 2 below where the lipase yield of *Aspergillus oryzae* HowB430 is normalized to 1.0.

TABLE 2

| Strain | Fermentation Results (Relative LU/ml) |
| --- | --- |
| HowB430 | 1.0 |
| DEBY599.3 | 1.7 |
| 112T90.2.2 | 2.3 |
| 112T100.4.2 | 2.1 |
| 112T344.2.1 | 1.7 |
| 112T142.2 | 2.0 |
| 112T59.2 | 2.4 |

All five retransformants produced approximately the same level of lipase activity as the original tagged strain *Aspergillus oryzae* DEBY599.3 when grown under fermentation conditions. In order to determine if the pDSY112 had integrated at the same homologous locus in the genome, a Southern blot of *Aspergillus oryzae* HowB430, *Aspergillus oryzae* DEBY599.3 and the pDSY112 transformants genomic DNA preparations digested with BglII was prepared and analyzed according to the procedure described in Example 6. The blot was probed with the *Aspergillus oryzae* DEBY599.3 rescued flanking DNA at 42° C. in DIG Easy Hyb. The blot was washed and processed using protocols provided with a Genius Kit.

A BglII band of 2.7 kb from *Aspergillus oryzae* HowB430 hybridized with the probe, while an ~8 kb BglII band from *Aspergillus oryzae* DEBY599.3 hybridized to the probe. A wild-type BglII band of 2.7 kb and a second band corresponding to the transforming DNA hybridized to the probe in all of the transformants. Therefore, none of the retransformants had exact gene replacements.

Example 12

Characterization of *Aspergillus oryzae* DEBY10.3 Rescued Locus pDSY109

The 3.4 and 2.2 kb regions on either side of the integration event of the *Aspergillus oryzae* DEBY10.3 rescued locus pDSY109 were sequenced according to the procedure described in Example 2. The nucleic acid sequence suggested that the integration event occurred within the open reading frame of a palB gene. palB genes encode a cysteine protease involved in the signal transduction pathway that signals ambient pH.

The genomic library of *Aspergillus oryzae* HowB430 was constructed by first partially digesting *Aspergillus oryzae* HowB430 genomic DNA with Tsp509I. Four units of Tsp509 were used to digest 3.5 μg of *Aspergillus oryzae* HowB430 genomic DNA using conditions recommended by the manufacturer. The reaction was carried out at 65 ° C, and samples were taken at 5 minute intervals (from 0 to 50 minutes). The reactions were placed on ice and stopped by the addition of EDTA to 10 mM. These digests were then run on a 1% agarose gel with ethidium bromide, and the region of the gel containing DNA from 3 kb to 9 kb was excised. The DNA was then purified from the gel slice using Beta-Agarase I using a protocol provided by the manufacturer (New England Biolabs, Beverly, Mass.). The size-selected DNA was then ligated into Lambda ZipLox EcoRI arms according to the manufacturer's instructions at 16° C. overnight using conditions recommended by the manufacturer. The ligation reaction was packaged and titered using a Gigapack GoldIII Packaging Kit according to the manufacturer's protocol. 8×10$^6$ recombinant plaques were obtained, and the library was amplified using a protocol provided by the manufacturer.

The genomic library was screened to obtain a genomic clone of palB. Appropriate dilutions of the genomic library were made to obtain 7000 plaques per 150 mm petri plate as described in the protocols provided with the Lambda ZipLox arms. The plaques were lifted to Hybond-N plus circular filters using standard protocols (Sambrook et al., 1989, supra). The filters were fixed using UV crosslinking, and prehybridized at 42° C. in DIG Easy Hyb. The filters were hybridized with a DIG-labeled 0.25 kb palB probe. The probe was labeled with dioxygenin using a Genius Kit and PCR amplified with the following primers synthesized with an Applied Biosystems Model 394 DNA/RNA Synthesizer according to the manufacturer's instructions:

5' CTGCCGTCGAAGGTGTCCAAG-3' (SEQ ID NO:14)

5' ATTGTGGCCCCTATGTGGATT-3' (SEQ ID NO:15)

The parameters for PCR are as described in Example 2. The filters were washed and processed post-hybridization using protocols provided with the Genius Kit. Several positive plaques were identified and purified to homogeneity using standard protocols (Sambrook et al., 1989, supra).

The nucleotide sequence was determined for the palB gene according to the method described in Example 2. The nucleic acid sequence (SEQ ID NO:16) and the deduced amino acid sequence (SEQ ID NO:17) are shown in FIG. 10. The open reading frame was interrupted by 3 introns. The Aspergillus oryzae PalB protein (SEQ ID NO:17) shared 66.4% identity with the Aspergillus nidulans PalB protein (SEQ ID NO:18). The site of insertion also contained a highly conserved domain of 37 amino acids (SEQ ID NO:19) similar to that derived from the Neurospora crassa NADH dehydrogenase (SEQ ID NO:20) which was probably a piece of mitochondrial DNA that inserted during transformation or rescue in E. coli.

A Southern blot of Aspergillus oryzae DEBY10.3 and Aspergillus oryzae HowB101 genomic DNA digested with BglII was prepared according to the emthod described in Example 6. The blot was probed with the Aspergillus oryzae DEBY10.3 rescued flanking DNA to confirm that the rescued flanking DNA was the gene disrupted in Aspergillus oryzae DEBY10.3.

A BglII band of ~7.5 kb from Aspergillus oryzae HowB101 hybridized to the probe while a band of 12 kb from Aspergillus oryzae DEBY10.3 hybridized to the probe. The size difference was the expected size for one plasmid copy being integrated confirming the locus rescued was disrupted in Aspergillus oryzae DEBY 10.3.

Because the integration event in Aspergillus oryzae DEBY10.3 would be predicted to lead to a nonfunctional PalB protein, Aspergillus oryzae DEBY10.3 was tested for growth at pH 8.0 and pH 6.5. Aspergillus nidulans palB minus strains are unable to grow at pH 8.0 but are able to grow at pH 6.5. Aspergillus oryzae HowB430 and Aspergillus oryzae DEBY10.3 were grown in Minimal medium with 10 mM uridine at either pH 8.0 or pH 6.5. As predicted, Aspergillus oryzae DEBY10.3 was unable to grow at pH 8.0.

Example 13

Construction of pMT1936 pMT1936 was constructed to contain a disruption cassette of palB using the following primers synthesized with an Applied Biosystems Model 394 DNA/RNA Synthesizer according to the manufacturer's instructions.

100752:
5'-GGTTGCATGCTCTAGACTTCGTCACCTTATTAGCC-3' (SEQ ID NO:21)

100753:5'-TTCGCGCGCATCAGTCTCGAGATCGTGT GTCGCGAGTACG-3' (SEQ ID NO:22)

100754: 5'-GATCTCGAGACTAGTGCGCGCGAACA GACATCACAGGAACC-3' (SEQ ID NO:23)

100755: 5'-CAACATATGCGGCCGCGAATTCACTTC ATTCCCACTGCGTGG-3' (SEQ ID NO:24)

The Aspergillus oryzae palB 5' flanking sequence and the sequence encoding the N-terminal part of the palB product were PCR amplified from genomic DNA of Aspergillus oryzae A1560 obtained according to the method described in Example 2. Approximately 0.05 μg of DNA template and 5 pmole of each of the two primers 100755 and 100754 were used. Amplification was performed with the polymerase Pwo as described by the manufacturer (Boehringer Mannheim, Indianapolis, Ind.). Amplification proceeded through 40 cycles. Part of the reaction product was phenol extracted, ethanol precipitated, digested with restriction enzymes EcoRI and XhoI and a fragment of approximately 1.05 kb was isolated by agarose gel electrophoresis.

The Aspergillus oryzae palB 3' flanking sequence and the sequence encoding the C-terminal part of the palB gene product were obtained as described above except that primers 100753 and 100752 were used for amplification and the PCR product was digested with restriction enzymes XhoI and XbaI before gel electrophoresis to recover a fragment of approximately 1.50 kb.

Figure 11:
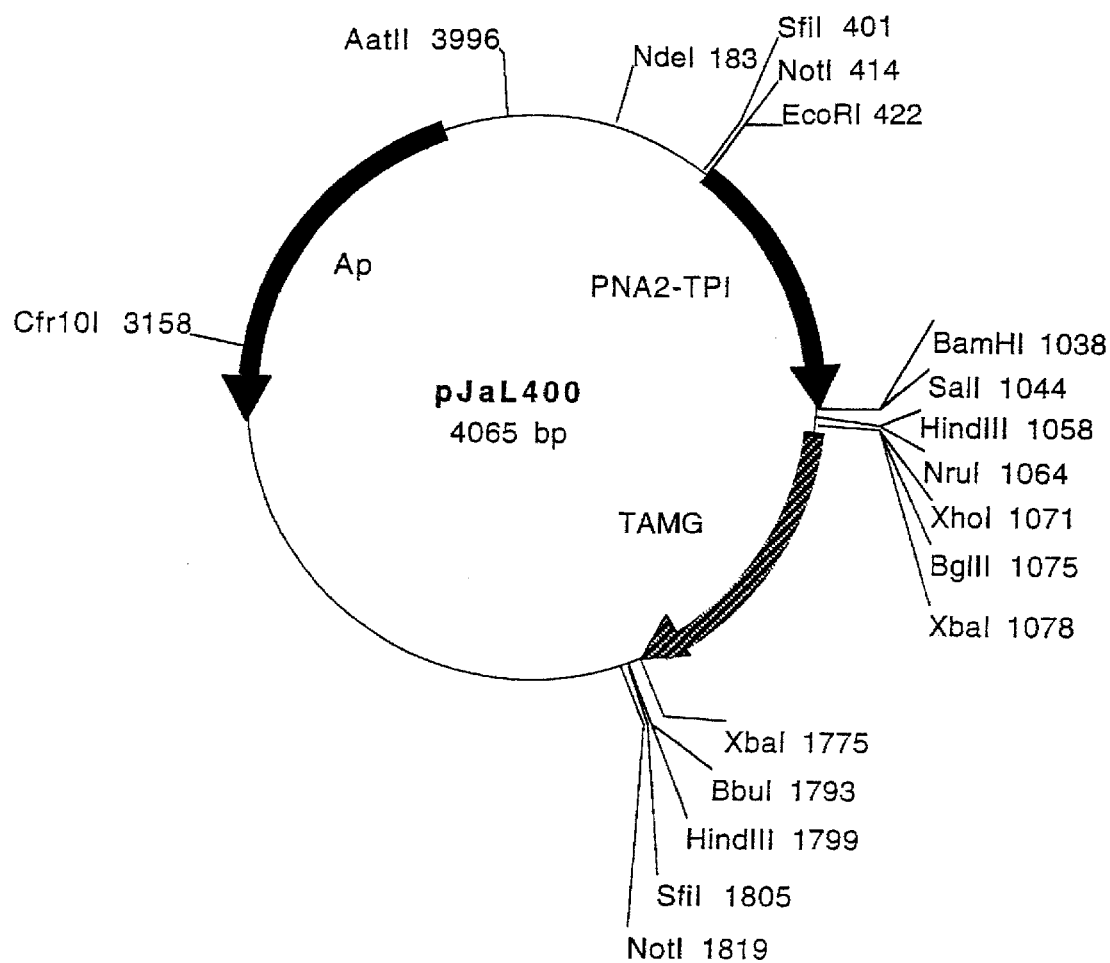
FIG. 11 is a restriction map of pJaL400.
Figure 12:
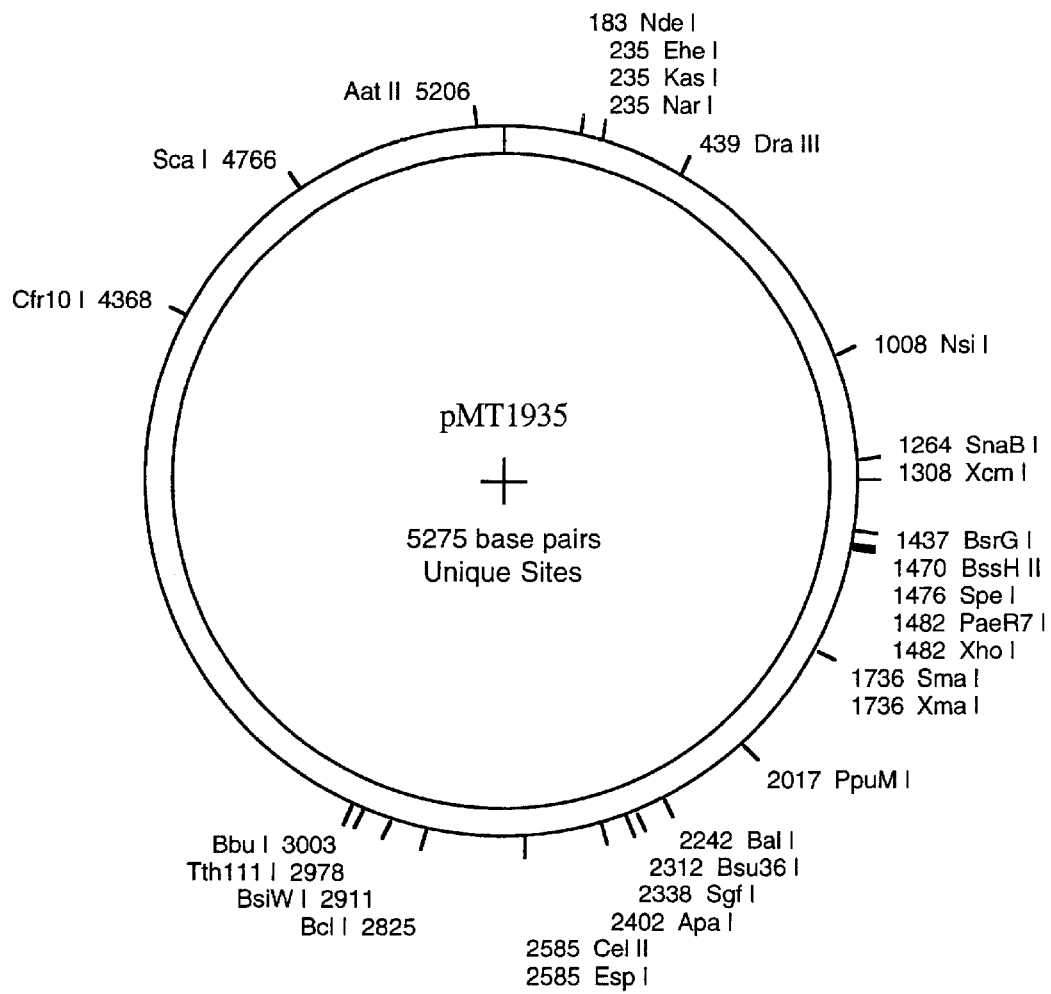
FIG. 12 is the construction of pMT1935.

The two digested and purified PCR fragments described above were ligated in a three part ligation with the purified 2.7 kb EcoRI-XbaI fragment from the vector pJaL400 (FIG. 11) to produce pMT1935 (FIG. 12). The palB 5' and 3' flanks of pMT1935 are separated by BssHII, SpeI, and XhoI sites introduced via PCR primers 100754 and 100753.

Figure 13:
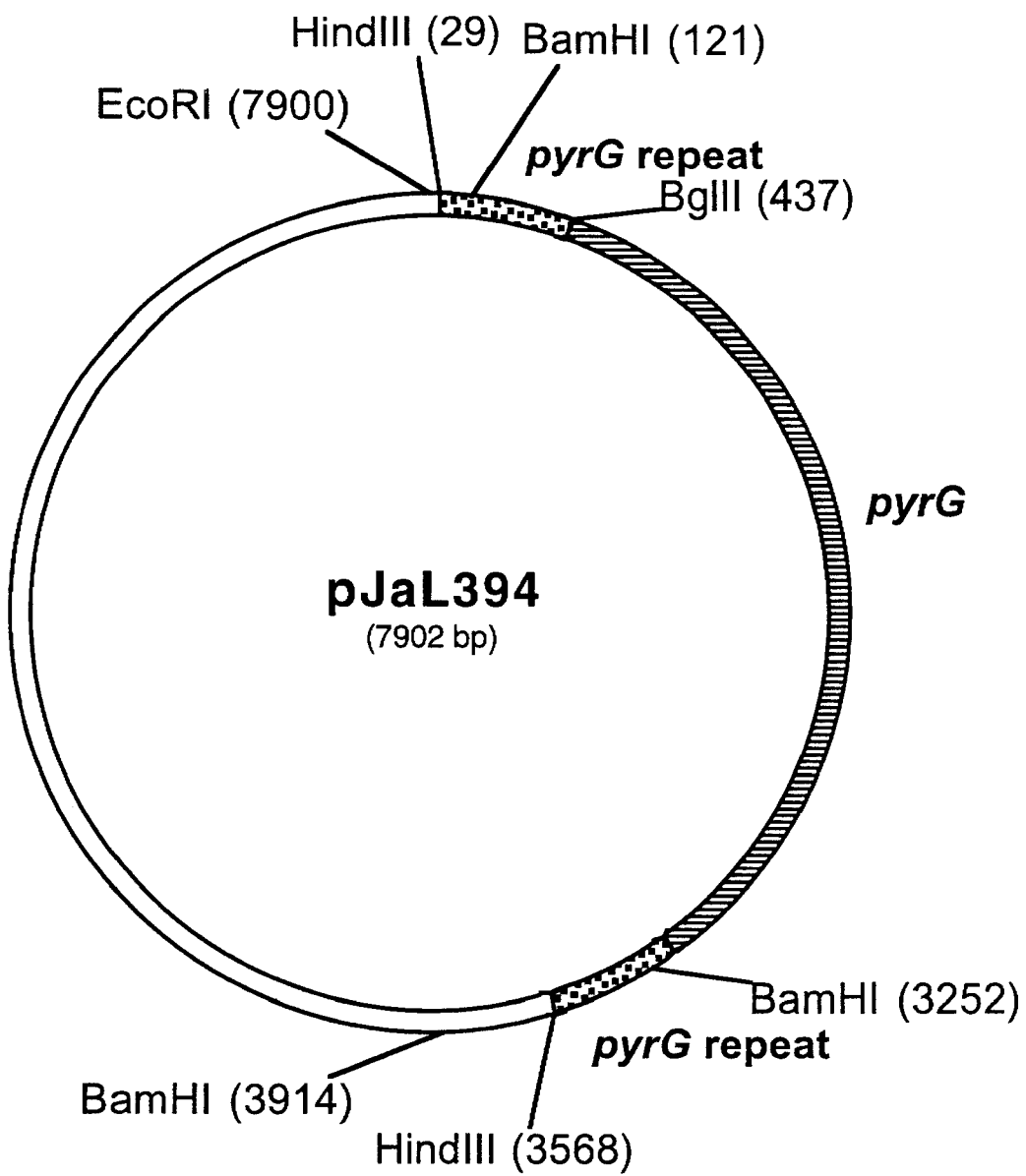
FIG. 13 is a restriction map of pJaL394.
Figure 14:
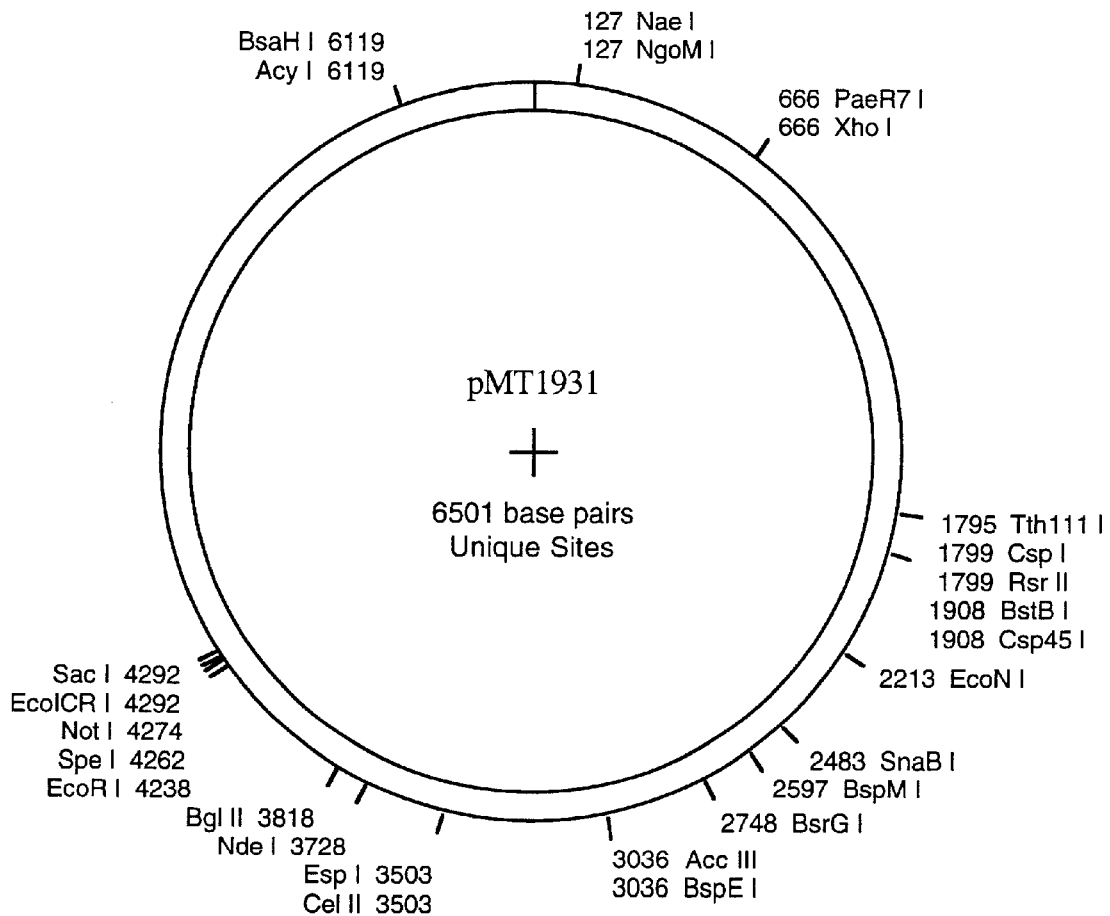
FIG. 14 is a restriction map of pMT1931.
Figure 15:
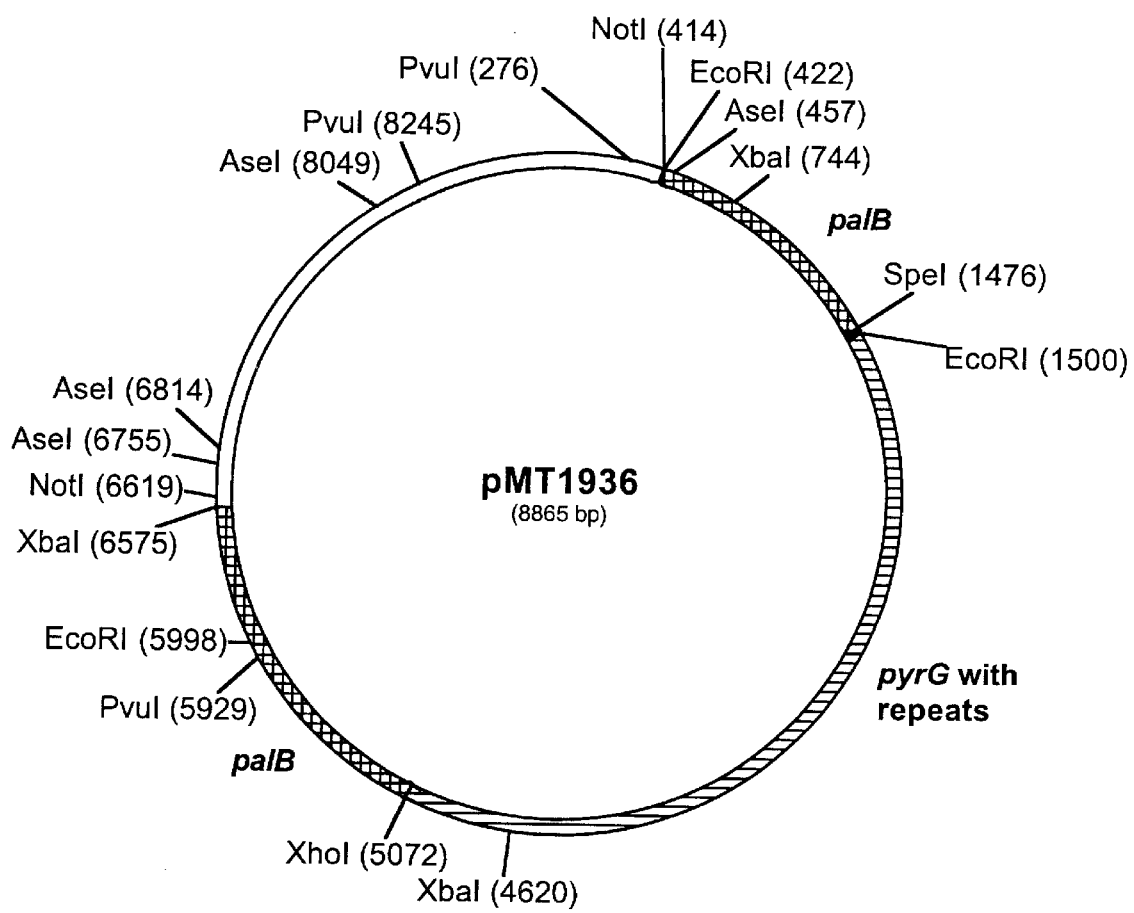
FIG. 15 is a restriction map of pMT1936.

To insert an Aspergillus oryzae pyrG gene between the palB 5' flank and the 3' flank of pMT1935, the 3.5 kb HindIII fragment of pJaL394 (FIG. 13) containing the repeat flanked pyrG gene was cloned into HindIII cut, dephosphorylated and purified pBluescript II SK (–). Plasmids with inserts in either orientation were obtained. One plasmid, pMT1931 (FIG. 14), was selected in which the SpeI site of the pBluescript polylinker was downstream of the pyrG gene and the XhoI site was upstream of the pyrG gene. The pyrG gene was isolated as a 3.5 kb SpeI-XhoI fragment and inserted in SpeI and XhoI digested and purified pMT1935 to produce the disruption plasmid pMT1936 (FIG. 15).

The pyrG selectable palB disruption cassette can be isolated from pMT1936 as a 6.2 kb NotI fragment (NotI cutting in polylinkers) or as a 5.5 kb AseI-PvuI fragment (AseI and PvuI cutting within the actual palB 5' and 3' flanking sequences).

Example 14

Aspergillus oryzae Transformation with AseI/PvuI palB Disruption Cassette from pMT1936 and Lipase Screening Aspergillus oryzae HowB430 was transformed using the same transformation procedure described in Example 5 with a 5.5 kb AseI/PvuI fragment obtained from pMT1936. The linear fragment for transformation was isolated by digestion of pMT1936 with AseI and PvuI and separation of the fragment on a 1% agarose gel using a QIAquick Gel Extraction Kit according to the manufacturer's instructions. The transformants were then tested for growth on Minimal medium plates at pH 6.5 or pH 8.0.

The results showed that 13 of the 128 transformants tested possessed the palB minus phenotype as indicated by the inability to grow at pH 8.0. The 13 palB minus strains and 13 of the transformants that were able to grow at pH 8.0 were spore purified and then evaluated in 24-well plate and shake flask cultures for lipase production using the methods described in Examples 7 and 8, respectively. The results are shown in Table 3 below.

Southern blots of the genomic DNA from an *Aspergillus oryzae* palB minus mutant, an *Aspergillus oryzae* palB plus strain, and *Aspergillus oryzae* HowB430 were performed to determine if the AsnI/PvuI transforming DNA fragment had integrated as a clean replacement into the palB locus. The genomic DNAs were prepared according to the procedure described in Example 9, digested with PvuI, and electrophoresed on a 0.8% agarose gel. The DNAs were transferred to a Hybond N+ membrane using 0.4 N NaOH and capillary action. The blot was UV crosslinked prior to prehybridization at 65° C. in Rapid Hyb. The blot was then probed with a 0.9 kb AsnI/SpeI fragment from pMT1936. The 0.9 kb fragment was isolated from an agarose gel slice using QiaQuick spin column after electrophoreses on a 1% agarose gel. The fragment was labeled using Vistra ECF Random Prime Labeling Kit. The blots were prehybridized and hybridized at 65° C. in Rapid Hyb (Amersham, Cleveland, Ohio), and then washed twice for 5 minutes in 2×SSC, 0.1% SDS at 65° C. and twice for 10 minutes in 0.2×SSC, 0.1% SDS at 65° C. Following the washes, the blot was processed for detection using the Vistra ECF Signal Amplification Kit (Amersham, Cleveland, Ohio) and the STORM860 Imaging System (Molecular Dynamics, Sunnyvale, Calif.).

The Southern blot results demonstrated that the probe hybridized to a band of 6 kb from *Aspergillus oryzae* HowB430. A clean disruption would be expected to hybridize to about an 8 kb PvuI band. The Southern blot results further showed that some of the palB minus strains had clean disruptions while others did not. The Southern blot results are summarized in Table 3.

Three of the palB minus strains were also run under fermentation conditions according to the procedure described in Example 8. The results obtained are shown in Table 3 below where the lipase yield of *Aspergillus oryzae* HowB430 is normalized to 1.0. The three palB minus strains performed better or close to the same as the original tagged mutant *Aspergillus oryzae* DEBY10.3.

TABLE 3

| Strain | PalB phenotype | 24 well LU/ml | Shake flasks LU/ml | Fermentation results LU/ml | Southern pattern |
|---|---|---|---|---|---|
| HowB430 | plus | 1.0 | 1.0 | 1.0 | wild type |
| palB3-1 | plus | 1.2 | 1.1 | 1.7 | wild-type and other |
| palB4-1 | plus | 1.0 | 0.8 | 1.4 | wild-type and other |
| palB5-1 | minus | 1.4 | 1.4 | 2.0 | disrupted |
| palB8-1 | plus | 0.9 | 1.0 | NA | wild-type and other |
| palB18-1 | plus | 0.9 | NA | NA | wild-type and other |
| palB27-1 | plus | 1.0 | NA | NA | wild-type and other |
| palB29-1 | minus | 0.8 | NA | NA | other |
| palB30-1 | plus | 0.9 | NA | 1.0 | wild-type and other |
| palB31-1 | minus | 1.3 | NA | NA | other |
| palB37-1 | plus | 0.8 | NA | NA | wild-type and other |
| palB39-1 | plus | 0.9 | NA | NA | wild-type and other |
| palB41-1 | plus | 1.0 | 0.8 | NA | wild-type and other |
| palB42-1 | plus | 1.2 | 1.0 | NA | wild-type and other |
| palB43-1 | minus | 1.3 | 1.2 | NA | other |
| palB69-1 | plus | 1.2 | 1.4 | NA | wild-type and other |
| palB71-1 | minus | 1.2 | 1.3 | 1.8 | other |
| palB72-1 | minus | 1.5 | 1.6 | 2.0 | other |
| palB75-1 | minus | 1.3 | 1.4 | 1.3 | other |
| palB76-1 | minus | 1.6 | 1.3 | 2.0 | clean disruption |
| palB79-1 | plus | 1.2 | 1.0 | NA | wild-type and other |

Example 15

Characterization of *Aspergillus oryzae* DEBY932 Rescued Locus pDSY138

Figure 16B:
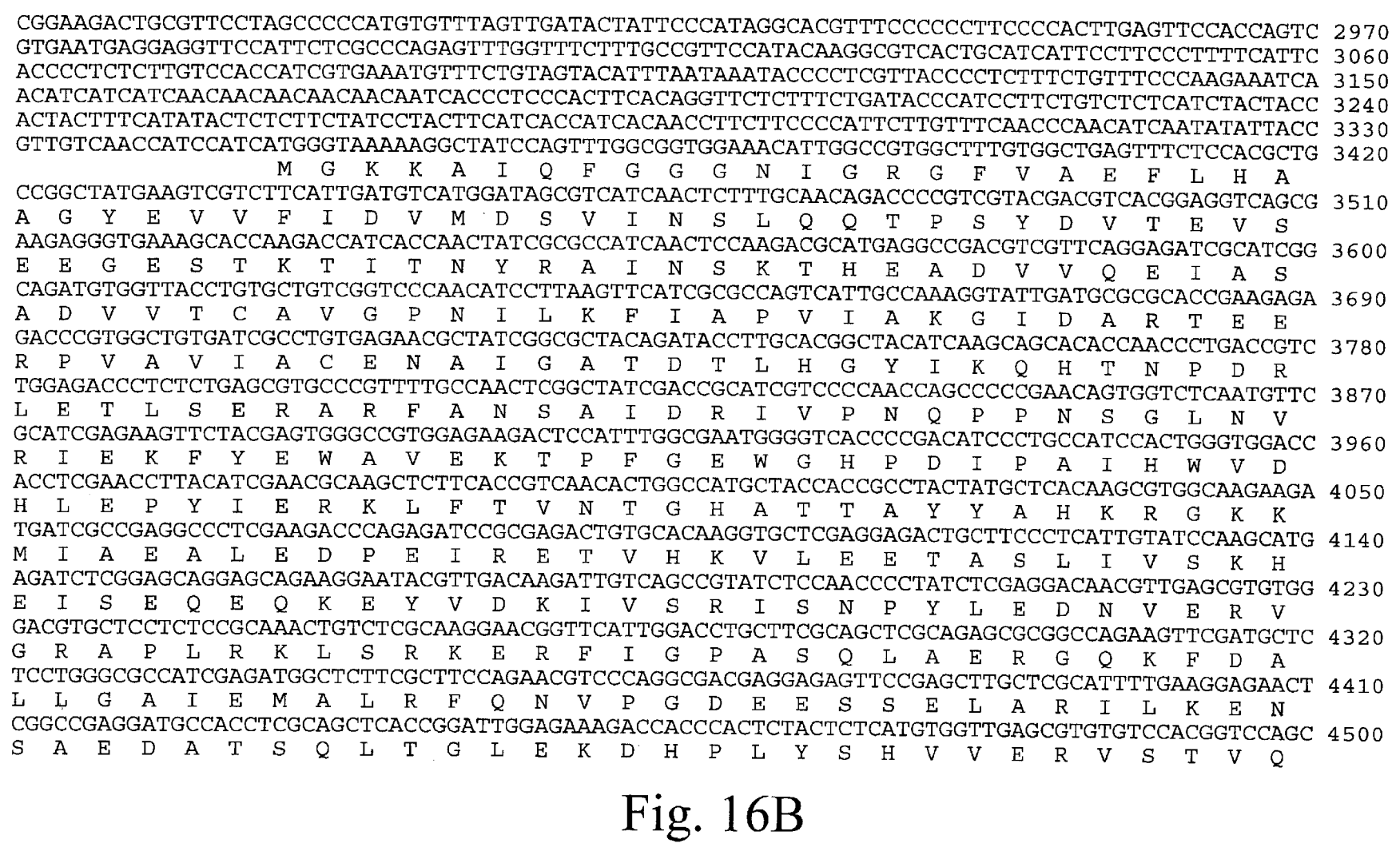
Figure 16C:
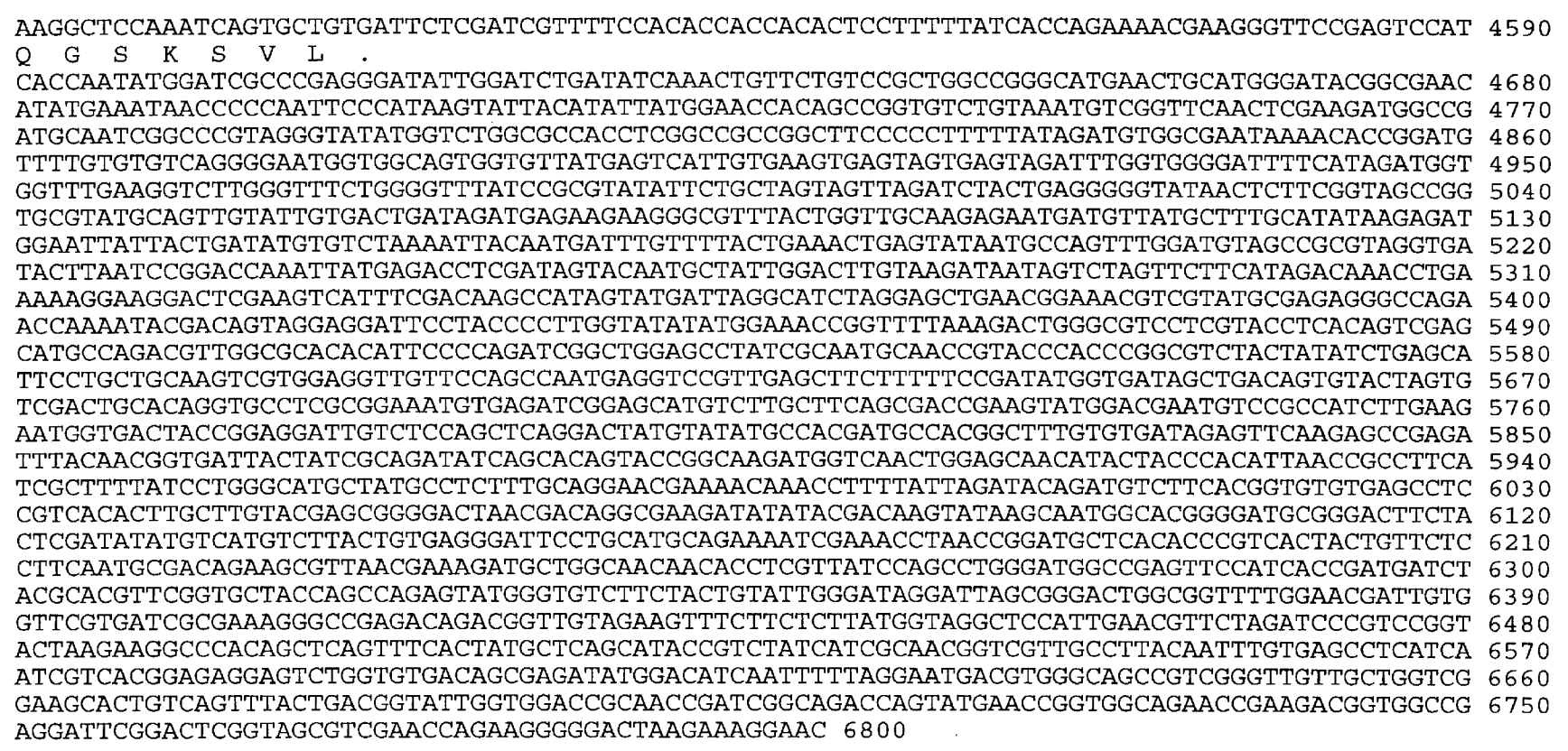

The *Aspergillus oryzae* DEBY932 rescued locus pDSY138 containing 1625 bp was sequenced according to the method described in Example 2. The nucleic acid sequence (SEQ ID NO:25) and deduced amino acid sequence (SEQ ID NO:26) are shown in FIG. 16. The nucleic acid sequence showed that the EcoRI site of the REMI integration was 810 bp upstream of the ATG start codon for an open reading frame and the deduced amino acid sequence (SEQ ID NO:26) had significant identity to mannitol-1-phosphate dehydrogenases from *E. coli* and *Bacillus subtilis*. The open reading frame coded for a predicted protein of 319 amino acids, and shared 13.3% and 34.7% identity with the *E. coli* (SEQ ID NO:27) and the *Bacillus subtilis* (SEQ ID NO:28) mannitol-1-phosphate dehydrogenases, respectively.

A Southern blot of *Aspergillus oryzae* DEBY932 and *Aspergillus oryzae* HowB430 genomic DNA preparations digested with NdeI was prepared and analyzed according to the method described in Example 14. The blot was probed with the *Aspergillus oryzae* DEBY932 rescued flanking DNA to confirm that the rescued flanking DNA is the gene disrupted in DEBY932.

An NdeI band of approximately 5 kb from *Aspergillus oryzae* HowB430 hybridized to the rescued locus while a band of approximately 10 kb from *Aspergillus oryzae* DEBY932 hybridized to the probe confirming that the rescued locus was the disrupted locus in *Aspergillus oryzae* DEBY932.

Example 16

*Aspergillus oryzae* Transformation with NdeI Linearized pDSY138 and Lipase Expression Screening

*Aspergillus oryzae* HowB430 was transformed with NdeI digested pDSY138 and the transformants were recovered using the methods described in Example 5. Totally, 180 recovered transformants were grown in 24 well microtiter plates in 1/100 strength MY25, and samples were taken at 4 and 6 days for lipase assays as described in Example 7. The top 11 highest lipase producing and 1 average lipase producing transformants were spore purified and retested in 24 well microtiter cultures. These purified transformants were also evaluated in shake flasks in full-strength MY25 as described in Example 8. The top two producers were also grown in a 2 liter fermentor as described in Example 8. Lipase activity was measured as described in Example 7.

The results obtained are shown in Table 4 below where the lipase yield of *Aspergillus oryzae* HowB430 was normalized to 1.0. The top two lipase producers produced essentially the same amount of lipase activity as the original tagged mutant *Aspergillus oryzae* DEBY932.

TABLE 4

| Strain | Fermentation Results (Relative LU/ml) | Southern Results |
|---|---|---|
| HowB430 | 1.0 | Wild-type |
| DEBY932.3.3 | 2.1 | Disrupted |
| 138T83.1.1 | 2.2 | Disrupted |
| 138T102.1.1 | 1.9 | Disrupted |

A Southern blot of *Aspergillus oryzae* DEBY932, *Aspergillus oryzae* HowB430 and pDSY138 genomic DNA preparations digested with NdeI was prepared and analyzed as described in Example 14 to determine if pDSY138 had integrated at the homologous locus producing gene replacements in the transformants using the *Aspergillus oryzae* DEBY932 rescued flanking DNA as a probe.

The Southern blot showed that an NdeI band of approximately 5 kb from *Aspergillus oryzae* HowB430 hybridized to the rescued locus while a band of approximately 10 kb from *Aspergillus oryzae* DEBY932 hybridized to the probe. In Table 4, the column labeled Southern results indicated whether the transformants had a wild-type NdeI fragment of the size observed in the parent strain *Aspergillus oryzae* HowB430 or whether the transformants had a band corresponding to the disrupted size observed in *Aspergillus oryzae* DEBY932.

Example 17

Characterization of *Aspergillus oryzae* DEBY1058 Rescued Locus pDSY141

The *Aspergillus oryzae* DEBY1058 rescued locus pDSY141 containing approximately 1 kb was sequenced according to the method described in Example 2. The nucleic acid sequence demonstrated that the rescued locus contained flanking DNA from only one side of the BamHI REMI integration event, and the pDSY141 sequence had rearranged.

A Southern blot of *Aspergillus oryzae* DEBY1058 genomic DNA digested with BamHI was probed with the *Aspergillus oryzae* DEBY1058 rescued flanking DNA was prepared and analyzed as described in Example 14 to confirm that the rescued flanking DNA is the gene disrupted in *Aspergillus oryzae* DEBY1058.

The Southern analysis showed that the pDSY82 DNA had integrated as a REMI event at a BamHI site, but more than one copy of pDSY82 had integrated which suggested why the rescued plasmid had rearranged and only contained one side of the flanking DNA.

In order to obtain the other flanking piece, a genomic clone (pDSY163) was isolated from the *Aspergillus oryzae* HowB430 genomic library, prepared as described in Example 6, using a $^{32}$P-labeled 0.5 kb fragment of the rescued genomic DNA from *Aspergillus oryzae* DEBY1058. The probe was labeled using a Prime-It Kit according to the manufacturer's instructions (Stratagene, La Jolla, Calif.). Five plates of approximately 7000 plaques each were plated, and the plaques were lifted to Hybond-N$^+$ as described in Example 12. The filters were prehybridized at 42° C. in 50% formamide, 5×SSPE, 0.3% SDS and 200 µg/ml of sheared and denatured salmon sperm DNA for 1 hour. The denatured probe was added, and the filters were hybridized overnight at 42° C. The filters were washed in 1×SSC, 0.1% SDS for 5 minutes at 65° C. twice, in 0.1×SSC, 0.1% SDS at 65° C. for 15 minutes twice, and in 2×SSC at room temperature for 10 minutes. The filters were exposed to X-ray film, and 12 positive plaques were picked and purified using standard protocols (Sambrook et al., 1989, supra). Plasmid DNA was isolated from the purified genomic clones using the excision protocol provided with the Lambda ZipLox EcoRI Arms Kit.

The nucleotide sequence of 3.6 kb of the genomic clone was determined as described in Example 2. The nucleic acid sequence (SEQ ID NO:29) and deduced amino acid sequence (SEQ ID NO:30) are shown in FIG. 17. The nucleic acid sequence showed that the BamHI site of integration in the mutant is 250 bp downstream of the stop codon for an open reading frame that encodes a protein (SEQ ID NO:30) which shared significant identity with manganese superoxide dismutase from *Saccharomyces cerevisiae* (SEQ ID NO:31).

Since the site of integration in *Aspergillus oryzae* DEBY1058 was 250 bp downstream of the stop codon for the manganese superoxide dismutase gene, the effect of this integration on expression of the manganese superoxide dismutase was determined. *Saccharomyces cerevisiae* strains lacking a functional manganese superoxide dismutase are sensitive to paraquat when grown in the presence of oxygen. *Aspergillus oryzae* DEBY1058 and *Aspergillus oryzae* HowB430 were grown in 24 well microtiter plates in 1 ml of YEG medium supplemented with 10 mM uridine and either 0, 2, 4, 6, 8, 10 or 20 mM paraquat at 34° C. with shaking. *Aspergillus oryzae* HowB430 grew at concentrations of paraquat up to 8 mM while growth of *Aspergillus oryzae* DEBY1058 was inhibited by 2 mM paraquat. The data indicated that the integration event 250 bp downstream of the stop codon for manganese superoxide dismutase in *Aspergillus oryzae* DEBY1058 reduced expression of manganese superoxide dismutase.

Example 18

Construction of pDSY162 pDSY162 was constructed to contain a disruption cassette for manganese superoxide dismutase by PCR amplification of a 3179 bp XbaI/KpnI fragment of genomic DNA containing the manganese superoxide dismutase gene using the following primers synthesized with an Applied Biosystems Model 394 DNA/RNA Synthesizer according to the manufacturer's instructions.

970738: 5'-GCTCTAGATCGTCGGAGCTCATGTC GGCGATTTTAC-3' (SEQ ID NO:32)

970739: 5'-GCGGTACCACGCCTAGAGCAAAGT ATAAATAAGGAA-3' (SEQ ID NO:33)

The amplification reaction (100 µl) contained the following components: 0.2 µg of the pDSY163, 48.4 pmol of primer 970738, 48.4 pmol of primer 979739, 1 mM each of dATP, dCTP, dGTP, and dTTP, 1×Taq polymerase buffer, and 2.5 U of Taq polymerase. The reaction was incubated in an Ericomp Thermal Cycler programmed as follows: One cycle at 95° C. for 5 minutes followed by 30 cycles each at 95° C. for 1 minute, 55° C for minute, and 72° C. for 2 minutes. Two µl of the reaction were electrophoresed on an agarose gel to confirm the amplification of the PCR product of approximately 3179 bp.

The PCR product was subcloned into pCR®TOPO using a TOPO TA Cloning Kit (Invitrogen, San Diego, Calif.). The transformants were then screened by extracting plasmid DNA from the transformants using a QIAwell–8 Plasmid Kit according to the manufacturer's instructions, restriction digesting the plasmid DNA using XbaI/KpnI to confirm the presence of the correct size fragment, and sequencing the DNA according to the method described in Example 2 to confirm the PCR product.

Figure 18:
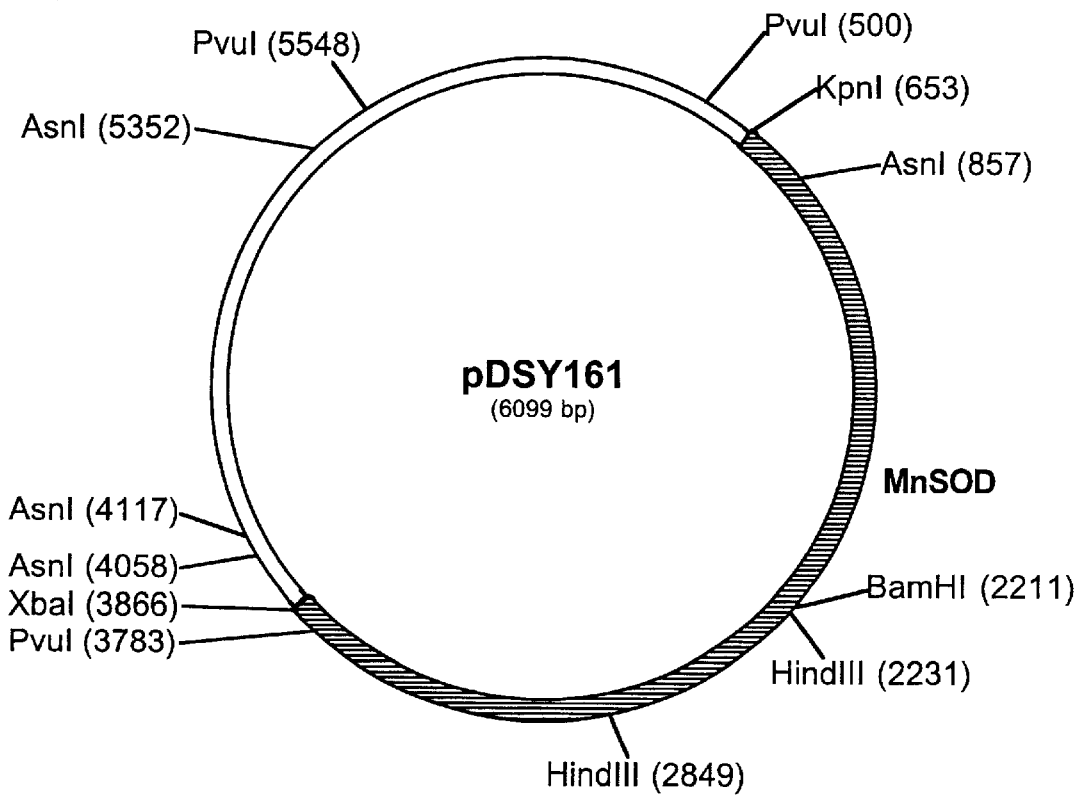
FIG. 18 is a restriction map of pDSY161.

The plasmids containing the manganese superoxide dismutase insert were digested with XbaI and KpnI and separated on a 1% agarose gel. A 3.1 kb manganese superoxide dismutase fragment was purified using a QIAquick Gel Extraction Kit according to the manufacturer's instructions. The purified fragment was ligated with pBluescript SK– digested with XbaI and KpnI to produce pDSY161 (FIG. 18). The ligation reaction was used to transform *E. coli* DH5α.

Figure 19:
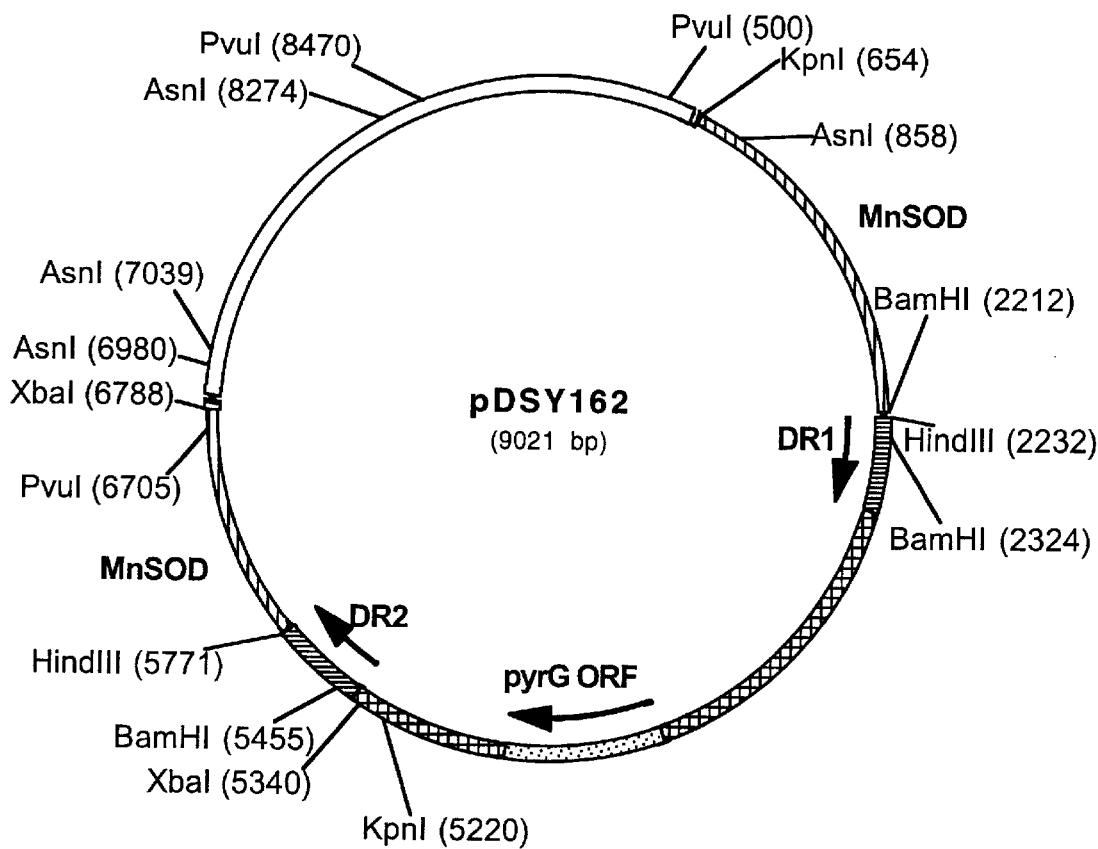
FIG. 19 is a restriction map of pDSY162.

The transformants were then screened by extracting plasmid DNA from the transformants using a QIAwell-8 Plasmid Kit according to the manufacturer's instructions and digesting the plasmids with HindIII to determine which clones were correct.

pDSY161 was digested with HindIII to remove a 600 bp fragment, and the digestion was electrophoresed on a 1% agarose gel. A 5.4 kb vector fragment was isolated using a QIAquick Gel Extraction Kit according to the manufacturer's instructions, and ligated to the 3.5 kb HindIII fragment from pJaL394 (FIG. 13) containing a pyrG gene repeat to produce pDSY162 (FIG. 19). The ligation reaction was used to transform *E. coli* DH5α.

The transformants were then screened by extracting plasmid DNA from the transformants using a QIAwell-8 Plasmid Kit according to the manufacturer's instructions and digesting them with HindIII to determine which plasmids contained the expected 3.5 kb HindIII fragment in pDSY162.

Example 19

*Aspergillus oryzae* Transformation with AsnI/PvuI Manganese Superoxide Dismutase Disruption Cassette and Lipase Screening

*Aspergillus oryzae* HowB430 was transformed with a 5.8 kb AseI/PvuI fragment containing the manganese superoxide dismutase disruption cassette using the same transformation procedure described in Example 5. The linear fragment for transformation was isolated by digestion of pDSY162 with AseI and PvuI and separation of the fragment on a 1% agarose gel using a QIAquick Gel Extraction Kit according to the manufacturer's instructions. The transformants were then tested for growth on Minimal medium plates at pH 6.5.

Six transformants were obtained and were tested for sensitivity to paraquat as described in Example 17. Four of the 6 transformants were paraquat sensitive indicative of the manganese superoxide dismutase disruption minus phenotype although the four paraquat sensitive strains were not equally sensitive to paraquat. As shown in Table 5 below, a dash means not sensitive to paraquat, ++ means sensitive means sensitive to intermediate levels of paraquat and +++ means inhibited by even 2 mM paraquat. All of the transformants were spore purified and tested in 24 well and shake flask cultures for lipase production according to the procedures described in Examples 7 and 8. The results tabulated in Table below show that following transformation of *Aspergillus oryzae* HowB430 with the manganese superoxide dismutase disruption cassette, transformants sensitive to paraquat on average produced higher LIPOLASE™ levels than *Aspergillus oryzae* HowB430.

Southern blots of the genomic DNA from an *Aspergillus oryzae* manganese superoxide dismutase minus mutant, an *Aspergillus oryzae* manganese superoxide dismutase plus strain, and *Aspergillus oryzae* HowB430 were performed as described in Example 14 to determine if the AsnI/PvuI transforming DNA fragment had integrated as a clean replacement into the manganese superoxide dismutase locus.

The results of the Southern blot (Table 5) showed that strains sensitive to even 2 mM paraquat were disrupted at the manganese superoxide dismutase locus while those sensitive to intermediate levels of paraquat have both a wild-type locus and the disrupted cassette locus. The Souther blot and LIPOLASE™ yield results together suggests that expression of both full length and truncated manganese superoxide dismutase in the same cell leads to an intermediate sensitivity to paraquat and an increase in LIPOLASE™ production. This can be explained by the fact that manganese superoxide dismutase is a homodimer so expression of the wild-type and truncated forms coded for by the wild-type and disrupted cassette, respectively, leads to heterodimers which are either non-functional or partially functional.

TABLE 5

| Strain | Paraquat sensitivity | 24 well results (Relative LU/ml) | Shake flasks results (Relative LU/ml) | Southern Results |
|---|---|---|---|---|
| HowB430 | – | 1.0 | 1.0 | wild-type |
| 430162T1 | – | 1.0 | 1.1 | wild-type & other |
| 430162T2 | ++ | 1.3 | 2.5 | wild-type & other |
| 430162T3 | ++ | 1.4 | 3.0 | wild-type & other |
| 430162T4 | +++ | 1.2 | 2.1 | disrupted |
| 430162T5 | +++ | 1.0 | 1.5 | disrupted |
| 430162T6 | – | 0.9 | 1.2 | wild-type & other |

Example 20

Characterization of *Aspergillus oryzae* DEBY1204.3.3 Rescued Locus pSMO1204

The *Aspergillus oryzae* DEBY1204.3.3 rescued locus pSMO1204 containing 2.0 kb was sequenced according to the procedure described in Example 2. The nucleic acid sequence (SEQ ID NO:34) as shown in FIG. 20 had no sequence homology to any published sequences.

Southern analysis and sequencing of a genomic clone was used to confirm that no deletions had taken place when the tagged mutant was generated. A Southern blot of *Aspergillus oryzae* HowB430 genomic DNA digested with various restriction endonucleases (BamHI, BglII, SalI and SphI) was prepared and analyzed as described in Example 14. Probes from both ends of the rescued plasmid were generated by PCR using the primers described below. The primers were synthesized with an Applied Biosystems Model 394 DNA/ RNA Synthesizer according to the manufacturer's instructions.

970052 5'-CTATGATTGGCCGATAGG-3' (SEQ ID NO:35)

970053 5'-CCAGGCTCGCACGCTTTC-3' (SEQ ID NO:36)

970054 5'-CTTGCAACTAACGGGGTT-3' (SEQ ID NO:37)

970055 5'-TGAGAAAGACCAAGAATG-3' (SEQ ID NO:38)

Probe 1 was generated from one end of the rescued locus by PCR using primer 970052 and primer 970053. Probe 2 was generated from the other end of the rescued locus by PCR using primer 970054 and primer 970055. The amplification/labeling reaction (50 µl) contained the following conponents: 10 ng rescued plasmid pSMO1204, 50 pmole each of primer 970052 and 970053 for probe 1 or 50 pmole each of primer 970054 and primer 970055 for probe 2, 1×DIG labeling mix (Boehringer Mannheim, Indianapolis, Ind.), 1×Taq polymerase buffer, and 2.5 U of Taq polymerase. The reaction was incubated in an Ericomp Thermal Cycler programmed as follows: One cycle at 95° C. for 5 minutes followed by 30 cycles each at 95° C. for 1 minute, 58° C. for 1 minute, and 72° C. for 1.5 minutes Southern blots of *Aspergillus oryzae* HowB430 genomic DNA digested with various restriction enzymes were prepared and analyzed according to the procedure described in Example 14. The blots were hybridized independently to probe 1 and probe 2. Identical banding patterns of the digests with both probes would suggest that a deletion had not occurred. Conditions of the Southern analysis were as follows: Blots were prehybridized for 1 hour and hybridized overnight at 42° C. in Easy Hyb. Blots were washed in 2×SSC, 0.1% SDS twice at room temperature for 15 minutes each, then washed twice at 65° C. in 0.1×SSC, 0.1% SDS for 15 minutes each. Detection continued with buffers and reagents from Boehringer Mannheim's DIG Wash Block Buffer System. CDP star (Boehringer Mannheim, Indianapolis, Ind.) was used to detect the chemiluminescent reaction. Film was exposed for approximately 1 hour.

The Southern blot results showed identical banding patterns with the different digests suggesting a direct insertion of the tagged plasmid. A genomic clone was obtained by probing an *Aspergillus oryzae* HowB430 Ziplox library obtained as described in Example 12 with the probe from the tagged mutant *Aspergillus oryzae* DEBY1204. The Ziplox library of *Aspergillus oryzae* HowB430 was screened with probe 1. A genomic clone was isolated and sequenced (Example 2) confirming that no deletions had occurred during the tagging event and the tagged plasmid had inserted at an EcoRI site.

Example 21

Characterization of *Aspergillus oryzae* Mutant HIN603 Rescued Locus pSMO603

The *Aspergillus oryzae* HIN603 rescued locus pSMO603 containing 1.0 kb was sequenced according to the procedure described in Example 2. The nucleic acid sequence (SEQ ID NO:39) as shown in FIG. 21 showed no homology to any published sequences.

A Southern blot of *Aspergillus oryzae* HowB430 genomic DNA digested with the restriction enymes SphI, SalI, and BamHI was hybridized to probes made from both ends of the rescued plasmid. Probe 3 was generated by PCR using primer 970858 and primer 970859 shown below synthesized with an Applied Biosystems Model 394 DNA/RNA Synthesizer according to the manufacturer's instructions. Probe 4 was generated by PCR using primer 970860 and primer 970861. The template for the 50 µl PCR labeling reaction was 10 ng of the rescued plasmid pSMOH603. PCR cycles and conditions were as described in Example 20. Southern conditions were as described in Example 20.

970858: 5'-TGTAGTCTGACTAGCATG-3' (SEQ ID NO:40)

970859: 5'-GGATCTTCACCTAGATCC-3' (SEQ ID NO:41)

970860: 5'-CATAGTGTCGACCAAGC-3' (SEQ ID NO:42)

970861: 5'-CAATCGAGCTTGCCTATG-3' (SEQ ID NO:43)

Different banding patterns on the Southern suggested that a deletion had taken place where the tagging occurred. When 500 ng of *Aspergillus oryzae* HowB430 genomic DNA was used as a template in a PCR reaction with primers 090858 and 090860, a 3 kb product was amplified suggesting a 2.5 kb deletion had occurred. Southern analysis of genomic DNA prepared from the tagged *Aspergillus oryzae* HIN603 strain, digested with HindIII, and probed with the NheI fragment from *Aspergillus oryzae* pyrG suggested that the tagged mutant had not been generated by a REMI event.

Example 22

Construction of *Aspergillus oryzae* HowB432

Figure 22:
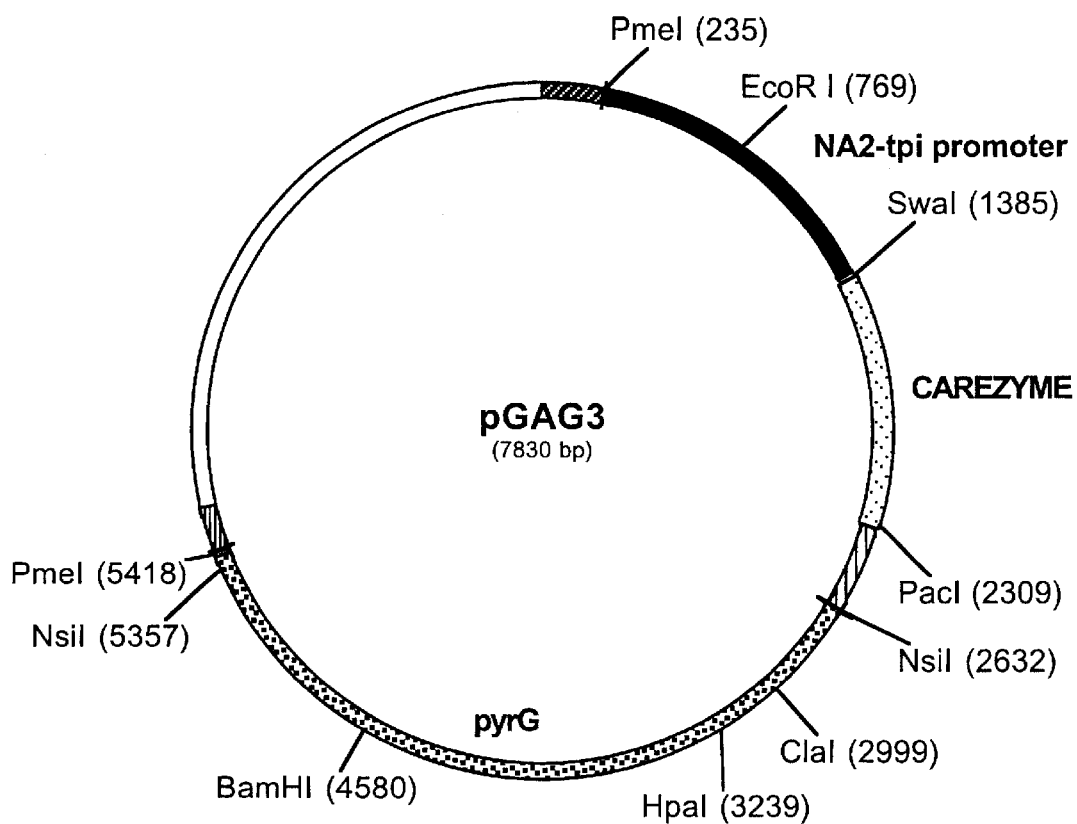
FIG. 22 is a restriction map of pGAG3.

*Aspergillus oryzae* HowB432 was generated by transformation of *Aspergillus oryzae* JaL250 with a linear fragment containing the NA2-tpi promoter, a cellulase gene from Humicola lanuginosa (CAREZYME™ gene, Novo Nordisk A/S, Bagsværd, Denmark), and the AMG terminator obtained from plasmid pGAG3 (FIG. 22).

Figure 23:
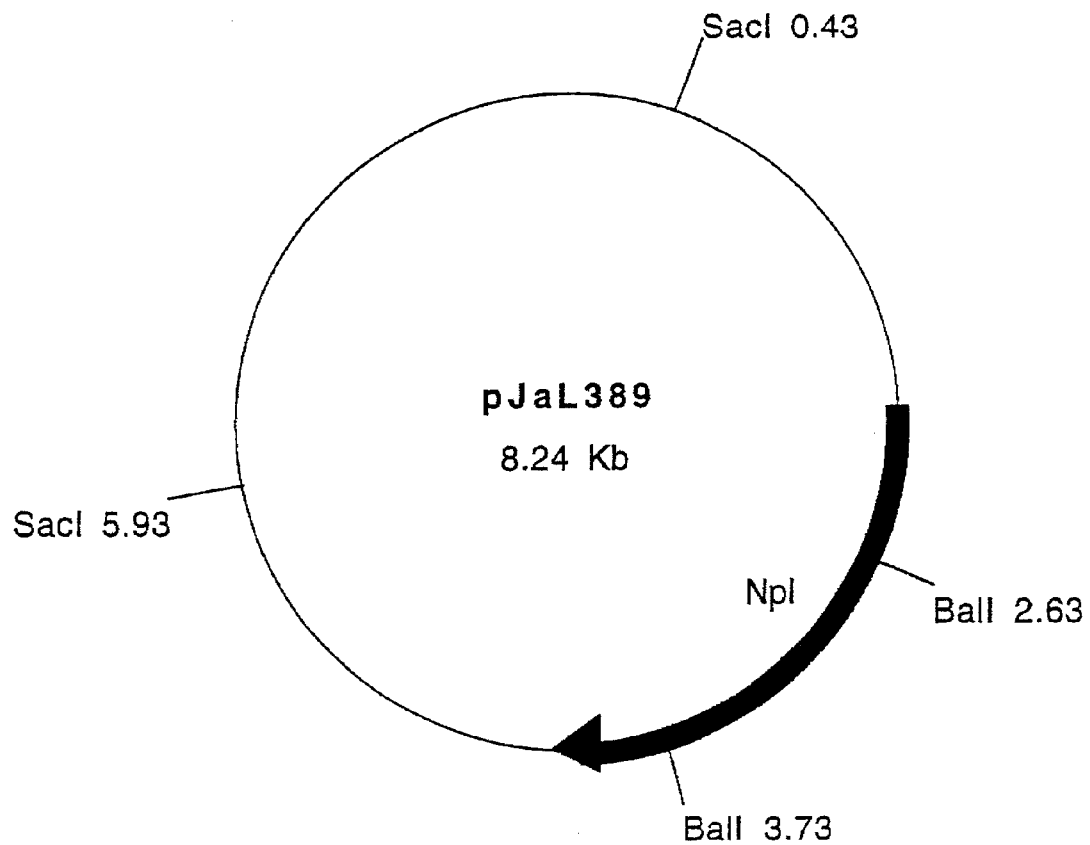
FIG. 23 is a restriction map of pJaL389.
Figure 24:
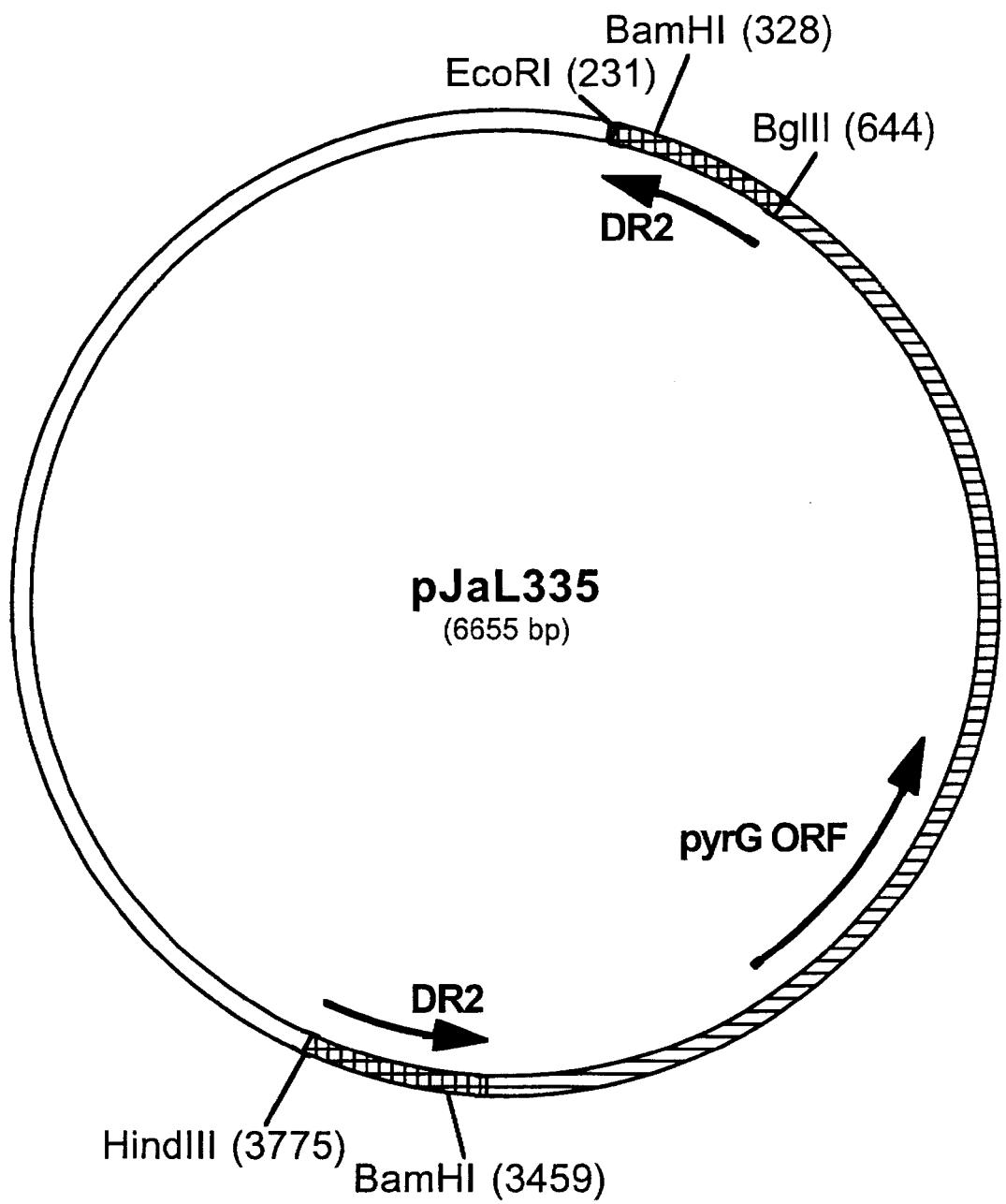
FIG. 24 is a restriction map of pJaL335.
Figure 25:
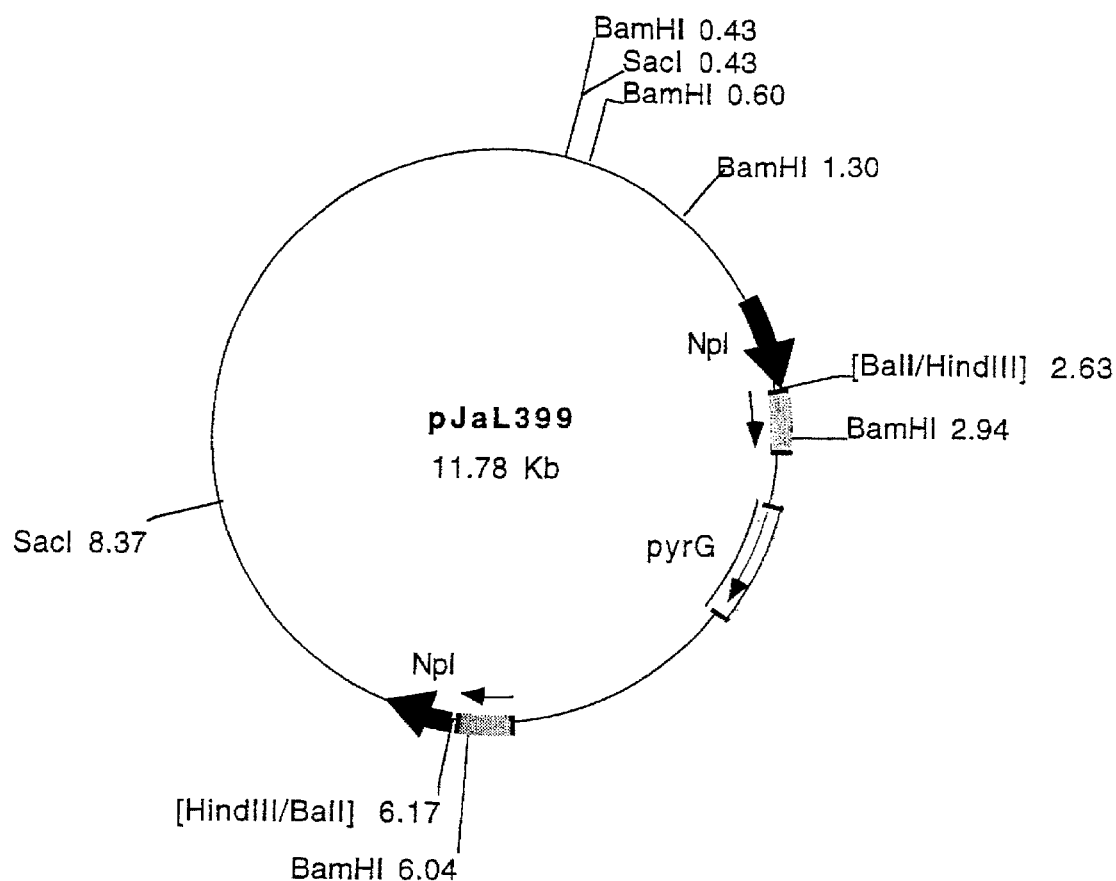
FIG. 25 is a restriction map of pJaL399.

*Aspergillus oryzae* JaL250 was constructed from *Aspergillus oryzae* JaL142 (Christensen et al., 1988, Bio/Technology 6: 1419–1422) by deleting the neutral protease I gene (npI). The npI deletion plasmid was constructed by exchanging a 1.1 kb BalI fragment coding for the central part of the npI gene in plasmid pJaL389 (FIG. 23), which contained a 5.5 kb SacI genomic fragment encoding the npI gene, with a 3.5 kb HindIII fragment from pJaL335 (FIG. 24) containing the pyrG gene flanked by repeats, thereby creating plasmid pJaL399 (FIG. 25). *Aspergillus oryzae* JaL142 was transformed with the 7.9 kb SacI fragment. Transformants were selected by relief of the uridine requirement on Minimal medium plates. The transformants were analyzed by Southern analysis as described in Example 14 and by IEF protease profile analysis according to standard methods.

Two out of 35 transformants possessed an altered Southern profile compared to the parent strain and displayed no neutral protease I activity by IEF. Furthermore, Southern analysis showed that one of the two transformants had a clean deletion of the npI gene and was designated *Aspergillus oryzae* JaL228.

Figure 26:
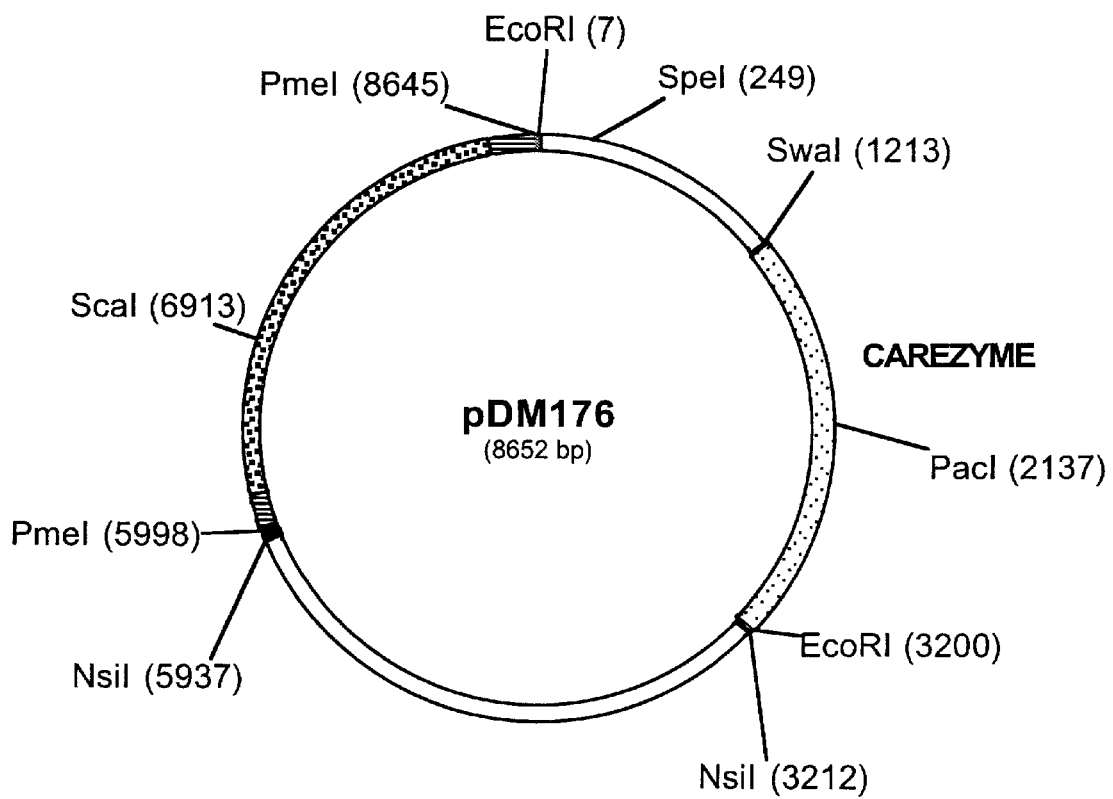
FIG. 26 is a restriction map of pDM176.

Totally, $2.3 \times 10^7$ conidiospores of *Aspergillus oryzae* JaL228 were spread on Minimal medium plates supplemented with 0.1% 5-fluoro-orotic acid (FOA) and 10 mM uridine. Eight FOA resistant colonies were obtained. A Southern blot of BamHI digested genomic DNA from the eight colonies probed with a 401 bp pyrG repeated region demonstrated that the pyrG gene had been excised by recombination at the repeated regions. *Aspergillus oryzae* JaL228 showed two bands of the expected size of 2.7 and 3.1 kb originating from the two copies of the repeated region. If the pyrG gene had been lost by recombination between the repeated regions, the 3.1 kb band would have disappeared and only the 2.7 kb would have remained. All 8 FOA resistant colonies showed this pattern of bands. Sequencing of a PCR fragment covering the junctions between the npI gene and the copy of the 401 bp repeat remaining in the 8 colonies confirmed that the pyrG gene was excised by recombination between the repeats. One of the colonies was designated *Aspergillus oryzae* JaL250.

pGAG3 was constructed by isolating from pDM176 (FIG. 26) a SwaI/PacI fragment containing the *Humicola lanuginosa* cellulase gene and ligating the fragment into SwaI/PacI digested pBANe6. The SwaI/PacI fragment from pDMI76 and SwaI/PacI digested pBANe6 were separated on a 1% agarose gel, and isolated using a QIAquick Gel Extraction Kit (Qiagen Inc., Chatsworth, Calif.) according to the manufacturer's instructions prior to ligation. The ligation was used to transform *E. coli* DH5α cells, and the transformants were then screened by extracting plasmid DNA from the transformants using a QIAwell-8 Plasmid Kit according to the manufacturer's instructions, restriction digesting the plasmid DNA to confirm the presence of the correct size fragment, and sequencing the DNA according to the method described in Example 2.

pGAG3 was then digested with PmeI and the linear expression cassette was isolated by preparative agarose electrophoresis using TAE buffer. The linear cassette was then used to transform *Aspergillus oryzae* JaL250.

Transformation of *Aspergillus oryzae* JaL250 for amdS selection was conducted with protoplasts at a concentration of $2 \times 10^7$ protoplasts per ml prepared as described in Example 2. Ten $\mu$g of the linear fragment described above were added to 100 $\mu$l of protoplasts. A volume of 250 $\mu$l of PEG (60% PEG 4000–10 mM CaCl$_2$-10 mM Tris-HCl pH 8.0) was then added, and the mixture was placed at 37° C. for 30 minutes. Three ml of STC medium was added and the mixture was plated on Cove plates supplemented with 10 mM uridine for amdS selection. The plates were incubated 7–10 days at 34° C. Transformants were then transferred to plates of the same medium and incubated 3–5 days at 37° C. The transformants were purified by streaking spores and picking isolated colonies using the plates of the same medium without sucrose.

Example 23

*Aspergillus oryzae* Transformation with HpaI Linearized pDSY112 and Cellulase Expression Screening

*Aspergillus oryzae* HowB432 was transformed with HpaI digested pDSY112 and the transformants were recovered using the methods described in Example 5. Totally, 104 recovered transformants were grown in 24 well microtiter plates in ¼ strength MY25. Samples were taken at 5 and 7 days and assayed for cellulase activity as described below.

Cellulase activity was measured according to the following protocol which is derived from Novo Nordisk method AF 302.1/1-GB which is available from Novo Nordisk A/S, Bagsværd, Denmark upon request. A substrate solution containing 2% azo-arboxymethylcellulose was prepared by dissolving the material in 100 mM MOPS pH 7.0 uffer at 80° C. for 10 minutes. CAREZYME™ (Novo Nordisk A/S, Bagsærd, Denmark) was used as a standard. Stock solutions of 2.5 to 25 ECU per ml were prepared to construct a standard curve by diluting accordingly CAREZYMET™ in 100 mM MOPS pH 7.0 buffer. Five $\mu$l aliquots of the standards and samples (diluted for shakeflasks and fermentations) were pipetted into individual wells of a 96 well plate. A volume of 65 $\mu$l of the 2% azo-carboxymethylcellulose solution was pipetted into each of the wells and mixed. The reactions were incubated at 45° C. for 30 minutes and then stopped by the addition of 215 $\mu$l of stop reagent followed by mixing. The stop reagent was prepared by first suspending 0.2 g of ZnCl$_2$ in 20 ml of 250 mM MOPS pH 7.0 and adding the suspension to 80 ml of acidified ethanol containing 1.1 ml of concentrated HCl per liter of ethanol. The plate containing the stopped reaction was then centrifuged at 3000 rpm for 10 minutes. A 100 $\mu$l aliquot of each supernatant was pipetted into a 96 well plate and the absorbance measured at 600 nm. Using linear regression, the slope, intercept, and correlation coefficient were determined for the standards and samples.

The top ten cellulase producing transformants from the 24 well cultures were spore purified, and regrown in 24 well cultures as above and assayed for cellulase activity. The purified strains were also grown in MY25 in 125 ml shake flasks in MY25 pH 6.5 at 34° C. and samples were taken at 3 and 5 days for cellulase assays. *Aspergillus oryzae* HowB432 pDSY112 84-1-1 and *Aspergillus oryzae* HowB432 pDSY112 94-1-1 were also grown in fermentors (2 liters) as described in Example 8. Cellulase activities were measured as described above.

The results from the 24 well and shake flasks cultures are presented in Table 6 where the cellulase yield of *Aspergillus oryzae* HowB432 was normalized to 1.0.

TABLE 6

| Strain | 24 well (ECU/ml) | Shake flasks (ECU/ml) | Fermentation results (ECU/ml) |
| --- | --- | --- | --- |
| HowB432 | 1.0 | 1.0 | 1.0 |
| C112T50.1.1 | 2.0 | 0.9 | NA |
| C112T84.1.1 | 2.1 | 2.0 | 1.3 |
| C112T86.1.1 | 2.3 | 2.4 | NA |
| C112T94.1.1 | 2.5 | 1.3 | 1.4 |
| C112T95.1.1 | 2.1 | 1.3 | NA |
| C112T100.1.1 | 2.3 | 1.6 | NA |
| C112T101.1.1 | 1.9 | 1.6 | NA |
| C112T102.1.1 | 2.0 | 2.1 | NA |
| C112T103.1.1 | 1.5 | 2.0 | NA |
| C112T104.1.1 | 2.2 | 2.3 | NA |

A Southern blot of *Aspergillus oryzae* HowB432, *Aspergillus oryzae* DEBY599.3 and the pDSY112 transformants genomic DNAs digested with BglII was prepared and analyzed as described in Example 14 performed to determine whether pDSY112 had integrated at the homologous locus in the genome using the *Aspergillus oryzae* DEBY599.3 rescued flanking DNA as a probe.

A BglII band of 2.7 kb from *Aspergillus oryzae* HowB432 hybridized with the probe, while an ~8 kb BglII band from *Aspergillus oryzae* DEBY599.3 hybridized to the probe. In all of the transformants a wild-type BglII band of 2.7 kb and a second band corresponding to the transforming DNA hybridized to the probe. Therefore, none of the retransformants had exact gene replacements.

Example 24

*Aspergillus oryzae* Transformation with NdeI Linearized pDSY138 and Cellulase Expression Screening

*Aspergillus oryzae* HowB432 was transformed with NdeI digested pDSY138 using the method described in Example 5. Totally, 240 transformants were recovered which were grown in 24 well microtiter plates in ¼ strength MY25 as described in Example 8 except samples were taken at days 3 and 5 and assayed for cellulase activity as described in Example 23. The top 20 cellulase producing transformants were spore purified and retested in 24 well microtiter cultures. The top 8 cellulase producing once purified transformants were spore purified a second time and tested in shake flasks in full-strength MY25 as described in Example 8. The top 2 producers were also grown in a 2 liter fermentor as described in Example 8. Cellulase activity was measured as described in Example 23.

The results obtained are shown in Table 7 below where the cellulase yield of *Aspergillus oryzae* HowB432 is normalized to 1.0.

TABLE 7

| Strain | ECU/ml | Southern Results |
|---|---|---|
| HowB432 | 1.0 | wild-type |
| C138T21.1.1 | 1.15 | disrupted allele |
| C138T205.1.1 | 1.5 | wild-type and disrupted alleles |

A Southern blot of *Aspergillus oryzae* DEBY932, *Aspergillus oryzae* HowB432, and pDSY138 genomic DNA preparations digested with NdeI was prepared and analyzed as described in Example 14 to determine if the pDSY138 DNA had integrated at the homologous locus producing gene replacements in the transformants using the *Aspergillus oryzae* DEBY932 rescued flanking DNA as a probe.

The results of the Southern blot demonstrated that an NdeI band of approximately 5 kb from *Aspergillus oryzae* HowB432 hybridized to the rescued locus while a band of approximately 10 kb from *Aspergillus oryzae* DEBY932 hybridized to the probe. In Table 7, the column labeled Southern results indicated whether the transformants had a wild-type NdeI fragment of the size observed in the parent strain *Aspergillus oryzae* HowB432 or whether the transformants had a band corresponding to the disrupted size observed in *Aspergillus oryzae* DEBY932.

Example 25

*Aspergillus oryzae* Transformation with AseI/PvuI palB Disruption Cassette from pMT1936 and Cellulase Screening

*Aspergillus oryzae* HowB432 was transformed using the same transformation procedure described in Example 5 with a 5.5 kb AseI/PvuI fragment containing the palB disruption cassette. The linear fragment for transformation was isolated by digestion of pMT1936 with AseI and PvuI and separation of the fragment on a 1% agarose gel using a QIAquick Gel Extraction Kit according to the manufacturer's instructions. The transformants obtained were then evaluated for growth on Minimal medium plates at pH 6.5 or pH 8.0.

The results showed that 10 of the 312 transformants tested were unable to grow at pH 8.0 indicative of the palB minus phenotype. The 10 palB minus transformants and 10 of the transformants that were able to grow at pH 8.0 were spore purified and tested in 24 well and shake flask cultures for cellulase production according to the procedures described in Example 23. The results tabulated in Table 8 below demonstrated that palB minus strains were better cellulase producers than the palB plus strains.

Southern blots of the genomic DNA from an *Aspergillus oryzae* palB minus mutant, an *Aspergillus oryzae* palB plus strain, and *Aspergillus oryzae* HowB432 were performed as described in Example 14 to determine if the AseI/PvuI transforming DNA fragment had integrated as a clean replacement into the palB locus.

The results of the Southern blot (Table 8) demonstrated that some of the palB minus rains had clean disruptions while others did not.

TABLE 8

| Strain | PalB phenotype | Shake flasks (ECU/ml) | Southern pattern |
|---|---|---|---|
| HowB432 | plus | 1.0 | wild-type |
| CpalB5-1 | plus | 1.0 | wild-type and other |
| CpalB6-1 | plus | 1.2 | wild-type and other |
| CpalB7-1 | plus | 1.1 | wild-type and other |
| CpalB24-1 | plus | 1.7 | wild-type and other |
| CpalB28-1 | minus | 1.6 | other |
| CpalB34-1 | minus | 1.6 | disruption |
| CpalB45-1 | minus | 1.4 | disruption |
| CpalB47-1 | plus | 1.1 | wild-type and other |
| CpalB72-1 | plus | 1.3 | wild-type and other |
| CpalB76-1 | minus | 1.6 | disruption |
| CpalB89-1 | minus | 1.6 | disruption |
| CpalB153-1 | minus | 1.1 | disruption |
| CpalB161-1 | plus | 1.2 | wild-type and other |
| CpalB163-1 | minus | 1.9 | other |
| CpalB185-1 | minus | 1.8 | other |
| CpalB190-1 | minus | 1.4 | disruption |

Example 26

*Aspergillus oryzae* Transformation with AsnI/PvuI Manganese Superoxide Dismutase Disruption Cassette and Cellulase Screening

*Aspergillus oryzae* HowB432 was transformed with a 5.8 kb AsnI/PvuI fragment containing the manganese superoxide dismutase disruption cassette according to the same procedure described in Example 5.

Twenty transformants were obtained and tested for sensitivity to paraquat as described in Example 17. Seven of the 20 transformants were paraquat sensitive indicative of the manganese superoxide dismutase minus phenotype although they are sensitive to different levels of paraquat as indicated in Table 9 below. Those indicated as +++ for paraquat sensitivity are sensitive to as low as 2 mM paraquat, while those labeled–and ++ are not sensitive to paraquat and sensitive to intermediate levels of paraquat, respectively. All of the transformants were spore purified and tested in 24 well cultures for cellulase production as described in Example 23. The strains were also tested in 125 ml shake flasks cultures as described in Example 23. The results are shown in Table 9 below. The strains that are paraquat sensitive produce on average more CAREZYME™ than those strains that are not paraquat sensitive.

Southern blots of the transformants and *Aspergillus oryzae* HowB432 were prepared and analyzed as described in Example 14 to determine if the AsnI/PvuI manganese superoxide dismutase disruption cassette had integrated to give a clean replacement into the manganese superoxide dismutase disruption cassette locus.

The results of the Southern blot shown in Table 9 below indicate that the strains sensitive to 2 mM paraquat have only the disrupted locus of manganese superoxide dismutase, while those sensitive to intermediate levels of paraquat have both the wild-type locus and the disrupted cassette. The intermediate sensitivity to paraquat may be explained by the fact that manganese superoxide dismutase is a homodimer, and those cells expressing the wild-type and truncated manganese superoxide dismutase coded for by the disruption cassette would be producing heterodimers that are probably not functional.

TABLE 9

| Strain | Paraquat sensitivity | Shake flasks (Relative LU/ml) | Southern Results |
|---|---|---|---|
| HowB432 | − | 1.00 | wild-type |
| 432162T3 | +++ | 1.26 | disrupted |
| 432162T7 | ++ | 1.24 | wild-type & other |
| 432162T8 | − | 1.21 | wild-type & other |
| 432162T9 | − | 0.61 | wild-type & other |
| 432162T10 | ++ | 1.14 | wild-type & other |
| 432162T11 | ++ | 1.04 | wild-type & other |
| 432162T12 | ++ | 1.12 | wild-type & other |
| 432162T15 | − | 0.44 | wild-type & other |
| 432162T16 | ++ | 1.10 | wild-type & other |
| 432162T17 | +++ | 1.53 | — |
| 432162T18 | − | 1.12 | — |
| 432162T19 | +++ | 1.44 | — |

Example 27

Construction of Glucose Transporter Gene Overexpression Plasmids pHB218 and pDSY153 and Stop Control Plasmids pDSY152 and pDSY155

Plasmids to overexpress the glucose transporter rescued locus from *Aspergillus oryzae* DEBY599.3 were constructed to determine if overexpression of the glucose transporter would lead to an increase in the yields of *Humicola lanuginlosa* lipase and cellulase. The glucose transporter open reading frame was PCR amplified to place SwaI and PacI sites at the 5' and 3' end of the ORF, respectively. The following primers synthesized with an Applied Biosystems Model 394 DNA/RNA Synthesizer according to the manufacturer's instructions were used in combination with 0.2 μg of pDSY112 in the amplification:

961176: 5'-ATTTAAATGGTCCTCGGTGGATCAAGC-3' (SEQ ID NO:44)

961177: 5'-TTAATTAATTAGTCCTGTCTGCGCTGGT-3' (SEQ ID NO:45)

Figure 27:
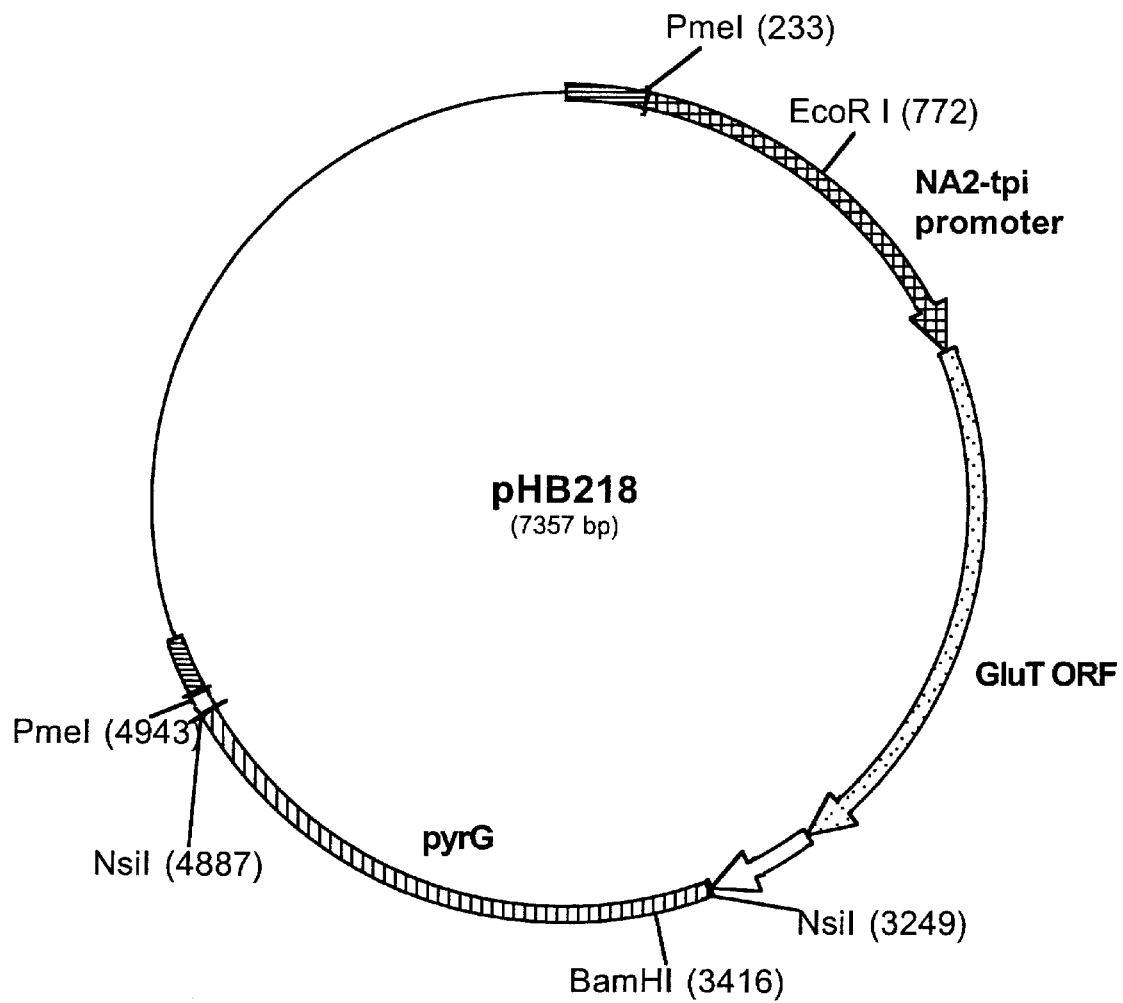
FIG. 27 is a restriction map of pHB218.

The conditions and parameters used for the amplification are described in Example 2. Ten μl of the PCR reaction was electrophoresed on an agarose gel, and a 1.5 kb product was obtained as expected. The PCR product was cloned using a pPCR-Script™ Kit (Stratagene, La Jolla, Calif.) according to the manufacturer's protocols. The ligation reaction was used to transform *E. coli* DH5α cells, and plasmid DNA was isolated from several of the transformants using the QIAwell-8 Plasmid Kit. The plasmids were digested with NotI and EcoRI to determine which clones had the 1.5 kb insert. Six of the 11 clones analyzed had the correct size insert as determined by electrophoreses on an agarose gel. One of the clones, pDSY119, was digested with PacI and SwaI, and the digest was run on an agarose gel. The 1.5 kb SwaI/Pac I band was excised from the gel, and DNA was purified from the gel slice using the QIAQuick Gel Extraction Kit. The 1.5 kb fragment was ligated with SwaI/PacI cut pBANel3 (FIG. 3) using standard conditions (Sambrook et al., 1989, supra). The ligation was used to transform *E. coli* DH5α cells, and plasmid DNA was isolated from several of the transformants. The plasmids were digested with SwaI/PacI to determine which clones had the expected 1.5 kb insert. The final plasmid was designated pHB218 (FIG. 27).

As a control for the overexpression experiments, a derivative of pHB218 in which a stop codon was inserted at amino acid 9 in the glucose transporter open reading frame was made using site-directed mutagenesis. A MORPH™ Site-Specific Plasmid DNA Mutagenesis kit from 5 Prime→3 Prime was used for the mutagenesis, and protocols provided with the kit were followed. The reaction contained pHB218 as template, and the mutagenic primer used was:

970545: 5'-CGGTGGATCAAGCGGTTAATTAATCAC TCCGTACCTGAT-3' (SEQ ID NO:46)

Several *E. coli* colonies were obtained after following the protocols, and plasmid DNA was isolated from the colonies using the QIA-Well8 plasmid kit. The plasmids were digested with PacI since the mutagenic primer introduced a PacI site which served as a marker for the mutagenesis. Two of the plasmids with the extra PacI site indicative of a successful mutagenesis were sequenced as described in Example 2 to confirm the presence of the stop codon at amino acid 9 in the ORF. The pHB218 derivative with the stop codon at amino acid 9 was, designated pDSY152.

Figure 28:
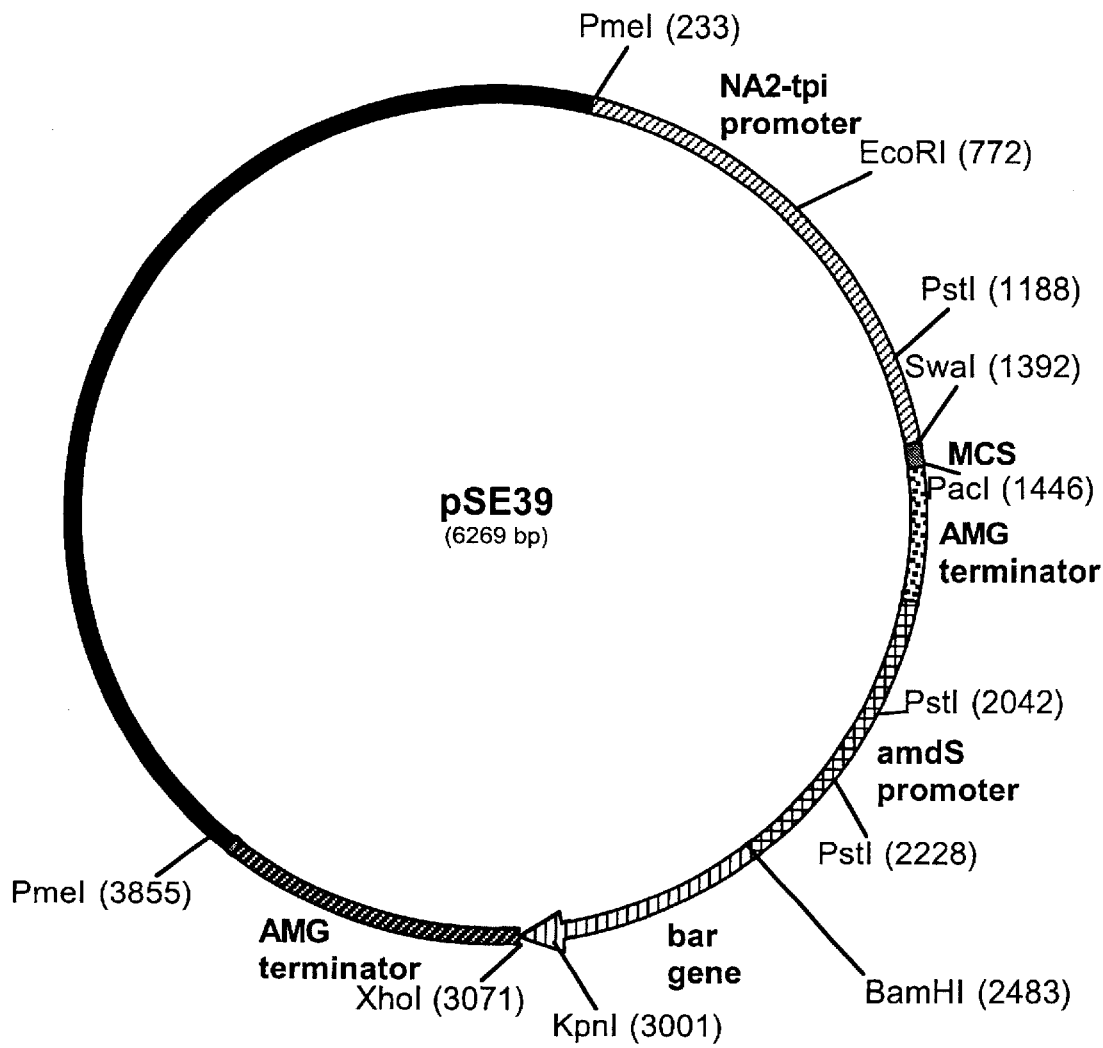
FIG. 28 is a restriction map of pSE39.
Figure 29:
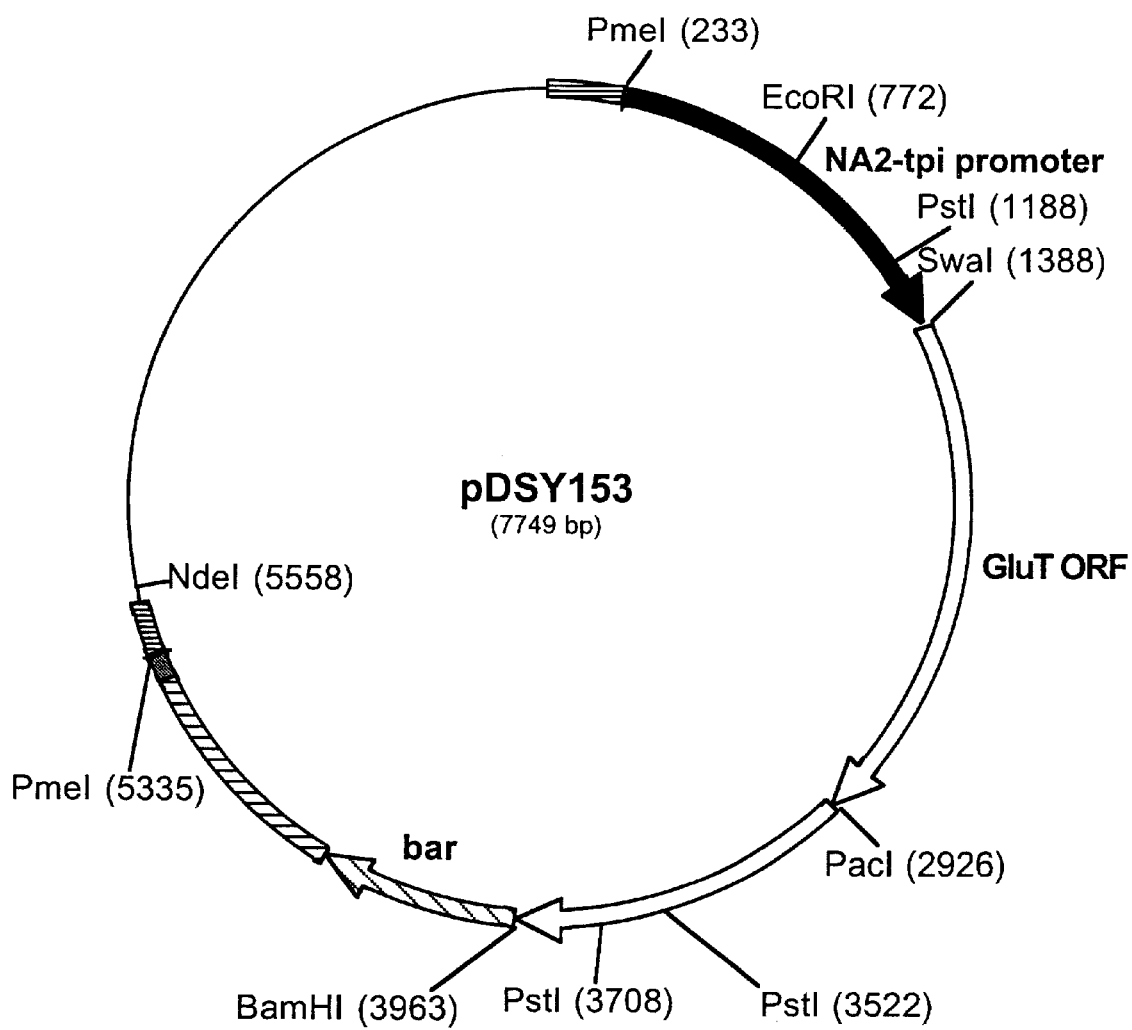
FIG. 29 is a restriction map of pDSY153.

Versions of pHB218 and pDSY152 in which the selectable marker was the bar gene were constructed for transformation of strains which are pyrG plus. The SwaI/PacI inserts from pHB218 and pDSY152 were isolated by restriction digestion, electrophoresed on an agarose gel, and purified using QIAQuick Gel Extraction Kit. The inserts were ligated into pSE39 (FIG. 28) and digested with SwaI/PacI. The ligation reaction was used to transform *E. coli* DH5α, and plasmid DNA was isolated from the colonies as described above. The plasmids were digested with SwaI/PacI to determine which clones contained the expected 1.5 kb insert. The plasmids were sequenced as described in Example 2 to confirm the presence or absence of the stop codon at amino acid 9 in pDSY155 and pDSY153 (FIG. 29), respectively. The only difference between pDSY155 and pDSY153 was the stop codon at amino acid 9 of the glucose transporter ORF in pDSY155.

Example 28

Transformation of *Aspergillus oryzae* HowB430 and *Aspergillus oryzae* HowB432 with pHB218 and pDSY152 and Lipase and Cellulase Screening, Respectively.

*Aspergillus oryzae* HowB430 was transformed with pHB218 or pDSY152, and the transformants were recovered using the methods described in Example 5. One hundred and twenty transformants each with pHB218 and pDSY152 were recovered, grown in 24-well microtiter plates in ¹⁄₁₀₀ strength MY25 and assayed for lipase activity after 3 and 5 days as described in Example 8. The assay results showed that there was a slight shift towards higher lipase production in the pHB218 transformants versus the pDSY152 transformants supporting the idea that overexpression of the glucose transporter has a positive effect on lipase expression.

*Aspergillus oryzae* HowB432 was transformed with pHB218 and pDSY152, and the transformants were recovered using the methods described in Example 5. One hundred transformants each with pHB218 and pDSY152 were recovered, grown in 24-well microtiter plates in ¼ strength MY25 and assayed for cellulase activity after 3 and 5 days as described in Example 23. The assay results showed that there was a shift towards higher cellulase production in the pHB218 transformants versus the pDSY152 transformants indicating that overexpression of the glucose transporter had a positive effect on cellulase expression.

Example 29

Transformation of *Aspergillus oryzae* DEBY10.3 with pDSY153 and pDSY155 and Lipage Screening.

*Aspergillus oryzae* DEBY10.3 was transformed with pDSY153 and pDSY155, and the transformants were recovered using the methods described in Example 5. Two hundred sixteen and 144 transformants with pDSY153 and pDSY155, respectively, were recovered, grown in 24-well microtiter plates in 1/100 strength MY25, and assayed for lipase activity on days 4 and 6 as described in Example 8. There was shift towards higher lipase production in the pDSY153 transformants when compared to the pDSY155 transformants indicating that overexpression of the glucose transporter led to an increase in lipase production and also suggesting that the palB minus effect and the glucose transporter overexpression were additive.

Example 30

Identification of Tagged Event in *Aspergillus oryzae* HowL795

Genomic DNA was prepared from *Aspergillus oryzae* HowL795 according to Example 9. One μg of DNA was digested with either SnaB1 or NsiI. Both enzymes cleave within the pyrG gene contained on the tagging construct. The DNA was then diluted to 4 ng/μl and recircularized with T4 Ligase at 22° C. for 18 hours. Inverse PCR was then performed using approximately 500 ng of recircularized DNA using the primers shown below which were synthesized with an Applied Biosystems Model 394 DNA/RNA Synthesizer according to the manufacturer's instructions. Both were located downstream of the NsiI and SnaBI sites.

Primer x: 5'-GCACTCGAATGACTACT-3' (SEQ ID NO:47)

Primer y: 5'-CGCATCATACTTGCGACA-3' (SEQ ID NO:48)

The inverse PCR amplification reaction contained the following components: 500 ng of recircularized DNA, 150 pmoles of primer x, 150 pmoles of primer y, 1 mM each of dATP, dCTP, dGTP, and dTTP, 1×Taq polymerase buffer, and 2.5 U of Taq polymerase. The reaction was incubated in an Ericomp Thermal Cycler programmed as follows: One cycle at 95° C. for 5 minutes followed by 30 cycles each at 95° C. for 1 minute, 55° C. for minute and 72° C. for 2 minutes. The PCR product was isolated by electrophoresis on a 1% agarose gel.

PCR of the religated SnaBI DNA amplified a 4 kb fragment whereas PCR of the religated NsiI DNA amplified a 2 kb fragment. PCR confirmed that the smaller NsiI fragment was contained within the larger SnaBI fragment.

DNA sequence analysis was performed according to the procedure described in Example 2 using primer A. The analysis identified that the insertion of pSO122 had occurred in the 3' non-translated region of the amdS gene contained within plasmid pBANe8.

Example 31

Construction of *Aspergillus oryzae* MStr107

Figure 30:
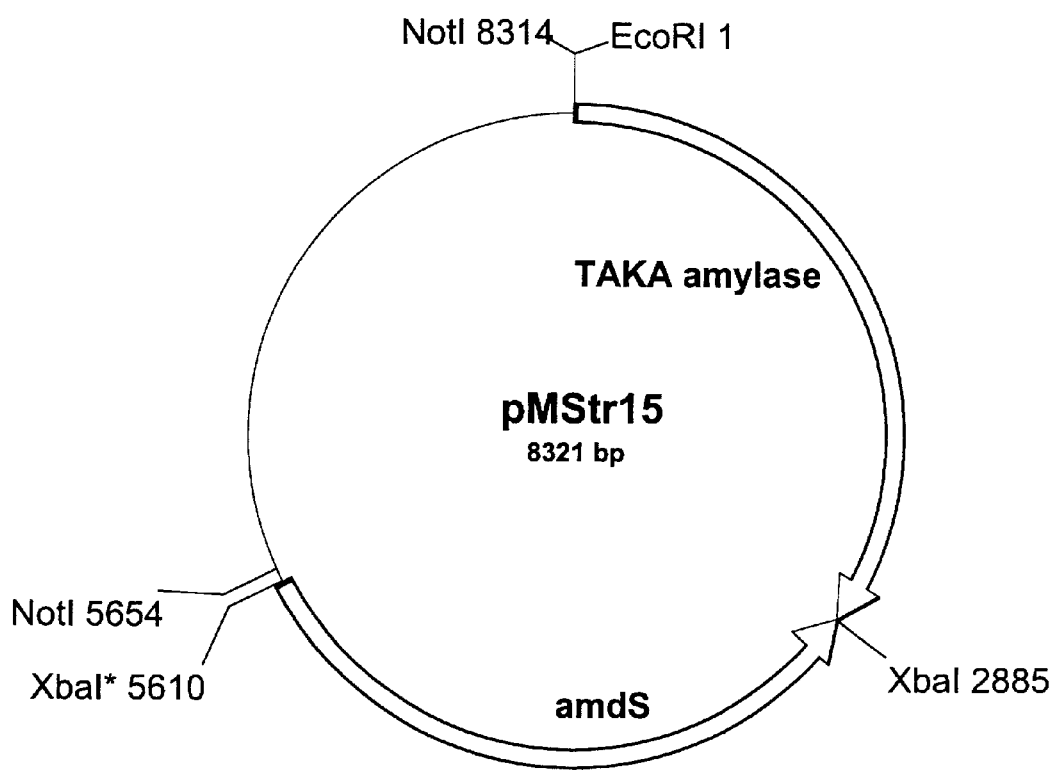
FIG. 30 is a restriction map of pCaHj505.

*Aspergillus oryzae* MStr107 was constructed to contain extra copies of one of the native alpha-amylase (TAKA) genes (FUNGAMYL™ gene, Novo Nordisk A/S, Bagsværd, Denmark), by transforming *Aspergillus oryzae* HowB101 with a DNA fragment from pMStrl5. pMStr15 was constructed from pCaHj505 and pTAKA17 as described below. Standard methods were employed (Sambrook et al., 1989, supra) except where noted.

pCaHj505 (FIG. 30) was constructed to contain the *Aspergillus oryzae* NA-14 alpha-amylase (TAKA) promoter, the *Aspergillus niger* glucoamylase (AMG) terminator, and the *Aspergillus nidulans* amdS gene from the following fragments:

a) The vector pToC65 (WO 91/17243) digested with EcoRI and XbaI.

b) A 2.7 kb XbaI fragment from *Aspergillus nidulans* carrying the amdS gene (Corrick et al., 1987, Gene 53: 63–71). The amdS gene was used as a selective marker in fungal transformations. The amdS gene was modified so that the BamHI site normally present in the gene was destroyed. This was done by introducing a silent point mutation using the primer: AGAAATCGGG-TATCCTTTCAG (SEQ ID NO:49).

c) A 0.6 kb EcoRI-BamHI fragment carrying the *Aspergillus oryzae* NA-14 alpha-amylase promoter.

d) A 675 bp XbaI fragment carrying the *Aspergillus niger* glucoamylase transcription terminator. The fragment was isolated from the plasmid pICAMG/Term (EP 238 023).

Figure 31:
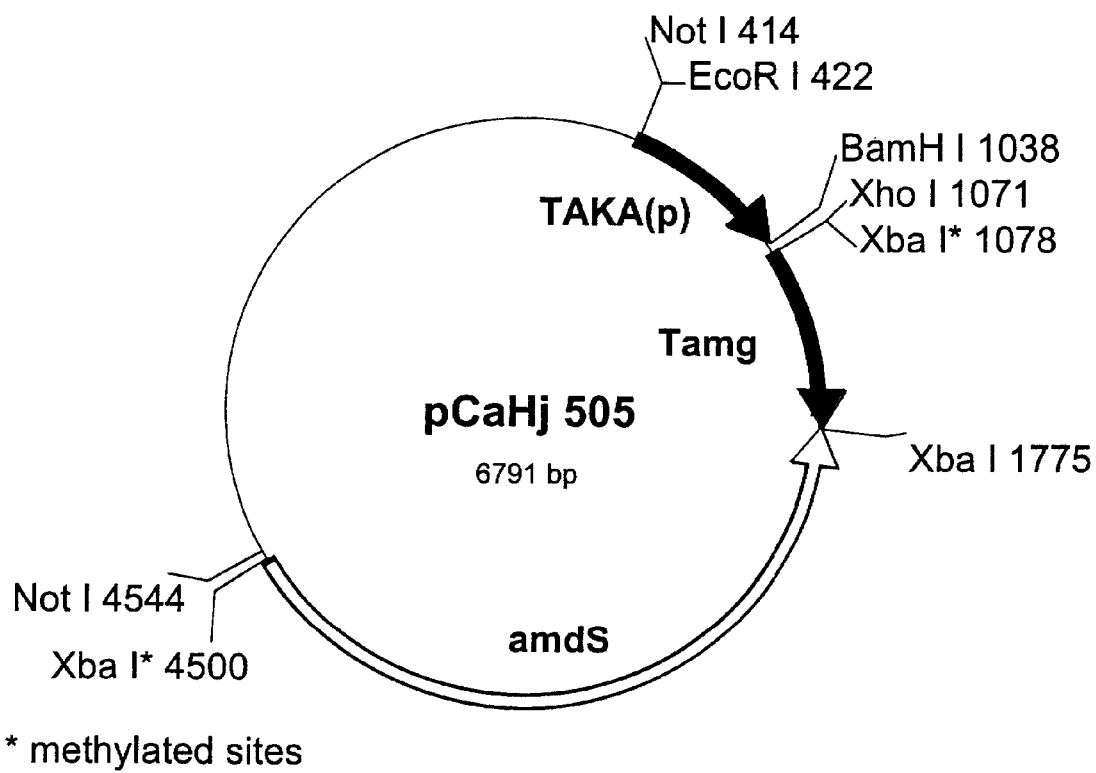
FIG. 31 is a restriction map of pMStr107.

The BamHI site of fragment c was connected to the XbaI site in front of the transcription terminator on fragment d via the pIC19R linker (BamHI to XbaI) (Boehringer Mannheim, Indianapolis, Ind.).

pMStr15 (FIG. 31) was constructed to contain the *Aspergillus oryzae* NA-14 alpha-amylase promoter, gene and terminator and the *Aspergillus nidulans* amdS gene. The alpha-amylase gene with promoter and terminator was excised from pTAKA17 (European patent 0238 023) as a 2.9 kb EcoRI-HindIII fragment and cloned adjacent to the amdS gene in the vector pCaHj505 by replacing the EcoRI-XbaI promoter/terminator fragment in pCaHj505. To facilitate cloning, the recessed 3' termini generated by HindIII and XbaI digestion were filled in.

A single linear DNA fragment containing both the alpha-amylase gene and the amdS gene was obtained by digesting pMStr15 with NotI, resolving the vector and insert sequences using agarose gel electrophoresis, excising the appropriate DNA band from the gel, and purifying the DNA from the agarose using GenElute™ Agarose Spin Columns according to the manufacturer's directions (Supelco, Bellefonte, Pa.). This 5.6 kb NotI fragment was used to transform *Aspergillus oryzae* HowB101 to construct *Aspergillus oryzae* MStr107, using the transformation protocol and selective medium described in Example 2. Transformants were propagated from single colonies twice in succession on COVE medium with 0.1% Triton X100 before performing additional screens.

Aspergillus or,yzae MStr107 was selected from among the transformants based on its ability to produce more alpha-amylase than *Aspergillus oryzae* HowB101. The ability of the transformants to produce alpha-amylase was determined by culturing them in 10 ml of YPM medium for 4 days at 30° C. with shaking and resolving 5 μl of the culture medium by SDS-PAGE according to standard methods. The strain producing the most alpha-amylase under these conditions was selected as *Aspergillus oryzae* MStr107, and was compared in a 3 liter fermentation culture to *Aspergillus oryzae* HowB101. The medium was composed of maltose syrup, yeast extract, $KH_2PO_4$, $K_2SO_4$, $(NH_4)_2SO_4$, citric acid, $MgSO_4$, trace metals and uridine. Under these conditions, *Aspergillus oryzae* MStr107 produced 360% of *Aspergillus oryzae* HowB101.

Example 32

*Aspergillus oryzae* Mstr107 Transformation with Linearized pDSY82

Protoplasts of *Aspergillus oryzae* Mstr107 were prepared as described in Example 2. A 5–15 μl aliquot of pDSY82 (6

µg) linearized with 1.25 U of XbaI was added to 0.1 ml of the protoplasts at a concentration of $2 \times 10^7$ protoplasts per ml in a 14 ml Falcon polypropylene tube followed by 250 µl of 60% PEG 4000–10 mM $CaCl_2$-10 mM Tris-HCl pH 7, gently mixed, and incubated at 37° C. for 30 minutes. Three ml of SPTC were then added and the suspension was gently mixed. The suspension was mixed with 12 ml of molten overlay agar (1×COVE salts, 1% NZ amine, 0.8 M sucrose, 0.6% Noble agar) or 3 ml of STC medium and the suspension was poured onto a Minimal medium plate. The plates were incubated at 37° C. for 3–5 days.

The transformation frequency of *Aspergillus oryzae* MStr107 with pDSY82 and XbaI was approximately 200 transformants/µg of DNA. A library of approximately 30,000 transformants was obtained. Spores from 70 pools with approximately 400 transformants in each pool were collected and stored in a 20% glycerol, 0.1% Tween 80 at −80° C. The pools and transformants from these libraries were designated with the letter "x".

Example 33

Characterization of Integration Events in "REMI" *Aspergillus oryzae* MStr107 Transformants Transformants of *Aspergillus oryzae* MStr107 with pDSY82 and XbaI (library "x") were analyzed as described in Example 6. Genomic DNA was isolated from 40 transformants, 20 from one pool (×15) and 20 from 20 various pools. DNA samples were cut with HindIII, resolved, blotted and probed with radiolabeled pDSY82. Thirty-three of 40 displayed apparently novel band patterns, suggesting that plasmid integrations were distributed to different sites in the genome. For 19 of the 40 transformants the band patterns suggested that only one copy of pDSY82 integrated in the genome, while more than one copy was observed in the remaining 21 transformants. DNA from the 20 transformants taken from various pools was also cut with XbaI, resolved, blotted and probed with radiolabeled pDSY82 as described in Example 6. A single, plasmid-sized band was observed indicating REMI had occurred at an XbaI site in 9 of the transformants.

Example 34

FUNGAMYL™ Expression Screening

The *Aspergillus oryzae* MStr107 tagged mutant library "x" pools described in Example 32 were assayed for FUNGAMYL™ expression.

For 96-well plate screens, MTBCDYU medium was used. For 24-well plate methods, 4×MTBCDYU medium was used.

Primary 96-well plate screens involved the dilution of spores from distinct pools into MTBCDYU so that one spore on average was inoculated per well when 100 µl of medium was dispensed into the wells. After inoculation, the 96-well plates were grown for 3–4 days at 34° C. under static conditions. Cultures were then assayed for FUNGAMYL™ activity as described below. Mutants of interest were isolated twice on YPG or Cove plates, and single colonies transferred to Cove agar slants. Spores from Cove slants were inoculated into 24-well plates containing 4×MTBCDYU with approximately $10^3$ spores per well and grown under static conditions for 4 days at 34° C. Cultures were then assayed for FUNGAMYL™ activity as described below.

The FUNGAMYL™ assay substrate (4-nitrophenyl-alpha-D-maltoheptasid-4,6-O-ethyliden, EPS) was prepared as a ½ strength solution relative to the instructions given by the manufacturer (Boehringer Mannheim, Indianapolis, Ind.). The substrate was prepared in HEPES pH 7.0 buffer. A FUNGAMYL™ standard (FUNGAMYL™, Novo Nordisk A/S, Bagsærd, Denmark) was prepared to contain 2 FAU/mi in HEPES pH 7.0 buffer. The standard was stored at −20° C. until use. FUNGAMYL™ stock was diluted appropriately to obtain a standard series ranging from 0.02 to 0.2 FAU/ml just before use. Broth samples were diluted in HEPES buffer and 25 µl aliquots were dispensed to wells in 96-well plates followed by 180 µl of diluted substrate. Using a plate reader, the absorbance at 405 nm was recorded as the difference of two readings taken at approximately 1 minute intervals. FUNGAMYL™ units/ml (FAU/ml) were calculated relative to the FUNGAMYL™ standard solutions.

The results of the 96-well screen followed by the 24-well screen identified for further evaluation 51 transformants from the pDSY82 and XBaI transformations. These identified transformants produced higher levels of FUNGAMYL™ than the control strain *Aspergillus oryzae* MStr107.

Example 35

Shake Flask and Fermentation Evaluation

The highest FUNGAMYL™-producing DNA-tagged mutants described in Example 34 were evaluated in shake flasks and fermentors.

Shake flask evaluations were performed by inoculating half the spore content of a COVE slant suspended in a suitable volume of sterile water containing 0.02% TWEEN-80 into 100 ml of G1-gly medium at pH 7.0 in a 500 ml shake flask. The G1-gly shake flasks were incubated at 34° C. for 1 day at 270 rpm. Next, 5 ml of the G1-gly cultures were inoculated into 100 ml of 1/5MDU2BP at pH 6.5 in 500 ml shake flasks. Samples were taken at day 3, and FUNGAMYL™ activity was measured as described in Example 34.

The DNA-tagged mutant X70–25 and 257D11 were grown in a 3 liter lab fermentor containing a medium composed of Nutriose, yeast extract, $MgSO_4$, $KH_2PO4$, citric acid, $K_2SO_4$, $(NH_4)_2SO_4$ and trace metals solution. The fermentation was performed at a temperature of 34° C., a pH of 7, and the agitation was maintained between 1000–1200 rpm for 5 days. FUNGAMYL™ activity was measured by partial degradation of EPS to $G_2$ and $G_3$ derivatives (G=glucose). The $G_2$ and $G_3$ derivatives were then degraded to glucose and yellowish colored p-nitrophenolate anion by the addition of a surplus of alpha-glucosidase. The analytical output was determined as the change in absorbance at 405 nm per unit time (3 minutes) at 37° C. and pH 7.1 after a preincubation for 2.5 minutes. FUNGAMYL™ was used as standard.

The results obtained are shown in Table 10 below where the FUNGAMYL™ yield of *Aspergillus oryzae* MStr107 as a control is normalized to 1.0.

TABLE 10

FUNGAMYL ™ Expression by DNA Tagged Mutants

| Strain Description | Pool | # Screened | 24-well in 96-well Plates (FAU/ml) | Shake Flask Plates Results (FAU/ml) | Fermentation Results (FAU/ml) |
|---|---|---|---|---|---|
| HowB101 | NA | NA | 0.4 | 0.4 | 0.3 |
| MStr107 | NA | NA | 1.0 | 1.0 | 1.0 |
| X70-25 | x70 | 580 | 1.4 | 1.3 | 1.2 |
| 257D11 | x6 | 480 | 1.5 | 1.4 | 1.0 |
| X70-42 | x70 | 580 | 1.3 | 1.3 | ND |
| 263A3 | x6 | 480 | 1.4 | 1.6 | ND |
| X69-246 | x69 | 350 | 1.6 | 1.4 | ND |
| X59-122 | x59 | 580 | 1.3 | 1.3 | ND |
| X49-233 | x49 | 460 | 1.4 | 1.4 | ND |

As shown in Table 10, the mutants produced approximately 30–60% more FUNGAMYL™ than the control strain *Aspergillus oryzae* MStr107 when grown in 24-well plates and when grown in shake flasks. The mutant, *Aspergilius oryzae* X70–25 produced approximately 20% more FUNGAMYLTM than the control strain *Aspergillus oryzae* MStr107 when grown in fermentors.

Example 36

Screening for Morphological Mutants

The 5 "e" pools and 5 "b" pools described in Example 5 were screened for altered morphology by plating on CM-1 agar and incubating at 34° C. for 4 days.

Twenty-four colonies having altered plate morphology and covering the morphological variation within the pool were transferred to fresh CM-1 plates and incubated 5 days at 34° C. for single colony isolation. Each morphology (in most cases 1) on a plate, was transferred from a single colony to the center of a CM-1 plate and a PDA plate, and incubated 6–8 days at 34° C. before the morphology was evaluated, i.e., the diameter and the appearance. A total of 218 morphological mutants was transferred to COVE plates and incubated at 34° C. for 1–2 week to generate spores.

Example 37

Evaluation of Morphological Mutants

The morphological mutants isolated in Example 36 were evaluated in 24-well plates for lipase production according to the procedure described in Example 7. The highest yielding mutants were compared with respect to plate morphology on CM-1 agar, and 23 mutants covering the observed morphological variation were further tested in shake flasks containing CD medium to evaluate lipase production.

Approximately 0.25 ml of spore suspension from a CM-1 plate was inoculated into 25 ml of G1-gly medium in a 125 ml PP flask and incubated at 34° C. for 24 hours. Then 0.5 ml of the 24 hour seed flask was transferred to 50 ml of CD medium supplemented with 1.0 µl of FUNGAMYL™ 800L (Novo Nordisk A/S, Bagværd, Denmark) in a 125 ml PP flask, and incubated at 34° C., 200 rpm. The culture was sampled after 2 and 3 days and assayed for lipase activity as described in Example 7.

The isolated mutants were also tested in the following manner in oxygen limited media. *Aspergillus oryzae* HowL536.3 was run as a control since the strain possessed the wild type morphology and did not require uridine for growth. Approximately 250 µl of spore suspension was inoculated into a 125 ml shake flask containing 25 ml OL-1 medium and incubated at 34° C., 200 rpm until residual glucose was <<1 g/l measured using DIASTIX™ (Bayer, Elkhart, Ind.). Then 75 ml OL-6 medium was added to each flask and further incubated at 34° C., 200 rpm for approximately 25 hours until residual glucose in the *Aspergillus oryzae* HowL536.3 flask was approximately 5 g/l. At that time, all the flasks were assayed for residual glucose, and the flasks with significantly lower glucose (0–2 g/l) were considered positive. The majority of the flasks averaged around 5–10 g/l.

Twenty mutants converting the glucose faster than average were considered likely to be easier to aerate and were further tested in shake flasks containing CD medium as described above to evaluate lipase expression.

Based on these tests, 14 mutants were identified and further evaluated in lab fermentors according to the procedure described in Example 8. The morphological mutants listed below in Table 11 were identified.

TABLE 11

Morphological mutants

| Strain | Construction | Pool | Description |
|---|---|---|---|
| P2-7.10 | pDSY82 + BamHI | b2 | colonial, easy to aerate, 50% yield increase in fermentors |
| P3-2.1 | pDSY82 + BamHI | b3 | flat, yield 40% yield increase in fermentors |
| P4-8.1 | pDSY82 + BamHI | b5 | easy to aerate, 30% yield increase in fermentors |
| P5-7.1 | pDSY82 + BamHI | b6 | easy to aerate, 60% yield increase in fermentors |
| P7-14.1 | pDSY81 + EcoRI | e2 | colonial, easy to aerate, 50% yield increase in fermentors |
| P8-10.1 | pDSY81 + EcoRI | e3 | easy to aerate, yield increased 50% in fermentors |

Example 38

Rescue of Plasmid DNA and Flanking DNA from Morphological Mutants

The plasmid DNA and genomic flanking loci were isolated from mutants *Aspergillus oryzae* P4-8.1 and P7-14.1 using the procedure described in Example 9 except for the restriction endonuclease(s) used. Transformant *E. coli* HB101 p4-8.1 contained a BglII rescued locus from mutant *Aspergillus oryzae* P4-8.1. Transformant *E. coli* HB101 p7-14.1 contained a NarI rescued locus from mutant *Aspergillus oryzae* P7-14.1.

The plasmid DNA and genomic flanking loci were isolated from mutants *Aspergillus oryzae* DEBY7-17.2, DEBY3-2.1, DEBY5-7.1, and DEBY8-10.1. The rescued plasmids were generated as previously described in Example 9 with the exception that rescues pSMO717, pSMO321, pHowB571, and pSMO810 were isolated from transformed *E. coli* DH5α cells.

Transformant *E. coli* DH5α pSMO717 contained the BglII rescued locus from mutant *Aspergillus oryzae* DEBY7-17.2. Transformant *E. coli* DH5α pSMO321 contained the BglII rescued locus from mutant *Aspergilus oryzae* DEBY3-2.1. Transformant *E. coli* DH5α pHowB571 contained the NdeI rescued locus from mutant *Aspergillus oryzae* DEBY5-7.1. Transformant *E. coli* DH5α pSMO810 contained the NdeI rescued locus from mutant *Aspergillus oryzae* DEBY8-10.1.

Example 39

Characterization of Morphological Mutant Aspergillus oryzae P4-8.1 Rescued Locus p4-8.1

The *Aspergillus oryzae* P4-8.1 rescued locus p4-8.1 containing 915 and 665 bp regions on either side of the integration event was sequenced according to the procedure described in Example 2. The nucleic acid sequence (SEQ ID NO:50) and the deduced amino acid sequence (SEQ ID NO:51) are shown in FIG. 32. The nucleic acid sequence suggested that the integration event occurred within an open reading frame for a homologue of the *Saccharomyces cerevisiae* YHM4 Heat Shock protein gene. The deduced amino acid sequence (SEQ ID NO:51) showed 40.2% identity to the *Saccharomyces cerevisiae* YHM4 Heat Shock protein (SEQ ID NO:52) and 41.8% identity to a *Schizzosaccharomyces pompe* Heat Shock Protein 70 (SEQ ID NO:53).

Example 40

Aspergillus oryzae Transformation with BglII Linearized p4-8.1 and Morphology Screening To verify the link between the observed plate morphology for *Aspergillus oryzae* P4-8.1 and the rescued genomic locus, *Aspergillus oryzae* HowB430 was transformed with the BglII linearized rescued locus of *Aspergillus oryzae* P4-8.1, p4-8.1, using the procedure described in Example 5.

Sixty-six transformants were obtained, transferred to CM-1 agar, and incubated at 34° C. for 3–4 days to evaluate the morphology. Sixteen transformants with the correct plate morphology were transferred to fresh CM-1 plates as center colonies, and 12 transformants maintaining the plate morphology after 4 days at 34° C. were analyzed by Southern blot analysis with a PCR amplified 300 bp fragment of the rescued locus as a probe. The fragment was PCR amplified using the primers below synthesized with an Applied Biosystems Model 394 DNA/RNA Synthesizer according to the manufacturer's instructions.

HSP-1: 5'-TACGGTTGACAGTGGAGC-3' (SEQ ID NO:54)

HSP-3r: 5'-CACTGACTTCTCCGATGC-3' (SEQ ID NO:55)

The amplification reaction (50 µl) contained the following components: 0.2 ng of p4-8.1, 50 pmol of primer HSP-1, 50 pmol of primer HSP-3r, 0.25 mM each of dATP, dCTP, dGTP, and dTTP, 1×Taq polymerase buffer, and 2.5 U of Taq polymerase. The reaction was incubated in an Ericomp Thermal Cycler programmed as follows: One cycle at 95° C. for 3 minutes; 30 cycles each at 95° C. for 1 minute, 58° C. for 1 minute, and 72° C. for 1.5 minutes; and 1 cycle at 72° C. for 5 minutes. The PCR product was isolated by electrophoresis on a 1% agarose gel.

Samples of the genomic DNA were obtained from each of the 12 transformants obtained according to the method described in Example 9. The genomic DNAs were digested with BglII and submitted to Southern analysis according to the procedure described in Example 14.

All 12 transformants were affected at the rescued locus, suggesting a connection between this locus and the observed plate morphology.

Example 41

Characterization of Morphological Mutant Aspergillus oryzae P7-14.1 Rescued Locus p7-14.1

The *Aspergillus oryzae* P7-14.1 rescued locus p7-14.1 containing 1040 and 520 bp regions on either side of the integration event was sequenced according to the procedure described in Example 2. The nucleic acid sequence (SEQ ID NO:56) and the deduced amino acid sequence (SEQ ID NO:57) are shown in FIG. 33. The nucleic acid sequence suggested that the integration event occurred within an open reading frame for a homologue of the *Aspergillus nidulans* chitin synthase B (chsB) gene and the *Aspergillus fumigatus* chitin synthase G (chsG) gene. Identities of 94% and 80% were found when the deduced amino acid sequences of the two sides of the rescued locus (SEQ ID NO:57), the chsB gene (SEQ ID NO:58), and the chsG gene (SEQ ID NO:59) were compared.

Disruption of the chsB gene in *Aspergillus nidulans* is known to change the morphology significantly (Yanai et al., 1994, Biosci. Biotech. Biochem. 58: 1828–1835), and in *Aspergillus fumigatus* disruption of the chsG gene is known to cause colonial morphology (Mellado et al., 1996, *Molecular Microbiology* 20: 667–679), which is the observed phenotype of *Aspergillus oryzae* P7-14.1.

Example 42

Aspergillus oryzae Transformation with a Linear chs Fragment and Morphology Screening A 1.9 kb DNA fragment was generated by PCR using as the template *Aspergillus oryzae* HowB430 genomic DNA prepared as described in Example 6. Primer A, 5'-CACCAAGTCAGAGCGTC-3' (SEQ ID NO:60), was derived from the rescued chs *Aspergillus oryzae* homolog. Primer 5, 5'-GGICCITTYGAYGAYCCICA-3' (SEQ ID NO:61), was degenerate based on the consensus sequence of the *Aspergillus fumigatus* chsG and *Aspergillus nidulans* chsB genes. The amplification reaction (50 µl) contained the following components: 10 ng of pHB220, 48.4 pmol of each primer, 1 mM each of dATP, dCTP, dGTP, and dTTP, and the Advantage-GC™ Tth Polymerase Mix (Clontech, Palo Alto, Calif.). The reaction was incubated in an Ericomp Thermal Cycler programmed as follows: One cycle at 95° C. for 3 minutes; 30 cycles each at 95° C. for 1 minute, 58° C. for 1 and 72° C. for 3 minutes; and 1 cycle at 72° C. for 5 minutes. The PCR product was isolated by electrophoresis on a 1% agarose gel.

Figure 34:
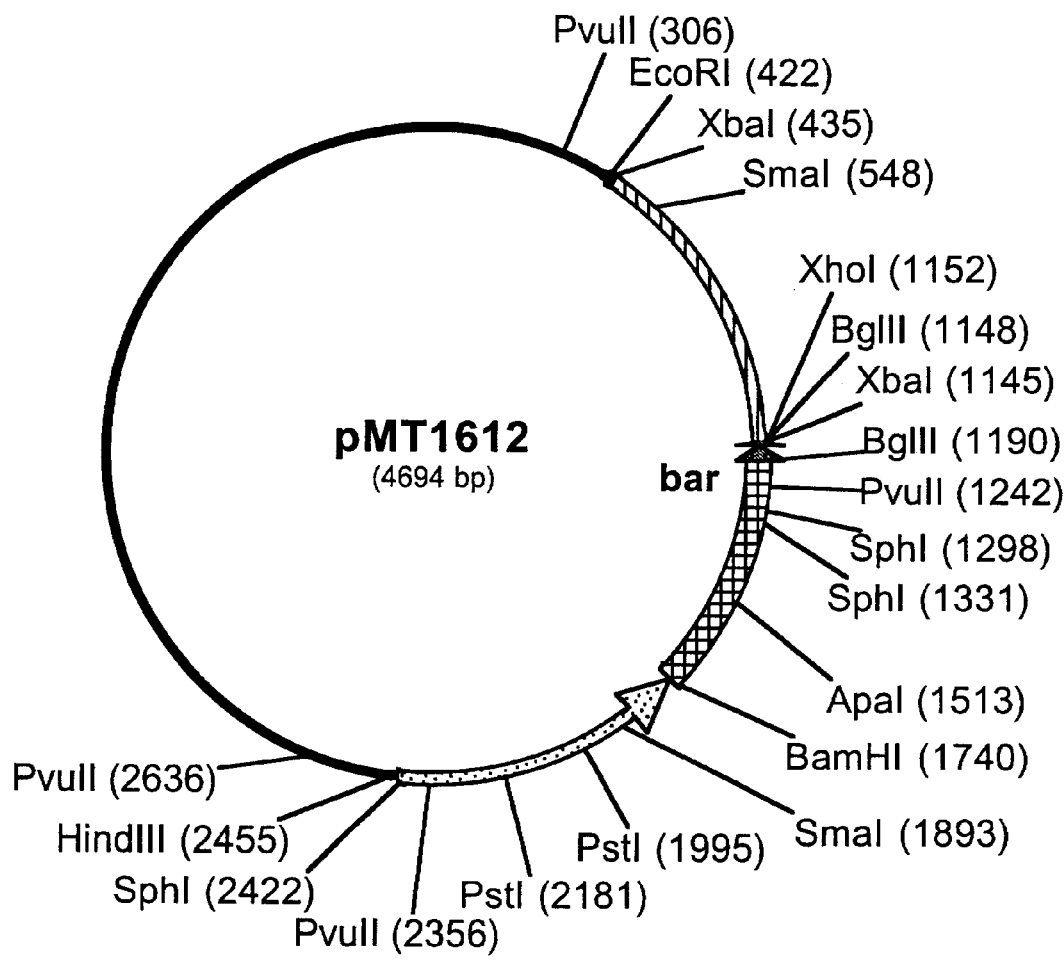
FIG. 34 is a restriction map of pMT1612.

The DNA fragment was cloned into the PCR-Blunt Cloning Vector (Invitrogen, San Diego, Calif.). A HindIII site in the multicloning site was destroyed by filling in with the Klenow fragment of DNA Polymerase I. A 2 kb HindIII-EcoRI fragment containing the Basta gene conferring resistance to Bialaphos was obtained from pMT1612 (FIG. 34) and inserted into the chs HindIII site located approximately 0.7 kb within the chs fragment. The resultant plasmid was labelled pHB220.

Using pHB220 as template, a 4 kb PCR fragment was generated using primer A and 5'-GGGCCGTTTGACAATCCGCAT-3' (SEQ ID NO:62). The amplification reaction was performed as described above except the reaction was incubated in an Ericomp Thermal Cycler programmed as follows: One cycle at 95° C. for 3 minutes; 30 cycles each at 95° C. for 1 minute, 58° C. for 1 minute, and 72° C. for 6 minutes; and 1 cycle at 72° C. for minutes. The PCR product was isolated by electrophoresis on a 1% agarose gel.

The PCR fragment was then used directly to transform protoplasts prepared from *Aspergillus oryzae* HowL795 according to the procedure described in Example 5. Of 100 transformants, three transformants appeared to have a "colonial" plate morphology on Minimal medium plates and PDA plates.

Southern analysis was performed on the three transformants and *Aspergillus oryzae* HowB430 as a control using the 2 kb DIG-labelled chs fragment as probe. Genomic DNA was prepared from the three strains and control strain as described in Example 9. Samples of the genomic DNA from each of the 3 transformants digested with HindIII was submitted to Southern analysis according to the procedure described in Example 14.

The Southern analysis showed that each of the three transformants had undergone a gene replacement substituting the chs/basta construct with the wild-type chs gene. The results confirmed that the colonial morphology observed in the chs tagged strain *Aspergillus oryzae* P7–14.1 was associated with a mutation of the chs gene.

An apparent effect of the chs gene on colony morphology was observed in shake flask cultures containing MY25 medium performed as described in Example 8. The pellet mass of the colonies in the broth appeared less dense in the chs mutants of *Aspergillus oryzae* HowL795 compared to *Aspergillus oryzae* HowL795.

Fermentations were also performed as described in Example 8 on two derivatives of *Aspergillus oryzae* HowL795 containing gene disruptions of the chs gene. Lipase yields in both strains were approximately 21% greater than *Aspergillus oryzae* HowL795. The kinetics of enzyme production appeared to be increased in the chs mutants in the later stages of fermentation suggesting that these strains exhibited a more optimal tank morphology. Example 43: Characterization of morphological mutant *Aspergillus oryzae* DEBY7-17.2 rescued locus pSMO717

The *Aspergillus oryzae* DEBY7-17.2 rescued locus pSMO717 containing 400 bp was sequenced according to the method described in Example 2. The nucleic acid sequence (SEQ ID NO:63) and the deduced amino acid sequence (SEQ ID NO:64) are shown in FIG. 35. The deduced amino acid sequence (SEQ ID NO:64) showed 44% identity to the deduced amino acid sequence of an ORF of *Aspergillus nidulans* (AC000133) (SEQ ID NO:65).

Example 44

Characterization of Morphological Mutant
*Aspergillus oryzae* DEBY3-2.1 Rescued Locus
pSMO321

The *Aspergillus oryzae* DEBY3-2.1 rescued locus pSMO321 containing 1.0 kb was sequenced according to the method described in Example 2. The nucleic acid sequence (SEQ ID NO:66) shown in FIG. 36 showed no homology to any published sequences.

Probes from either end of the rescued plasmid pSMO321 were generated by PCR. Probe 5 was generated with primers 970850 and 970851 shown below. Probe 6 was generated with primers 970852 and primer 970853 shown below. The primers were synthesized with an Applied Biosystems Model 394 DNA/RNA Synthesizer according to the manufacturer's instructions. The template for the 50 µl PCR labeling reaction was 10 ng of the rescued plasmid pSMO321. PCR cycles and conditions were as described in Example 20.

970850: 5'-GTTCTATTGAGATACGCG-3' (SEQ ID NO:67)

970851: 5'-ACAAGCCGACCGGTTTTG-3' (SEQ ID NO:68)

970852: 5'-CGATAAGGACTCCAAGAG-3' (SEQ ID NO :69)

970853: 5'-GTCGCGCATAATATGAAG-3' (SEQ ID NO:70)

Southern blots of *Aspergillus oryzae* HowB430 genomic DNA digested with SphI, SalI and BamHI were prepared and analyzed according to the method described in Example 14. The blots were hybridized independently to probes 5 and 6 made from the ends of the rescued plasmid.

Analysis of the Southern blots suggested no deletions had occurred. When PCR was performed using 500 ng of genomic DNA from *Aspergillus oryzae* HowB43d with primers 090850 and 090852, a 500 bp product was amplified as predicted verifying that no deletions had taken place.

Genomic DNA was prepared from the tagged mutant strain *Aspergillus oryzae* DEBY3-2.1 as described in Example 9, digested with the restriction enzyme used for REMI (BamnHI), blotted and probed with the NheI fragment from *Aspergillus oryzae* pyrG. Southern analysis of this blot suggested the tagged plasmid had inserted into a BamHI site in the genome.

Example 45

Characterization of Morphological Mutant
*Aspergillus oryzae* DEBY 5-7.1 Rescued Locus
pHowB571

The *Aspergillus oryzae* DEBY5-7.1 rescued locus pHowB571 containing 600 bp was sequenced according to the method described in Example 2. The nucleic acid sequence (SEQ ID NO:71) shown in FIG. 37 showed no homology to any published sequences.

To test if a deletion occurred during tagging, a Southern blot was preapared and analyzed according to the method described in Example 14 using genomic DNA from *Aspergillus oryzae* HowB43D digested with SphI, SalI and BamHI. Probes from either end of the rescued tagged plasmid pSMO571 were generated by PCR. Probe 7 was generated with primer 970936 and primer 970937 shown below. Probe 8 was generated with primer 970938 and primer 970939 shown below. The primers w ere synthesized with an Applied Biosystems Model 394 DNA/RNA Synthesizer according to the manufacturer's instructions. The template for the PCR labeling reaction was 10 ng of pSMO571. PCR cycles and conditions were as described in Example 20.

970936: 5'-CTTCCTCATAAACCACCC-3' (SEQ ID NO:72)

970937: 5'-AACTGACAGGACAAGACC-3' (SEQ ID NO:73)

970938: 5'-GACTTGCATCACTTCCTC-3' (SEQ ID NO:74)

970939: 5'-TGAAGCTGAGAGTAGGTG-3' (SEQ ID NO:75)

The results showed identical banding patterns from both probes suggesting no deletions had occurred. PCR was used to verify that no deletions had occurred using the method described in Example 20. A total of 500 ng of genomic DNA from *Aspergillus oryzae* HowB430 was used as template with primer 970936 and primer 970939. A 550 bp product was amplified as predicted. Southern data from genomic DNA obtained from the tagged mutant *Aspergillus oryzae* DEBY5-7.1 digested with BamHI, hybridized to the NheI fragment of pyrG suggested that the tagged plasmid had inserted into a BamHI site in the genome. Southern blot conditions are described as above.

Southern and PCR analysis demonstrated the tagged plasmid had inserted directly into a BamHI site. Cloning with TOPO pCRll vector and subsequent sequencing according to Example 2 of the PCR product generated using *Aspergillus oryzae* HowB430 genomic DNA with primers from the rescued ends of *Aspergillus oryzae* DEBY5-7.1 confirmed this result.

Example 46

Characterization of Morphological Mutant *Aspergillus oryzae* DEBY8-10.1 pSMO810

The *Aspergillus oryzae* DEBY8-10.1 rescued locus pSMO810 containing 750 bp was sequenced according to the method described in Example 2. The nucleic acid sequence (SEQ ID NO:76) shown in FIG. 38 showed no homology to any published sequences.

Probes from either end of the rescued plasmid pSMO810 were generated by PCR. Probe 9 was generated with primer 970854 and primer 970855 shown below. Probe 10 was generated with primer 970856 and primer 970857 shown below. The primers were synthesized with an Applied Biosystems Model 394 DNA/RNA Synthesizer according to the manufacturer's instructions. The template for the PCR labeling reaction was 10 ng of pSMO810. The PCR reaction and conditions were as described in Example 20.

970854: 5'-GTTTCGGTATTGTCACTG-3' (SEQ ID NO:77)

970855: 5'-ACAGGTGAACAACTGAGG-3' (SEQ ID NO:78)

970856: 5'-CGACCAAACTAGACAAGC-3' (SEQ ID NO:79)

970857: 5'-CTTTCCTCTTGGACACAC-3' (SEQ ID NO:80)

Southern analysis was performed as described in Example 14. Southern analysis of genomic DNA from *Aspergillus oryzae* HowB430 digested with SphI, SalI, and BamHI hybridized independently with probes 9 and 10 suggested no deletions had occurred during the insertion of the tagged plasmid. PCR using 500 ng of *Aspergillus oryzae* HowB430 genomic DNA as template with primers 090854 and 090856 amplified a 500 bp product as expected with no deletions. Southern analysis of genomic DNA prepared from mutant *Aspergillus oryzae* DEBY8-10.1, digested with EcoRI, and probed to the NheI fragment of pyrG suggested that the plasmid integrated into an EcoRI site in the genome. Cloning with TOPO pCR11 vector and subsequent sequencing according to Example 2 of the PCR product generated using *Aspergillus oryzae* HowB430 genomic DNA with primers from the rescued ends of *Aspergillus oryzae* DEBY8-10.1 confirmed this result.

Example 47

Screening on a Poor Carbon Source for High Producers

Eighteen pools of *Aspergillus oryzae* HowB430 transformants, 11 generated with HindIII digested pDSY81 and in the presence of HindIII, and 7 generated with SalI digested pDSY81 and in the presence of SalI (see Example 5) were screened on poor carbon sources to identify mutants which were high producers of lipase. Glycerol was used as poor carbon source, since the expression of lipase is very low on glycerol, but a number of other carbon sources, e.g., xylose, sucrose, and polyols such as mannitol and sorbitol could be used in a similar way.

The primary 96-well plate screen was performed as described in Example 7, but with GLY25 medium composed of 100 ml of 10% yeast extract, 100 ml of 25% glycerol, 100 ml of 2% urea per liter diluted 50-fold. Lipase assays were performed as described in Example 7.

Mutants of interest were then inoculated directly into 24-well plates containing the same medium as above and grown 6 days at 34° C. and 100 rpm. Cultures were then assayed for lipase activity as described in Example 7, and mutants of interest were plated on COVE plates to produce spores, spread on PDA plates to produce single colonies, and then 4 single isolates of each mutant were grown on CM-glycerol agar (as CM-1 agar, but maltose was replaced by glycerol as carbon source) to produce spores for inoculation of 24-well plates as above.

After the 24-well plates, 10 transformants were identified for further evaluation in shake flasks. The shake flasks contained 50 ml of medium at pH 6.5 composed of 1 g of $MgSO_4$-$7H_2O$, 1 g/l $K_2SO_4$, 15 g of $KH_2PO_4$, 0.25 ml of trace metals solution, 0.7 g of yeast extract, 3 ml of 50% urea, 2 ml of 15% $CaCl_2$-$2H_2O$, and 2% carbon source (either maltose, glucose, sucrose, or glycerol). The shake flasks containing 50 ml of medium in a 125 PP flask were inoculated with 0.5 ml G1-gly overnight culture, incubated at 34° C. and 200 rpm, and sampled after 2 and 3 days. Lipase activity was measured as above.

The results are shown in Table 12 where lipase production by *Aspergillus oryzae* HowB430 grown on glycerol as carbon source is normalized to 1.0.

TABLE 12

| Strain | Pool | Glycerol | Maltose | Glucose | Sucrose |
| --- | --- | --- | --- | --- | --- |
| HowB430 | NA | 1.0 | 152 | 44 | 1.1 |
| HINL880.1 | Hin-5 | 1.5 | 182 | 49 | 10 |
| HINL895.3 | Hin-20 | 8.4 | 140 | 38 | 11 |
| HINL918.4 | Hin-24 | 5.7 | 163 | 45 | 8.8 |
| SALL587.4 | Sal-4 | 1.6 | 178 | 89 | 22 |
| SALL591.2 | Sal-4 | 1.3 | 232 | 126 | 33 |
| SALL631.2 | Sal-5 | 16.6 | 72 | 35 | 25 |
| SALL631.3 | Sal-5 | 18.3 | 67 | 42 | 29 |
| SALL664.2 | Sal-15 | 6.1 | 70 | 79 | 9.2 |
| SALL683.3 | Sal-16 | 1.6 | 186 | 77 | 20 |
| SALL692.2 | Sal-16 | 2.7 | 148 | 63 | 24 |

The relative expression of lipase responded differently to different carbon sources, suggesting that the regulation of the lipase expression was altered in these transformants.

Example 48

Screening for α-cyclopiazonic Acid Mutants The pools e1–e26 from the EcoRI library described in Example 5 was used in screening for a-cyclopiazonic acid negative strains.

The spore number in the vials containing the different pools was determined by counting an appropriate dilution in a haemocytometer and a dilution series was constructed in such a way that approximately 30–50 spore derived colonies were present on each 9 cm screening plate. The screening medium was composed per liter of 30 g of mannitol, 10 g of glucose, 10 g of succinic acid, 3 g of Casamino acids, 1 g of $KH_2PO_4$, 0.3 g of $MgSO_4$-$7H_2O$, 0.2 g of $FeSO_4$-$7H_2O$, 100 μl of Triton x100, and 20 g of Difco Bacto Agar. The pH was adjusted to 5.6 with 14% $NH_4OH$ before autoclaving. The ferrous ion forms a red complex with a-cyclopiazonic acid. This complex is seen on the reverse side of the colonies.

Approximately 2000–2500 colonies were screened from each pool. Colonies with no red coloration on the reverse side after 7 days incubation at 34° C. were reisolated on the screening medium and incubated for 7 days at 34° C. Ten colonies originating from 6 different pools exhibited non-red reverse coloration and were subsequently inoculated onto Cove-N slants made as follows: 20 ml of Cove salt solution, 4.2 g of NaNO$_3$, and 60 g of glucose were dissolved in deionised water and the volume made up to 1000 ml. The medium was solidified by 2% Difco Bacto Agar.

Five ml of a spore suspension, made from a Cove slant by adding 10 ml of aqueous 0.01% Tween 80, was inoculated into 500 ml baffled shake flasks containing 100 ml of MDU1B shake flask medium. At the time of inoculation, 1.3 ml of 50% sterile filtered urea was added to each shake flask. The shake flasks were incubated at 250 rpm for 5 days at 34° C.

Ten µl of supernatant from the 5 day old shake flask cultures were applied to the opposite edges of a 20 cm×20 cm TLC plate (Merck Silica Gel 60). The plate was then run for 15 minutes in a chloroform:acetone:propan-2-ol (85:15:20) solvent system (CAP) allowed to dry, turned around and the opposite side was run in a toluene: ethyl acetate: formic acid (5:4:1) solvent system (TEF) for 15 minutes. The plate was allowed to dry thoroughly for 1 hour in a fume hood before spraying with Ehrlich reagent (2 g of 4-dimethylaminobenzaldehyde in 85 ml of 96% ethanol plus 15 ml of 37% hydrochloric acid). α-Cyclopiazonic acid was seen as bluish-violet mushroom shaped spots with a typical low Rf value in the CAP solvent system (a neutral system) whereas the acidic TEF solvent system yielded a typical high Rf value prolonged smear. Solutions of 30, 15, and 7.5 ppm of α-cyclopiazonic acid (Sigma Chemical Co., St. Louis, Mo.) in a 1:1:1 solution of ethanol, methanol, and chloroform were used as standards.

The TLC analysis of ten putative α-cyclopiazonic acid-free transformants showed no sign of α-cyclopiazonic acid. The remaining contents of the shake flasks were filtered through Miracloth and 10 ml of 0.1 M hydrochloric acid were added to 60 ml of each filtrate. The acidified filtrates were then vigorously shaken for 3–5 minutes with 50 ml chloroform. The bottom phases (approximately 25 ml) were each transferred to a 300 ml beaker after phase separation (3 hrs) and the chloroform allowed to evaporate. The residues were each redissolved in 300 µl of chloroform and 10 µl of each concentrate was analyzed by TLC as described above.

None of the 10 strain extracts contained any detectable oe-cyclopiazonic acid.

DEPOSIT OF BIOLOGICAL MATERIALS

The following strains have been deposited according to the Budapest Treaty in the Agricultural Research Service Patent Culture Collection (NRRL), Northern Regional Research Laboratory, 1815 University Street, Peoria, Ill. 61604, USA.

| Strain | Accession Number | Deposit Date |
| --- | --- | --- |
| E. coli HB101 pDSY109 | NRRL B-21623 | September 5, 1996 |
| E. coli DH5α pMT1936 | NRRL B-21832 | September 8, 1997 |
| E. coli HB101 pDSY112 | NRRL B-21622 | September 5, 1996 |
| E. coli HB101 pDSY138 | NRRL B-21833 | September 8, 1997 |
| E. coli DH5α pDSY162 | NRRL B-21831 | September 8, 1997 |
| E. coli DH5α pDSY163 | NRRL B-21830 | September 8, 1997 |
| E. coli DH5α pSMO1204 | NRRL B-21820 | September 8, 1997 |
| E. coli DH5α pSMOH603 | NRRL B-21821 | September 8, 1997 |
| E. coli HB101 p4-8.1 | NRRL B-21823 | September 8, 1997 |
| E. coli HB101 p7-14.1 | NRRL B-21824 | September 8, 1997 |
| E. coli DH5α pHB220 | NRRL B-21825 | September 8, 1997 |
| E. coli DH5α pSMO717 | NRRL B-21826 | September 8, 1997 |
| E. coli DH5α pSMO321 | NRRL B-21827 | September 8, 1997 |
| E. coli DH5α pHowB571 | NRRL B-21828 | September 8, 1997 |
| E. coli DH5α pSMO810 | NRRL B-21829 | September 8, 1997 |

The strains have been deposited under conditions that assure that access to the culture will be available during the pendency of this patent application to one determined by the Commissioner of Patents and Trademarks to be entitled thereto under 37 C.F.R. §1.14 and 35 U.S.C. §122. The deposits represent a substantially pure culture of each deposited strain. The deposits are available as required by foreign patent laws in countries wherein counterparts of the subject application, or its progeny are filed. However, it should be understood that the availability of a deposit does not constitute a license to practice the subject invention in derogation of patent rights granted by governmental action.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

All publications mentioned herein are incorporated herein by reference for the purpose of describing and disclosing the particular information for which the publication was cited. The publications discussed above are provided solely for their disclosure prior to the filing date of the present application. Nothing herein is to be construed as an admission that the inventors are not entitled to antedate such disclosure by virtue of prior invention.

It is to be understood that this invention is not limited to the particular methods and compositions described as such may, of course, vary. It is also to be understood that the terminology used herein is for the purpose of describing particular embodiments only, and is not intended to be limiting since the scope of the present invention will be limited only by the appended claims.

Unless defined otherwise all technical and scientific terms used herein have the same meaning as commonly understood by one of ordinary skill in the art to which this invention belongs. Although any materials or methods similar or equivalent to those described herein can be used in the practice or testing of the present invention, the preferred methods and materials are described.

What is claimed is:

1. A method of producing a polypeptide comprising:
   (a) cultivating a mutant cell under conditions conducive for production of the polypeptide, wherein
      (i) the mutant cell is related to a parent cell, wherein the parent cell comprises a first DNA sequence encoding the polypeptide, by the introduction of a nucleic acid construct into the genome of the parent cell at a locus which is not within the first DNA sequence and not within a second DNA sequence encoding a protein that positively regulates transcription translation or secretion of the polypeptide; and
      (ii) the mutant cell produces less of the polypeptide than the parent cell when both cells are cultivated under the conditions; and
   (b) recovering the polypeptide.

2. The method of claim 1, wherein the nucleic acid construct has less than 40% homology with the first DNA sequence.

3. The method of claim 1, wherein the nucleic acid construct has less than 40% homology with the locus.

4. The method of claim 1, wherein the locus is on a different chromosome than the first DNA sequence or on the same chromosome but at least 3,000 bps from the 5' or 3' terminus of the first DNA sequence.

5. The method of claim 1, wherein the nucleic acid construct is introduced by restriction enzyme-mediated integration.

6. The method of claim 1, wherein the nucleic acid construct comprises a selectable marker.

7. The method of claim 6, wherein the selectable marker is amdS, argB, bar, hygB, niaD, pyrG, sC, or trpC.

8. The method of claim 1, wherein the parent cell is a mammalian cell.

9. The method of claim 1, wherein the parent cell is a bacterial cell.

10. The method of claim 1, wherein the parent cell is a fungal cell.

11. The method of claim 10, wherein the fungal cell is a filamentous fungal or yeast cell.

12. The method of claim 1, wherein the polypeptide is a recombinant polypeptide.

13. The method of claim 1, wherein the polypeptide is a heterologous polypeptide.

14. The method of claim 1, wherein the polypeptide is a hormone, hormone variant, enzyme, receptor, antibody, or reporter.

15. The method of claim 14, wherein the enzyme is an oxidoreductase, transferase, hydrolase, lyase, isomerase, or ligase.

16. The method of claim 1, wherein the mutant cell has an altered morphology relative to the parent cell.

17. The method of claim 1, wherein the mutant cell exhibits an altered growth rate relative to the parent cell.

18. The method of claim 1, wherein the mutant cell can tolerate lower oxygen concentration conditions than the parent cell.

19. A method of producing a polypeptide, comprising
   (a) cultivating a mutant cell under conditions conducive for production of the polypeptide, wherein
      (i) the mutant cell is related to a parent cell, wherein the parent cell comprises a DNA sequence encoding the polypeptide, by the introduction of a nucleic acid construct into the genome of the parent cell at a locus which is not within the DNA sequence, wherein the introduction of the nucleic acid construct specifically decreases transcription, translation or secretion of the polypeptide; and
      (ii) the mutant cell produces less of the polypeptide than the parent cell when both cells are cultivated under the conditions; and
   (b) recovering the polypeptide.

* * * * *

SEQUENCE LISTING (1) GENERAL INFORMATION:

(iii) NUMBER OF SEQUENCES: 80

(2) INFORMATION FOR SEQ ID NO:1:

(i) SEQUENCE CHARACTERISTICS:
       (A) LENGTH: 24 base pairs
       (B) TYPE: nucleic acid
       (C) STRANDEDNESS: single
       (D) TOPOLOGY: linear (xi) SEQUENCE DESCRIPTION: SEQ ID NO:1:

ATGCATCTGG AAACGCAACC CTGA                                          24

(2) INFORMATION FOR SEQ ID NO:2:

(i) SEQUENCE CHARACTERISTICS:
       (A) LENGTH: 24 base pairs
       (B) TYPE: nucleic acid
       (C) STRANDEDNESS: single
       (D) TOPOLOGY: linear (xi) SEQUENCE DESCRIPTION: SEQ ID NO:2:

ATGCATTCTA CGCCAGGACC GAGC                                          24

(2) INFORMATION FOR SEQ ID NO:3:

(i) SEQUENCE CHARACTERISTICS:
       (A) LENGTH: 21 base pairs
       (B) TYPE: nucleic acid
       (C) STRANDEDNESS: single
       (D) TOPOLOGY: linear (xi) SEQUENCE DESCRIPTION: SEQ ID NO:3:

TGGTGTACAG GGGCATAAAA T                                             21

(2) INFORMATION FOR SEQ ID NO:4:

(i) SEQUENCE CHARACTERISTICS:
       (A) LENGTH: 34 base pairs
       (B) TYPE: nucleic acid
       (C) STRANDEDNESS: single
       (D) TOPOLOGY: linear (xi) SEQUENCE DESCRIPTION: SEQ ID NO:4:

ATTTAAATCC AGTTGTGTAT ATAGAGGATT GTGG                               34

(2) INFORMATION FOR SEQ ID NO:5:

(i) SEQUENCE CHARACTERISTICS:
       (A) LENGTH: 30 base pairs
       (B) TYPE: nucleic acid
       (C) STRANDEDNESS: single
       (D) TOPOLOGY: linear (xi) SEQUENCE DESCRIPTION: SEQ ID NO:5:

ATTTAAATGA TGAGGAGCTC CCTTGTGCTG                                    30

(2) INFORMATION FOR SEQ ID NO:6:

(i) SEQUENCE CHARACTERISTICS:
       (A) LENGTH: 29 base pairs
       (B) TYPE: nucleic acid
       (C) STRANDEDNESS: single (D) TOPOLOGY: linear (xi) SEQUENCE DESCRIPTION: SEQ ID NO:6:

TTAATTAACT AGAGTCGACC CAGCCGCGC                                                    29

(2) INFORMATION FOR SEQ ID NO:7:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:7:

GCGGGATCCC TAGAGTAGGG GGTGGTGG                                                     28

(2) INFORMATION FOR SEQ ID NO:8:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:8:

GCGGGATCCC CCCTAAGGAT AGGCCCTA                                                     28

(2) INFORMATION FOR SEQ ID NO:9:

(i) SEQUENCE CHARACTERISTICS:
        (A) LENGTH: 3000 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

ACACGGCCTG GACAATGAGA CAACTCTTCT AAAGAGTTCA GATTTAGTAT ATATACTAGC        60

CAGGACGGAC TTTCCAAATA TTATGTAAAT TAAAGTGTCG TTGTGAAGTG CTACCTATAA       120

TGCTTAGTAT GTGTATGTCT GGATGCAACG GGCTAATATT ACACATCAAG AAGTCCACTC       180

AATAAGCCAC TGGTGCAAAT TAACTGAATA CACATGTATC TATATCCGGA GCAATAAAAA       240

CTAACGATAA TAATGGCAAG GGTCACTTAT AACAAACTCA TACTGGACAA AAAGTATGGA       300

GAAACAATAG ATTAAAAAGG TCCCGTTCTA TATTTAATCC TCCCGCGACG GAGTTTCCTT       360

ATCCCGATAG ATACGATAAG GATCCAGGTA ACGTCATTCC ATCCCGTGAG ATAAAGAGGA       420

CTCCACCTCA ACAACTAATC ATCAAATCTC CAATCAATAT CAATGAACCC ATAACAACTT       480

AAAAAGCTCT CGGAAAAGTA AAAAGAGCTT CTATCAGCAT ATACACCATG GTCCTCGGTG       540

GATCAAGCGG GTCAAAGGTC ACTCCGTACC TGATCTACCT TGTGTTTATC ACAACTTTGG       600

GGCCACTTCA ATTCGGATAT CATTTGGTAT TACACGGAGC TTGGTCTATG CTGGAGGCTT       660

CAATACATCG GCTGACAATA TATTATGATA GGCTGAGCTC AATGCCCCCC AGGCCGTGAT       720

AACTTGCGAG CGGAAAAGCA TCCATTCGAC AACAACACGG GGTCTCCCGC AATGCATACC       780

TATGAACCCA TCCCAATTCG GCCTGGTCTC CTCTATATAC ACCCTTGGGG GCTTGCTAGG       840

GGCTCTCCTG GCAGGTCCAG TTTCCACCAA GCATGGCCGC TTGTTCACAC TGCGAGCGAC       900

CACCATCTTC TTCATCCTAG GCCCTATAGC AGAAACATTT GCGCCCAGTA TACCCGTATT       960

GAGTATGGGT AGGCTTTTAT CTGGTGTTGG TGCGGGCGCT TCTATCGTCG TGGGTCCGAT      1020

-continued

```
ATATATCTCT GAGATTGCTC CTCCTAGTGC TAAGGGTCTT TTCGGCGCTT TTACGCAAAT      1080

CATGACTAAT GTCGGTATTC TGTTGACACA GTCCCTTGGT TACTTCTTGA GTAAAGGAAG      1140

TATGTGGAGA GTTATACTTG CAATTGCTGG CGCGATCGGA TGCCTTGAGC TTCTGGGCCT      1200

CTTCTTAGTC CCAGAAAGCC CCATCTGGCT TGCAGATCAC CAGAAAGGGA ATGTGGCTAG      1260

ACAGGTGCTA CAACGTATAC GGGGCAGGGA TGCAGACATC GAGCCAGAGG TTGAAGGCTG      1320

GAGAACATCT GCAGCGCCTG AACACAGCTC TGGGGAAGAG CAGTCCCTAC TATCACCCCC      1380

ATCTGGAAAT ATGCCACCCA AGCAACCTCC GGTTACCATG ATGCGAGCTA TTACTGATTC      1440

TTTTTACCGC CCTGCCATCA TTGCAGTGGT CGGAGTCATG GTTTCCCAGC AGTTCACTGG      1500

TGTCAACAGC ATCATCATGT ACAGCGTTTC CCTCTTACAG ACCATCCTTC CCACCACTGC      1560

AGCCCTGTTG TCGGTGATCA TCTCGGCTAT CAATCTTGTA ATCACTCTGG CCTGCTCACC      1620

ACTACCTGAT AAGATTGGTA GACGCTCCTG CCTGCTTCTA AGTATCAGCG GCATGGGTCT      1680

TAATTCCGTC CTACTGGCGC TAGCCATCTA CTTCAACCTG AAAGCCTTAT CCGCCATAGC      1740

AGTTCTACTT TTCGTTGCTT CTTTCGCCGC CGGTCTAGGC CCAGTCCCCT TCATTTTAGC      1800

CTCTGAACTC GTTGGCCCGG AGGCTGTCGG CGCCGCACAG AGCTGGGCGC TGGGAGCGAA      1860

CTGGATTGCC ACGTTCATCG TGGCACAATT TTTTCCGATG TTAAACGATT TGTTGGGCGG      1920

ACGAGGCAAG ATCTACTGGA TCTTTGCAGC GATGGCCTGT CTCCTCGGAA GTTTCATCTA      1980

CTGGTGGGTG CCGGAGACCA AGGGGAAGGC TAACGCCGAC GAAGTTTGGG GAAGGACCAA      2040

CCAGCGCAGA CAGGACTAAT TTTTCTGGCC TCTTTGATTT TTTTTTTCTG GGCCTTACTC      2100

TGCTGCCAAC ATTCAGATTA TCAATTAGTA GTCAATCTGT GACTATCCTC TCCGAGGGAT      2160

AGCTTGCAAA GGTGTGACCT CCACAGAGGA ATCTATCGTG TGACAGTATC AAAGACAATA      2220

GAATAGCAAT AATTGGTGCT CTCTACCTAG GAGCATTCGG TGAGAGTGAA AGAGTCATAC      2280

TTGCCTCGGC TTGTTCATCC CAGTCGATCA GTCAGGTTTA GCTCGGCAGT AAAAGCAATA      2340

CCGGTCTACT TCCATCTTCA AACTGTACCG CGGAAACAAA GAGTAAAGGA GGGGTCATGA      2400

TACCTCTAAA TAATGTATAA GTCGTTGACA ATGCTCTTTA TCACCACCCG TTGAAGACGT      2460

CCTTTGATGT CTTGATCATC ACAAGCAGGT TGATCATCTG CGATCGACGT CACTTCGCAC      2520

CGCACACTGC ATGACAAGTG CGGGGCAGAG GGGCCAACAG GCCCAAAAAT TTAGTGATTT      2580

TGAAGCAATG TTGTTACACC CTTTTACCCC TCAATCCATG ATAAGGGAAA AAGAGATGCT      2640

GAGAGAGGGT CACTGCCACG CTAGACTGGA TTGGTCCGTA TATGCAGGTT TATGCACGCA      2700

CAGGGGGGCT TCGTTCTTCT TGGCTATGCA CTATGGATTA GTAGGGTGTA TTCAACCACG      2760

TAGATAGATT GGCGTGTCCG GTGCAGGATA TGTAGAAGAC AATGAGGTTC GGGCTTTCGG      2820

AAATGAGGAA AGAATGTTGG ACAGATGAAA AACGGTACTG CTGTTGCAAG GGGGCGCTGT      2880

TTGAGATATT TTAAGTGCCT GTCATGTAAT TTTGCAACGG TGAGACATTT ATCTAGGGTA      2940

AAATCCAAGA AGAACCTAGG GAAGAGTAAA GCCACAACGA AGATTACGTG AGAGGAAGAG      3000
```

(2) INFORMATION FOR SEQ ID NO:10:

(i) SEQUENCE CHARACTERISTICS:
        (A) LENGTH: 488 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:10:

-continued

```
Met Val Leu Gly Gly Ser Ser Gly Ser Lys Val Thr Pro Tyr Leu Ile
 1               5                  10                  15

Tyr Leu Val Phe Ile Thr Thr Leu Gly Pro Leu Gln Phe Gly Tyr His
             20                  25                  30

Leu Ala Glu Leu Asn Ala Pro Gln Ala Val Ile Thr Cys Glu Arg Lys
         35                  40                  45

Ser Ile His Ser Thr Thr Thr Arg Gly Leu Pro Gln Cys Ile Pro Met
 50                  55                  60

Asn Pro Ser Gln Phe Gly Leu Val Ser Ile Tyr Thr Leu Gly Gly
 65                  70                  75                  80

Leu Leu Gly Ala Leu Leu Ala Gly Pro Val Ser Thr Lys His Gly Arg
                 85                  90                  95

Leu Phe Thr Leu Arg Ala Thr Thr Ile Phe Phe Ile Leu Gly Pro Ile
                100                 105                 110

Ala Glu Thr Phe Ala Pro Ser Ile Pro Val Leu Ser Met Gly Arg Leu
            115                 120                 125

Leu Ser Gly Val Gly Ala Gly Ala Ser Ile Val Val Gly Pro Ile Tyr
        130                 135                 140

Ile Ser Glu Ile Ala Pro Pro Ser Ala Lys Gly Leu Phe Gly Ala Phe
145                 150                 155                 160

Thr Gln Ile Met Thr Asn Val Gly Ile Leu Leu Thr Gln Ser Leu Gly
                165                 170                 175

Tyr Phe Leu Ser Lys Gly Ser Met Trp Arg Val Ile Leu Ala Ile Ala
                180                 185                 190

Gly Ala Ile Gly Cys Leu Glu Leu Leu Gly Leu Phe Leu Val Pro Glu
        195                 200                 205

Ser Pro Ile Trp Leu Ala Asp His Gln Lys Gly Asn Val Ala Arg Gln
210                 215                 220

Val Leu Gln Arg Ile Arg Gly Arg Asp Ala Asp Ile Glu Pro Glu Val
225                 230                 235                 240

Glu Gly Trp Arg Thr Ser Ala Ala Pro Glu His Ser Ser Gly Glu Glu
                245                 250                 255

Gln Ser Leu Leu Ser Pro Pro Ser Gly Asn Met Pro Pro Lys Gln Pro
                260                 265                 270

Pro Val Thr Met Met Arg Ala Ile Thr Asp Ser Phe Tyr Arg Pro Ala
            275                 280                 285

Ile Ile Ala Val Val Gly Val Met Val Ser Gln Gln Phe Thr Gly Val
        290                 295                 300

Asn Ser Ile Ile Met Tyr Ser Val Ser Leu Leu Gln Thr Ile Leu Pro
305                 310                 315                 320

Thr Thr Ala Ala Leu Leu Ser Val Ile Ile Ser Ala Ile Asn Leu Val
                325                 330                 335

Ile Thr Leu Ala Cys Ser Pro Leu Pro Asp Lys Ile Gly Arg Arg Ser
            340                 345                 350

Cys Leu Leu Leu Ser Ile Ser Gly Met Gly Leu Asn Ser Val Leu Leu
        355                 360                 365

Ala Leu Ala Ile Tyr Phe Asn Leu Lys Ala Leu Ser Ala Ile Ala Val
    370                 375                 380

Leu Leu Phe Val Ala Ser Phe Ala Ala Gly Leu Gly Pro Val Pro Phe
385                 390                 395                 400

Ile Leu Ala Ser Glu Leu Val Gly Pro Glu Ala Val Gly Ala Ala Gln
                405                 410                 415

Ser Trp Ala Leu Gly Ala Asn Trp Ile Ala Thr Phe Ile Val Ala Gln
```

-continued

```
                    420                 425                 430
Phe Phe Pro Met Leu Asn Asp Leu Leu Gly Gly Arg Gly Lys Ile Tyr
            435                 440                 445

Trp Ile Phe Ala Ala Met Ala Cys Leu Leu Gly Ser Phe Ile Tyr Trp
    450                 455                 460

Trp Val Pro Glu Thr Lys Gly Lys Ala Asn Ala Asp Glu Val Trp Gly
465                 470                 475                 480

Arg Thr Asn Gln Arg Arg Gln Asp
                485
```

(2) INFORMATION FOR SEQ ID NO:11:

(i) SEQUENCE CHARACTERISTICS:
        (A) LENGTH: 488 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:11:

```
Met Ala Glu Thr Glu Arg Leu Met Pro Asn Gly Gly Ser Arg Glu Thr
1               5                   10                  15

Lys Pro Leu Ile Thr Gly His Leu Ile Leu Gly Thr Ile Val Ala Cys
            20                  25                  30

Leu Gly Ser Ile Gln Tyr Gly Tyr His Ile Ala Glu Leu Asn Ala Pro
        35                  40                  45

Gln Glu Phe Leu Ser Cys Ser Arg Phe Glu Ala Pro Asp Glu Asn Ile
    50                  55                  60

Ser Tyr Asp Asp Thr Trp Val Gly Gln His Gly Leu Lys Gln Cys Ile
65                  70                  75                  80

Ala Leu Thr Asp Ser Gln Tyr Gly Ala Ile Thr Ser Ile Phe Ser Ile
                85                  90                  95

Gly Gly Leu Phe Gly Ser Tyr Tyr Ala Gly Asn Trp Ala Asn Arg Tyr
            100                 105                 110

Gly Arg Lys Tyr Val Ser Met Gly Ala Ser Ala Met Cys Met Val Ser
        115                 120                 125

Ser Leu Leu Leu Phe Phe Ser Asn Ser Tyr Leu Gln Leu Leu Phe Gly
    130                 135                 140

Arg Phe Leu Val Gly Met Ser Cys Gly Thr Ala Ile Val Ile Thr Pro
145                 150                 155                 160

Leu Phe Ile Asn Glu Ile Ala Pro Val Glu Trp Arg Gly Ala Met Gly
                165                 170                 175

Ser Met Asn Gln Val Ser Ile Asn Leu Gly Ile Leu Leu Thr Gln Thr
            180                 185                 190

Leu Ala Leu Lys Tyr Ala Asp Ser Tyr Asn Trp Arg Trp Leu Leu Phe
        195                 200                 205

Ser Gly Ser Val Ile Ala Val Ala Asn Ile Leu Ala Trp Leu Lys Val
    210                 215                 220

Asp Glu Ser Pro Arg Trp Leu Val Ser His Gly Phe Val Ser Glu Ala
225                 230                 235                 240

Glu Thr Ala Leu Phe Lys Leu Arg Pro Gly Thr Tyr Gln Gln Ala Lys
                245                 250                 255

Gln Glu Ile Gln Asp Trp Gln Arg Ser His Gly His Asn Arg Asp Pro
            260                 265                 270

Glu Ser Ser Glu Glu Thr His Ser Gly Pro Thr Leu Trp Gln Tyr Val
```

-continued

```
                275                 280                 285
Thr Asp Pro Ser Tyr Lys Lys Pro Arg Thr Val Ile Leu Ala Ile Leu
    290                 295                 300
Ser Cys Gln Gln Phe Cys Gly Ile Asn Ser Ile Ile Phe Tyr Gly Val
305                 310                 315                 320
Lys Val Ile Gly Lys Ile Leu Pro Asp Tyr Ser Ile Gln Val Asn Phe
                325                 330                 335
Ala Ile Ser Ile Leu Asn Val Val Thr Leu Ala Ala Ser Ala Ile
                340                 345                 350
Ile Asp His Val Gly Arg Arg Pro Leu Leu Leu Ala Ser Thr Thr Val
                355                 360                 365
Met Thr Ala Met Ser Leu Leu Ile Ser Val Gly Leu Thr Leu Ser Val
    370                 375                 380
Ser Phe Leu Leu Val Thr Ala Thr Phe Val Tyr Ile Ala Ala Phe Ala
385                 390                 395                 400
Ile Gly Leu Gly Pro Ile Pro Phe Leu Ile Ile Gly Glu Leu Ser Tyr
                405                 410                 415
Pro Gln Asp Ala Ala Thr Ala Gln Ser Phe Gly Thr Val Cys Asn Trp
                420                 425                 430
Leu Ala Thr Phe Ile Val Gly Tyr Leu Phe Pro Ile Gly His Gly Leu
                435                 440                 445
Met Gly Gly Tyr Val Phe Ala Ile Phe Ala Ala Ile Ala Ala Met Phe
    450                 455                 460
Ala Thr Tyr Val Tyr Lys Arg Val Pro Glu Thr Lys Gly Lys Thr Thr
465                 470                 475                 480
Tyr Ser Glu Val Trp Ala Gly Tyr
                485
```

(2) INFORMATION FOR SEQ ID NO:12:

(i) SEQUENCE CHARACTERISTICS:
        (A) LENGTH: 524 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:12:

```
Met Thr Glu Asp Lys Val Thr Gly Thr Leu Val Phe Thr Val Ile Thr
1               5                   10                  15
Ala Val Leu Gly Ser Phe Gln Phe Gly Tyr Asp Ile Gly Val Ile Asn
                20                  25                  30
Ala Pro Gln Gln Val Ile Ile Ser His Tyr Arg His Val Leu Gly Val
                35                  40                  45
Pro Leu Asp Asp Arg Lys Ala Ile Asn Asn Tyr Val Ile Asn Ser Thr
    50                  55                  60
Asp Glu Leu Pro Thr Ile Ser Tyr Ser Met Asn Pro Lys Pro Thr Pro
65                  70                  75                  80
Trp Ala Glu Glu Glu Thr Val Ala Ala Ala Gln Leu Ile Thr Met Leu
                85                  90                  95
Trp Ser Leu Ser Val Ser Ser Phe Ala Val Gly Gly Met Thr Ala Ser
                100                 105                 110
Phe Phe Gly Gly Trp Leu Gly Asp Thr Leu Gly Arg Ile Lys Ala Met
                115                 120                 125
Leu Val Ala Asn Ile Leu Ser Leu Val Gly Ala Leu Leu Met Gly Phe
```

-continued

```
            130                 135                 140
Ser Lys Leu Gly Pro Ser His Ile Leu Ile Ile Ala Gly Arg Ser Ile
145                 150                 155                 160

Ser Gly Leu Tyr Cys Gly Leu Ile Ser Gly Leu Val Pro Met Tyr Ile
                165                 170                 175

Gly Glu Ile Ala Pro Thr Ala Leu Arg Gly Ala Leu Gly Thr Phe His
                180                 185                 190

Gln Leu Ala Ile Val Thr Gly Ile Leu Ile Ser Gln Ile Ile Gly Leu
                195                 200                 205

Glu Phe Ile Leu Gly Asn Tyr Asp Leu Trp His Ile Leu Leu Gly Leu
                210                 215                 220

Ser Gly Val Arg Ala Ile Leu Gln Ser Leu Leu Leu Phe Phe Cys Pro
225                 230                 235                 240

Glu Ser Pro Arg Tyr Leu Tyr Ile Lys Leu Asp Glu Glu Val Lys Ala
                245                 250                 255

Lys Gln Ser Leu Lys Arg Leu Arg Gly Tyr Asp Asp Val Thr Lys Asp
                260                 265                 270

Ile Asn Glu Met Arg Lys Glu Arg Glu Glu Ala Ser Ser Glu Gln Lys
                275                 280                 285

Val Ser Ile Ile Gln Leu Phe Thr Asn Ser Ser Tyr Arg Gln Pro Ile
290                 295                 300

Leu Val Ala Leu Met Leu His Val Ala Gln Gln Phe Ser Gly Ile Asn
305                 310                 315                 320

Gly Ile Phe Tyr Tyr Ser Thr Ser Ile Phe Gln Thr Ala Gly Ile Ser
                325                 330                 335

Lys Pro Val Tyr Ala Thr Ile Gly Val Gly Ala Val Asn Met Val Phe
                340                 345                 350

Thr Ala Val Ser Val Phe Leu Val Glu Lys Ala Gly Arg Arg Ser Leu
                355                 360                 365

Phe Leu Ile Gly Met Ser Gly Met Phe Val Cys Ala Ile Phe Met Ser
370                 375                 380

Val Gly Leu Val Leu Leu Asn Lys Phe Ser Trp Met Ser Tyr Val Ser
385                 390                 395                 400

Met Ile Ala Ile Phe Leu Phe Val Ser Phe Phe Glu Ile Gly Pro Gly
                405                 410                 415

Pro Ile Pro Trp Phe Met Val Ala Glu Phe Phe Ser Gln Gly Pro Arg
                420                 425                 430

Pro Ala Ala Leu Ala Ile Ala Ala Phe Ser Asn Trp Thr Cys Asn Phe
                435                 440                 445

Ile Val Ala Leu Cys Phe Gln Tyr Ile Ala Asp Phe Cys Gly Pro Tyr
                450                 455                 460

Val Phe Phe Leu Phe Ala Gly Val Leu Leu Ala Phe Thr Leu Phe Thr
465                 470                 475                 480

Phe Phe Lys Val Pro Glu Thr Lys Gly Lys Ser Phe Glu Glu Ile Ala
                485                 490                 495

Ala Glu Phe Gln Lys Lys Ser Gly Ser Ala His Arg Pro Lys Ala Ala
                500                 505                 510

Val Glu Met Lys Phe Leu Gly Ala Thr Glu Thr Val
                515                 520
```

(2) INFORMATION FOR SEQ ID NO:13:

(i) SEQUENCE CHARACTERISTICS:
        (A) LENGTH: 584 amino acids

```
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:13:

Met Gly Ile His Ile Pro Tyr Leu Thr Ser Lys Thr Ser Gln Ser Asn
 1               5                  10                  15

Val Gly Asp Ala Val Gly Asn Ala Asp Ser Val Glu Phe Asn Ser Glu
            20                  25                  30

His Asp Ser Pro Ser Lys Arg Gly Lys Ile His Ile Glu Ser His Glu
            35                  40                  45

Ile Gln Arg Ala Pro Ala Ser Asp Asp Glu Asp Arg Ile Gln Ile Lys
 50                      55                  60

Pro Val Asn Asp Glu Asp Asp Thr Ser Val Met Ile Thr Phe Asn Gln
 65                  70                  75                  80

Ser Leu Ser Pro Phe Ile Ile Thr Leu Thr Phe Val Ala Ser Ile Ser
                85                  90                  95

Gly Phe Met Phe Gly Tyr Asp Thr Gly Tyr Ile Ser Ser Ala Leu Ile
                100                 105                 110

Ser Ile Gly Thr Asp Leu Asp His Lys Val Leu Thr Tyr Gly Glu Lys
            115                 120                 125

Glu Ile Val Thr Ala Ala Thr Ser Leu Gly Ala Leu Ile Thr Ser Ile
 130                 135                 140

Phe Ala Gly Thr Ala Ala Asp Ile Phe Gly Arg Lys Arg Cys Leu Met
 145                 150                 155                 160

Gly Ser Asn Leu Met Phe Val Ile Gly Ala Ile Leu Gln Val Ser Ala
                165                 170                 175

His Thr Phe Trp Gln Met Ala Val Gly Arg Leu Ile Met Gly Phe Gly
                180                 185                 190

Val Gly Ile Gly Ser Leu Ile Ala Pro Leu Phe Ile Ser Glu Ile Ala
            195                 200                 205

Pro Lys Met Ile Arg Gly Arg Leu Thr Val Ile Asn Ser Leu Trp Leu
 210                 215                 220

Thr Gly Gly Gln Leu Val Ala Tyr Gly Cys Gly Ala Gly Leu Asn Tyr
225                 230                 235                 240

Val Asn Asn Gly Trp Arg Ile Leu Val Gly Leu Ser Leu Ile Pro Thr
            245                 250                 255

Ala Val Gln Phe Thr Cys Leu Cys Phe Leu Pro Asp Thr Pro Arg Tyr
                260                 265                 270

Tyr Val Met Lys Gly Asp Leu Ala Arg Ala Thr Glu Val Leu Lys Arg
            275                 280                 285

Ser Tyr Thr Asp Thr Ser Glu Glu Ile Ile Glu Arg Lys Val Glu Glu
 290                 295                 300

Leu Val Thr Leu Asn Gln Ser Ile Pro Gly Lys Asn Val Pro Glu Lys
305                 310                 315                 320

Val Trp Asn Thr Ile Lys Glu Leu His Thr Val Pro Ser Asn Leu Arg
            325                 330                 335

Ala Leu Ile Ile Gly Cys Gly Leu Gln Ala Ile Gln Gln Phe Thr Gly
            340                 345                 350

Trp Asn Ser Leu Met Tyr Phe Ser Gly Thr Ile Phe Glu Thr Val Gly
            355                 360                 365

Phe Lys Asn Ser Ser Ala Val Ser Ile Ile Val Ser Gly Thr Asn Phe
 370                 375                 380
```

```
Ile Phe Thr Leu Val Ala Phe Phe Ser Ile Asp Lys Ile Gly Arg Arg
385                 390                 395                 400

Thr Ile Leu Leu Ile Gly Leu Pro Gly Met Thr Met Ala Leu Val Val
            405                 410                 415

Cys Ser Ile Ala Phe His Phe Leu Gly Ile Lys Phe Asp Gly Ala Val
            420                 425                 430

Ala Val Val Val Ser Ser Gly Phe Ser Ser Trp Gly Ile Val Ile Ile
            435                 440                 445

Val Phe Ile Ile Val Phe Ala Ala Phe Tyr Ala Leu Gly Ile Gly Thr
450                 455                 460

Val Pro Trp Gln Gln Ser Glu Leu Phe Pro Gln Asn Val Arg Gly Ile
465                 470                 475                 480

Gly Thr Ser Tyr Ala Thr Ala Thr Asn Trp Ala Gly Ser Leu Val Ile
            485                 490                 495

Ala Ser Thr Phe Leu Thr Met Leu Gln Asn Ile Thr Pro Ala Gly Thr
            500                 505                 510

Phe Ala Phe Phe Ala Gly Leu Ser Cys Leu Ser Thr Ile Phe Cys Tyr
            515                 520                 525

Phe Cys Tyr Pro Glu Leu Ser Gly Leu Glu Leu Glu Val Gln Thr
530                 535                 540

Ile Leu Lys Asp Gly Phe Asn Ile Lys Ala Ser Lys Ala Leu Ala Lys
545                 550                 555                 560

Lys Arg Lys Gln Gln Val Ala Arg Val His Glu Leu Lys Tyr Glu Pro
                565                 570                 575

Thr Gln Glu Ile Ile Glu Asp Ile
            580
```

(2) INFORMATION FOR SEQ ID NO:14:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:14:

CTGCCGTCGA AGGTGTCCAA G                                    21

(2) INFORMATION FOR SEQ ID NO:15:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:15:

ATTGTGGCCC CTATGTGGAT T                                    21

(2) INFORMATION FOR SEQ ID NO:16:

(i) SEQUENCE CHARACTERISTICS:
        (A) LENGTH: 4700 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:16:

-continued

```
ACAGCGACTG GGATGGTGAA TATCTGAGCG ATAGCCCCCG ACACAGCACC AAGGGTAAGC    60

TCCATAGCGG TTCCAGGTGG CTTAGATACG CTCTTCGATG CCATATAAAG GCTTCTAACC   120

ACGCTGTACC AGTAGAAGTA CGCAAAGTTG GTCGAGGCCA CGCCAAGCAA AGAACCAACC   180

ATCCCGGAAT ATAAACCTTC AATTCCCTCT TTCTCCACAA TCTTGTTGAT GGCATCTAGG   240

GTCGACTCGT AATGTACTAC ATCTCCGCTT TTCGATTCAG GTGCGTTCTT CACTTGGACT   300

TGAAGTTTGG TTTTGACACT AAAGATTAGG AACGAGTCAG TCTCAGTCTA CACCACTAAG   360

CCAACTGGCA AGGCTATGTA CGCACAGGTC CAGTGGATAG ACGATAGCAT TTGCGAGAAC   420

AGCACCAGTT GCACCTGCGA CAGCACTACC CCAAGGGGAG AGCGCGGGTT TCGATTGGCC   480

GGCCATTATG CAGGATGAGC TAAAGTGCCT CTGCCAATTC CGTCAGAAAG AATAGTATAA   540

GAGCACAAAT ACTGGTAAAA CCAAGACCGG CGAATGAGGC AGGACTCTGT GCGATTCGGG   600

GGGTTTAGCG TTCGGCTTGA AGGCTTACCG GATCGACTGA TAGAAAAGTT GAATGCCGAG   660

TAAGGTGAAA AGACCCCAGC TCCCAAGCAG CAACAGTAAG TGGAAGAGCT TAAGGATAGA   720

AAAAATAAAT TAGGATTAAG AAAAAAAGAA GAACCTCAAG ACTGGTCACA CAGTCCCGGC   780

ATCCTGAACG TAAAATGCGG GAAGGATAGA GTCGGCAGGG CCAGGGCAGT TGCACCTCGG   840

CGCTCTGGTT TGCGCATGAC GAAATGAGCC GAGGTTCGTT TTTTGGAGGC CAATTTCTGA   900

ACACCGACCT TCGAATTCCC GTTCCTCCCC ACCGACACGC TAGTGAATGA TCCAGCAAGC   960

ATACTTGGTG TTGTTTTGAC CTCATTCCAC TGCGTGTGAA TTAGCATTAA TTTAAGTTTA  1020

TGATTAACAG TCAATTGCTA TACGCGAAAA TCATCATCGT CTTGATTGGC CCTTCATAAA  1080

ACTTGACAAG GAAGTTTGAT CGACCTCGGA TGTCGCGCTT TCGGAAATTT CACGGAGCCC  1140

TTCGGACGGG TCACAAGCAA GGTGTCTGAC TGTCTCGTTT AGTCGGATAG ACGCTAGTTG  1200

AACTGTTATG CCTATCGCGG GGAAGATCTC GGAGTGTCAC GGTGTTTGAA GATCCCAGGC  1260

GCTCGTCAAA ATACTGCCCG GCCTGCCAGT ATGTCTAGAC CGAACGCCTC AGCCCAGAAG  1320

TCCTTTATAA CTCAGGCACT GGTACTTGAC CCTTTTTTTT TATGGTTTTT TGTTTCTTTC  1380

TTGTTACACC TTATTTTTCT TCTTCTCGTT TTTTGTAGAT AATACTGACC ACTGGCTAGA  1440

AAGCCGAGCG GGATGTATCG TCCGCCACTT CTCAAAGGCA AGCTTTAGAA GCTGCCATTG  1500

ATGCTGCTGA ACACTATATG AAAGCCTTAA ATCTGGCATC TGTTCAGAAA GACAAACATG  1560

CATTGGATGC AAAGTGTAAA GAATGGCTCA CAAGAGCGGA AAAGATCAAA GAATCTAAGG  1620

ACTGGCAAGC TGCTGCCCGT TTCCATGACA AAACTGTTCC AGAGCCACGG TTGCCTGTAT  1680

CTACTCGTAA GCTCACCACA CGGGAGGAGA TCATTCTGCT AGAGGGAGCC AAGTTGAATG  1740

GCTTCATATT CCCTCCATGG TCCACCTCCC CAGGCTCTGA CGAGTTCAAA CGAGAGGATG  1800

GTGAATCCCC GTTTACGTAA GTTCTGGTGG TCTGCATCGT CAATGTTGCA TGTATACCCA  1860

GATGACTGCT GGATATTCTA ACCGATAACA GCGACAAACC CGATCTTCAT CTATCTTATC  1920

CTCAAAGGAA AGTTTTTGAT GGCTGGAAAC GACCTTCCGA GCTTCTCGCG AAAGACACGG  1980

AAGATGTGTA CACAAAGGTG GTTCCTGTGA GTGTCTGTTCC AGGAAAGACA GATCTAGTCC  2040

AGGATATGCT GACGGACTGT TCTGTCGTTG CTAGCCTTTG TGCTACTACG TCAATGCTAG  2100

AACGCGGCCA GTGTACTGTA AGAAGATTGA TCCCTTCCGG CTGACCTGCA TGGTTCGCTG  2160

TGACTAATAG GTGTAGCATT TTCTTCCAAT GATATACCCT AGCCGGGGGA GCTCTCAGCC  2220

TTCACCGTCA GGCAAGTATA TATTTCGCTT TTATTTCAAT GGGTGCTTCC GGAAAGTCAT  2280

CATTGACGAC CGTTTGCCAT CGTCTAAGAC ATCAAGATCA CTCCACGTGA TCGACCGGAA  2340

AAATCCCAAT TTCCTTTGGC CGGCGCTCGT AGAGAAGGCG TATTTGAAAT TGCGCGGAGG  2400
```

-continued

```
CTATGATTTT CCCGGAAGCA ATTCCGGGAC AGATCTCTGG GTGCTGACAG GTTGGATTCC    2460
CGAGCAAGTC TTTCTCCATA ATGACGATGT GACTGGCGAC CAGCTCTGGA AGCGACTTTA    2520
CAGATCCTTT CACCAAGGAG ATGTTCTCTT GACTATAGGT ACCGGTGAAC TCACTGAGAG    2580
GGAACAAAGA GAACTAGGCC TCGTGAGTGA GCATGATTAT GCTATTCTGG ATATGAAGGA    2640
ATCTAAAGGT CGCCGACAAT TACTCGTGAA AAACCCTTGG GCTGGAGCAG ATACTGCCCC    2700
CGGCGACAAT GGAAGCCTCT CTGCATCGCA GGATTTACCC CATAACCCGC CCTCATTTGA    2760
GCCGGGTACC TTTTGGATGG ATTGCGAAAA GCTGCTTCAA CATTTTGAAA ACCTCTATTT    2820
GAATTGGAAC CCTGAGATTT TCAAATACCG CGAAGACGTC CACTTTACGT GGGACCTCAA    2880
CAACGGGAGA GGTGTAGCCG GCTGTTTTGT GAATAACCCG CAGTTCGCAG TGTCAACCGA    2940
GAACGGTGGG ATTGTCTGGT TACTTCTAGG CAAGCATTTC AGAACAACAG GGCAGCCGGA    3000
ACGACCTCTT GACGAATACC AAGCGAATGA GGAGTCGGCT TTTATAAGCA TATATGTCTT    3060
TAACGCAGAT GGCAAACGGG TCTCTTTGAG TGATGGGGCT CTACATCGTG GCCCCTATGT    3120
GGATTCCCCT AATACGCTCA TGAGGTTAGA GATGCCCCCC AGAACAACAT ACACAGTCGT    3180
GGTCTCCGAG CAATCACTGC CATCTTTGAA TCAAAACTTT ACTTTGTCTG CCTTCTCTAC    3240
CTGCCCTGTA CGGATGGCAA AAGCCCAAGA TAAATACATG TGTGTCAGGA AGATTCAAGG    3300
GTCTTGGACA CCTTCGACGG CAGGTGGGAA TGCCGAATCT TCTCGATATC CACTCAACCC    3360
CCAATTTAGG TTGGAGATAG AGAATGACAC AGATGTTTCA CTCCTGCTGG AATGCCCAAA    3420
CACGGAACTC GCGACCCATG TTAAGTTATT CTGGTCCAAT GGAAATCGTG TGTCGCGAGT    3480
ACGCAGTCGC GACATAATCG CTGATAGTGG TGACTATCGC CGTGGTGGCT CCCTTGTGGA    3540
AAAGAAGGCT CTGGAACCGG GCTCATATAC AATCGTCTGT TCCACATTCG CGCCGGATCA    3600
ACTTGGCCGA TTCACGCTCT GGGTATCCTC CTTAGTTCCT TGCAAGACGA GCCCGCTCCC    3660
ACCAGAGGCA GCAGGTCGAC GAACGGTCAT TTCAGATATT GGCGTACTGC CTCCCGGGAG    3720
AGACCGAATG TTAGCTTCTC TGCAAGTGCC GCGGCTTACG AGGATCAAGC TCATCACCCG    3780
AAGTAGGCAA TCCATCATCG GGAGCCATCC TGTTGGACCC TCGCCCGTTT TAATGACAGT    3840
GGAGCTCGGG CAAGGGCCAT ACAAACAGAT CCTGGCGACT TCGGAAGATG GAACTCACAG    3900
TGATGCTGTA TCGGGGTAC GTGTTGAGGA CTTTGACTTG CAGCCTGGGC TAGAGGAGAG    3960
TGGTGGTATT TGGATTGTTA TTGAGAGGAT TGGGGGTCCT GGAGGGCAGG TAGAGGACCA    4020
CTTTGAGGTG GAAGCTTTGG CTGAAGAGAG GGTTGAGATT GGGGAGTGGA TACTTGAAGA    4080
TGCTTGATCT CTTATCCTGC AGAAGCTCTG AAGCTCTGGA CGGTCTTAGT TGAGCTTTTT    4140
TGATCGTCGT TGTGATTAGC ACGTTAGAGT AGAAGAGCGG AAACAATGAT AGACATGAAT    4200
TTCTCTTATT GTCTCTATTG GCCAGAAGAG AAAGAAGGCA TTAAATCAAT ACATTAAAAG    4260
CAAGAGTTTA TCTATAGATA CCGAGCAGCC TCAGGATTTG AGCTGAGGTT TGTCGCGATC    4320
GCGACCGCCA AAATGGAGTT AGCTTGCTTT ACTCCGCATA AATTAAATCC TCGGCTCGGG    4380
GCCCGAATTC CCCTCCCGAG TGCTTTCAAC GTCATCCCGT TTGCTGTGTG CATTGTGCCT    4440
CCCCACCTTT AACAATTGGA GCTCTGTCCA AGGACAAATC CTTATTCTCG CGGCCTCCAT    4500
GGCGACTAAT ATTCCTGCTG CTCTGAAGTC TGCGGACATT GGGCGCTTTG CCGTCAGAGC    4560
AGCTCAGCTT GAACGTGTAA AGCCCGTGGT CGCCTACTGG TGTGAGTATT GTGTGATTAT    4620
ACCCAGTACG AACTACAGC TGATGAGCGG CCTCTGCTGA TCGCAGGCAA CTTCTGGATC    4680
GTCAACCAGA TTATTGAGAA                                                4700
```

(2) INFORMATION FOR SEQ ID NO:17:

(i) SEQUENCE CHARACTERISTICS:
        (A) LENGTH: 854 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:17:

```
Met Ser Arg Pro Asn Ala Ser Ala Gln Lys Ser Phe Ile Thr Gln Ala
 1               5                  10                  15

Leu Lys Ala Glu Arg Asp Val Ser Ser Ala Thr Ser Gln Arg Gln Ala
            20                  25                  30

Leu Glu Ala Ala Ile Asp Ala Ala Glu His Tyr Met Lys Ala Leu Asn
        35                  40                  45

Leu Ala Ser Val Gln Lys Asp Lys His Ala Leu Asp Ala Lys Cys Lys
50                  55                  60

Glu Trp Leu Thr Arg Ala Glu Lys Ile Lys Glu Ser Lys Asp Trp Gln
65                  70                  75                  80

Ala Ala Ala Arg Phe His Asp Lys Thr Val Pro Glu Pro Arg Leu Pro
                85                  90                  95

Val Ser Thr Arg Lys Leu Thr Thr Arg Glu Glu Ile Ile Leu Leu Glu
            100                 105                 110

Gly Ala Lys Leu Asn Gly Phe Ile Phe Pro Pro Trp Ser Thr Ser Pro
        115                 120                 125

Gly Ser Asp Glu Phe Lys Arg Glu Asp Gly Ser Pro Phe Thr Asp
130                 135                 140

Lys Pro Asp Leu His Leu Ser Tyr Pro Gln Arg Lys Val Phe Asp Gly
145                 150                 155                 160

Trp Lys Arg Pro Ser Glu Leu Leu Ala Lys Asp Thr Glu Asp Val Tyr
                165                 170                 175

Thr Lys Val Val Pro Val Met Ser Val Pro Gly Lys Thr Asp Leu Val
            180                 185                 190

Gln Asp Met Leu Thr Asp Cys Ser Val Ala Ser Leu Cys Ala Thr
        195                 200                 205

Thr Ser Met Leu Glu Arg Gly Gln Cys Thr His Phe Leu Pro Met Ile
210                 215                 220

Tyr Pro Ser Arg Gly Ser Ser Gln Pro Ser Pro Ser Gly Lys Tyr Ile
225                 230                 235                 240

Phe Arg Phe Tyr Phe Asn Gly Cys Phe Arg Lys Val Ile Ile Asp Asp
                245                 250                 255

Arg Leu Pro Ser Ser Lys Thr Ser Arg Ser Leu His Val Ile Asp Arg
            260                 265                 270

Lys Asn Pro Asn Phe Leu Trp Pro Ala Leu Val Glu Lys Ala Tyr Leu
        275                 280                 285

Lys Leu Arg Gly Gly Tyr Asp Phe Pro Gly Ser Asn Ser Gly Thr Asp
290                 295                 300

Leu Trp Val Leu Thr Gly Trp Ile Pro Glu Gln Val Phe Leu His Asn
305                 310                 315                 320

Asp Asp Val Thr Gly Asp Gln Leu Trp Lys Arg Leu Tyr Arg Ser Phe
                325                 330                 335

His Gln Gly Asp Val Leu Leu Thr Ile Gly Thr Gly Glu Leu Thr Glu
            340                 345                 350
```

```
Arg Glu Gln Arg Glu Leu Gly Leu Val Ser Glu His Asp Tyr Ala Ile
            355                 360                 365

Leu Asp Met Lys Glu Ser Lys Gly Arg Arg Gln Leu Leu Val Lys Asn
        370                 375                 380

Pro Trp Ala Gly Ala Asp Thr Ala Pro Gly Asp Asn Gly Ser Leu Ser
385                 390                 395                 400

Ala Ser Gln Asp Leu Pro His Asn Pro Ser Phe Glu Pro Gly Thr
                405                 410                 415

Phe Trp Met Asp Cys Glu Lys Leu Leu Gln His Phe Glu Asn Leu Tyr
            420                 425                 430

Leu Asn Trp Asn Pro Glu Ile Phe Lys Tyr Arg Glu Asp Val His Phe
        435                 440                 445

Thr Trp Asp Leu Asn Asn Gly Arg Gly Val Ala Gly Cys Phe Val Asn
    450                 455                 460

Asn Pro Gln Phe Ala Val Ser Thr Glu Asn Gly Gly Ile Val Trp Leu
465                 470                 475                 480

Leu Leu Gly Lys His Phe Arg Thr Thr Gly Gln Pro Glu Arg Pro Leu
                485                 490                 495

Asp Glu Tyr Gln Ala Asn Glu Glu Ser Ala Phe Ile Ser Ile Tyr Val
            500                 505                 510

Phe Asn Ala Asp Gly Lys Arg Val Ser Leu Ser Asp Gly Ala Leu His
        515                 520                 525

Arg Gly Pro Tyr Val Asp Ser Pro Asn Thr Leu Met Arg Leu Glu Met
    530                 535                 540

Pro Pro Arg Thr Thr Tyr Thr Val Val Ser Glu Gln Ser Leu Pro
545                 550                 555                 560

Ser Leu Asn Gln Asn Phe Thr Leu Ser Ala Phe Ser Thr Cys Pro Val
                565                 570                 575

Arg Met Ala Lys Ala Gln Asp Lys Tyr Met Cys Val Arg Lys Ile Gln
            580                 585                 590

Gly Ser Trp Thr Pro Ser Thr Ala Gly Gly Asn Ala Glu Ser Ser Arg
        595                 600                 605

Tyr Pro Leu Asn Pro Gln Phe Arg Leu Glu Ile Glu Asn Asp Thr Asp
    610                 615                 620

Val Ser Leu Leu Leu Glu Cys Pro Asn Thr Glu Leu Ala Thr His Val
625                 630                 635                 640

Lys Leu Phe Trp Ser Asn Gly Asn Arg Val Ser Arg Val Arg Ser Arg
                645                 650                 655

Asp Ile Ile Ala Asp Ser Gly Asp Tyr Arg Arg Gly Gly Ser Leu Val
            660                 665                 670

Glu Lys Lys Ala Leu Glu Pro Gly Ser Tyr Thr Ile Val Cys Ser Thr
        675                 680                 685

Phe Ala Pro Asp Gln Leu Gly Arg Phe Thr Leu Trp Val Ser Ser Leu
    690                 695                 700

Val Pro Cys Lys Thr Ser Pro Leu Pro Glu Ala Ala Gly Arg Arg
705                 710                 715                 720

Thr Val Ile Ser Asp Ile Gly Val Leu Pro Pro Gly Arg Asp Arg Met
                725                 730                 735

Leu Ala Ser Leu Gln Val Pro Arg Leu Thr Arg Ile Lys Leu Ile Thr
            740                 745                 750

Arg Ser Arg Gln Ser Ile Ile Gly Ser His Pro Val Gly Pro Ser Pro
        755                 760                 765

Val Leu Met Thr Val Glu Leu Gly Gln Gly Pro Tyr Lys Gln Ile Leu
```

-continued

```
                770                 775                 780
Ala Thr Ser Glu Asp Gly Thr His Ser Asp Ala Val Ser Gly Val Arg
785                 790                 795                 800

Val Glu Asp Phe Asp Leu Gln Pro Gly Leu Glu Glu Ser Gly Gly Ile
                805                 810                 815

Trp Ile Val Ile Glu Arg Ile Gly Gly Pro Gly Gly Gln Val Glu Asp
                820                 825                 830

His Phe Glu Val Glu Ala Leu Ala Glu Glu Arg Val Glu Ile Gly Glu
            835                 840                 845

Trp Ile Leu Glu Asp Ala
    850
```

(2) INFORMATION FOR SEQ ID NO:18:

(i) SEQUENCE CHARACTERISTICS:
        (A) LENGTH: 842 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:18:

```
Met Ser Arg Thr Ser Ser Ala Pro Ser Gln Lys Ser Leu Ile Ser Arg
1               5                   10                  15

Ala Leu Lys Ala Glu Arg Asp Val Ile Thr Ala Ser Ser Gln Ser Gln
            20                  25                  30

Ala Leu Asp Ala Ala Ile Asp Ala Ala Glu His Tyr Met Lys Ala Leu
            35                  40                  45

Ala Leu Thr Ser Ser Ser Lys Asp Arg Asn Val Leu Asp Ala Lys Cys
50                      55                  60

Lys Glu Trp Leu Thr Arg Ala Glu Lys Ile Lys Gly Ser Glu Asp Trp
65                  70                  75                  80

Arg Ser Val Ala Gln Ser Arg Arg Ser Arg Leu Arg Thr Pro Ala Ser
                85                  90                  95

Thr Arg Lys Leu Thr Thr Arg Glu Asp Ile Ile Leu Leu Gln Gly Ala
                100                 105                 110

Lys Leu Asn Gly Phe Ile Phe Pro Pro Trp Lys Ala Glu Pro Ser Leu
            115                 120                 125

Thr Glu Phe Glu Thr Gly Thr Asn Gly Asp Val Leu Phe Thr Asp Lys
130                 135                 140

Pro Asp Leu His Leu Ser Asn Leu Gln Arg Asp Ile Phe Ala Gly Trp
145                 150                 155                 160

Lys Arg Pro His Glu Leu Leu Ser Gly Gln Val Asp Asp Ala Gly Met
                165                 170                 175

Pro Leu Asn Pro Val Met Thr Val Ser Gly Asn Thr Asp Leu Val Gln
            180                 185                 190

Asp Val Leu Thr Asp Cys Ser Val Val Ala Ser Leu Cys Ala Thr Thr
            195                 200                 205

Ser Arg Ser Glu Arg Gly Leu Asp Asp Thr Leu Leu Pro Ile Val Tyr
210                 215                 220

Pro Cys Ile His Asn Ser Met Lys Ser Asp Ile Ser Pro Ser Gly Lys
225                 230                 235                 240

Tyr Ile Phe Arg Phe Tyr Phe Asn Gly Cys Phe Arg Lys Val Val Ile
                245                 250                 255

Asp Asp Arg Leu Pro Ser Ser Lys Thr Ser Arg Ser Leu Tyr Met Ile
```

-continued

```
                260                    265                    270
Asp Arg Asn His Arg Asn Phe Met Trp Pro Ala Leu Val Glu Lys Ala
            275                    280                    285
Tyr Leu Lys Leu Arg Gly Gly Tyr Glu Phe Pro Gly Ser Asn Ser Gly
290                    295                    300
Thr Asp Leu Trp Val Leu Thr Gly Trp Ile Pro Glu Gln Val Phe Leu
305                    310                    315                    320
His Ser Asp Glu Val Thr Ala Asp Gln Ile Trp Ser Asp Leu Phe Lys
            325                    330                    335
Ser Phe His Ser Gly Asp Val Leu Leu Thr Ile Gly Thr Gly Lys Leu
            340                    345                    350
Thr Glu Arg Glu Gln Lys Glu Leu Gly Leu Val Ser Glu His Asp Tyr
            355                    360                    365
Ala Ile Leu Asp Met Lys Glu Leu Lys Gly Arg Arg Gln Phe Leu Ile
            370                    375                    380
Lys Asn Pro Trp Ala Gly Thr Asp Ala Val Tyr Pro Ala Leu Phe Ala
385                    390                    395                    400
Asp Pro Gly Pro Phe Pro Asn Ser Pro Phe Leu Ser Pro Gly Thr Phe
                    405                    410                    415
Trp Met Asp Cys Glu Met Val Leu Gln Asn Phe Glu Asn Leu Tyr Leu
            420                    425                    430
Asn Trp Asn Pro Gly Ile Phe Ala Tyr Gln Glu Asp Ile His Phe Thr
            435                    440                    445
Trp Asp Leu Ser Thr Gly Lys Gly Met Ala Gly Cys Phe Val Lys Asn
            450                    455                    460
Pro Gln Phe Ser Val Tyr Thr Glu Arg Gly Gly Val Val Trp Leu Leu
465                    470                    475                    480
Leu Gly Arg His Leu Arg Thr Ile Glu Ser Arg Ala Ser Glu Glu Asp
                    485                    490                    495
Glu Arg Phe Gly Phe Ile Ser Ile Tyr Val Phe Lys Gly Gly Lys Arg
                    500                    505                    510
Val Ala Leu Ser Asp Gly Ala Leu His Arg Gly Pro Tyr Val Asp Ser
            515                    520                    525
Pro Asn Thr Leu Met Lys Leu Asp Val Pro Pro Arg Ser Thr Tyr Thr
            530                    535                    540
Ala Val Val Ser Glu Glu Ser Leu Pro Arg Val Ser Gln Asn Phe Thr
545                    550                    555                    560
Ile Ser Ala Phe Ser Asp Ser Pro Val Arg Ile Ser His Ala Pro Asn
                    565                    570                    575
Lys Tyr Ile Cys Val Thr Lys Val Gln Gly Ser Trp Thr Pro Thr Thr
            580                    585                    590
Ala Gly Gly Asn Ala Glu Ser Ala Arg Tyr Ser Leu Asn Pro Gln Phe
            595                    600                    605
Ser Ile Val Leu Ser Asp Pro Thr Asp Ile Ser Ile Val Leu Glu Pro
610                    615                    620
Ser Asp Gln Glu Leu Ala Thr His Val Lys Leu Phe Trp Ser Gly Gly
625                    630                    635                    640
Lys Arg Ile Ala Arg Val Arg Ser Arg Asp Ile Val Ala Asp Ser Gly
                    645                    650                    655
Asp Tyr Arg Arg Gly Gly Ser Leu Val Glu Lys Gln Asp Leu Asp Pro
                    660                    665                    670
Gly Glu Tyr Thr Ile Val Val Ser Thr Phe Ala Pro Asp Gln Tyr Gly
            675                    680                    685
```

Ser Phe Thr Leu Trp Val Ser Thr Asn Ile Thr Cys Glu Val Thr Gln
    690                 695                 700

Leu Pro Ser Glu Ala Ala Gly Arg Arg Ala Val Leu Ser Asp Ile Gly
705                 710                 715                 720

Val Leu Leu Pro Gly Gln Asp Arg Met Leu Ala Pro Leu Thr Thr Pro
                725                 730                 735

Arg Leu Thr Arg Val Lys Leu Ile Ala Arg Ser Arg Glu Ser Arg Ile
            740                 745                 750

Gly Asn Arg Pro Val Gly Pro Ser Pro Leu Leu Met Thr Val Glu Leu
            755                 760                 765

Gly Gln Gly Pro Tyr Lys Glu Ile Leu Ala Thr Ser Glu Asp Gly Asp
        770                 775                 780

His Ser Asp Ser Ile Ser Gly Val Arg Val Glu Asp Phe Asp Leu Gln
785                 790                 795                 800

Pro Gly Leu Glu Glu Arg Gly Gly Val Trp Ile Val Leu Glu Arg Ile
                805                 810                 815

Gly Gly Leu Ala Val Lys Trp Lys Ile Ile Ser Lys Trp Lys Leu Trp
            820                 825                 830

Glu Lys Arg Glu Trp Arg Leu Gly Asn Gly
        835                 840

(2) INFORMATION FOR SEQ ID NO:19:

(i) SEQUENCE CHARACTERISTICS:
        (A) LENGTH: 38 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:19:

Gly Ile Leu Leu Ala Gly Ser Ala Asn Ser Lys Tyr Ala Phe Leu Gly
1               5                   10                  15

Ser Leu Arg Ser Thr Ala Gln Leu Ile Ser Tyr Glu Leu Ile Leu Ser
            20                  25                  30

Ser Val Ile Leu Leu Val
        35

(2) INFORMATION FOR SEQ ID NO:20:

(i) SEQUENCE CHARACTERISTICS:
        (A) LENGTH: 371 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:20:

Met Phe Tyr Ser Leu Thr Ile Ile Ser Ile Leu Glu Val Leu Leu Val
1               5                   10                  15

Leu Val Pro Ser Leu Leu Ala Val Ala Tyr Val Thr Val Ala Glu Arg
            20                  25                  30

Lys Thr Met Ala Ser Met Gln Arg Arg Leu Gly Pro Asn Ala Val Gly
        35                  40                  45

Tyr Leu Gly Leu Leu Gln Ala Phe Ala Asp Ala Leu Lys Leu Leu Leu
    50                  55                  60

Lys Glu Tyr Val Ala Leu Thr Gln Ala Asn Met Thr Leu Phe Phe Leu

```
65                  70                  75                  80
Gly Pro Val Ile Thr Leu Ile Phe Ser Leu Leu Gly Tyr Ala Val Ile
                85                  90                  95
Pro Tyr Gly Pro Ser Leu Val Ile Gln Asp Val Asn Leu Gly Ile Leu
               100                 105                 110
Tyr Met Leu Ala Val Ser Ser Leu Ala Thr Tyr Gly Ile Leu Leu Ala
               115                 120                 125
Gly Trp Ser Ala Asn Ser Lys Tyr Ala Phe Leu Gly Ser Leu Arg Ser
       130                 135                 140
Ala Ala Gln Leu Ile Ser Tyr Glu Leu Val Leu Ser Ser Ala Ile Leu
145                 150                 155                 160
Leu Val Ile Met Leu Thr Gly Ser Phe Asn Leu Gly Val Asn Thr Glu
               165                 170                 175
Ser Gln Arg Ala Val Leu Phe Val Leu Pro Leu Leu Pro Ile Phe Ile
               180                 185                 190
Ile Phe Phe Ile Gly Ser Ile Ala Glu Thr Asn Arg Ala Pro Phe Asp
       195                 200                 205
Leu Ala Glu Ala Glu Ser Glu Leu Val Ser Gly Phe Met Thr Glu His
       210                 215                 220
Ala Ala Val Val Phe Val Phe Phe Leu Ala Glu Tyr Gly Ser Ile
225                 230                 235                 240
Val Leu Met Cys Ile Leu Thr Ser Ile Leu Phe Leu Gly Gly Tyr Leu
               245                 250                 255
Phe Ile Asn Leu Lys Asp Val Phe Asn Ile Leu Asp Phe Val Tyr Ser
               260                 265                 270
Asn Leu Phe Ile Phe Glu Ile Asn Trp Met Val Ser Glu Arg Ser Tyr
               275                 280                 285
Thr Glu Asp Phe Phe Asn Asn Tyr Lys Ser Ile Leu Glu Gly Trp Leu
       290                 295                 300
Tyr Gly Trp Ile Ile Gly Leu Lys Ser Ser Ile Met Ile Phe Ile Phe
305                 310                 315                 320
Ile Leu Gly Arg Ala Ser Phe Pro Arg Ile Arg Tyr Asp Gln Leu Met
               325                 330                 335
Gly Phe Cys Trp Thr Val Leu Leu Pro Ile Ile Phe Ala Leu Ile Ile
               340                 345                 350
Leu Val Pro Cys Ile Leu Glu Ser Phe Tyr Ile Leu Pro Trp Asn Leu
               355                 360                 365
Asn Leu Phe
    370

(2) INFORMATION FOR SEQ ID NO:21:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:21:

GGTTGCATGC TCTAGACTTC GTCACCTTAT TAGCCC                               36

(2) INFORMATION FOR SEQ ID NO:22:

(i) SEQUENCE CHARACTERISTICS:
        (A) LENGTH: 40 base pairs
        (B) TYPE: nucleic acid
        (C) STRANDEDNESS: single
```

(D) TOPOLOGY: linear (xi) SEQUENCE DESCRIPTION: SEQ ID NO:22:

TTCGCGCGCA TCAGTCTCGA GATCGTGTGT CGCGAGTACG                    40

(2) INFORMATION FOR SEQ ID NO:23:

(i) SEQUENCE CHARACTERISTICS:
            (A) LENGTH: 41 base pairs
            (B) TYPE: nucleic acid
            (C) STRANDEDNESS: single
            (D) TOPOLOGY: linear (xi) SEQUENCE DESCRIPTION: SEQ ID NO:23:

GATCTCGAGA CTAGTGCGCG CGAACAGACA TCACAGGAAC C                  41

(2) INFORMATION FOR SEQ ID NO:24:

(i) SEQUENCE CHARACTERISTICS:
            (A) LENGTH: 42 base pairs
            (B) TYPE: nucleic acid
            (C) STRANDEDNESS: single
            (D) TOPOLOGY: linear (xi) SEQUENCE DESCRIPTION: SEQ ID NO:24:

CAACATATGC GGCCGCGAAT TCACTTCATT CCCACTGCGT GG                 42

(2) INFORMATION FOR SEQ ID NO:25:

(i) SEQUENCE CHARACTERISTICS:
            (A) LENGTH: 6800 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:25:

TATTCTGCTA GTAGTTAGAT CTACTGAGGG GGTATAACTC TTCGGTAGCC GGTGCGTATG    60

CAGTTGTATT GTGACTGATA GATGAGAAGA AGGGCGTTTA CTGGTTGCAA GAGAATGATG   120

TTATGCTTTG CATATAAGAG ATGGAATTAT TACTGATATG TGTCTAAAAT TACAATGATT   180

TGTTTTACTG AAACTGAGTA TAATGCCAGT TTGGATGTAG CCGCGTAGGT GATACTTAAT   240

CCGGACCAAA TTATGAGACC TCGATAGTAC AATGCTATTG GACTTGTAAG ATAATAGTCT   300

AGTTCTTCAT AGACAAACCT GAAAAGGAA GGACTCGAAG TCATTTCGAC AAGCCATAGT    360

ATGATTAGGC ATCTAGGAGC TGAACGGAAA CGTCGTATGC GAGAGGGCCA GAACCAAAAT   420

ACGACAGTAG GAGGATTCCT ACCCCTTGGT ATATATGGAA ACCGGTTTTA AAGACTGGGC   480

GTCCTCGTAC CTCACAGTCG AGCATGCCAG ACGTTGGCGC ACACATTCCC CAGATCGGCT   540

GGAGCCTATC GCAATGCAAC CGTACCCACC CGGCGTNTAC TATATCTGAG CATTCCTGCT   600

GCAAGTCGTG GAGGTTGTTC CAGCCAATGA GGTCCGTTGA GCTTCTTTTT CCGATATGGT   660

GATAGCTGAC AGTGTACTAG TGTCGACTGC ACAGGTGCCT CGCGGAAATG TGAGATCGGA   720

GCATGTCTTG CTTCAGCGAC CGAAGTATGG ACGAATGTCC GCCATCTTGA AGAATGGTGA   780

CTACCGGAGG ATTGTCTCCA GCTCAGGACT ATGTATATGC CACGATGCCA CGGCTTTGTG   840

TGATAGAGTT CAAGAGCCGA GATTTACAAC GGTGATTACT ATCGCAGATA TCAGCACAGT   900

ACCGGCAAGA TGGTCAACTG GAGCAACATA CTACCCACAT TAACCGCCTT CATCGCTTTT   960

ATCCTGGGCA TGCTATGCCT CTTTGCAGGA ACGAAAACAA ACCTTTTATT AGATACAGAT  1020

```
GTCTTCACGG TGTGTGAGCC TCCGTCACAC TTGCTTGTAC GAGCGGGGAC TAACGACAGG    1080

CGAAGATATA TACGACAAGT ATAAGCAATG GCACGGGGAT GCGGGACTTC TACTCGATAT    1140

ATGTCATGTC TTACTGTGAG GGATTCCTGC ATGCAGAAAA TCGAAACCTA ACCGGATGCT    1200

CACACCCGTC ACTACTGTTC TCCTTCAATG CGACAGAAGC GTTAACGAAA GATGCTGGCA    1260

ACAACACCTC GTTATCCAGC CTGGGATGGC CGAGTTCCAT CACCGATGAT CTACGCACGT    1320

TCGGTGCTAC CAGCCAGAGT ATGGGTGTCT TCTACTGTAT TGGGATAGGA TTAGCGGGAC    1380

TGGCGGTTTT GGAACGATTG TGGTTCGTGA TCGCGAAAGG GCCGAGACAG ACGGTTGTAG    1440

AAGTTTCTTC TCTTATGGTA GGCTCCATTG AACGTTCTAG ATCCCGTCCG GTACTAAGAA    1500

GGCCCACAGC TCAGTTTCAC TATGCTCAGC ATACCGTCTA TCATCGCAAC GGTCGTTGCC    1560

TTACAATTTG TGAGCCTCAT CAATCGTCAC GGAGAGGAGT CTGGTGTGAC AGCGAGATAT    1620

GGACATCAAT TTTTAGGAAT GACGTGGGCA GCCGTCGGGT TGTTGCTGGT CGGAAGCACT    1680

GTCAGTTTAC TGACGGTATT GGTGGACCGC AACCGATCGG CAGACCAGTA TGAACCGGTG    1740

GCAGAACCGA AGACGGTGGC CGAGGATTCG GACTCGGTAG CGTCGAACCA GAAGGGGGAC    1800

TAAGAAAGGA ACAGAATGGA GAGGAATAAT CATAAGAGAA AAAAGGGGG AAATTAACCA    1860

AAGCAGGAAA AGTAGGGAAA AAAAAAAGAA GAAGACCGGA GAAAGCCAAG GAAAGGGAAC    1920

GAATCGGGAG GAGTGTTTCT TGTTTGCAAA TACGTTGGAT TGGAGCCCAA TATTGAATAT    1980

ACTCCGTACT GTAGTCGAAA GAAAGGACAA GAGCCCCACC AAACCTCGAC CGTTCCATAG    2040

CAGAAATTCC ATGACTATCT GTTAATATTT TCTGATCGAT GATGTTGTAA CAGTGGTTGA    2100

AGTGGACCTT ATTTTTCGCA ATACAATAGC AGCATGGCTT GTGGGAAGGG GTCTTGAGAT    2160

CATAGTCATA GTGTAAGAAA AAATTGGGTC TCCCGCGGAT GGCGACGTCA CGAGTGGACC    2220

CGGGAAAAGG TCTCGCCAAA TGAGGCAACC CGGTTCCCTC CGTTCCAACC GCTATGCCTG    2280

CGATTCTATC AATGATAGTG GGTCACTCGA TGGATTCAAG GGATGTCAAA TGATGACGTT    2340

AAGTTGACTA CGACTGTTGC TGTCATGCAC TGGAAATTTA TCGGGAGGAA TTGACCAGTC    2400

TTATTCGCGG AGGAGGGAGT GAAGAGACTA GGAGTCGTTC AGTTCAGTCT TGCAGGAAAT    2460

CCACTCGGGG ATGAGCAGGG GTTAACCTCA TGGACGACTG AACTACTCCG TACAGGACGG    2520

AGTACAGAAT GTCGAATTCA CCCGTTCGGC TAAAGATGAG TCCGTTTTAT GGTCACCTAG    2580

CGGAGTGCAA CCCCGACTGG ATAACTGTTA GGAAAAGAGA GAATTAGGAT CGGGTGACAA    2640

TTGGGTCTCT AAGTTCCTGC GTAACGTGAT ACCGAATCAA ATCCATGACC CTATCGCCAG    2700

GACGATCACG GAATGGTCCG GATCAGAAAT TCTGAGGTTC TGGTTGGATT GATGACCTGA    2760

ACTAATACCC AATATCATGA CGAAAACCAA TCCCCTCATT TCCTGTTTTT GCACGGGAAT    2820

AGCCACAATT TCCCCCCCCC CCCCCCCCCC CCAGAAAACC GAAATGAAGT CTGAGCCCTC    2880

CGGAAGACTG CGTTCCTAGC CCCCATGTGT TTAGTTGATA CTATTCCCAT AGGCACGTTT    2940

CCCCCCTTCC CCACTTGAGT TCCACCAGTC GTGAATGAGG AGGTTCCATT CTCGCCCAGA    3000

GTTTGGTTTC TTTGCCGTTC CATACAAGGC GTCACTGCAT CATTCCTTCC CTTTTCATTC    3060

ACCCCTCTCT TGTCCACCAT CGTGAAATGT TTCTGTAGTA CATTTAATAA ATACCCCTCG    3120

TTACCCCTCT TTCTGTTTCC CAAGAAATCA ACATCATCAT CAACAACAAC AACAACAATC    3180

ACCCTCCCAC TTCACAGGTT CTCTTTCTGA TACCCATCCT TCTGTCTCTC ATCTACTACC    3240

ACTACTTTCA TATACTCTCT TCTATCCTAC TTCATCACCA TCACAACCTT CTTCCCCATT    3300

CTTGTTTCAA CCCAACATCA ATATATTACC GTTGTCAACC ATCCATCATG GGTAAAAAGG    3360

CTATCCAGTT TGGCGGTGGA AACATTGGCC GTGGCTTTGT GGCTGAGTTT CTCCACGCTG    3420
```

```
CCGGCTATGA AGTCGTCTTC ATTGATGTCA TGGATAGCGT CATCAACTCT TTGCAACAGA   3480

CCCCGTCGTA CGACGTCACG GAGGTCAGCG AAGAGGGTGA AAGCACCAAG ACCATCACCA   3540

ACTATCGCGC CATCAACTCC AAGACGCATG AGGCCGACGT CGTTCAGGAG ATCGCATCGG   3600

CAGATGTGGT TACCTGTGCT GTCGGTCCCA ACATCCTTAA GTTCATCGCG CCAGTCATTG   3660

CCAAAGGTAT TGATGCGCGC ACCGAAGAGA GACCCGTGGC TGTGATCGCC TGTGAGAACG   3720

CTATCGGCGC TACAGATACC TTGCACGGCT ACATCAAGCA GCACACCAAC CCTGACCGTC   3780

TGGAGACCCT CTCTGAGCGT GCCCGTTTTG CCAACTCGGC TATCGACCGC ATCGTCCCCA   3840

ACCAGCCCCC GAACAGTGGT CTCAATGTTC GCATCGAGAA GTTCTACGAG TGGGCCGTGG   3900

AGAAGACTCC ATTTGGCGAA TGGGGTCACC CCGACATCCC TGCCATCCAC TGGGTGGACC   3960

ACCTCGAACC TTACATCGAA CGCAAGCTCT TCACCGTCAA CACTGGCCAT GCTACCACCG   4020

CCTACTATGC TCACAAGCGT GGCAAGAAGA TGATCGCCGA GGCCCTCGAA GACCCAGAGA   4080

TCCGCGAGAC TGTGCACAAG GTGCTCGAGG AGACTGCTTC CCTCATTGTA TCCAAGCATG   4140

AGATCTCGGA GCAGGAGCAG AAGGAATACG TTGACAAGAT TGTCAGCCGT ATCTCCAACC   4200

CCTATCTCGA GGACAACGTT GAGCGTGTGG GACGTGCTCC TCTCCGCAAA CTGTCTCGCA   4260

AGGAACGGTT CATTGGACCT GCTTCGCAGC TCGCAGAGCG CGGCCAGAAG TTCGATGCTC   4320

TCCTGGGCGC CATCGAGATG GCTCTTCGCT TCCAGAACGT CCCAGGCGAC GAGGAGAGTT   4380

CCGAGCTTGC TCGCATTTTG AAGGAGAACT CGGCCGAGGA TGCCACCTCG CAGCTCACCG   4440

GATTGGAGAA AGACCACCCA CTCTACTCTC ATGTGGTTGA GCGTGTGTCC ACGGTCCAGC   4500

AAGGCTCCAA ATCAGTGCTG TGATTCTCGA TCGTTTTCCA CACCACCACA CTCCTTTTTA   4560

TCACCAGAAA ACGAAGGGTT CCGAGTCCAT CACCAATATG GATCGCCCGA GGGATATTGG   4620

ATCTGATATC AAACTGTTCT GTCCGCTGGC CGGGCATGAA CTGCATGGGA TACGGCGAAC   4680

ATATGAAATA ACCCCCAATT CCCATAAGTA TTACATATTA TGGAACCACA GCCGGTGTCT   4740

GTAAATGTCG GTTCAACTCG AAGATGGCCG ATGCAATCGG CCCGTAGGGT ATATGGTCTG   4800

GCGCCACCTC GGCCGCCGGC TTCCCCCTTT TTATAGATGT GGCGAATAAA ACACCGGATG   4860

TTTTGTGTGT CAGGGGAATG GTGGCAGTGG TGTTATGAGT CATTGTGAAG TGAGTAGTGA   4920

GTAGATTTGG TGGGGATTTT CATAGATGGT GGTTTGAAGG TCTTGGGTTT CTGGGGTTTA   4980

TCCGCGTATA TTCTGCTAGT AGTTAGATCT ACTGAGGGGG TATAACTCTT CGGTAGCCGG   5040

TGCGTATGCA GTTGTATTGT GACTGATAGA TGAGAAGAAG GGCGTTTACT GGTTGCAAGA   5100

GAATGATGTT ATGCTTTGCA TATAAGAGAT GGAATTATTA CTGATATGTG TCTAAAATTA   5160

CAATGATTTG TTTTACTGAA ACTGAGTATA ATGCCAGTTT GGATGTAGCC GCGTAGGTGA   5220

TACTTAATCC GGACCAAATT ATGAGACCTC GATAGTACAA TGCTATTGGA CTTGTAAGAT   5280

AATAGTCTAG TTCTTCATAG ACAAACCTGA AAAAGGAAGG ACTCGAAGTC ATTTCGACAA   5340

GCCATAGTAT GATTAGGCAT CTAGGAGCTG AACGGAAACG TCGTATGCGA GAGGGCCAGA   5400

ACCAAAATAC GACAGTAGGA GGATTCCTAC CCCTTGGTAT ATATGGAAAC CGGTTTTAAA   5460

GACTGGGCGT CCTCGTACCT CACAGTCGAG CATGCCAGAC GTTGGCGCAC ACATTCCCCA   5520

GATCGGCTGG AGCCTATCGC AATGCAACCG TACCCACCCG GCGTCTACTA TATCTGAGCA   5580

TTCCTGCTGC AAGTCGTGGA GGTTGTTCCA GCCAATGAGG TCCGTTGAGC TTCTTTTTCC   5640

GATATGGTGA TAGCTGACAG TGTACTAGTG TCGACTGCAC AGGTGCCTCG CGGAAATGTG   5700

AGATCGGAGC ATGTCTTGCT TCAGCGACCG AAGTATGGAC GAATGTCCGC CATCTTGAAG   5760
```

-continued

```
AATGGTGACT ACCGGAGGAT TGTCTCCAGC TCAGGACTAT GTATATGCCA CGATGCCACG    5820

GCTTTGTGTG ATAGAGTTCA AGAGCCGAGA TTTACAACGG TGATTACTAT CGCAGATATC    5880

AGCACAGTAC CGGCAAGATG GTCAACTGGA GCAACATACT ACCCACATTA ACCGCCTTCA    5940

TCGCTTTTAT CCTGGGCATG CTATGCCTCT TTGCAGGAAC GAAAACAAAC CTTTTATTAG    6000

ATACAGATGT CTTCACGGTG TGTGAGCCTC CGTCACACTT GCTTGTACGA GCGGGGACTA    6060

ACGACAGGCG AAGATATATA CGACAAGTAT AAGCAATGGC ACGGGATGC GGGACTTCTA     6120

CTCGATATAT GTCATGTCTT ACTGTGAGGG ATTCCTGCAT GCAGAAAATC GAAACCTAAC    6180

CGGATGCTCA CACCCGTCAC TACTGTTCTC CTTCAATGCG ACAGAAGCGT TAACGAAAGA    6240

TGCTGGCAAC AACACCTCGT TATCCAGCCT GGGATGGCCG AGTTCCATCA CCGATGATCT    6300

ACGCACGTTC GGTGCTACCA GCCAGAGTAT GGGTGTCTTC TACTGTATTG GGATAGGATT    6360

AGCGGGACTG GCGGTTTTGG AACGATTGTG GTTCGTGATC GCGAAAGGGC CGAGACAGAC    6420

GGTTGTAGAA GTTTCTTCTC TTATGGTAGG CTCCATTGAA CGTTCTAGAT CCCGTCCGGT    6480

ACTAAGAAGG CCCACAGCTC AGTTTCACTA TGCTCAGCAT ACCGTCTATC ATCGCAACGG    6540

TCGTTGCCTT ACAATTTGTG AGCCTCATCA ATCGTCACGG AGAGGAGTCT GGTGTGACAG    6600

CGAGATATGG ACATCAATTT TTAGGAATGA CGTGGGCAGC CGTCGGGTTG TTGCTGGTCG    6660

GAAGCACTGT CAGTTTACTG ACGGTATTGG TGGACCGCAA CCGATCGGCA GACCAGTATG    6720

AACCGGTGGC AGAACCGAAG ACGGTGGCCG AGGATTCGGA CTCGGTAGCG TCGAACCAGA    6780

AGGGGGACTA AGAAAGGAAC                                                6800
```

(2) INFORMATION FOR SEQ ID NO:26:

(i) SEQUENCE CHARACTERISTICS:
        (A) LENGTH: 391 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:26:

```
Met Gly Lys Lys Ala Ile Gln Phe Gly Gly Gly Asn Ile Gly Arg Gly
 1               5                  10                  15

Phe Val Ala Glu Phe Leu His Ala Ala Gly Tyr Glu Val Val Phe Ile
                20                  25                  30

Asp Val Met Asp Ser Val Ile Asn Ser Leu Gln Gln Thr Pro Ser Tyr
            35                  40                  45

Asp Val Thr Glu Val Ser Glu Glu Gly Glu Ser Thr Lys Thr Ile Thr
        50                  55                  60

Asn Tyr Arg Ala Ile Asn Ser Lys Thr His Glu Ala Asp Val Val Gln
65                  70                  75                  80

Glu Ile Ala Ser Ala Asp Val Val Thr Cys Ala Val Gly Pro Asn Ile
                85                  90                  95

Leu Lys Phe Ile Ala Pro Val Ile Ala Lys Gly Ile Asp Ala Arg Thr
                100                 105                 110

Glu Glu Arg Pro Val Ala Val Ile Ala Cys Glu Asn Ala Ile Gly Ala
            115                 120                 125

Thr Asp Thr Leu His Gly Tyr Ile Lys Gln His Thr Asn Pro Asp Arg
        130                 135                 140

Leu Glu Thr Leu Ser Glu Arg Ala Arg Phe Ala Asn Ser Ala Ile Asp
145                 150                 155                 160
```

-continued

```
Arg Ile Val Pro Asn Gln Pro Asn Ser Gly Leu Asn Val Arg Ile
            165                 170                 175

Glu Lys Phe Tyr Glu Trp Ala Val Lys Thr Pro Phe Gly Glu Trp
            180                 185                 190

Gly His Pro Asp Ile Pro Ala Ile His Trp Val Asp His Leu Glu Pro
            195                 200                 205

Tyr Ile Glu Arg Lys Leu Phe Thr Val Asn Thr Gly His Ala Thr Thr
    210                 215                 220

Ala Tyr Tyr Ala His Lys Arg Gly Lys Met Ile Ala Glu Ala Leu
225                 230                 235                 240

Glu Asp Pro Glu Ile Arg Glu Thr Val His Lys Val Leu Glu Thr
                245                 250                 255

Ala Ser Leu Ile Val Ser Lys His Glu Ile Ser Glu Gln Glu Gln Lys
            260                 265                 270

Glu Tyr Val Asp Lys Ile Val Ser Arg Ile Ser Asn Pro Tyr Leu Glu
            275                 280                 285

Asp Asn Val Glu Arg Val Gly Arg Ala Pro Leu Arg Lys Leu Ser Arg
    290                 295                 300

Lys Glu Arg Phe Ile Gly Pro Ala Ser Gln Leu Ala Glu Arg Gly Gln
305                 310                 315                 320

Lys Phe Asp Ala Leu Leu Gly Ala Ile Glu Met Ala Leu Arg Phe Gln
                325                 330                 335

Asn Val Pro Gly Asp Glu Glu Ser Ser Glu Leu Ala Arg Ile Leu Lys
            340                 345                 350

Glu Asn Ser Ala Glu Asp Ala Thr Ser Gln Leu Thr Gly Leu Glu Lys
            355                 360                 365

Asp His Pro Leu Tyr Ser His Val Val Glu Arg Val Ser Thr Val Gln
    370                 375                 380

Gln Gly Ser Lys Ser Val Leu
385                 390
```

(2) INFORMATION FOR SEQ ID NO:27:

(i) SEQUENCE CHARACTERISTICS:
        (A) LENGTH: 195 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:27:

```
Met Val Asp Gln Ala Gln Asp Thr Leu Arg Pro Asn Asn Arg Leu Ser
1               5                   10                  15

Asp Met Gln Ala Thr Met Glu Gln Thr Gln Ala Phe Glu Asn Arg Val
            20                  25                  30

Leu Glu Arg Leu Asn Ala Gly Lys Thr Val Arg Ser Phe Leu Ile Thr
        35                  40                  45

Ala Val Glu Leu Leu Thr Glu Ala Val Asn Leu Val Leu Gln Val
    50                  55                  60

Phe Arg Lys Asp Asp Tyr Ala Val Lys Tyr Ala Val Glu Pro Leu Leu
65                  70                  75                  80

Asp Gly Asp Gly Pro Leu Gly Asp Leu Ser Val Arg Leu Lys Leu Ile
                85                  90                  95

Tyr Gly Leu Gly Val Ile Asn Arg Gln Glu Tyr Glu Asp Ala Glu Leu
                100                 105                 110
```

```
Leu Met Ala Leu Arg Glu Glu Leu Asn His Asp Gly Asn Glu Tyr Ala
            115                 120                 125

Phe Thr Asp Asp Glu Ile Leu Gly Pro Phe Gly Glu Leu His Cys Val
        130                 135                 140

Ala Ala Leu Pro Pro Pro Gln Phe Glu Pro Ala Asp Ser Ser Leu
145                 150                 155                 160

Tyr Ala Met Gln Ile Gln Arg Tyr Gln Gln Ala Val Arg Ser Thr Met
                165                 170                 175

Val Leu Ser Leu Thr Glu Leu Ile Ser Lys Ile Ser Leu Lys Lys Ala
            180                 185                 190

Phe Gln Lys
        195

(2) INFORMATION FOR SEQ ID NO:28:

(i) SEQUENCE CHARACTERISTICS:
        (A) LENGTH: 366 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:28:

Met Ile Ala Leu His Phe Gly Ala Gly Asn Ile Gly Arg Gly Phe Ile
1               5                   10                  15

Gly Ala Leu Leu His His Ser Gly Tyr Asp Val Val Phe Ala Asp Val
            20                  25                  30

Asn Glu Thr Met Val Ser Leu Leu Asn Glu Lys Lys Glu Tyr Thr Val
        35                  40                  45

Glu Leu Ala Glu Glu Gly Arg Ser Ser Glu Ile Ile Gly Pro Val Ser
50                  55                  60

Ala Ile Asn Ser Gly Ser Gln Thr Glu Glu Leu Tyr Arg Leu Met Asn
65                  70                  75                  80

Glu Ala Ala Leu Ile Thr Thr Ala Val Gly Pro Asn Val Leu Lys Leu
            85                  90                  95

Ile Ala Pro Ser Ile Ala Glu Gly Leu Arg Arg Arg Asn Thr Ala Asn
            100                 105                 110

Thr Leu Asn Ile Ile Ala Cys Glu Asn Met Ile Gly Gly Ser Ser Phe
        115                 120                 125

Leu Lys Lys Glu Ile Tyr Ser His Leu Thr Glu Ala Glu Gln Lys Ser
        130                 135                 140

Val Ser Glu Thr Leu Gly Phe Pro Asn Ser Ala Val Asp Arg Ile Val
145                 150                 155                 160

Pro Ile Gln His His Glu Asp Pro Leu Lys Val Ser Val Glu Pro Phe
                165                 170                 175

Phe Glu Trp Val Ile Asp Glu Ser Gly Phe Lys Gly Lys Thr Pro Val
            180                 185                 190

Ile Asn Gly Ala Leu Phe Val Asp Asp Leu Thr Pro Tyr Ile Glu Arg
        195                 200                 205

Lys Leu Phe Thr Val Asn Thr Gly His Ala Val Thr Ala Tyr Val Gly
        210                 215                 220

Tyr Gln Arg Gly Leu Lys Thr Val Lys Glu Ala Ile Asp His Pro Glu
225                 230                 235                 240

Ile Arg Arg Val Val His Ser Ala Leu Leu Glu Thr Gly Asp Tyr Leu
            245                 250                 255
```

```
Val Lys Ser Tyr Gly Phe Lys Gln Thr Glu His Glu Gln Tyr Ile Lys
            260                 265                 270

Asn Gln Arg Ser Leu Leu Lys Ser Phe His Phe Gly Arg Cys Asp Pro
            275                 280                 285

Arg Ser Glu Val Thr Ser Gln Lys Thr Gly Arg Lys Cys Arg Leu Val
            290                 295                 300

Gly Pro Ala Lys Lys Ile Lys Glu Pro Asn Ala Leu Ala Glu Gly Ile
305                 310                 315                 320

Ala Ala Ala Leu Arg Phe Asp Phe Thr Gly Asp Pro Glu Ala Val Glu
                325                 330                 335

Leu Gln Ala Leu Ile Glu Glu Lys Asp Thr Ala Ala Tyr Phe Lys Arg
            340                 345                 350

Cys Ala Ala Phe Ser Pro Met Asn Arg Cys Thr Pro Ser Phe
            355                 360                 365

(2) INFORMATION FOR SEQ ID NO:29:

(i) SEQUENCE CHARACTERISTICS:
        (A) LENGTH: 3300 base pairs
        (B) TYPE: nucleic acid
        (C) STRANDEDNESS: single
        (D) TOPOLOGY: linear (xi) SEQUENCE DESCRIPTION: SEQ ID NO:29:
```

| | | | | | |
|---|---|---|---|---|---|
| GGATTGGCTG | ACTGCGTGTT | GTTACTCCAG | GGATTGCGAC | GAGCACTTCC | TAAGCCACCG | 60 |
| TGCGACGGAG | GCGACTCTGA | GCGTGACGAT | GCCCTAGCGA | ACCCGCGGAA | GCCCATCGTG | 120 |
| GGGCGAAAAT | CTTCTTCGTC | GGAGCTCATG | TCGGCGATTT | TACGTTTTTG | GCCGGCGGAT | 180 |
| GGTGAGGCCG | GGGGAGAATC | CGAATCCATG | ACCGATCGCA | GATGTCAGGA | TAAGGTGTAA | 240 |
| GTAGTAACTC | AGAGTCGTCG | GAGAGGTTCG | AAAGGCAATG | AAACGGTCAA | ACGACACGTT | 300 |
| TGAGAGCCAC | GAAGGAGCTG | TGGGTTGAGA | TACGCACGAT | AACGAGAAAG | GAAAGTTGAT | 360 |
| TATCGGACAT | TTCGGCGCGG | GGAAAATTCA | AGTCCGAGGG | GCCGAGCAAC | AATGACGTTC | 420 |
| GTTGCATCGA | ATCCCCTTC | CGGTTATTTT | TCCCTCTTCT | TCTCCTCTTC | TTCTTTTCTT | 480 |
| CTTTACCCTC | TCCTCTCTTT | GGCATTTCGT | CACTACTTTG | TAACGTAACT | CAATTCTATT | 540 |
| GATACATAAA | AATCACATAT | CAACTATGGC | TGCCTCTCTT | ATCCGTACCT | CTGCCCGTAC | 600 |
| CGCTCTTCGC | GCTGGAGCTT | CGGCTACTCC | TAAAGCTGCG | GGTGTTGCGG | GTTTGACCTT | 660 |
| TGCCCGTGGC | AAGGCCACTC | TGCCTGACCT | GGCTTGTATG | GCTCTCCCCT | TCCCTTGATG | 720 |
| TCGTCAATTT | GCCCCTCTGT | TGTGTTATCT | TCCGTTTTGT | CATCTTTCTC | GGCTATTTTG | 780 |
| GCAGTGCGAA | TGAGTAGATG | GGTTACGCTT | GTCGCTCATG | ACGCCCCGGA | AGCACGTAAT | 840 |
| GCAATGGTTG | GTTGACTGAA | TAACAGATGA | CTATGGCGCC | CTTGAGCCCT | CTATCTCCGG | 900 |
| AAAGATCATG | GAGCTTCACC | ACAAGAACCA | CCACCAGACC | TATGTCAACA | GCTACAACAC | 960 |
| CGCCATCGAA | CAGCTCCAGG | AGGCCGTCGC | CAAGGAGGAC | ATCACCACTC | AGATCAACCT | 1020 |
| CAAGCCCCTG | ATCAACTTCC | ACGGTGGTGG | CCACATCAAC | CACACTCTTT | TCTGGGAGAA | 1080 |
| CCTTGCCCCT | AAGAGCCAGG | GCGGTGGTGA | GCCCCCATCT | GGAGCTTTGG | CCAAGGCCAT | 1140 |
| CGACGAAAGC | TTCGGCAGCT | TGGGAGAGTT | CCAGAGCAAG | ATGAACGCCG | CCCTCGCTGG | 1200 |
| TATTCAGGGA | AGCGGATGGG | CTTGGCTCGT | CAAGGACAAG | CAGACCGGAA | ACATCGGCAT | 1260 |
| CAAGACCTAT | GCCGTAAGTT | CCTCCTTGTG | AGCGCCTAAG | GATACAGGTA | GCTAACTCCC | 1320 |
| GACCAGAACC | AGGACCCTGT | CGTTGGTCAG | TTCCAGCCTC | TTCTCGGTAT | TGATGCTTGG | 1380 |
| GAGCACGCCT | ACTAGTAAGT | TTTCTTGGAC | TAGATATCTA | CCAAGCAATA | ACTAATGCCG | 1440 |

```
TGTTAGCCTT CAATACCAGA ACCGCAAGGC TGAGTACTTC AGCGCCATCT GGGACGTCAT    1500

CAACTGGAAG GCGGTTGAGA AGCGCTTCTC GTAAGCGTGC AAAAGTGTTG TGAATTGACG    1560

CAGCTTGATG AGCGCTTTGT TTCAGTTGTG CCCAGAGTGA TACTGTGTAA TGTCTGATCA    1620

AGCTGTACTT GTAGCCCTAA TGCAATTGGA TACGCCTCGT GTATATATAA ACTCATGTTC    1680

GTTGAACGTA AATAATTTTG GGGAAGCTGC ACCAGCCACA GTGGCTGGAT CACATGCTCC    1740

CGTAGCATTC CCGCAGTTTC CGGCAAGCTT ATTTTCTTAG TTTGGGATCC GCTCCGCCCT    1800

CTCCGGATCT TCTTCCCTCA TCTCACCTCT CAAGCGATCA ATTCTCTCGA AATGTCTGCA    1860

GAAAGCCCGG GAGAAAAGCG CGGTGGGTTT CGGGCGTTCT TCGCCGGCGC CCTCCGACCT    1920

AAGAAATCCC GTCAGGTCCT CCGAAAGGCA TCGACACCGA ATCTAAAGGA AGGTCTACAA    1980

AGCAAAGATG ACGTCCCGGC GATGCCTTCA CTGACCCCAT GGAGGCCCA CCGACTCAAA     2040

TACCGAGAAG TAAATCTTCA GAAAGACACA CAGCTAGGCG AAACCCACGA TCATACCGCA    2100

ATGCTGCATT CAATCGGTGT TGGAGAGCTC GATCCGTCCG ATCCACACGC GCAACTACAC    2160

GAATTCGACA ATAGACCCCC AGGCGAGCCT ATGATTGCGA GCTTAACATC GGACCTCTGG    2220

GCCAAGGTCA CCGAGTATCT CAATCCCGCC GAAAGAGCCA GTCTTGCCTT CTCCAGCCGA    2280

ACACTATACG CTCGTCTGGG CCGCGAGCCC TGGATAACAA TAAACCTCCC AGAAAACCAC    2340

GACTACAAAG CGGACTTTCT CATCTCCCAA GATAGACTAC TCCCTCACCA TCTCCTCTGT    2400

TTCCCCTGCG GCAAATACCA CCGCCGCACA CAAGAAGGCT ACGAAAAGCT CCAACCCGCA    2460

GACATAATCA ACCCGCTCTT CGATTGCCCC AACGCCCGCA ACAACGCCCT CCCAGCACCC    2520

CGCCACCGCA TCACCCACGG CCGAGTCCTT TACTTCACCT TCCACCAGCT AGTCATGCGC    2580

GCATACCGAT TTGGACCCCG CTACGGCATC TCAGCCGACT CTCTATCCCG TCGCTGGCGC    2640

CGGGACGGCT GGTCCCACCA AACCCGATAC CACATCCATC AGGGTCGACT GCTCATGCGA    2700

GTCGTGAGCA CCTGCTTCGC CGAACCAGGC CTCAGCGCCA GCCAACAGCG ACTCCTCCTC    2760

TACTCGCGCG ACGACTACTG GCCGTACTTC TCCGTCTGCG CGCACTGGCG GGATGGCGAA    2820

CTTATGAACG TTTGCAAATG CGCCCTCGGC CACATCCCCG TCCCCGCAC CACGAACGGC     2880

CTGCAGGGCC TCGAACACCG CGCAAAAGAT ATGTACCACC GTCGAGAGCA CAATCCCAAC    2940

GCCCTCGCGT CGCTCTGCGG TAAGTGTCGA CCTATGCGTC GCTGCCCCGA GTGTCCCTCC    3000

GAGTATCTGG TCGAGGTCAA GCTCACCGAG GACCGGAGTG GTTCGCATCG CAACTTATTC    3060

CGGCATGCGA TTGTGGTGAC ACGGTGGAGT GATTTGGGGG ATGGGCGGTC GCCGCGGCTA    3120

TCGAAGGAGT GGGCGGCGAT TAATGGGGAC GAGGCGGGTG AGGGGTATGA TTCTTTTGAG    3180

AAAATAGGGA AGAGGGCTAT TTCGGGGATT TTTGAGTCGG CTATTACCGA TGATACTTTG    3240

CCTGGGCAGA GGATTCTTTC AATGAATCCT AAGGGAAAGA AGTTGGGTGA GGCTGGGAAT    3300
```

(2) INFORMATION FOR SEQ ID NO:30:

(i) SEQUENCE CHARACTERISTICS:
  (A) LENGTH: 230 amino acids
  (B) TYPE: amino acid
  (C) STRANDEDNESS: single
  (D) TOPOLOGY: linear (ii) MOLECULE TYPE: None (xi) SEQUENCE DESCRIPTION: SEQ ID NO:30:

```
Met Ala Ala Ser Leu Ile Arg Thr Ser Ala Arg Thr Ala Leu Arg Ala
 1               5                  10                  15
```

```
Gly Ala Ser Ala Thr Pro Lys Ala Ala Gly Val Ala Gly Leu Thr Phe
             20                  25                  30

Ala Arg Gly Lys Ala Thr Leu Pro Asp Leu Ala Tyr Asp Tyr Gly Ala
             35                  40                  45

Leu Glu Pro Ser Ile Ser Gly Lys Ile Met Glu Leu His His Lys Asn
 50                  55                  60

His His Gln Thr Tyr Val Asn Ser Tyr Asn Thr Ala Ile Glu Gln Leu
 65                  70                  75                  80

Gln Glu Ala Val Ala Lys Glu Asp Ile Thr Thr Gln Ile Asn Leu Lys
             85                  90                  95

Pro Leu Ile Asn Phe His Gly Gly His Ile Asn His Thr Leu Phe
                100                 105                 110

Trp Glu Asn Leu Ala Pro Lys Ser Gln Gly Gly Glu Pro Pro Ser
            115                 120                 125

Gly Ala Leu Ala Lys Ala Ile Asp Glu Ser Phe Gly Ser Leu Gly Glu
            130                 135                 140

Phe Gln Ser Lys Met Asn Ala Ala Leu Ala Gly Ile Gln Gly Ser Gly
145                 150                 155                 160

Trp Ala Trp Leu Val Lys Asp Lys Gln Thr Gly Asn Ile Gly Ile Lys
                165                 170                 175

Thr Tyr Ala Asn Gln Asp Pro Val Val Gly Gln Phe Gln Pro Leu Leu
                180                 185                 190

Gly Ile Asp Ala Trp Glu His Ala Tyr Tyr Leu Gln Tyr Gln Asn Arg
                195                 200                 205

Lys Ala Glu Tyr Phe Ser Ala Ile Trp Asp Val Ile Asn Trp Lys Ala
                210                 215                 220

Val Glu Lys Arg Phe Ser
225                 230

(2) INFORMATION FOR SEQ ID NO:31:

(i) SEQUENCE CHARACTERISTICS:
        (A) LENGTH: 233 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:31:

Met Phe Ala Lys Thr Ala Ala Asn Leu Thr Lys Lys Gly Gly Leu
 1               5                  10                  15

Ser Leu Leu Ser Thr Thr Ala Arg Arg Thr Lys Val Thr Leu Pro Asp
             20                  25                  30

Leu Lys Trp Asp Phe Gly Ala Leu Glu Pro Tyr Ile Ser Gly Gln Ile
             35                  40                  45

Asn Glu Leu His Tyr Thr Lys His His Gln Thr Tyr Val Asn Gly Phe
 50                  55                  60

Asn Thr Ala Val Asp Gln Phe Gln Glu Leu Ser Asp Leu Leu Ala Lys
 65                  70                  75                  80

Glu Pro Ser Pro Ala Asn Ala Arg Lys Met Ile Ala Ile Gln Gln Asn
             85                  90                  95

Ile Lys Phe His Gly Gly Gly Phe Thr Asn His Cys Leu Phe Trp Glu
                100                 105                 110

Asn Leu Ala Pro Glu Ser Gln Gly Gly Gly Glu Pro Pro Thr Gly Ala
            115                 120                 125
```

```
Leu Ala Lys Ala Ile Asp Glu Gln Phe Gly Ser Leu Asp Glu Leu Ile
    130                 135                 140

Lys Leu Thr Asn Thr Lys Leu Ala Gly Val Gln Gly Ser Gly Trp Ala
145                 150                 155                 160

Phe Ile Val Lys Asn Leu Ser Asn Gly Gly Lys Leu Asp Val Val Gln
                165                 170                 175

Thr Tyr Asn Gln Asp Thr Val Thr Gly Pro Leu Val Pro Leu Val Ala
                180                 185                 190

Ile Asp Ala Trp Glu His Ala Tyr Tyr Leu Gln Tyr Gln Asn Lys Lys
            195                 200                 205

Ala Asp Tyr Phe Lys Ala Ile Trp Asn Val Val Asn Trp Lys Glu Ala
        210                 215                 220

Ser Arg Arg Phe Asp Ala Gly Lys Ile
225                 230
```

(2) INFORMATION FOR SEQ ID NO:32:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:32:

```
GCTCTAGATC GTCGGAGCTC ATGTCGGCGA TTTTAC                              36
```

(2) INFORMATION FOR SEQ ID NO:33:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:33:

```
GCGGTACCAC GCCTAGAGCA AAGTATAAAT AAGGAA                              36
```

(2) INFORMATION FOR SEQ ID NO:34:

(i) SEQUENCE CHARACTERISTICS:
        (A) LENGTH: 346 base pairs
        (B) TYPE: nucleic acid
        (C) STRANDEDNESS: single
        (D) TOPOLOGY: linear (xi) SEQUENCE DESCRIPTION: SEQ ID NO:34:

```
ATATCGACTG TAGTAATATC TCAGGTCTCT GGGATAGCTG ATGGAATGTT AAGTGAATAA     60

TATTGATTTA AAGTTCCTCT AGTTCCAAGC TCTTATGTAG CTTCATTTTC TATATATATA    120

TATTCTATTT AGTGGTGTTG CAGGCGGTGA GCCTATCGGC CAATCATAGT AAAAAACCCG    180

TTAGTTGCAA TACCCTGTTA GTTGCAAGGC GAATTCCTGG CTGATATCCT TGCAACTAAC    240

GGGGTTTCTC AGTACTCGAA TTGAATATAT ATTTCGCACA AAGTTATTTC GCAAACTTGG    300

GGGCCCTGGG GTCATACAAC CCAAGCCACA AGCTTTATTT AATTCG                   346
```

(2) INFORMATION FOR SEQ ID NO:35:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:35:

CTATGATTGG CCGATAGG                                                          18

(2) INFORMATION FOR SEQ ID NO:36:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:36:

CCAGGCTCGC ACGCTTTC                                                          18

(2) INFORMATION FOR SEQ ID NO:37:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:37:

CTTGCAACTA ACGGGGTT                                                          18

(2) INFORMATION FOR SEQ ID NO:38:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:38:

TGAGAAAGAC CAAGAATG                                                          18

(2) INFORMATION FOR SEQ ID NO:39:

(i) SEQUENCE CHARACTERISTICS:
        (A) LENGTH: 188 base pairs
        (B) TYPE: nucleic acid
        (C) STRANDEDNESS: single
        (D) TOPOLOGY: linear (xi) SEQUENCE DESCRIPTION: SEQ ID NO:39:

GATTTAATGA CTACCTTGAT GATACTGCCA ATATAGTTAG ATAATACAAA TCCTGGCTGC            60

CATATAACGC CCTCGCAAAC GACATCTTGT TCTTATTNTC CCTCAATCGA GCTTGCCTAT           120

GCCCAAGCTT CGAACTATAC GAGCATTGTA AATTGATTTT GATACGGCCT GCCATATCAG           180

ATTGACTC                                                                   188

(2) INFORMATION FOR SEQ ID NO:40:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:40:

TGTAGTCTGA CTAGCATG                                                          18

(2) INFORMATION FOR SEQ ID NO:41:

(i) SEQUENCE CHARACTERISTICS:

(A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:41:

GGATCTTCAC CTAGATCC                                                         18

(2) INFORMATION FOR SEQ ID NO:42:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:42:

CATAGTGTCG ACCAAGC                                                          17

(2) INFORMATION FOR SEQ ID NO:43:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:43:

CAATCGAGCT TGCCTATG                                                         18

(2) INFORMATION FOR SEQ ID NO:44:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:44:

ATTTAAATGG TCCTCGGTGG ATCAAGC                                               27

(2) INFORMATION FOR SEQ ID NO:45:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:45:

TTAATTAATT AGTCCTGTCT GCGCTGGT                                              28

(2) INFORMATION FOR SEQ ID NO:46:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:46:

CGGTGGATCA AGCGGTTAAT TAATCACTCC GTACCTGAT                                  39

(2) INFORMATION FOR SEQ ID NO:47:

(i) SEQUENCE CHARACTERISTICS:
        (A) LENGTH: 17 base pairs

```
    (B) TYPE: nucleic acid
    (C) STRANDEDNESS: single
    (D) TOPOLOGY: linear (xi) SEQUENCE DESCRIPTION: SEQ ID NO:47:
```

GCACTCGAAT GACTACT                                                    17

(2) INFORMATION FOR SEQ ID NO:48:

```
(i) SEQUENCE CHARACTERISTICS:
    (A) LENGTH: 18 base pairs
    (B) TYPE: nucleic acid
    (C) STRANDEDNESS: single
    (D) TOPOLOGY: linear (xi) SEQUENCE DESCRIPTION: SEQ ID NO:48:
```

CGCATCATAC TTGCGACA                                                   18

(2) INFORMATION FOR SEQ ID NO:49:

```
(i) SEQUENCE CHARACTERISTICS:
    (A) LENGTH: 21 base pairs
    (B) TYPE: nucleic acid
    (C) STRANDEDNESS: single
    (D) TOPOLOGY: linear (xi) SEQUENCE DESCRIPTION: SEQ ID NO:49:
```

AGAAATCGGG TATCCTTTCA G                                               21

(2) INFORMATION FOR SEQ ID NO:50:

```
(i) SEQUENCE CHARACTERISTICS:
    (A) LENGTH: 1132 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:50:
```

AACCCTGTAT GTGAGCCTGA TTCAAGACTT CGGATTTACT TTCAAGGCTT CGAATCACTG      60

TTAAGGCAGA AGAAAGTAGT ACTAATGGTT ATCAATATAT AGGAGGGCAA GCGGGAGGTT     120

ATCGCCAACG AAGAAGGAGG TTAGTCCACT ACTGCTTGGT GGCGGGTAAT CTTAAGAGCA     180

CAAACTAACG GATACACAGA TCGTCAAATC CCTTCCGTCC TTTCATACAT TGATGGTGAG     240

GAGTACCACG GTACTCAAGC CAAGGCCCAG TTGGTCCGCA ACTCCCAGAA CACTGTCGCA     300

TACTTCAGAG ATTACCTTGG CAAGGAGTTC AAGTCGATAG ACGCCACACC ATGCCATAAC     360

TCGGCGCATC CTCAGCCTCA CGAGTCTACC GTTGCTTTCT CCATTGTGGA CTCTACCAAC     420

GAGACCCCCA GCACTGTCAC CGTCTCCGAG ATTGCCACCC GCCATCTCCG TCGTTTGAAG     480

CAGTCCGCCT CTGACTACCT GGGCAAGGAA GTCAATGCCG CCGTCATCAC TGTCCCCACT     540

GACTTCTCCG ATGCTCAGCG CGAGGCTTTG ACCGCTTCCG CTAAGGCTGC TGGCCTTGAG     600

GTCCTCCAGC TCATCCATGA GCCTGTTGCC GCTGCCCTGG CTTACGATGC CAGGCCCGAG     660

GCTACTGTTA CTGACAAGCT TGTTGTCGTC GCCGACCTCG GTGGTACCCG ATCCGACGCT     720

GCTGTTCTCG CTTGCCGTGG TGGCATGTAC AGTATCCTCG CAACTGCTCA TGACTACGAG     780

TTGGGTGGAG CTTCGTTGGA CAAGATCATC ATCGACCATT CGCCAAGGA GTTCATTAAG      840

AAGCACAAGA CCGATCCTCG CGAGAACGCT CGTGGTCTCG CCAAGTTGAA GCTTGAGGGT     900

GAGGCTGCTC GCAAGACCTT GAGCTTGGGT ACCAACGCCA GCTTGAGCAT TGAGATCTTC     960

```
GCAGATGGCA TTGATTTCGG CTCCACTGTC AACCGTACTC GNTACGAACT TCTTTCCGGC      1020

AAGACCTTCG CCCAGTTCAC CGGCTTGATC GAGCAGGTTA TCCAGAAGGC TGGTTTGGAT      1080

GTTTTGGACA TTGACGAGGT TAGTCCCTTG TGATTTTTTT TTTTTTTTTC AG             1132
```

(2) INFORMATION FOR SEQ ID NO:51:

(i) SEQUENCE CHARACTERISTICS:
        (A) LENGTH: 374 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:51:

```
Asn Pro Val Cys Glu Pro Asp Ser Arg Leu Arg Ile Tyr Phe Gln Gly
 1               5                  10                  15

Phe Glu Ser Leu Leu Arg Gln Lys Lys Val Val Leu Met Val Ile Asn
             20                  25                  30

Ile Glu Gly Lys Arg Glu Val Ile Ala Asn Glu Glu Gly Gly Ser Thr
         35                  40                  45

Thr Ala Trp Trp Arg Val Ile Leu Arg Ala Gln Thr Asn Gly Tyr Thr
     50                  55                  60

Asp Arg Gln Ile Pro Ser Val Leu Ser Tyr Ile Asp Gly Glu Glu Tyr
65                  70                  75                  80

His Gly Thr Gln Ala Lys Ala Gln Leu Val Arg Asn Ser Gln Asn Thr
                 85                  90                  95

Val Ala Tyr Phe Arg Asp Tyr Leu Gly Lys Glu Phe Lys Ser Ile Asp
            100                 105                 110

Ala Thr Pro Cys His Asn Ser Ala His Pro Gln Pro His Glu Ser Thr
        115                 120                 125

Val Ala Phe Ser Ile Val Asp Ser Thr Asn Glu Thr Pro Ser Thr Val
    130                 135                 140

Thr Val Ser Glu Ile Ala Thr Arg His Leu Arg Arg Leu Lys Gln Ser
145                 150                 155                 160

Ala Ser Asp Tyr Leu Gly Lys Glu Val Asn Ala Ala Val Ile Thr Val
                165                 170                 175

Pro Thr Asp Phe Ser Asp Ala Gln Arg Glu Ala Leu Thr Ala Ser Ala
            180                 185                 190

Lys Ala Ala Gly Leu Glu Val Leu Gln Leu Ile His Glu Pro Val Ala
        195                 200                 205

Ala Ala Leu Ala Tyr Asp Ala Arg Pro Glu Ala Thr Val Thr Asp Lys
    210                 215                 220

Leu Val Val Val Ala Asp Leu Gly Gly Thr Arg Ser Asp Ala Ala Val
225                 230                 235                 240

Leu Ala Cys Arg Gly Gly Met Tyr Ser Ile Leu Ala Thr Ala His Asp
                245                 250                 255

Tyr Glu Leu Gly Gly Ala Ser Leu Asp Lys Ile Ile Ile Asp His Phe
            260                 265                 270

Ala Lys Glu Phe Ile Lys Lys His Lys Thr Asp Pro Arg Glu Asn Ala
        275                 280                 285

Arg Gly Leu Ala Lys Leu Lys Leu Glu Gly Glu Ala Ala Arg Lys Thr
    290                 295                 300

Leu Ser Leu Gly Thr Asn Ala Ser Leu Ser Ile Glu Ile Phe Ala Asp
305                 310                 315                 320
```

```
Gly Ile Asp Phe Gly Ser Thr Val Asn Arg Thr Arg Tyr Glu Leu Leu
                325                 330                 335

Ser Gly Lys Thr Phe Ala Gln Phe Thr Gly Leu Ile Glu Gln Val Ile
            340                 345                 350

Gln Lys Ala Gly Leu Asp Val Leu Asp Ile Asp Glu Val Ser Pro Leu
        355                 360                 365

Phe Phe Phe Phe Phe Ser
    370

(2) INFORMATION FOR SEQ ID NO:52:

(i) SEQUENCE CHARACTERISTICS:
        (A) LENGTH: 339 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:52:

Met Ser Lys Ala Val Gly Ile Asp Leu Gly Thr Thr Tyr Ser Cys Val
1               5                   10                  15

Ala His Phe Ala Asn Asp Arg Val Asp Ile Ile Ala Asn Asp Gln Gly
            20                  25                  30

Asn Arg Thr Thr Pro Ser Phe Val Ala Phe Thr Asp Thr Glu Arg Leu
        35                  40                  45

Ile Gly Asp Ala Ala Lys Asn Gln Ala Ala Met Asn Pro Ser Asn Thr
50                  55                  60

Val Phe Asp Ala Lys Arg Leu Ile Gly Arg Asn Phe Asn Asp Pro Glu
65                  70                  75                  80

Val Gln Ala Asp Met Lys His Phe Pro Phe Lys Leu Ile Asp Val Asp
                85                  90                  95

Gly Lys Pro Gln Ile Gln Val Glu Phe Lys Gly Glu Thr Lys Asn Phe
            100                 105                 110

Thr Pro Glu Gln Ile Ser Ser Met Val Leu Gly Lys Met Lys Glu Thr
        115                 120                 125

Ala Glu Ser Tyr Leu Gly Ala Lys Val Asn Asp Ala Val Val Thr Val
130                 135                 140

Pro Ala Tyr Phe Asn Asp Ser Gln Arg Gln Ala Thr Lys Asp Ala Gly
145                 150                 155                 160

Thr Ile Ala Gly Leu Asn Val Leu Arg Ile Ile Asn Glu Pro Thr Ala
                165                 170                 175

Ala Ala Ile Ala Tyr Gly Leu Asp Lys Lys Gly Lys Glu Glu His Val
            180                 185                 190

Leu Ile Phe Asp Leu Gly Gly Gly Thr Phe Asp Val Ser Leu Leu Phe
        195                 200                 205

Ile Glu Asp Gly Ile Phe Glu Val Lys Ala Thr Ala Gly Asp Thr His
210                 215                 220

Leu Gly Gly Glu Asp Phe Asp Asn Arg Leu Val Asn His Phe Ile Gln
225                 230                 235                 240

Glu Phe Lys Arg Lys Asn Lys Lys Asp Leu Ser Thr Asn Gln Arg Ala
                245                 250                 255

Leu Arg Arg Leu Arg Thr Ala Cys Glu Ser Gln Glu Asn Phe Val Ser
            260                 265                 270

Ser Ala Gln Thr Ser Val Glu Ile Asp Ser Lys Asn Glu Gly Ile Asp
        275                 280                 285
```

```
Phe Tyr Thr Ser Ile Thr Arg Ala Arg Phe Glu Glu Leu Cys Ala Asp
    290                 295                 300

Leu Phe Arg Ser Thr Leu Asp Pro Val Glu Lys Val Leu Arg Asp Ala
305                 310                 315                 320

Lys Leu Asp Lys Ser Gln Val Asp Glu Ile Val Leu Val Gly Gly Ser
                325                 330                 335

Thr Arg Ile (2) INFORMATION FOR SEQ ID NO:53:

(i) SEQUENCE CHARACTERISTICS:
        (A) LENGTH: 560 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:53:

Lys Thr Leu Pro Phe Ser Glu Asn Phe Ile Met Ala Asp Ser Glu Glu
1               5                   10                  15

Tyr Lys Thr Val Ile Gly Ile Ser Phe Gly Asn Gln Asn Ser Ser Ile
                20                  25                  30

Ala Phe Asn Arg Asp Gly Lys Thr Asp Val Leu Ala Asn Glu Glu Gly
                35                  40                  45

Asn Arg Gln Ile Pro Ser Ile Leu Pro Tyr His Gly Asp Gln Glu Tyr
50                  55                  60

His Gly Val Gln Ala Arg Gly Gln Leu Val Arg Asn Ala Asp Asn Ser
65                  70                  75                  80

Val Thr Asn Phe Arg Asp Leu Leu Gly Lys Ser His Asp Glu Leu Thr
                85                  90                  95

His His His Cys His Tyr Ser Ser Asn Pro Val Asn Val Glu Gly Gln
                100                 105                 110

Ile Gly Phe Lys Ile Thr Val Gln Glu Gly Glu Glu Ser Asp Pro Lys
                115                 120                 125

Glu Lys Ile Leu Thr Ala His Glu Ala Ser Val Arg His Leu Arg Arg
130                 135                 140

Leu Thr Glu Ser Ala Glu Asp Phe Leu Gly Thr Lys Val Asn Gly Cys
145                 150                 155                 160

Val Met Ser Val Pro Val Tyr Phe Thr Asp Ala Gln Arg Lys Ala Leu
                165                 170                 175

Glu Ser Ala Ala Asn Glu Ala Gly Leu Pro Val Leu Gln Leu Ile His
                180                 185                 190

Asp Pro Ala Ala Val Ile Leu Ala Leu Met Tyr Ser Glu Glu Val Leu
                195                 200                 205

Ile Asp Lys Thr Val Val Ala Asn Phe Gly Ala Thr Arg Ser Glu
                210                 215                 220

Val Ser Val Val Ser Val Lys Gly Gly Leu Met Thr Ile Leu Ala Ser
225                 230                 235                 240

Val His Asp Glu Asn Leu Gly Gly Glu Gln Leu Thr Asp Val Leu Val
                245                 250                 255

Asn Phe Phe Ala Lys Glu Phe Lys Lys Asn Gly Ile Asp Pro Arg
                260                 265                 270

Lys Asn Ala Arg Ser Leu Val Lys Leu Arg Ala Gln Cys Glu Ile Thr
                275                 280                 285

Lys Arg Val Leu Ser Asn Gly Thr Thr Ala Ser Ala Ala Val Asp Ser
```

```
             290                 295                 300
Leu Ala Asp Gly Ile Asp Phe His Ser Ser Ile Asn Arg Leu Arg Tyr
305                 310                 315                 320

Asp Leu Ala Ala Ser Ala Thr Leu Asn Arg Met Ala Asp Leu Val Thr
                325                 330                 335

Glu Ala Val Glu Lys Ala Asn Met Glu Pro Phe Asp Ile Ser Glu Val
                340                 345                 350

Ile Leu Ala Gly Gly Ala Ser Asn Thr Pro Lys Leu Thr Ser Leu Met
                355                 360                 365

Glu Ser Ile Phe Pro Glu Gln Thr Ile Ile Arg Ser Ser Ser Ser Val
370                 375                 380

Thr Pro Leu Gln Leu Asp Pro Ser Glu Leu Thr Ala Ile Gly Ser Gly
385                 390                 395                 400

Val Gln Ala Ser Leu Ile Gly His Phe Asp Ala Ala Asp Ile Ala Ala
                405                 410                 415

Ser Thr Asp Ala Gln Val Val Asp Val Pro His Leu Thr Ala Pro Ile
                420                 425                 430

Gly Ile Asn Glu Gly Glu Asn Phe Val Thr Ile Phe Asp Ile Glu Thr
                435                 440                 445

Ala Leu Pro Ala Arg Lys Thr Val Glu Val Ile Ala Pro Lys Glu Gly
450                 455                 460

Ala Ala Phe Ile Pro Ile Tyr Glu Ala Glu Arg Ser Val Lys Val Thr
465                 470                 475                 480

Lys Val Glu Pro Glu Pro Ile Asp Glu Glu Ala Phe Ser Asp Asp
                485                 490                 495

Glu Glu Glu Glu Pro Glu Glu Ile Lys Glu Arg Ile Ala Ile Pro Lys
                500                 505                 510

Thr Leu Ile Ala Thr Ile Thr Leu Pro Asp Val Ser Pro Asn Ala Lys
                515                 520                 525

Ile Glu Leu Val Leu Gln Ile Asp Ala Glu Gly Lys Leu Thr Ala Ser
530                 535                 540

Ala Arg Pro Lys Asp Gly Lys Gly Thr Asn Val Arg Gly Ser Thr Ala
545                 550                 555                 560
```

(2) INFORMATION FOR SEQ ID NO:54:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:54:

TACGGTTGAC AGTGGAGC                                                    18

(2) INFORMATION FOR SEQ ID NO:55:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:55:

CACTGACTTC TCCGATGC                                                    18

(2) INFORMATION FOR SEQ ID NO:56:

```
        (i) SEQUENCE CHARACTERISTICS:
            (A) LENGTH: 501 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:56:

ATTTCCCAGC GTCGTCGTTG GTTGAACGGT TCTTTTGCGG CCGGTCTCTA TTCGCTCATG      60

CATTTCGGTC GGATGTACAA GAGTGGACAT AACATCATCC GTATGTTCTT CTTGCACATT     120

CAGATGTTGT ACAACGTTTT CAACACTATC CTTACATGGT TCTCCCTGGC ATCTTACTGG     180

TTGACCACCA CCGTCATCAT GGACTTGGTC GGAACGCCCA GTGAGAGCAA CGGTAACAAA     240

GGATTCCCCT TCGGTAAATC GGCGACCCCT ATTATCAACA CAATTGTGAA GTATGTCTAC     300

CTCGGATTGT TGCTCTTGCA GTTCATTCTC GCTCTCGGTA ACCGCCCCAA GGGATCCCGC     360

TTCTCGTACC TGACATCTTT CGTCGTATTC GGTATCATTC AAATCTACGT TGTCGTCGAC     420

GCTCTGTACT TGGTGGTTCG TGCATTCAAG GTGTTGGCGA ATTCCTCAAG TCGTTCTTCT     480

CGTCTTCCGG CGCCAGCGCC A                                              501

(2) INFORMATION FOR SEQ ID NO:57:

(i) SEQUENCE CHARACTERISTICS:
            (A) LENGTH: 178 amino acids
            (B) TYPE: amino acid
            (C) STRANDEDNESS: single
            (D) TOPOLOGY: linear (ii) MOLECULE TYPE: None (xi) SEQUENCE DESCRIPTION: SEQ ID NO:57:

Ile Ser Gln Arg Arg Arg Trp Leu Asn Gly Ser Phe Ala Ala Gly Leu
 1               5                  10                  15

Tyr Ser Leu Met His Phe Gly Arg Met Tyr Lys Ser Gly His Asn Ile
            20                  25                  30

Ile Arg Met Phe Phe Leu His Ile Gln Met Leu Tyr Asn Val Phe Asn
        35                  40                  45

Thr Ile Leu Thr Trp Phe Ser Leu Ala Ser Tyr Trp Leu Thr Thr Thr
    50                  55                  60

Val Ile Met Asp Leu Val Gly Thr Pro Ser Glu Ser Asn Gly Asn Lys
65                  70                  75                  80

Gly Phe Pro Phe Gly Lys Ser Ala Thr Pro Ile Ile Asn Thr Ile Val
                85                  90                  95

Lys Tyr Val Tyr Leu Gly Leu Leu Leu Gln Phe Ile Leu Ala Leu
            100                 105                 110

Gly Asn Arg Pro Lys Gly Ser Arg Phe Ser Tyr Leu Thr Ser Phe Val
        115                 120                 125

Val Phe Gly Ile Ile Gln Ile Tyr Val Val Asp Ala Leu Tyr Leu
    130                 135                 140

Val Val Arg Ala Phe Thr Asn Ser Asp Ala Ile Asp Phe Val Thr Asp
145                 150                 155                 160

Gln Gly Val Gly Glu Phe Leu Lys Ser Phe Phe Ser Ser Gly Ala
                165                 170                 175

Ser Ala (2) INFORMATION FOR SEQ ID NO:58:
```

(i) SEQUENCE CHARACTERISTICS:
        (A) LENGTH: 916 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:58:

Met Ala Tyr His Gly Ser Gly Pro Gln Ser Pro Gly Glu His Thr Tyr
1               5                   10                  15

Asp Asp Gly His Gln Leu Arg Asp Leu Ser His Ser Asn Thr Ser Tyr
            20                  25                  30

Glu Glu Glu Ala Ser His Gly Leu Leu Ser Ser Gln Gln Ser Pro Phe
            35                  40                  45

Ala Gly Pro Phe Asp Asp Pro His Gln Gln Arg Gly Leu Thr Ala Ser
50                  55                  60

Pro Val Gln Arg Pro Thr Ser Gly Tyr Ser Leu Thr Glu Ser Tyr Ala
65                  70                  75                  80

Pro Asp Ala Ala Tyr His Asp Pro Tyr Ser Ala Asn Gln Ser Val Tyr
            85                  90                  95

Ser Gly His Ser Glu Asn Pro Ala Ala Ala Phe Gly Val Pro Gly Arg
            100                 105                 110

Val Ala Ser Pro Tyr Ala Arg Ser Glu Thr Ser Ser Thr Glu Ala Trp
            115                 120                 125

Arg Gln Arg Gln Ala Gly Ala Arg Arg Gly Gly Asn Gly Leu Arg Arg
130                 135                 140

Tyr Ala Thr Arg Lys Val Lys Leu Val Gln Gly Ser Val Leu Ser Val
145                 150                 155                 160

Asp Tyr Pro Val Pro Ser Ala Ile Gln Asn Ala Ile Gln Ala Lys Tyr
            165                 170                 175

Arg Asn Asp Leu Glu Gly Gly Ser Glu Phe Thr His Met Arg Tyr
            180                 185                 190

Thr Ala Ala Thr Cys Asp Pro Asn Glu Phe Thr Leu His Asn Gly Tyr
            195                 200                 205

Asn Leu Arg Pro Ala Met Tyr Asn Arg His Thr Glu Leu Leu Ile Ala
210                 215                 220

Ile Thr Tyr Tyr Asn Glu Asp Lys Thr Leu Thr Ala Arg Thr Leu His
225                 230                 235                 240

Gly Val Met Gln Asn Ile Arg Asp Ile Val Asn Leu Lys Lys Ser Glu
            245                 250                 255

Phe Trp Asn Lys Gly Gly Pro Ala Trp Gln Lys Ile Val Val Cys Leu
            260                 265                 270

Val Phe Asp Gly Ile Asp Pro Cys Asp Lys Asp Thr Leu Asp Val Leu
            275                 280                 285

Ala Thr Val Gly Ile Tyr Gln Asp Gly Val Met Lys Arg Asp Val Asp
            290                 295                 300

Gly Lys Glu Thr Val Ala His Ile Phe Glu Tyr Thr Thr Gln Leu Ser
305                 310                 315                 320

Val Thr Pro Asn Gln Gln Leu Ile Arg Pro Thr Asp Asp Gly Pro Ser
            325                 330                 335

Thr Leu Pro Pro Val Gln Met Met Phe Cys Leu Lys Gln Lys Asn Ser
            340                 345                 350

Lys Lys Ile Asn Ser His Arg Trp Leu Phe Asn Ala Phe Gly Arg Ile
            355                 360                 365

```
-continued

Leu Asn Pro Glu Val Cys Ile Leu Asp Ala Gly Thr Lys Pro Gly
    370             375             380

Pro Lys Ser Leu Leu Tyr Leu Trp Glu Ala Phe Tyr Asn Asp Lys Asp
385             390             395                 400

Leu Gly Gly Ala Cys Gly Glu Ile His Ala Met Leu Gly Lys Gly Trp
                405             410             415

Lys Lys Leu Leu Asn Pro Leu Val Ala Ala Gln Asn Phe Glu Tyr Lys
            420             425             430

Ile Ser Asn Ile Leu Asp Lys Pro Leu Glu Ser Ser Phe Gly Tyr Val
            435             440             445

Ser Val Leu Pro Gly Ala Phe Ser Ala Tyr Arg Phe Arg Ala Ile Met
        450             455             460

Gly Arg Pro Leu Glu Gln Tyr Phe His Gly Asp His Thr Leu Ser Lys
465             470             475             480

Gln Leu Gly Lys Lys Gly Ile Glu Gly Met Asn Ile Phe Lys Lys Asn
                485             490             495

Met Phe Leu Ala Glu Asp Arg Ile Leu Cys Phe Glu Leu Val Ala Lys
            500             505             510

Ala Gly Ser Lys Trp His Leu Ser Tyr Val Lys Ala Ser Lys Gly Glu
        515             520             525

Thr Asp Val Pro Glu Gly Ala Pro Glu Phe Ile Ser Gln Arg Arg Arg
530             535             540

Trp Leu Asn Gly Ser Phe Ala Ala Gly Ile Tyr Ser Leu Met His Phe
545             550             555             560

Gly Arg Met Tyr Lys Ser Gly His Asn Ile Val Arg Met Phe Phe Leu
                565             570             575

His Leu Gln Met Leu Tyr Asn Trp Phe Ser Thr Phe Leu Thr Trp Phe
            580             585             590

Ser Leu Ala Ser Tyr Trp Leu Thr Thr Ser Val Ile Met Asp Leu Val
        595             600             605

Gly Thr Pro Ser Ser Ser Asn Gly Tyr Thr Ala Phe Pro Phe Gly Lys
610             615             620

Thr Ala Thr Pro Ile Ile Asn Thr Leu Val Lys Tyr Ile Tyr Leu Ala
625             630             635             640

Phe Leu Leu Leu Gln Phe Ile Leu Ala Leu Gly Asn Arg Pro Lys Gly
                645             650             655

Ser Lys Leu Ser Tyr Leu Ala Ser Phe Ala Phe Gly Ile Ile Gln
            660             665             670

Leu Tyr Val Val Val Asp Ala Leu Tyr Leu Val Val Arg Ala Phe Thr
        675             680             685

Gly Gly Ala Pro Met Asp Phe Asn Thr Asp Asp Gly Ile Gly Ala Phe
690             695             700

Leu Ser Ser Phe Phe Gly Ser Ser Gly Ala Gly Ile Ile Ile Ile Ala
705             710             715             720

Leu Ala Ala Thr Phe Gly Leu Tyr Phe Val Ala Ser Phe Met Tyr Leu
                725             730             735

Asp Pro Trp His Met Phe Thr Ser Phe Pro Ala Tyr Met Ala Val Gln
            740             745             750

Ser Ser Tyr Ile Asn Ile Leu Asn Val Tyr Ala Phe Ser Asn Trp His
        755             760             765

Asp Val Ser Trp Gly Thr Lys Gly Ser Asp Lys Ala Asp Ala Leu Pro
770             775             780

Ser Ala Lys Thr Thr Gly Gly Lys Gly Glu Glu Ala Val Ile Glu Glu
```

-continued

```
                785                 790                 795                 800
Ile Asp Lys Pro Gln Ala Asp Ile Asp Ser Gln Phe Glu Ala Thr Val
                    805                 810                 815

Lys Arg Ala Leu Thr Pro Tyr Val Pro Pro Glu Glu Lys Glu Glu Lys
                    820                 825                 830

Ser Leu Asp Asp Ser Tyr Lys Ser Phe Arg Thr Arg Leu Val Thr Leu
                    835                 840                 845

Trp Leu Phe Ser Asn Gly Leu Leu Ala Val Cys Ile Thr Ser Glu Gly
                    850                 855                 860

Leu Asp Lys Phe Gly Phe Thr Asn Thr Ser Thr Glu Arg Thr Ser Arg
865                 870                 875                 880

Phe Phe Gln Ala Leu Leu Trp Ser Asn Ala Val Val Ala Leu Ile Arg
                    885                 890                 895

Phe Ile Gly Ala Thr Trp Phe Leu Gly Lys Thr Gly Leu Leu Cys Cys
                    900                 905                 910

Phe Ala Arg Arg
                    915

(2) INFORMATION FOR SEQ ID NO:59:

(i) SEQUENCE CHARACTERISTICS:
        (A) LENGTH: 911 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:59:

Met Ala Tyr Gln Gly Ser Gly Ser His Ser Pro Pro His Tyr Asp Asp
1               5                   10                  15

Asn Gly His Arg Leu Gln Asp Leu Pro His Gly Ser Tyr Glu Glu Glu
                    20                  25                  30

Ala Ser Arg Gly Leu Leu Ser His Gln Gln Gly Pro Phe Thr Gly Pro
                    35                  40                  45

Phe Asp Asp Pro Gln Gln His Gly Ser Ser Thr Thr Arg Pro Val Ser
            50                  55                  60

Gly Tyr Ser Leu Ser Glu Thr Tyr Ala Pro Glu Ala Ala Tyr His Asp
65                  70                  75                  80

Pro Tyr Thr Gln Pro Ser Pro Gly Ser Val Tyr Ser Ala Gln Ser Ala
                    85                  90                  95

Glu Asn Pro Ala Ala Ala Phe Gly Val Pro Gly Arg Val Ala Ser Pro
                    100                 105                 110

Tyr Ala Arg Ser Asp Thr Ser Ser Thr Glu Ala Trp Arg Gln Arg Gln
                    115                 120                 125

Ala Pro Gly Gly Pro Gly Leu Arg Arg Tyr Ala Thr Arg Lys
            130                 135                 140

Val Lys Leu Val Gln Gly Ser Val Leu Ser Val Asp Tyr Pro Val Pro
145                 150                 155                 160

Ser Ala Ile Gln Asn Ala Ile Gln Ala Lys Tyr Arg Asn Asp Leu Glu
                    165                 170                 175

Gly Gly Ser Glu Glu Phe Thr His Met Arg Tyr Thr Ala Ala Thr Cys
                    180                 185                 190

Asp Pro Asn Glu Phe Thr Leu His Asn Gly Tyr Asn Leu Arg Pro Ala
            195                 200                 205

Met Tyr Asn Arg His Thr Glu Leu Leu Ile Ala Ile Thr Tyr Tyr Asn
```

-continued

```
            210                 215                 220
Glu Asp Lys Thr Leu Thr Ser Arg Thr Leu His Gly Val Met Gln Asn
225                 230                 235                 240
Ile Arg Asp Ile Val Asn Leu Lys Lys Ser Glu Phe Trp Asn Lys Gly
                245                 250                 255
Gly Pro Ala Trp Gln Lys Ile Val Val Cys Leu Val Phe Asp Gly Ile
                260                 265                 270
Asp Pro Cys Asp Lys Asp Thr Leu Asp Val Leu Ala Thr Ile Gly Val
        275                 280                 285
Tyr Gln Asp Gly Val Met Lys Arg Asp Val Asp Gly Lys Glu Thr Val
        290                 295                 300
Ala His Ile Phe Glu Tyr Thr Thr Gln Leu Ser Val Thr Pro Asn Gln
305                 310                 315                 320
Gln Leu Ile Arg Pro Thr Asp Asp Gly Pro Ser Thr Leu Leu Pro Ser
                325                 330                 335
Lys Met Met Phe Cys Leu Lys Gln Lys Asn Ser Lys Lys Ile Asn Ser
                340                 345                 350
His Arg Trp Leu Phe Asn Ala Phe Gly Arg Ile Leu Asn Pro Glu Val
                355                 360                 365
Cys Ile Leu Leu Asp Ala Gly Thr Lys Pro Gly Pro Lys Ser Leu Leu
        370                 375                 380
Ser Leu Trp Glu Ala Phe Tyr Asn Asp Lys Asp Leu Gly Gly Ala Cys
385                 390                 395                 400
Gly Glu Ile His Ala Met Leu Gly Lys Gly Trp Lys Asn Leu Ile Asn
                405                 410                 415
Pro Leu Val Ala Ala Gln Asn Phe Glu Tyr Lys Ile Ser Asn Ile Leu
                420                 425                 430
Asp Lys Pro Leu Glu Ser Ser Phe Gly Tyr Val Ser Val Leu Pro Gly
                435                 440                 445
Ala Phe Ser Ala Tyr Arg Phe Arg Ala Ile Met Gly Arg Pro Leu Glu
        450                 455                 460
Gln Tyr Phe His Gly Asp His Thr Leu Ser Lys Gln Leu Gly Lys Lys
465                 470                 475                 480
Gly Ile Glu Gly Met Asn Ile Phe Lys Lys Asn Met Phe Leu Ala Glu
                485                 490                 495
Asp Arg Ile Leu Cys Phe Glu Leu Val Ala Lys Ala Gly Ser Lys Trp
                500                 505                 510
His Leu Thr Tyr Val Lys Ala Ser Lys Ala Glu Thr Asp Val Pro Glu
                515                 520                 525
Gly Ala Pro Glu Phe Ile Ser Gln Arg Arg Trp Leu Asn Gly Ser
        530                 535                 540
Phe Ala Ala Gly Ile Tyr Ser Leu Met His Phe Gly Arg Met Tyr Lys
545                 550                 555                 560
Ser Gly His Asn Ile Val Arg Met Phe Phe Leu His Ile Gln Met Leu
                565                 570                 575
Tyr Asn Ile Phe Ser Thr Val Leu Thr Trp Phe Ser Leu Ala Ser Tyr
                580                 585                 590
Trp Leu Thr Thr Thr Val Ile Met Asp Leu Val Gly Thr Pro Ser Asp
        595                 600                 605
Asn Asn Gly Asn Lys Ala Phe Pro Phe Gly Lys Thr Ala Thr Pro Ile
        610                 615                 620
Ile Asn Thr Ile Val Lys Tyr Val Tyr Leu Gly Phe Leu Leu Leu Gln
625                 630                 635                 640
```

```
Phe Ile Leu Ala Leu Gly Asn Arg Pro Lys Gly Ser Lys Phe Ser Tyr
                645                 650                 655
Leu Ala Ser Phe Val Val Phe Gly Ile Ile Gln Val Tyr Val Val Ile
            660                 665                 670
Asp Ala Leu Tyr Leu Val Val Arg Ala Phe Ser Gly Ser Ala Pro Met
            675                 680                 685
Asp Phe Thr Thr Asp Gln Gly Val Gly Glu Phe Leu Lys Ser Phe Phe
        690                 695                 700
Ser Ser Ser Gly Ala Gly Ile Ile Ile Ala Leu Ala Thr Phe
705                 710                 715                 720
Gly Leu Tyr Phe Val Ala Ser Phe Met Tyr Leu Asp Pro Trp His Met
                725                 730                 735
Phe Thr Ser Phe Pro Ala Tyr Met Cys Val Gln Ser Ser Tyr Ile Asn
                740                 745                 750
Ile Leu Asn Val Tyr Ala Phe Ser Asn Trp His Asp Val Ser Trp Gly
            755                 760                 765
Thr Lys Gly Ser Asp Lys Ala Asp Ala Leu Pro Ser Ala Lys Thr Thr
        770                 775                 780
Lys Asp Glu Gly Lys Glu Val Val Ile Glu Glu Ile Asp Lys Pro Gln
785                 790                 795                 800
Ala Asp Ile Asp Ser Gln Phe Glu Ala Thr Val Lys Arg Ala Leu Thr
                805                 810                 815
Pro Tyr Val Pro Pro Val Glu Lys Glu Glu Lys Thr Leu Glu Asp Ser
                820                 825                 830
Tyr Lys Ser Phe Arg Thr Arg Leu Val Thr Phe Trp Ile Phe Ser Asn
        835                 840                 845
Ala Phe Leu Ala Val Cys Ile Thr Ser Asp Gly Val Asp Lys Phe Gly
850                 855                 860
Phe Thr Asn Ser Ala Thr Asp Arg Thr Gln Arg Phe Phe Gln Ala Leu
865                 870                 875                 880
Leu Trp Ser Asn Ala Val Val Ala Leu Phe Arg Phe Ile Gly Ala Cys
                885                 890                 895
Trp Phe Leu Gly Lys Thr Gly Leu Met Cys Cys Phe Ala Arg Arg
                900                 905                 910
```

(2) INFORMATION FOR SEQ ID NO:60:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:60:

CACCAAGTCA GAGCGTC                    17

(2) INFORMATION FOR SEQ ID NO:61:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:61:

GGCCTTYGAY GAYCCCA                    17

(2) INFORMATION FOR SEQ ID NO:62:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:62:

```
GGGCCGTTTG ACAATCCGCA T                                              21
```

(2) INFORMATION FOR SEQ ID NO:63:

(i) SEQUENCE CHARACTERISTICS:
        (A) LENGTH: 251 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:63:

```
AGGGCCACAG CNTGTGCTAA GCGCCTTGAC GGGGACCCTG GACTTTCAA GTCTCCTTGG      60
ACCCGGAATT GAATCCTCAC AGAACAGCTT TCAACACTGC TCTAAGGCTG AACTGAGCTG    120
CGCGACTCCG TATCATGGCC AAGACAAATG CTGCTTCAAC TATCCCGGGG GGCAGTTCCT    180
TCAATCGCTG TTTTGGGACG CCGACCCGGC CATTGGACCG GAAGATTCCT GGACTATCCA    240
TGGCTTATGG T                                                        251
```

(2) INFORMATION FOR SEQ ID NO:64:

(i) SEQUENCE CHARACTERISTICS:
        (A) LENGTH: 83 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:64:

```
Gly Pro Gln Xaa Val Leu Ser Ala Leu Thr Gly Thr Leu Gly Leu Ser
  1               5                  10                  15

Ser Leu Leu Gly Pro Gly Ile Glu Ser Ser Gln Asn Ser Phe Gln His
                 20                  25                  30

Cys Ser Lys Ala Glu Leu Ser Cys Ala Thr Pro Tyr His Gly Gln Asp
             35                  40                  45

Lys Cys Cys Phe Asn Tyr Pro Gly Gly Gln Phe Leu Gln Ser Leu Phe
         50                  55                  60

Trp Asp Ala Asp Pro Ala Ile Gly Pro Glu Asp Ser Trp Thr Ile His
 65                  70                  75                  80

Gly Leu Trp
```

(2) INFORMATION FOR SEQ ID NO:65:

(i) SEQUENCE CHARACTERISTICS:
        (A) LENGTH: 83 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:65:

Gly Pro Gln Xaa Val Leu Ser Ala Leu Thr Gly Thr Leu Gly Leu Ser

```
              1               5                  10                  15
            Ser Leu Leu Gly Pro Gly Ile Glu Ser Ser Gln Asn Ser Phe Gln His
                            20                  25                  30

Cys Ser Lys Ala Glu Leu Ser Cys Ala Thr Pro Tyr His Gly Gln Asp
                        35                  40                  45

Lys Cys Cys Phe Asn Tyr Pro Gly Gly Gln Phe Leu Gln Ser Leu Phe
             50                      55                  60

Trp Asp Ala Asp Pro Ala Ile Gly Pro Glu Asp Ser Trp Thr Ile His
             65                  70                  75                  80

Gly Leu Trp
```

(2) INFORMATION FOR SEQ ID NO:66:

(i) SEQUENCE CHARACTERISTICS:
        (A) LENGTH: 214 base pairs
        (B) TYPE: nucleic acid
        (C) STRANDEDNESS: single
        (D) TOPOLOGY: linear (xi) SEQUENCE DESCRIPTION: SEQ ID NO:66:

```
CTACTGAACG CTTAAAGGTG CTTAAGGAGC AACTTCATAT TATGCGCGAC CAACGGATCC      60

AGGAAGTCTT GAGCAATAAG AAGGGTCGAA CGCAGCACGG ACACTCGCAC AAGCCGACCG     120

GTTTTGGGGG ACTCAACGGT TCTCGGCTAA AGGAGGCCTT TGTGGGACGT CGAATCGGGA     180

AGAATTCCAA GGCATTGGCC GAATTGGCCA CCCC                                 214
```

(2) INFORMATION FOR SEQ ID NO:67:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:67:

```
GTTCTATTGA GATACGCG                                                    18
```

(2) INFORMATION FOR SEQ ID NO:68:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:68:

```
ACAAGCCGAC CGGTTTTG                                                    18
```

(2) INFORMATION FOR SEQ ID NO:69:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:69:

```
CGATAAGGAC TCCAAGAG                                                    18
```

(2) INFORMATION FOR SEQ ID NO:70:

(i) SEQUENCE CHARACTERISTICS:
        (A) LENGTH: 18 base pairs (B) TYPE: nucleic acid
        (C) STRANDEDNESS: single
        (D) TOPOLOGY: linear (xi) SEQUENCE DESCRIPTION: SEQ ID NO:70:

GTCGCGCATA ATATGAAG                                                           18

(2) INFORMATION FOR SEQ ID NO:71:

(i) SEQUENCE CHARACTERISTICS:
        (A) LENGTH: 336 base pairs
        (B) TYPE: nucleic acid
        (C) STRANDEDNESS: single
        (D) TOPOLOGY: linear (xi) SEQUENCE DESCRIPTION: SEQ ID NO:71:

AGCACCTATA ATCTATGCTG TCCCACTATC ACACATCTAT ATGTTGTACA AGCCTGATAC              60

AATCAATAAT GATGTAATAA TTGACTCTGG AAAGTTGGCT ATAAAACTCA CCATACAAGT             120

CCAGATAACC CTGCCAAACT CCACTCCCAG GGCATTAATC TTCATTTATA TCGACCAGCC             180

ATACCTATGG TCAAATCACA CGCAACGCCA CAGATATATA TTTGAATCAA ATTTCTCTTT             240

TGAAGAAGAA AGGGTGGTTT ATGAGGAAGA ATATCCCAAT ATGCCAATCT GACTGTTCCG             300

GATTGGAATA ATGCACAAGC TTCGAATATA AATATA                                      336

(2) INFORMATION FOR SEQ ID NO:72:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:72:

CTTCCTCATA AACCACCC                                                           18

(2) INFORMATION FOR SEQ ID NO:73:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:73:

AACTGACAGG ACAAGACC                                                           18

(2) INFORMATION FOR SEQ ID NO:74:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:74:

GACTTGCATC ACTTCCTC                                                           18

(2) INFORMATION FOR SEQ ID NO:75:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:75:

TGAAGCTGAG AGTAGGTG                                                      18

(2) INFORMATION FOR SEQ ID NO:76:

(i) SEQUENCE CHARACTERISTICS:
        (A) LENGTH: 281 base pairs
        (B) TYPE: nucleic acid
        (C) STRANDEDNESS: single
        (D) TOPOLOGY: linear (xi) SEQUENCE DESCRIPTION: SEQ ID NO:76:

CAAGGGAACG GGAATAAAAT ACACATAACA AAGGATTCGA AGAAAGAAAA AAAAAGGGGG          60

GGAGGTGTGT CCAAGAGGAA AGAAGAAAAA AAATTTAATT TCGCCACCCT ATCGCGGAGT        120

GTTCCGCCTT CAGGAGAGAT AGAAAAGAGG AGGGAGAAGG GAGAAGGAAA AAAAAAAACA        180

GAATTCCCAC AGACAAGGAA AGCTTAACCG GGTCACGAAA AAGCACAATA CAGGTGAACA        240

ACTGAGGGGA AGGGGGCCAA AAAGAAAAAA ATAATTCCTA A                           281

(2) INFORMATION FOR SEQ ID NO:77:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:77:

GTTTCGGTAT TGTCACTG                                                      18

(2) INFORMATION FOR SEQ ID NO:78:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:78:

ACAGGTGAAC AACTGAGG                                                      18

(2) INFORMATION FOR SEQ ID NO:79:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:79:

CGACCAAACT AGACAAGC                                                      18

(2) INFORMATION FOR SEQ ID NO:80:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:80:

CTTTCCTCTT GGACACAC                                                      18